(12) United States Patent
Yuen et al.

(10) Patent No.: US 10,008,090 B2
(45) Date of Patent: Jun. 26, 2018

(54) METHODS AND SYSTEMS FOR METRICS ANALYSIS AND INTERACTIVE RENDERING, INCLUDING EVENTS HAVING COMBINED ACTIVITY AND LOCATION INFORMATION

(71) Applicant: Fitbit, Inc., San Francisco, CA (US)

(72) Inventors: Shelten Gee Jao Yuen, Berkeley, CA (US); James Park, Berkeley, CA (US); Hans Christiansen Lee, Carmel, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days. days.

(21) Appl. No.: 14/448,991

(22) Filed: Jul. 31, 2014

(65) Prior Publication Data
US 2014/0340221 A1    Nov. 20, 2014

Related U.S. Application Data

(60) Division of application No. 14/148,505, filed on Jan. 6, 2014, which is a continuation of application No.
(Continued)

(51) Int. Cl.
*G06K 9/00* (2006.01)
*G08B 21/18* (2006.01)
(Continued)

(52) U.S. Cl.
CPC ............ *G08B 21/18* (2013.01); *A61B 5/0002* (2013.01); *A61B 5/1112* (2013.01);
(Continued)

(58) Field of Classification Search
CPC .......... G06F 1/163; G06F 3/012; G06F 3/014; G06F 19/3481
(Continued)

(56) References Cited

U.S. PATENT DOCUMENTS

| 2,717,736 A | 9/1955 | Schlesinger |
| 2,827,309 A | 3/1958 | Fred |

(Continued)

FOREIGN PATENT DOCUMENTS

| CN | 101978374 | 2/2011 |
| CN | 102111434 | 6/2011 |

(Continued)

OTHER PUBLICATIONS

Fitbit Inc., "Fitbit Automatically Tracks Your Fitness and Sleep" published online at web.archive.org/web/20080910224820/http://www.fitbit.com, copyrighted 2008, 1 page.
(Continued)

*Primary Examiner* — Paul D Lee
(74) *Attorney, Agent, or Firm* — Knobbe, Martens, Olson & Bear, LLP

(57) ABSTRACT

A method includes receiving location data of a monitoring device when carried by a user and receiving motion data of the monitoring device. The motion data is associated with a time of occurrence and the location data. The method includes processing the received motion data to identify a group of the motion data having a substantially common characteristic and processing the location data for the group of the motion data. The group of motion data by way of processing the location data provides an activity identifier. The motion data includes metric data that identifies characteristics of the motion data. The method includes transferring the activity identifier and the characteristics of the motion data to a screen of a device for display. The activity identifier being a graphical user interface that receives an input for rendering more or less of the characteristics of the motion data.

30 Claims, 54 Drawing Sheets

Related U.S. Application Data

13/959,681, filed on Aug. 5, 2013, now Pat. No. 8,738,323, which is a continuation-in-part of application No. 13/693,334, filed on Dec. 4, 2012, now Pat. No. 8,548,770, which is a division of application No. 13/667,229, filed on Nov. 2, 2012, now Pat. No. 8,437,980, which is a division of application No. 13/469,027, filed on May 10, 2012, now Pat. No. 8,311,769, which is a division of application No. 13/246,843, filed on Sep. 27, 2011, now Pat. No. 8,180,591, which is a division of application No. 13/156,304, filed on Jun. 8, 2011, now Pat. No. 9,167,991, application No. 13/959,681, which is a continuation-in-part of application No. 13/759,485, filed on Feb. 5, 2013, now Pat. No. 8,543,351, which is a division of application No. 13/667,229.

(60) Provisional application No. 61/680,230, filed on Aug. 6, 2012, provisional application No. 61/388,595, filed on Sep. 30, 2010, provisional application No. 61/390,811, filed on Oct. 7, 2010.

(51) Int. Cl.

| | |
|---|---|
| G01C 22/00 | (2006.01) |
| A61B 5/11 | (2006.01) |
| A61B 5/22 | (2006.01) |
| H04W 4/02 | (2018.01) |
| *A61B 5/00* | (2006.01) |
| *A61B 5/0205* | (2006.01) |
| *A61B 5/021* | (2006.01) |
| *A61B 5/024* | (2006.01) |
| *G06F 19/00* | (2018.01) |

(52) U.S. Cl.
CPC ............ A61B 5/1118 (2013.01); A61B 5/1123 (2013.01); A61B 5/222 (2013.01); A61B 5/743 (2013.01); G01C 22/006 (2013.01); G06K 9/00342 (2013.01); H04W 4/02 (2013.01); *A61B 5/021* (2013.01); *A61B 5/024* (2013.01); *A61B 5/02055* (2013.01); *A61B 5/4806* (2013.01); *A61B 5/681* (2013.01); *A61B 5/6838* (2013.01); *A61B 5/7264* (2013.01); *A61B 5/744* (2013.01); *A61B 2560/0242* (2013.01); *A61B 2560/045* (2013.01); *A61B 2562/0219* (2013.01); *G06F 19/3481* (2013.01)

(58) Field of Classification Search
USPC .................................................. 702/150, 179
See application file for complete search history.

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Bloom |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,466,204 A | 8/1984 | Wu |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,224,059 A | 6/1993 | Nita et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,692,324 A | 12/1997 | Goldston et al. |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amino et al. |
| 6,287,262 B1 | 9/2001 | Amano et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,454,708 B1 | 9/2002 | Ferguson et al. |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,558,335 B1 | 5/2003 | Thede |
| 6,561,951 B2 | 5/2003 | Cannon et al. |
| 6,571,200 B1 | 5/2003 | Mault |
| 6,583,369 B2 | 6/2003 | Montagnino et al. |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,772,331 B1 | 8/2004 | Hind et al. |
| 6,788,200 B1 | 9/2004 | Jamel et al. |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 6,984,207 B1 | 1/2006 | Sullivan et al. |
| 7,020,508 B2 | 3/2006 | Stivoric et al. |
| 7,041,032 B1 | 5/2006 | Calvano |
| 7,062,225 B2 | 6/2006 | White |
| 7,099,237 B2 | 8/2006 | Lall |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |

(56) References Cited

U.S. PATENT DOCUMENTS

| | | | |
|---|---|---|---|
| 7,272,982 B2 | 9/2007 | Neuhauser et al. |
| 7,283,870 B2 | 10/2007 | Kaiser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shugg |
| 7,653,508 B1 | 1/2010 | Kahn et al. |
| 7,690,556 B1 | 4/2010 | Kahn et al. |
| 7,713,173 B2 | 5/2010 | Shin et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,827,000 B2 | 11/2010 | Stirling et al. |
| 7,865,140 B2 | 1/2011 | Levien et al. |
| 7,881,902 B1 | 2/2011 | Kahn et al. |
| 7,907,901 B1 | 3/2011 | Kahn et al. |
| 7,925,022 B2 | 4/2011 | Jung et al. |
| 7,927,253 B2 | 4/2011 | Vincent et al. |
| 7,941,665 B2 | 5/2011 | Berkema et al. |
| 7,942,824 B1 | 5/2011 | Kayyali et al. |
| 7,953,549 B2 | 5/2011 | Graham et al. |
| 7,983,876 B2 | 7/2011 | Vock et al. |
| 8,005,922 B2 | 8/2011 | Boudreau et al. |
| 8,028,443 B2 | 10/2011 | Case, Jr. |
| 8,036,850 B2 | 10/2011 | Kulach et al. |
| 8,055,469 B2 | 11/2011 | Kulach et al. |
| 8,059,573 B2 | 11/2011 | Julian et al. |
| 8,060,337 B2 | 11/2011 | Kulach et al. |
| 8,095,071 B2 | 1/2012 | Sim et al. |
| 8,099,318 B2 | 1/2012 | Moukas et al. |
| 8,103,247 B2 | 1/2012 | Ananthanarayanan et al. |
| 8,132,037 B2 | 3/2012 | Fehr et al. |
| 8,172,761 B1 | 5/2012 | Rulkov et al. |
| 8,177,260 B2 | 5/2012 | Tropper et al. |
| 8,180,591 B2 | 5/2012 | Yuen et al. |
| 8,180,592 B2 | 5/2012 | Yuen et al. |
| 8,190,651 B2 | 5/2012 | Treu et al. |
| 8,213,613 B2 | 7/2012 | Diehl et al. |
| 8,260,261 B2 | 9/2012 | Teague |
| 8,270,297 B2 | 9/2012 | Akasaka et al. |
| 8,271,662 B1 | 9/2012 | Gossweiler, III et al. |
| 8,289,162 B2 | 10/2012 | Mooring et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,638,228 B2 | 1/2014 | Amico et al. |
| 8,670,953 B2 | 3/2014 | Yuen et al. |
| 8,684,900 B2 | 4/2014 | Tran |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,825,445 B2 | 9/2014 | Hoffman et al. |
| 8,847,988 B2 | 9/2014 | Geisner et al. |
| 8,868,377 B2 | 10/2014 | Yuen et al. |
| 8,892,401 B2 | 11/2014 | Yuen et al. |
| 8,949,070 B1 | 2/2015 | Kahn et al. |
| 8,954,290 B2 | 2/2015 | Yuen et al. |
| 8,961,414 B2 | 2/2015 | Teller et al. |
| 8,968,195 B2 | 3/2015 | Tran |
| 9,047,648 B1 | 6/2015 | Lekutai et al. |
| 9,081,534 B2 | 7/2015 | Yuen et al. |
| 9,374,279 B2 | 6/2016 | Yuen et al. |
| 9,426,769 B2 | 8/2016 | Haro |
| 2001/0049470 A1* | 12/2001 | Mault et al. ............... 600/300 |
| 2001/0055242 A1 | 12/2001 | Deshmuhk et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0107575 A1 | 6/2003 | Cardno |
| 2003/0131059 A1 | 7/2003 | Brown et al. |
| 2003/0171189 A1 | 9/2003 | Kaufman |
| 2003/0208335 A1 | 11/2003 | Unuma et al. |
| 2003/0226695 A1 | 12/2003 | Mault |
| 2004/0054497 A1 | 3/2004 | Kurtz |
| 2004/0061324 A1 | 4/2004 | Howard |
| 2004/0117963 A1 | 6/2004 | Schneider |
| 2004/0122488 A1 | 6/2004 | Mazar et al. |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0186965 A1 | 8/2005 | Pagonis et al. |
| 2005/0187481 A1 | 8/2005 | Hatib |
| 2005/0195830 A1 | 9/2005 | Chitrapu et al. |
| 2005/0216724 A1 | 9/2005 | Isozaki |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064037 A1 | 3/2006 | Shalon et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0106535 A1 | 5/2006 | Duncan |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0189863 A1 | 8/2006 | Peyser |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0282021 A1 | 12/2006 | DeVaul et al. |
| 2006/0287883 A1 | 12/2006 | Turgiss et al. |
| 2006/0288117 A1 | 12/2006 | Raveendran et al. |
| 2007/0011028 A1 | 1/2007 | Sweeney |

(56) References Cited

U.S. PATENT DOCUMENTS

| | | |
|---|---|---|
| 2007/0049384 A1 | 3/2007 | King et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippo et al. |
| 2007/0083602 A1 | 4/2007 | Heggenhougen et al. |
| 2007/0123391 A1 | 5/2007 | Shin et al. |
| 2007/0135264 A1 | 6/2007 | Rosenberg |
| 2007/0136093 A1 | 6/2007 | Rankin et al. |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0179761 A1 | 8/2007 | Wren et al. |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katragadda et al. |
| 2008/0084823 A1 | 4/2008 | Akasaka et al. |
| 2008/0093838 A1 | 4/2008 | Tropper et al. |
| 2008/0097550 A1 | 4/2008 | Dicks et al. |
| 2008/0109158 A1 | 5/2008 | Huhtala |
| 2008/0114829 A1 | 5/2008 | Button et al. |
| 2008/0125288 A1 | 5/2008 | Case |
| 2008/0125959 A1 | 5/2008 | Doherty |
| 2008/0129457 A1 | 6/2008 | Ritter et al. |
| 2008/0134102 A1 | 6/2008 | Movold et al. |
| 2008/0139910 A1 | 6/2008 | Mastrototaro et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1* | 6/2008 | James .......................... 709/223 |
| 2008/0176655 A1 | 7/2008 | James et al. |
| 2008/0190202 A1 | 8/2008 | Kulach et al. |
| 2008/0214360 A1 | 9/2008 | Stirling et al. |
| 2008/0275309 A1 | 11/2008 | Stivoric et al. |
| 2008/0285805 A1 | 11/2008 | Luinge et al. |
| 2008/0287751 A1 | 11/2008 | Stivoric et al. |
| 2008/0300641 A1 | 12/2008 | Brunekreeft |
| 2009/0012418 A1 | 1/2009 | Gerlach |
| 2009/0018797 A1 | 1/2009 | Kasama et al. |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0054751 A1 | 2/2009 | Babashan et al. |
| 2009/0058635 A1 | 3/2009 | Lalonde et al. |
| 2009/0063193 A1 | 3/2009 | Barton et al. |
| 2009/0063293 A1 | 3/2009 | Mirrashidi et al. |
| 2009/0076765 A1 | 3/2009 | Kulach et al. |
| 2009/0088183 A1 | 4/2009 | Piersol |
| 2009/0093341 A1 | 4/2009 | James et al. |
| 2009/0098821 A1 | 4/2009 | Shinya |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Tropper et al. |
| 2009/0195350 A1 | 8/2009 | Tsern et al. |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu et al. |
| 2009/0307517 A1 | 12/2009 | Fehr et al. |
| 2009/0309742 A1 | 12/2009 | Alexander et al. |
| 2009/0313857 A1 | 12/2009 | Carnes et al. |
| 2010/0023348 A1 | 1/2010 | Hardee et al. |
| 2010/0043056 A1 | 2/2010 | Ganapathy |
| 2010/0056872 A1 | 3/2010 | Kahn |
| 2010/0058064 A1 | 3/2010 | Kirovski et al. |
| 2010/0059561 A1 | 3/2010 | Ellis et al. |
| 2010/0069203 A1 | 3/2010 | Kawaguchi et al. |
| 2010/0079291 A1 | 4/2010 | Kroll |
| 2010/0125729 A1 | 5/2010 | Baentsch et al. |
| 2010/0130873 A1 | 5/2010 | Yuen et al. |
| 2010/0158494 A1 | 6/2010 | King |
| 2010/0159709 A1 | 6/2010 | Kotani et al. |
| 2010/0167783 A1 | 7/2010 | Alameh et al. |
| 2010/0179411 A1 | 7/2010 | Holmström et al. |
| 2010/0185064 A1 | 7/2010 | Bandic et al. |
| 2010/0191153 A1 | 7/2010 | Sanders et al. |
| 2010/0205541 A1 | 8/2010 | Rapaport et al. |
| 2010/0217099 A1 | 8/2010 | LeBoeuf et al. |
| 2010/0222179 A1 | 9/2010 | Temple et al. |
| 2010/0261987 A1 | 10/2010 | Kamath et al. |
| 2010/0292050 A1 | 11/2010 | DiBenedetto |
| 2010/0292600 A1 | 11/2010 | DiBenedetto et al. |
| 2010/0295684 A1 | 11/2010 | Hsieh et al. |
| 2010/0298656 A1 | 11/2010 | McCombie et al. |
| 2010/0298661 A1 | 11/2010 | McCombie et al. |
| 2010/0304674 A1 | 12/2010 | Kim et al. |
| 2010/0311544 A1 | 12/2010 | Robinette et al. |
| 2010/0331145 A1 | 12/2010 | Lakovic et al. |
| 2011/0003665 A1 | 1/2011 | Burton et al. |
| 2011/0009051 A1 | 1/2011 | Khedouri et al. |
| 2011/0021143 A1 | 1/2011 | Kapur et al. |
| 2011/0022349 A1 | 1/2011 | Stirling et al. |
| 2011/0029241 A1 | 2/2011 | Miller et al. |
| 2011/0032105 A1 | 2/2011 | Hoffman et al. |
| 2011/0051665 A1 | 3/2011 | Huang |
| 2011/0080349 A1 | 4/2011 | Holbein et al. |
| 2011/0087076 A1 | 4/2011 | Brynelsen et al. |
| 2011/0106449 A1 | 5/2011 | Chowdhary et al. |
| 2011/0109540 A1 | 5/2011 | Milne et al. |
| 2011/0131005 A1 | 6/2011 | Ueshima et al. |
| 2011/0145894 A1 | 6/2011 | Garcia Morchon et al. |
| 2011/0153773 A1 | 6/2011 | Vandwalle |
| 2011/0167262 A1 | 7/2011 | Ross et al. |
| 2011/0193704 A1 | 8/2011 | Harper et al. |
| 2011/0197157 A1 | 8/2011 | Hoffman et al. |
| 2011/0214030 A1 | 9/2011 | Greenberg et al. |
| 2011/0221590 A1 | 9/2011 | Baker et al. |
| 2011/0224508 A1 | 9/2011 | Moon |
| 2011/0230729 A1 | 9/2011 | Shirasaki et al. |
| 2011/0258689 A1 | 10/2011 | Cohen et al. |
| 2011/0275940 A1 | 11/2011 | Nims et al. |
| 2012/0015778 A1* | 1/2012 | Lee .................. A63B 71/0622 482/8 |
| 2012/0035487 A1 | 2/2012 | Werner et al. |
| 2012/0046113 A1 | 2/2012 | Ballas |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kääriäinen et al. |
| 2012/0116684 A1 | 5/2012 | Ingrassia, Jr. et al. |
| 2012/0119911 A1 | 5/2012 | Jeon et al. |
| 2012/0150483 A1 | 6/2012 | Vock et al. |
| 2012/0165684 A1 | 6/2012 | Sholder |
| 2012/0166257 A1 | 6/2012 | Shiragami et al. |
| 2012/0179278 A1 | 7/2012 | Riley et al. |
| 2012/0183939 A1 | 7/2012 | Aragones et al. |
| 2012/0215328 A1 | 8/2012 | Schmelzer |
| 2012/0221634 A1 | 8/2012 | Treu et al. |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0245716 A1 | 9/2012 | Srinivasan et al. |
| 2012/0254987 A1 | 10/2012 | Ge et al. |
| 2012/0265477 A1 | 10/2012 | Vock et al. |

(56) References Cited

U.S. PATENT DOCUMENTS

| | | |
|---|---|---|
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0290109 A1 | 11/2012 | Enqelberq et al. |
| 2012/0296400 A1 | 11/2012 | Bierman et al. |
| 2012/0297229 A1 | 11/2012 | Desai et al. |
| 2012/0297440 A1 | 11/2012 | Reams et al. |
| 2012/0316456 A1 | 12/2012 | Rahman et al. |
| 2012/0317167 A1 | 12/2012 | Rahman |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0096843 A1 | 4/2013 | Yuen et al. |
| 2013/0102251 A1 | 4/2013 | Linde et al. |
| 2013/0103847 A1 | 4/2013 | Brown et al. |
| 2013/0106684 A1 | 5/2013 | Weast et al. |
| 2013/0132501 A1 | 5/2013 | Vandwalle et al. |
| 2013/0151193 A1 | 6/2013 | Kulach et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0187789 A1 | 7/2013 | Lowe |
| 2013/0190008 A1 | 7/2013 | Vathsancam et al. |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |
| 2013/0297220 A1 | 11/2013 | Yuen et al. |
| 2013/0310896 A1 | 11/2013 | Mass |
| 2013/0325396 A1 | 12/2013 | Yuen et al. |
| 2013/0331058 A1 | 12/2013 | Harvey |
| 2013/0337974 A1 | 12/2013 | Yanev et al. |
| 2013/0345978 A1 | 12/2013 | Lush et al. |
| 2014/0035761 A1 | 2/2014 | Burton et al. |
| 2014/0035764 A1 | 2/2014 | Burton et al. |
| 2014/0039804 A1 | 2/2014 | Park et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0085077 A1 | 3/2014 | Luna et al. |
| 2014/0094941 A1 | 4/2014 | Ellis et al. |
| 2014/0099614 A1 | 4/2014 | Hu et al. |
| 2014/0121471 A1 | 5/2014 | Walker |
| 2014/0125618 A1 | 5/2014 | Panther et al. |
| 2014/0156228 A1 | 6/2014 | Yuen et al. |
| 2014/0164611 A1 | 6/2014 | Molettiere et al. |
| 2014/0180022 A1 | 6/2014 | Stivoric et al. |
| 2014/0200691 A1 | 7/2014 | Lee et al. |
| 2014/0207264 A1 | 7/2014 | Quy |
| 2014/0213858 A1 | 7/2014 | Presura et al. |
| 2014/0275885 A1 | 9/2014 | Isaacson et al. |
| 2014/0278229 A1 | 9/2014 | Hong et al. |
| 2014/0316305 A1 | 10/2014 | Venkatraman et al. |
| 2014/0337451 A1 | 11/2014 | Choudhary et al. |
| 2014/0337621 A1 | 11/2014 | Nakhimov |
| 2014/0343867 A1 | 11/2014 | Yuen et al. |
| 2015/0026647 A1 | 1/2015 | Park et al. |
| 2015/0057967 A1 | 2/2015 | Albinali |
| 2015/0088457 A1 | 3/2015 | Yuen et al. |
| 2015/0102923 A1 | 4/2015 | Messenger et al. |
| 2015/0120186 A1 | 4/2015 | Heikes |
| 2015/0127268 A1 | 5/2015 | Park et al. |
| 2015/0137994 A1 | 5/2015 | Rahman et al. |
| 2015/0220883 A1 | 8/2015 | B'far et al. |
| 2015/0289802 A1 | 10/2015 | Thomas et al. |
| 2015/0324541 A1 | 11/2015 | Cheung et al. |
| 2015/0374267 A1 | 12/2015 | Laughlin |
| 2016/0058372 A1 | 3/2016 | Raghuram et al. |
| 2016/0061626 A1 | 3/2016 | Burton et al. |
| 2016/0063888 A1 | 3/2016 | McCallum et al. |
| 2016/0089572 A1 | 3/2016 | Liu et al. |
| 2016/0107646 A1 | 4/2016 | Kolisetty et al. |
| 2016/0259426 A1 | 9/2016 | Yuen et al. |
| 2016/0278669 A1 | 9/2016 | Messenger et al. |
| 2016/0285985 A1 | 9/2016 | Molettiere et al. |
| 2016/0323401 A1 | 9/2016 | Messenger et al. |

FOREIGN PATENT DOCUMENTS

| | | |
|---|---|---|
| CN | 102377815 | 3/2012 |
| CN | 102740933 | 10/2012 |
| CN | 102983890 | 3/2013 |
| CN | 103226647 | 7/2013 |
| EP | 1 721 237 | 11/2006 |
| JP | 11-347021 | 12/1999 |
| RU | 2178588 C1 | 1/2002 |
| WO | 200211019 A1 | 2/2002 |
| WO | 2006055125 A1 | 5/2006 |
| WO | 2006090197 A1 | 8/2006 |
| WO | WO 08/038141 | 4/2008 |
| WO | WO 09/042965 | 4/2009 |
| WO | 2012061438 A2 | 5/2012 |
| WO | 2012061438 A3 | 8/2012 |
| WO | WO 12/170586 | 12/2012 |
| WO | WO 12/170924 | 12/2012 |
| WO | WO 12/171032 | 12/2012 |
| WO | WO 15/127067 | 8/2015 |
| WO | WO 16/003269 | 1/2016 |

OTHER PUBLICATIONS

"Activator is One of the Best Cydia iPhone Hacks I Control your iPhone with Gestures," iphone-Tips-and-Advice.com, [retrieved on Jul. 9, 2013 at http://www.iphone-tips-and-advice.comlactivatior. html], 10 pp.

"Parts of Your Band," (Product Release Date Unknown, downloaded Jul. 22, 2013) Jawbone UP Band, 1 page.

Chandrasekar et al., Aug. 28-Sep. 1, 2012, Plug-and-Play, Single-Chip Photoplethysmography, 34th Annual International Conference of the IEEE EMBS, San Diego, California USA, 4 pages.

Chudnow, Alan (Dec. 3, 2012) "Basis Wristband Make Its Debut," The Wired Self, Living in a Wired World, published in Health [retrieved on Jul. 22, 2013 at http://thewiredself.com/health/basis-wrist-band-make-its-debut/], 3pp.

Clifford et al., Altimeter and Barometer System, Freescale Semiconductor Aplication Note AN1979, Rev. 3, Nov. 2006.

Definition of "Graphic" from Merriam-Webster Dictionary, downloaded from merriam-webster.com on Oct. 4, 2014, 3 pp.

Definition of "Graphical user interface" from Merriam-Webster Dictionary, downloaded from merriam-webster.com on Oct. 4, 2014, 2 pp.

DesMarais, Christina (posted on Sep. 3, 2013) "Which New Activity Tracker is Best for You?" Health and Home, Health & Fitness, Guides & Reviews, [Retrieved on Sep. 23, 2013 at http://www.techlicious.com/guide/which-new-activity-tracker-is-right-for--you/] 4 pp.

(56) References Cited

OTHER PUBLICATIONS

Empson, Rip, (Sep. 22, 2011) "Basis Reveals an Awesome New Affordable Heart and Health Tracker You Can Wear on Your Wrist," [retrieved on Sep. 23, 2013 at http://techcrunch.com/2011/09/22/basis-reveals-an-awesome-new . . . ], 3 pp.
Fang et al., Dec. 2005, Design of a Wireless Assisted Pedestrian Dead Reckoning System—The NavMote Experience, IEEE Transactions on Instrumentation and Measurement, 54(6):2342-2358.
Fitbit User's Manual, Last Updated Oct. 22, 2009, 15 pages.
Forerunner® 10 Owner's Manual (Aug. 2012), Garmin Ltd., 10 pp.
Forerunner® 110 Owner's Manual, (2010) "GPS-Enabled Sport Watch," Garmin Ltd., 16 pp.
Forerunner® 201 personal trainer owner's manual, (Feb. 2006) Garmin Ltd., 48 pp.
Forerunner® 205/305 Owner's Manual, GPS-enabled trainer for runners, (2006-2008), Garmin Ltd., 80 pp.
Forerunner® 210 Owner's Manual, (2010) "GPS-Enabled Sport Watch," Garmin Ltd., 28 pp.
Forerunner® 301 personal trainer owner's manual, (Feb. 2006) Garmin Ltd., 66 pp.
Forerunner® 310XT Owner's Manual, Multisport GPS Training Device, (2009-2013), Garmin Ltd., 56 pp.
Forerunner® 405 Owner's Manual, (Mar. 2011) "GPS-Enabled Sport Watch With Wireless Sync," Garmin Ltd., 56 pp.
Forerunner® 405CX Owner's Manual, "GPS-Enabled Sports Watch With Wireless Sync," (Mar. 2009), Garmin Ltd., 56 pp.
Forerunner® 410 Owner's Manual, (Jul. 2012) "GPS-Enabled Sport Watch With Wireless Sync," Garmin Ltd., 52 pp.
Forerunner® 50 with ANT+Sport.TM. wireless technology, Owner's Manual, (Nov. 2007) Garmin Ltd., 44 pp.
Forerunner® 910XT Owner's Manual, (Jan. 2013) Garmin Ltd., 56 pp.
Garmin Swim™ Owner's Manual (Jun. 2012), 12 pp.
Godfrey et al., 2008, Direct Measurement of Human Movement by Accelerometry, Medical Engineering & Physics, 30:1364-1386.
Godha et al., May 2008, Foot Mounted Inertia System for Pedestrian Navigation, Measurement Science and Technology, 19(7):1-9.
Intersema App., Using MS5534 for altimeters and barometers, Note AN501, Jan. 2006.
Ladetto et al. Sep. 2000, On Foot Navigation: When GPS alone is not Enough, Journal of Navigation, 53(2):279-285.
Lammel et al., Sep. 2009, Indoor Navigation with MEMS Sensors, Proceedings of the Eurosensors XIII conference, 1(1):532-535.
Lark/Larkpro, User Manual, (2012) "What's in the box," Lark Technologies, 7 pp.
Larklife, User Manual, (2012) Lark Technologies, 7 pp.
Lester et al., 2005, A Hybrid Discriminative/Generative Approach for Modeling Human Activities, Proc. of the Int'l Joint Conf. Artificial Intelligence, pp. 766-772.
Lester et al., 2009, Validated caloric expenditure estimation using a single body-worn sensor, Proc. of the Int'l Conf. on Ubiquitous Computing, pp. 225-234.
Minetti et al. Energy cost of walking and running at extreme uphill and downhill slopes. J Appl Physiol. 2002; 93:10-39-1046.
Nike+FuelBand GPS Manual, User's Guide (Product Release Date Unknown, downloaded Jul. 22, 2013), 26 pages.
Nike+SportBand User's Guide, (Product Release Date Unknown, downloaded Jul. 22, 2013), 36 pages.
Nike+SportWatch GPS Manual, User's Guide, Powered by TOMTOM, (Product Release Date Unknown, downloaded Jul. 22, 2013), 42 pages.
O'Donovan et al., 2009, A context aware wireless body area network (BAN), Proc. 3rd Intl. Conf. Pervasive Computing Technologies for Healthcare, pp. 1-8.
Ohtaki et al., Aug. 2005, Automatic classification of ambulatory movements and evaluation of energy consumptions utilizing accelerometers and barometer, Microsystem Technologies, 11(8-10:)1034-1040.
Parkka et al., Jan. 2006, Activity Classification Using Realistic Data From Wearable Sensors, IEEE Transactions on Information Technology in Biomedicine, 10(1):119-128.
Perrin et al., 2000, Improvement of Walking Speed Prediction by Accelerometry and Altimetry, Validated by Satellite Positioning, Medical & Biological Engineering & Computing, 38:164-168.
Polar WearLink® + Coded Transmitter 31 Coded Transmitter W.I.N.D. User Manual, POLAR@ Listen to Your Body, Manufactured by Polar Electro Oy, 11 pages.
Rainmaker, (Jun. 25, 2012, updated Feb. 16, 2013) "Garmin Swim watch in-Depth Review," [retrieved on Sep. 9, 2013 at http://www.dcrainmaker.com/2012/06/garmin-swim-in-depth-review.html, 38 pp.
Retscher, 2006, An Intelligent Multi-Sensor system for Pedestrian Navigation, Journal of Global Positioning Systems, 5(1):110-118.
Sagawa et al., Aug.-Sep. 1998, Classification of Human Moving Patterns Using Air Pressure and Acceleration, Proceedings of the 24.sup.th Annual Conference of the IEEE Industrial Electronics Society, 2:1214-1219.
Sagawa et al., Oct. 2000, Non-restricted measurement of walking distance, IEEE Int'l Conf. on Systems, Man, and Cybernetics, 3:1847-1852.
SCP 1000-D01/D11 Pressure Sensor as Barometer and Altimeter, VTI Technologies Application, Jun. 2006, Note 33.
Stirling et al., 2005, Evaluation of a New Method of Heading Estimation of Pedestrian Dead Reckoning Using Shoe Mounted Sensors, Journal of Navigation, 58:31-45.
Suunto LUMI User Guide, Jun. and Sep. 1997.
Tanigawa et al., Mar. 2008, Drift-free dynamic height sensor using MEMS IMU aided by MEMS pressure sensor, Workshop on Positioning, Navigation and Communication, pp. 191-196.
Thompson et al., (Jan. 1996) "Predicted and measured resting metabolic rate of male and female endurance athletes," Journal of the American Dietetic Association 96(1):30-34.
International Search Report dated Aug. 15, 2008, in related application PCT/IB07/03617.
Specification of the Bluetooth® System, version 4.1, Dec. 2013, vols. 0 and 1, 283 pages.

* cited by examiner

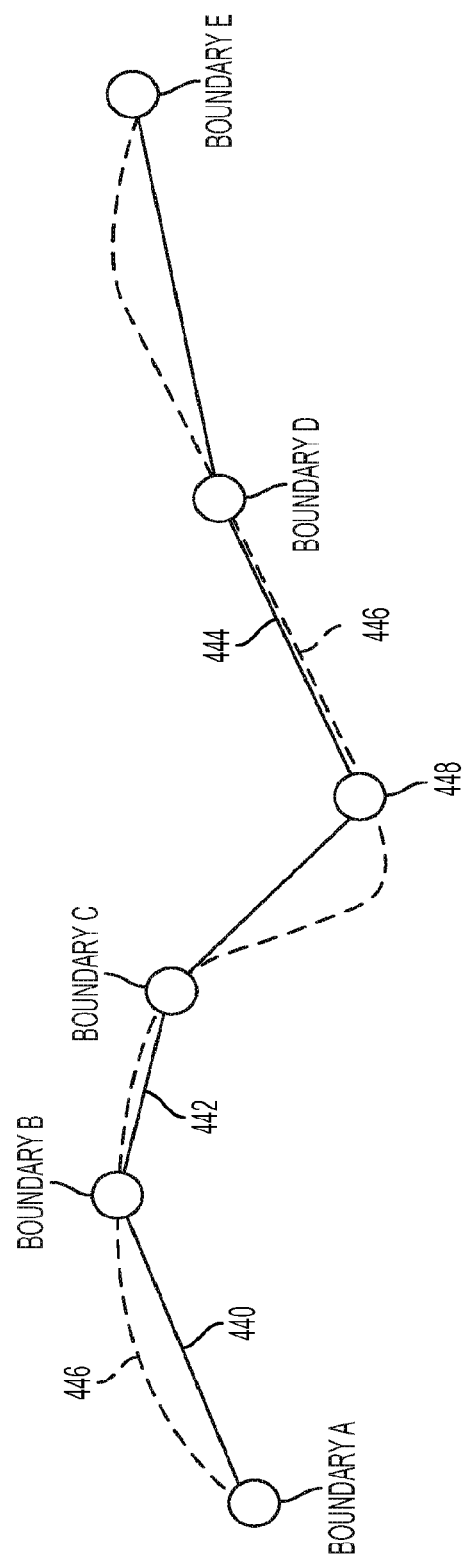

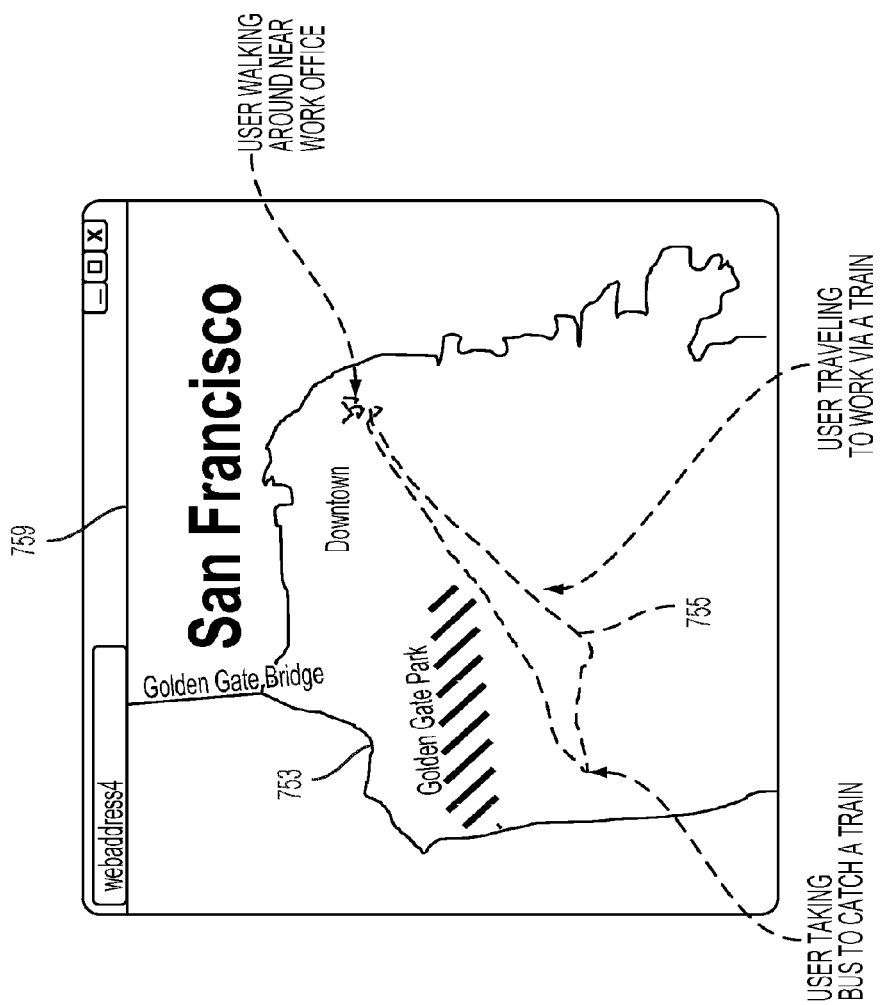

| Saturday, March 3 — 990 | Sunday, March 4 — 992 |
|---|---|
| I drove a lot. — 994₁  I sat around. — 994₂  I was up late. — 994₃ | I drove a lot. — 996₁  I sat around. — 996₂  I was up late. — 996₃ |
| Metrics { Description of Metric } | Metrics |
| Steps: 6K — 950 | Steps: 19K — 956 |
| Got Up: 10:00 AM — 952 | Got Up: 9:00 AM — 958 |
| To Bed: 11:26 PM — 954 | To Bed: 11:36 PM — 960 |
| Ran: 0 min — 962 | Ran: 0 min — 964 |
| Vehicle 201 min — 970 | Vehicle 156 min — 980 |
| Home Activity: 52 steps/min — 972 | Home Activity: 29 steps/min — 982 |
| Office Activity: N/A — 974 | Office Activity: N/A — 984 |
| Time at Home 0:11 hr — 976 | Time at Home 0:42 hr — 986 |
| Time at Work: 0:00 hr — 978 | Time at Work: 0:00 hr — 988 |
| Longest Sedentary: 1:05 hr — 966 | Longest Sedentary: 1:00 hr — 968 |

| Sunday, February 26 | Monday, February 27 | Tuesday, February 28 | Wednesday, February 29 |
|---|---|---|---|
| I walked a lot.<br>↙ 1004 | I did not walk a lot.<br>↙ 1006 | I was up late.<br>↙ 1008 | I went for a run! I drove a lot. I worked late. I was up late.<br>{ $1010_1$  $1010_2$ } |

| Thursday, March 1 | Friday, March 2 | Saturday, March 3 |
|---|---|---|
| I drove a lot. I walked a lot. I sat around. | I did not walk a lot. I worked late. I was up late. | I went for a run! I drove a lot. I walked a lot. I sat around. |

1002

From FIG.14-1

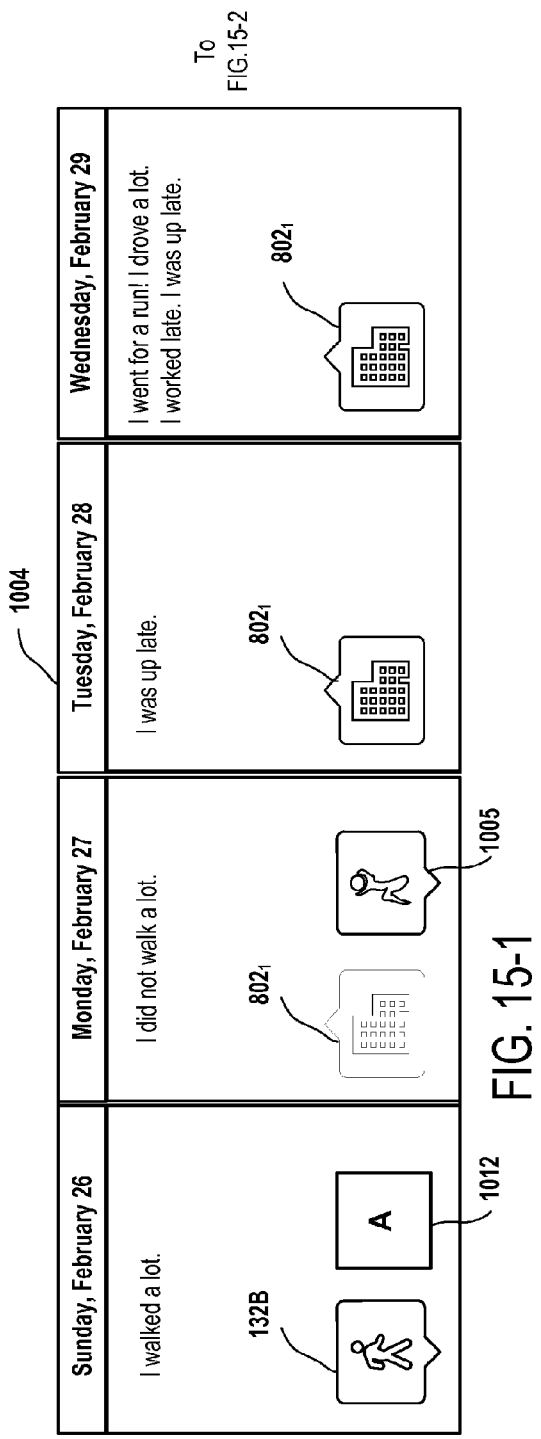

METHODS AND SYSTEMS FOR METRICS ANALYSIS AND INTERACTIVE RENDERING, INCLUDING EVENTS HAVING COMBINED ACTIVITY AND LOCATION INFORMATION

CLAIM OF PRIORITY

This application is a divisional application claiming priority from co-pending U.S. patent application Ser. No. 14/148,505, filed Jan. 6, 2014, entitled "Methods and Systems for Metrics Analysis and Interactive Rendering, including Events having Combined Activity and Location Information", which is a continuation of U.S. patent application Ser. No. 13/959,681, filed on Aug. 5, 2013, titled "Methods and Systems for Metrics Analysis and Interactive Rendering, including Events having Combined Activity and Location Information", now U.S. Pat. No. 8,738,323, all of which are incorporated by reference herein in their entirety.

The application Ser. No. 13/959,681 claims the benefit of and priority, under 35 U.S.C. 119 § (e), to a Provisional Patent Application No. 61/680,230, filed on Aug. 6, 2012, and entitled "GPS ENABLED ACTIVITY AND SLEEP TRACKER," which is incorporated by reference herein in its entirety.

The application Ser. No. 13/959,681 is a continuation-in-part of U.S. patent application Ser. No. 13/693,334, now U.S. Pat. No. 8,548,770, filed on Dec. 4, 2012, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. 119§ (e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

The application Ser. No. 13/959,681 is a continuation-in-part of U.S. patent application Ser. No. 13/759,485, now U.S. Pat. No. 8,543,351, filed on Feb. 5, 2013, titled "Portable Monitoring Devices and Methods for Operating Same", which is a divisional of U.S. patent application Ser. No. 13/667,229, filed on Nov. 2, 2012, titled "Portable Monitoring Devices and Methods for Operating Same", which is a divisional of U.S. patent application Ser. No. 13/469,027, now U.S. Pat. No. 8,311,769, filed on May 10, 2012, titled "Portable Monitoring Devices and Methods for Operating Same", which is a divisional of U.S. patent application Ser. No. 13/246,843, now U.S. Pat. No. 8,180,591, filed on Sep. 27, 2011, which is a divisional of U.S. patent application Ser. No. 13/156,304, filed on Jun. 8, 2011, titled "Portable Monitoring Devices and Methods for Operating Same", which claims the benefit of and priority to, under 35 U.S.C. § 119(e), to U.S. Provisional Patent Application No. 61/388,595, filed on Sep. 30, 2010, and titled "Portable Monitoring Devices and Methods for Operating Same" and to U.S. Provisional Patent Application No. 61/390,811, filed on Oct. 7, 2010, and titled "Portable Monitoring Devices and Methods for Operating Same", all of which are hereby incorporated by reference in their entirety.

FIELD

The present disclosure relates to systems and methods for capturing activity data over a period of time and associating the captured activity data into identification of locations of a user performing activities.

BACKGROUND

In recent years, the need for health and fitness has grown tremendously. The growth has occurred due to a better understanding of the benefits of good fitness to overall health and wellness. Unfortunately, although today's modern culture has brought about many new technologies, such as the Internet, connected devices and computers, people have become less active. Additionally, many office jobs require people to sit in front of computer screens for long periods of time, which further reduces a person's activity levels. Furthermore, much to today's entertainment options involve viewing multimedia content, computer social networking, and other types of computer involved interfacing. Although such computer activity can be very productive as well as entertaining, such activity tends to reduce a person's overall physical activity.

To provide users concerned with health and fitness a way of measuring or accounting for their activity or lack thereof, fitness tracker are often used. Fitness trackers are used to measure activity, such as walking, motion, running, sleeping, being inactive, bicycling, exercising on an elliptical trainer, and the like. Usually, the data collected by such fitness trackers can be transferred and viewed on a computing device. However, such data is often provided as a basic accumulation of activity data.

It is in this context that embodiments described herein arise.

SUMMARY

Embodiments described in the present disclosure provide systems, apparatus, computer readable media, and methods for segmenting a period of time into identification of locations of a user performing activities. This segmentation provides a way of identifying particular activities to particular locations. Using the segmentations, the systems and methods can identify one or more events that may have occurred during the period of time of activity. In one embodiment, the events can be displayed on a screen of a device, and a user is able to interactively view data concerning the events with contextual information, e.g., where certain events occurred.

In one embodiment, as described below, the events are automatically associated with locations, and the locations can be associated with contextual information concerning the locations. For instance, if a tracking device detects certain activity at a particular location (e.g., a map location), the mapping data or related databases can be queried to determine that the map location corresponds to a golf course. The system can then generate information that is graphically presented to the user, concerning the particular tracked activity as corresponding to golfing. In some embodiments, the locations can be identified over time, e.g., by received user feedback (e.g., this is my home, this is a coffee shop, this is my work).

In some embodiments, the locations can be inferred or learned based on the activities and times of day, and/or repeat activities over a period of time (e.g., based on an identifiable pattern). For example, if the user/tracker is typically experiencing low activity from 9:00 am and 11:55 am, Monday-Friday, it can be inferred using a rules database and learning logic that the user is at work or is working. In another embodiment, the user can be asked, "are you at work?" via a computing device or a tracking device, and based on the user's response, database can associate particular locations (e.g., geo-location) to particular actual location (e.g., work), and collect the activity data for presentation along with the most appropriate location.

In some embodiments, an activity that is performed by a user is inferred based on geo-locations of a monitoring device or a computing device used by the user. For example, a processor of the monitoring device, of the computing device, of a server, or of a virtual machine determines based on the geo-locations that a user is at a location, e.g., a gym, home, work, etc. The processor retrieves from an activity-location database one or more activities that may be performed by the user at the location. For example, the activity-location database indicates that the user may be performing one or more activities, e.g., using a treadmill, using an elliptical trainer, lifting weights to build resistance, swimming laps, etc., while at a gym. As another example, the activity-location database indicates that the user may be performing one or more activities, e.g., walking, climbing stairs, descending stairs, sleeping, etc., while at home. The processor retrieves one or more of the activities from the activity-location database that correspond to the location and determines that the user is performing one or more of the activities.

Broadly speaking, the systems and methods facilitate determination of an activity level of an activity performed by a user at a location. For example, the systems and methods can determine that the user is sedentary for a particular period of time when the user is at work. As another example, the systems and methods can determine that the user is active when the user is at home. The activity or lack of activity is therefore contextually associated to a particular location. The systems and methods determine activity levels of one or more activities performed by the user during a period of time. The user can view the activity levels of an activity performed at a location and decide whether to perform a different activity at the location, to perform an activity at another location, or to continue performing the activity when at the location. By providing the user location context to activities, the user is able to better view his or her actual activity performance and better health decisions can be made regarding and/or adjustments can be made in lifestyle. For instance, a user may find that walking to the train station can significantly improve his/her health, over taking a bus to the train. These simple decisions in activity can act to significantly increase a person's activity, but providing context as to what and where activity is taking place can provide better understanding as to how simple changes can have large impacts in overall fitness.

In some embodiments, a method includes receiving location data of a monitoring device when carried by a user. The method further includes receiving motion data of the monitoring device. The motion data is associated with a time of occurrence and the location data of the monitoring device. The method includes processing the received motion data to identify a group of the motion data having a substantially common characteristic and processing the location data for the group of motion data. The group of motion data, by way of processing the location data, provides an activity identifier. The motion data includes metric data that identifies characteristics of the motion data for the activity identifier. The method includes transferring the activity identifier and the characteristics of the motion data to a screen of a device for display. The activity identifier being a graphical user interface that receives an input for rendering more or less of the characteristics of the motion data.

In several embodiments, a method includes obtaining one or more locations of a monitoring device when used by a user. The method further includes determining one or more spatial positions of the monitoring device, determining one or more times of occurrence corresponding to the spatial positions and the locations, and characterizing a type of an activity based on the times of occurrence, the locations, and the spatial positions. Examples of a type of activity include walking, running, swimming, sleeping, training on an elliptical trainer, etc. The activity includes metric data that indicates levels for the activity.

In various embodiments, a method includes receiving one or more locations of a monitoring device, which is usable by a user. The method further includes receiving one or more spatial positions of the monitoring device, receiving one or more times of occurrence corresponding to the spatial positions and the geo-locations, and determining activity data based on the times of occurrence, the geo-locations, and the spatial positions. The activity data includes metric data that includes one or more activity levels. The activity data includes one or more classes of activities detected by the monitoring device. The method includes determining one or more locations of the monitoring device based on the times of occurrence, the geo-locations, and the spatial positions.

Other aspects will become apparent from the following detailed description, taken in conjunction with the accompanying drawings, illustrating by way of example the principles of embodiments described in the present disclosure.

BRIEF DESCRIPTION OF THE DRAWINGS

Various embodiments described in the present disclosure may best be understood by reference to the following description taken in conjunction with the accompanying drawings in which:

FIG. 7C is a diagram illustrating a method for establishing boundaries between two locations arrived at by a user over one or more periods of time, in accordance with one embodiment described in the present disclosure.

FIG. 7F-2 is a zoom-in of the GUI of FIG. 7F-1, in accordance with one embodiment described in the present disclosure.

FIG. 7G-1 is a diagram of a first portion of a daily journal GUI that includes one or more GUIs that include event data for periods of time, in accordance with one embodiment described in the present disclosure.

FIG. 7G-2 is a diagram of a second portion of the daily journal GUI, in accordance with one embodiment described in the present disclosure.

FIG. 7G-3 is a diagram of a third portion of the daily journal GUI, in accordance with one embodiment described in the present disclosure.

FIG. 7V is a diagram of an embodiment of a GUI that includes further details regarding the user's path of FIG. 7T, in accordance with one embodiment described in the present disclosure.

FIG. 13 is a diagram of calendar GUIs, in accordance with one embodiment described in the present disclosure.

FIG. 14-1 is a diagram of a first portion of a calendar, in accordance with one embodiment described in the present disclosure.

FIG. 14-2 is a diagram of a second portion of the calendar of FIG. 14-2, in accordance with one embodiment described in the present disclosure FIG. 15-1 is a diagram of a first portion of another calendar, in accordance with one embodiment described in the present disclosure.

FIG. 15-2 is a diagram of a second portion of the calendar of FIG. 15-1, in accordance with one embodiment described in the present disclosure.

FIG. 17-1 is a diagram of a first portion of a GUI that includes a calendar GUI and a group of event data, in accordance with one embodiment described in the present disclosure.

FIG. 17-2 is a diagram of a second portion of the GUI of FIG. 17-1, in accordance with one embodiment described in the present disclosure.

FIG. 18-1 is a diagram of a first portion of another GUI that includes a calendar GUI, a group of event data, and a map, in accordance with one embodiment described in the present disclosure.

FIG. 18-2 is a diagram of a second portion of the GUI of FIG. 18-1, in accordance with one embodiment described in the present disclosure.

DETAILED DESCRIPTION

Figure 1A:
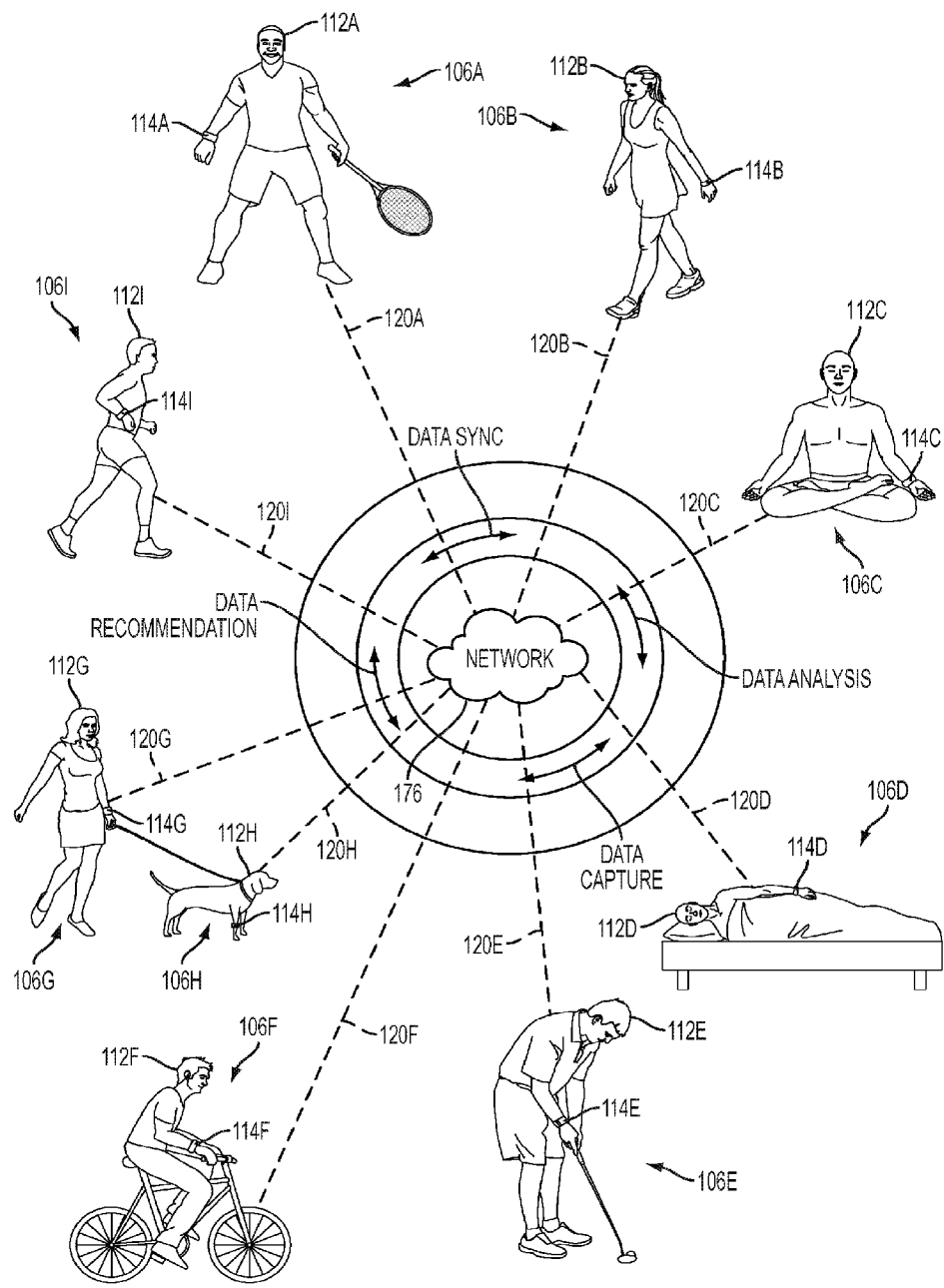
FIG. 1A illustrates a variety of situations in which a system for segmenting a period of time into identification of locations of a user performing activities is used, in accordance with one embodiment described in the present disclosure.

Embodiments described in the present disclosure provide systems, apparatus, computer readable media, and methods for analyzing tracked activity data and segmenting/associating the activity data to contextually identifiable locations where a user, wearing an activity tracker performed such activities. This segmentation provides a way of identifying events that associate the identified activities to particular locations. In one embodiment, the data is collected from an activity tracker and then transferred to a computing device. In some embodiments, the computing device can include a portable device, such as a smart phone, an internet connected watch, a tablet, a laptop, a desktop, etc. The computing device can then transfer the collected activity data to a server that is connected to the internet for processing.

In one embodiment, the term location refers to a geographic position. The geographic position can be identified on a map, identified on a coordinate identifier using global positioning data (e.g., GPS), identified using radio signal tower locator data (e.g., cell towers), identified using wireless internet router signal data (e.g., Wi-Fi signals), identified using router signal data for multi-floor identification (e.g., floor-to-floor locator data), or combinations thereof. In some embodiments, changes in location data include determining a difference between location identified data at various times (e.g., every minute, every few minutes, every half hour, every hour, at particular hour intervals or days). In some embodiments, the time at which location data is obtained can vary depending on sensed activity. For example, if less activity or motion is detected, fewer location data points need be taken.

In some embodiments, the various motions of the tracking device, movements, locations traversed, and activities performed, can all generate metric data. The metric data provides points of view of understanding the various activities performed by a user that wears, holds, or carries the monitoring device. The metric data can be processed to define detailed views or characteristics of data, which characterize the information in easy to understand forms. The metric data can be generated on the fly as the user is producing trackable data or from time to time. In some embodiments, the metric data is processed in accordance with rules or filters set by the user or set by the system. The rules or filters can define where the metric data is to be populated. For instance, the metric data can be populated to a screen of the tracking device itself, to a portable device (e.g., smart phone), or to any computer or computing device having access to the Internet.

In various embodiments, the processing of the data to produce metrics, can be done all or part on the local device (e.g., the monitoring device), all or part on a portable device, or all or part on a cloud based computing system. The data, once processed can be provided to users in various forms, on various GUIs, various form factors, using the same or different graphics, or custom graphics, layouts or renderings as defined by the user or set as defaults by the system. With this in mind, various examples of metric generation will now be described.

In one embodiment, the term location, location data, or locations may refer to one or more geographic positions. A geographic position can be identified on a map, identified on a coordinate identifier using global positioning data (e.g., GPS), identified using radio signal tower locator data (e.g., cell towers), identified using wireless internet router signal data (e.g., Wi-Fi signals), identified using router signal data for multi-floor identification (e.g., floor-to-floor locator data), or combinations thereof. In some embodiments, changes in location data include determining a difference between location identified data at various times (e.g., every minute, every few minutes, every half hour, every hour, at particular hour intervals or days). In some embodiments, the time at which location data is obtained can vary depending on sensed activity. For example, if less activity or motion is detected, fewer location data points need be taken.

The server can include one or more servers, which define a cloud processing system. The cloud processing a system includes logic, code, programs and/or software for processing the activity data to produce the identifiable events. The cloud processing system can provide a system for creating user accounts for users and their activity trackers. The user accounts enable users to view graphical users interfaces (GUIs) that render and display the events identified using the tracked activity data and the location data (e.g., geo-location data). Processing logic on the servers associated with the cloud processing system can process the tracked data, can access other Internet services (e.g., mapping services, social networking services, location context services, etc., to enable formulation or identification of a location for particular activities, which define an event). Broadly speaking, an event is defined to include a location and an activity.

In one embodiment, the events can be displayed on a screen of a device, and a user is able to interactively view data concerning the events with contextual information, e.g., where certain events occurred.

In some embodiments, locations can be automatically identified by accessing mapping services and other online databases that identify locations. The online databases can include mapping programs, data from social networks, tagged data, crowd-sourced data, etc.

In some embodiments, the locations can be inferred or learned based on the activities and times of day, and/or repeat activities over a period of time (e.g., based on an identifiable pattern). Databases of rules are constructed and such rules are refined over time. The rules are used to enable the system to infer locations and provide appropriate contextual identification to the locations. In some embodiments, the rules can shape themselves using learning systems, and can be tailored for specific users. In still other embodiments, learned patterns and behaviors of other users can be used to collaboratively identify rules, shape rules or determine locations or identify locations. For instance, if multiple users tag a location as a coffee bar, this information can be used to associate "coffee bar" to some range of geo-location. If over time, the location starts to get tagged as a breakfast bar, the rules can be adjusted to now associate that geo-location as "breakfast bar." As businesses or location contexts change over time, so can the rules.

In various embodiments, the shape rules are used to associate one or more geo-locations with a location. For example, a shape, e.g., a circle, a polygon, an oval, a square, etc., is used to identify a location on a graphical user interface. The graphical user interface may include event data, a route, a map, or a combination thereof. A user changes a size via a user interface of a monitoring device or via an input device of a computing device of a shape to change a number of geo-locations associated with the location. For example, a user increases a size of a circle to include more geo-locations within a location that is identified by the circle. As another example, a user decreases a size of a polygon to exclude a number of geo-locations from within a location that is identified by the polygon. As another example, a center of a shape is changed to associate a different set of geo-locations with a location than that already associated with the location. For example, a user drags via a user interface of a monitoring device or via an input device of a computing device a point associated with, e.g., a center of, a vertex of, etc., a shape to a different spot on a graphical user interface. When the point is dragged, the shape is also dragged to the difference spot and is associated with a difference set of geo-locations than that before the movement of the center. The graphical user interface may include event data, a route, a map, or a combination thereof.

In another embodiment, the user may be allowed to post details of particular locations. The user can identify locations with particular custom identifiers, e.g., "mom's house" or can select from predefined identifiers. In still other embodiments, the user can be asked to identify a location. In still another embodiment, the user can be asked via custom queries, such as: "Are you at work?"; "Is this your home?"; "Are you driving?"; "Do you need medical assistance? if so, say or type help" etc. Or, the queries can be presented to the user at a later time, such as when the user is viewing his or her past activity on a GUI. In some embodiments, the queries can be provided via a cloud program, when accessing a computer with cloud access, via push notifications, via voice requests, etc. Based on this returned feedback, the servers and databases of the cloud service can learn or associate location identification to particular locations, which are later identified by detecting the geo-location of the tracker.

In some embodiments, a user tags a location as being associated with a person known to the user. For example, a user logs into his/her user account and tags a location as being Mom's house, Eric's house, Jessica's house, Buddy's gym, etc. Examples of a person known to the user include a friend of the user, a work mate of the user, a special interest of the user, a relative of the user, an acquaintance of the user, or a family member of the user. The user tags via an input device of a computing device or via a user interface of a monitoring device. A processor, e.g., a processor of the monitoring device, a processor of the computing device, a processor of a server, a processor of a virtual machine, or a combination thereof, etc., determines that the tag indicates that the user knows the person. For example, the term "Mom" indicates that the person is a mom of the user. As another example, "Eric" indicates that the person is a friend, a relative, or an acquaintance of the user. The processor determines whether the person tagged has a user account. The user account is used to display event data that includes activities performed by the person and/or locations visited by the person while performing the activities, etc. The processor suggests to the user to add the person to a social group, e.g. a friend group, a work mate group, a special interest group, a relative group, an acquaintance group, a family member group, etc. When the user adds the person within the social group, the user account of the user indicates the addition of the person within the social group.

In general, the systems and methods facilitate determination of an activity level of an activity performed by a user at a location. For example, the systems and methods can determine that the user is sedentary for a particular period of time when the user is at work. As another example, the systems and methods can determine that the user is active when the user is at home. The activity or lack of activity is therefore contextually associated to a particular location. The location can be an address, map, or a combination of maps, addresses, activities, and/or predefined location identifiers or activities that occur at particular locations (e.g., golf occurs at a golf course, swimming occurs at a swimming pool, etc.). By providing the user location context to activities, the user is able to better view his or her actual activity performance and better health decisions can be made regarding and/or adjustments can be made in lifestyle.

In some embodiments, a calendar GUI is generated. The calendar GUI provides an integrated visual display of a calendar with activities performed by a user and metrics associated with the activities. For example, a calendar includes a number of steps walked by a user during a day, a latitude of a monitoring device, a longitude of a monitoring device, a latitude of a computing device, a longitude of a computing device, a speed of the user for a period of time, a name of a location of the user, an address of a location of the user, a start time at which the user reaches a location, a start time at which the user starts performing an activity, an end time at which the user leaves a location, an end time at which the user finishes performing an activity, a wake-up time of the user on that day, a bed time of the user on that day, an amount of time spent by the user at his/her home, a length of time for which an activity is performed by the user, an amount of time spent by the user performing an activity, an amount of time spent by the user at a location, an activity level at a location, an activity level of an activity, an amount of time spent by the user at his/her work, an amount of time spent by the user in his/her vehicle, etc. In several embodiments, a calendar provides the user with a summarized description of the metrics. For example, a calendar describes that "You did not walk much today", "You woke up late today", "You ran a lot this week", "You drove a lot this month", "You went to bed early today", etc. Each of "You did not walk much today", "You woke up late today", "You ran a lot this week", "You drove a lot this month", and "You went to bed early today" is an example of a sentence. The calendar helps the user view his/her activities. The user can view his/her activities and decide whether to increase, decrease, or maintain an activity level to achieve health and happiness.

In various embodiments, a start time of performing an activity is determined by a processor. For example, the processor of a monitoring device, a server, or a computing device receives a time at which an activity level of the user changes from a first level to a second level. Upon determining that the activity level changed from the first level to the second level, the processor receives, from a time measurement device, a time at which the activity level changed. Upon determining that the activity level changed at the time, the processor determines that the time is the start time at which the user started performing an activity having the second activity level.

The processor may confirm that the user has started performing an activity having the second activity level based on a geo-location of the user. The processor obtains a geo-location from a device locator. Upon determining that the geo-location corresponds to a location at which the activity having the second activity level is usually performed, the processor determines that the user has started performing an activity having the second activity level.

In several embodiments, an end time of performing an activity is determined by a processor. For example, the processor of a monitoring device, a server, or a computing device receives a time at which an activity level of the user changes from a third level to a fourth level. Upon determining that the activity level changed from the third level to the fourth level, the processor receives, from a time measurement device, a time at which the activity level changed. Upon determining that the activity level changed at the time, the processor determines that the time is the end time at which the user finished performing an activity having the third activity level.

The processor may confirm that the user has stopped performing an activity having the third activity level based on a geo-location of the user. Upon determining that the geo-location corresponds to a location at which the activity having the third activity level is not usually performed, the processor determines that the user has stopped performing an activity having the third activity level.

It should be noted that in a number of embodiments, a processor determines a time of performing an activity as a time period between a start time at which the activity started and an end time at which the activity finished.

In some embodiments, instead of each the first, second, third, and fourth activity levels, a statistical amount of activity level, e.g., maximum activity level, average activity level, median activity level, etc., is used. For example, an average activity level averaged over a period of time is used to determine whether the user has started or stopped performing an activity.

In various embodiments, a processor determines a time for which the user is at a location as being equal to time of entry of the location by the user and a time of exit of the location by the user.

In some embodiments, event data is represented with respect to the calendar GUI. For example, the event data is shown below the calendar GUI. In various embodiments, a map or a route is overlaid on the event data or the calendar GUI. The route is a route showing activities performed by a user and/or locations visited by the user while performing the activities.

In some instances, well known process operations have not been described in detail in order not to unnecessarily obscure various embodiments described in the present disclosure.

FIG. 1A illustrates a variety of situations/activities in which a system and/or method uses location data to segment a period of time into identifiable events, each event defining an activity for a period of time. In one embodiment, location data is obtained for a time when the activity is tracked, such as location data and/or characteristics of the activity used to identify an event. As noted in detail below, a period of time having associated tracking data can be segmented into one or more events.

In the example of FIG. 1A, a user 112A wears a monitoring device 114A on his arm while playing a sport, e.g., tennis. Other examples of a sport include badminton, golf, running, bicycling, vehicle racing, racquetball, squash, soccer, etc. It should be understood that the example of sports is provided, as such sports have particular identifiable activity patterns. However, any activity, whether sports related or not, can be tracked and associated to an event. For instance, another user 112B wears a monitoring device 114B on her arm while walking. Yet another user 112C wears a monitoring device 114C on his/her arm while doing yoga. Another user 112D wears a monitoring device 114D on his/her arm during sleep. Another user 112E wears a monitoring device 114E on his/her arm while playing golf. Yet another user 112F wears a monitoring device 114F on his/her clothing part while riding a bicycle. Another user 112G wears a monitoring device 114G on his/her foot while walking a user 112H, e.g., a dog. In some embodiments, the user 112G walks other animals, e.g., a tiger, a cat, etc. The user 112H also wears a monitoring device 114H on its arm. Another user 112I wears a monitoring device 114I on his arm during running.

In some embodiments, a user performs one or more of other activities, e.g., swimming, resistance training, rock climbing, skiing, snowboarding, hiking, skating, rollerblading, etc. It is noted that the activities described herein are not limiting and that other activities may be used.

It should be noted that in some embodiments, a user can wear, hold, append, strap-on, move, transport or carry a monitoring device while performing any type of activity, e.g., playing ping-pong, climbing stairs, descending stairs, hiking, sitting, resting, working, etc. Additionally, one user can be associated with more than one monitoring device, and such data can be processed and associated to the user's activity. In some embodiments, the data is selected from various devices of the user based on a priority algorithm. In some embodiments, data from more than one device can be blended or alternated together to define a more complete map of the activities.

Each monitoring device 114A, 114B, 114C, 114D, 114E, 114F, 114G, 114H, and 114I communicates with a network 176. In some embodiments, each monitoring device 114A, 114B, 114C, 114D, 114E, 114F, 114G, 114H, and 114I communicates with the network 176 via a computing device, e.g., a desktop computer, a laptop computer, a smart phone, a tablet, a smart watch, a smart television, etc.

Examples of the network 176 include the Internet and an Intranet. The network 176 may be a wide area network, a local area network, or a combination thereof. The network 176 may be coupled to one or more servers, one or more virtual machines, or a combination thereof.

A server, a virtual machine, a controller of a monitoring device, or a controller of a computing device is sometimes referred to herein as a computing resource. Examples of a controller include a processor and a memory device.

As used herein, a processor includes an application specific integrated circuit (ASIC), a programmable logic device (PLD), a processor, a central processing unit (CPU), or a combination thereof, etc. Examples of a memory device include a random access memory (RAM) and a read-only memory (ROM). A memory device may be a Flash memory, a redundant array of disks (RAID), a hard disk, or a combination thereof.

A computing resource performs data capture, which is reception of activity data from a monitoring device. Examples of activity data include, without limitation, calories burned by a user, blood pressure of the user, heart rate of the user, weight gained by a user, weight lost by a user, stairs ascended, e.g., climbed, etc., by a user, stairs descended by a user, steps taken by a user during walking or running, hours spent traveling, floors descended by a user, floors climbed by a user, a number of rotations of a bicycle pedal rotated by a user, sedentary activity data, a distance covered by a user during walking, running, or driving a vehicle, a number of golf swings taken by a user, a number of forehands of a sport played by a user, a number of backhands of a sport played by a user, or a combination thereof. In some embodiments, sedentary activity data is referred to herein as inactive activity data or as passive activity data. In some embodiments, when a user is not sedentary and is not sleeping, the user is active.

The data capture also includes capturing a geo-location of a monitoring device. For example, geographical location data 120A of the monitoring device 114A is determined by the monitoring device 114A and obtained by a computing resource. A geo-location is determined by a device locator, which is further described below. Examples of a geo-location include latitude, radius, longitude, altitude, landmark, city, country, state, county, village, eatery, commercial place, commercial building, province, public place, or a combination thereof. In some embodiments, the geo-location data is obtained not by the monitoring device, but by a companion device (e.g., such as a smart phone or other portable device with global positioning system (GPS) data collection capabilities).

In various embodiments, a device locator obtains a speed of a monitoring device or of a computing device. For example, a device locator of a computing device determines a speed of the computing device and a device locator of a monitoring device determines a speed of the monitoring device. In various embodiments, a device locator of a device, e.g., a monitoring device, a computing device, etc., obtains an orientation of the device. In various embodiments, an orientation of a device includes a degree of rotation of the device with respect to an x axis, a y axis, and a z axis.

Similarly, geographical location data 120B of the monitoring device 114B is determined by the monitoring device 114B and obtained by a computing resource, geographical location data 120C of the monitoring device 114C is determined by the monitoring device 114C and obtained by a computing resource, geographical location data 120D of the monitoring device 114D is determined by the monitoring device 114D and obtained by a computing resource, geographical location data 120E of the monitoring device 114E is determined by the monitoring device 114E and obtained by a computing resource, geographical location data 120F of the monitoring device 114F is determined by the monitoring device 114F and obtained by a computing resource, geographical location data 120G of the monitoring device 114G is determined by the monitoring device 114G and obtained by a computing resource, geographical location data 120H of the monitoring device 114H is determined by the monitoring device 114H and obtained by a computing resource, and geographical location data 120I of the monitoring device 114I is determined by the monitoring device 114I and obtained by a computing resource.

A geo-location of a monitoring device is used in conjunction with activity data by a computing resource to perform data analysis. The data analysis is performed by a processor.

For example, a level, e.g., an amount, etc., of an activity performed by a user at a geo-location is determined. Examples of activity level include a number of calories burned by a user, an amount of weight gained by a user, a heart rate of a user, an amount of blood pressure of a user, an amount of weight lost by a user, a number of stairs ascended by a user, a number of stairs descended by a user, a number of steps taken by a user during walking or running, a number of floors descended by a user, a number of floors climbed by a user, a number of rotations of a bicycle pedal rotated by a user, a distance covered by a vehicle operated by a user, a number of golf swings taken by a user, a number of forehands of a sport played by a user, a number of backhands of a sport played by a user, or a combination thereof, etc. The geo-location and the activity level are combined and displayed to a user to monitor activity and/or health of the user over a period of time. As another example, a geo-location is combined with an activity level to determine whether a user is still at a location, e.g., a house, a work place, an office, a gym, a sandwich shop, a coffee shop, etc. after performing the activity or has left the location after performing the activity. In this example, when it is determined that the user is at the location and the activity level has crossed from a first side of a threshold to a second side of the threshold, it is determined that the user has left the location. Moreover, in this example, when it is determined that the user is at the location and that the activity level has not crossed from the first side to the second side, it is determined that the user is still at the location. In some embodiments, the first side of the threshold is below the threshold and the second side of the threshold is above the threshold. In various embodiments, the first side of the threshold is above the threshold and the second side is below the threshold.

In some embodiments, a user indicates to a monitoring device or a computing device that the user has exited or entered a location. For example, the user logs into a user account and indicates via a user interface of a monitoring device or an input device of a computing device that the user is exiting or entering a location. A processor, e.g., a processor of a server, a processor of a virtual machine, a processor of the computing device, or a processor of the monitoring device, or a combination thereof, etc., receives the indication from the user. The processor determines a time at which the user indicates that the user is entering or exiting the location and indicates the time on a graphical user interface that includes event data. In various embodiments, upon determining that the user has entered a location, the processor accesses the activity-location database to determine one or more activities that may be performed by the user at the location and generates one or more activity identifiers of the activities.

In some embodiments, a computing resource performs data synchronization, which includes synchronization of activity data received from various users and synchronization of geo-locations of the users. For example, activity data from one user is displayed to another user when both the users are within one location. As another example, activity data of one user is displayed to another user when both users are performing the same activity, e.g., walking, running, etc. As yet another example, activity data of one user is displayed to another user when both users are performing the same activity at the same location. As another example, activity data is displayed to two or more users who perform similar activities in disparate locations (e.g., a virtually shared walk).

In various embodiments, a computing resource recommends data to a user based on activity data received from a monitoring device used by the user and based on a location of the user. For example, when it is determined that a user is at a golf course and has not taken a number of golf swings, the recommendation data indicates to the user that the user may take an additional amount of golf swings to achieve a goal. As another example, when it is determined that a user is not going to (or is unlikely to based on knowledge of the user's historical activity patterns) reach his/her activity goal, e.g., walking a number of steps over a time period, running a distance over a time period, climbing or descending a number of stairs over a time period, bicycling for an amount of distance over a time period, bicycling for a number of pedal rotations of a bicycle over a time period, lifting a weight for a number of times over a time period, hitting a forehand for a number of times over a time period, hitting a backhand for a number of times over a time period, etc., and it is determined that the user is at a location, the computing resource generates the recommendation data to indicate to the user to perform an activity or to extend performing the activity at the location or at another location that is within a distance of the location. These recommendations can be provided as electronic notifications to the user's device, the user's smart phone, to the tracking device, or some other user interface. The recommendations can also be provided as voice notifications, in case the user is occupied in a task that limits viewing a screen, such as driving. The determination that the user is driving can be made using data regarding the speed/motion of the device, location data (e.g., in a car), etc.

In some embodiments, a user may stand on a monitoring device that determines a physiological parameter of the user. For example, a user stands on a scale that measures a weight, a body fat percentage, a biomass index, or a combination thereof, of the user.

Figure 1B:
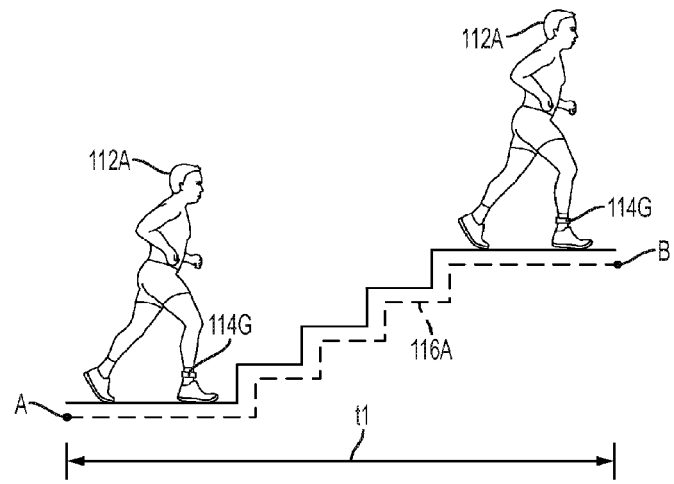
FIG. 1B is a diagram of a method for determining an amount of a type of movement of a monitoring device over a period of time, in accordance with one embodiment described in the present disclosure.

FIG. 1B is a diagram of an embodiment of a method for determining an amount of movement 116A of the monitoring device 114G, e.g., a number of stairs ascended by the monitoring device 114G, etc., over a period of time t1. The amount of movement 116A occurs when the user 112A is performing an activity of climbing stairs over the time period t1. A method of determining an amount of movement is performed by a position sensor of a monitoring device. Additionally, the method can simultaneously identify a location for the activity. The monitoring device 114G may be worn on the leg or foot (as depicted in FIG. 1B), or elsewhere on the body such as the wrist, forearm, upper arm, head, chest, or waist, or as an article of clothing such as a shirt, hat, pants, blouse, glasses, and the like.

A position sensor determines an amount of linear or angular movement of an arm of a user or of another body part of a user. For example, a position sensor determines that the user 112A wearing the monitoring device 114G on his leg has climbed a number of stairs, e.g., four, twenty, forty, etc., between positions A and B over the time period t1.

In some embodiments, instead of a number of stairs ascended, a position sensor determines a number of stairs descended by the monitoring device 114G.

Figure 1C:
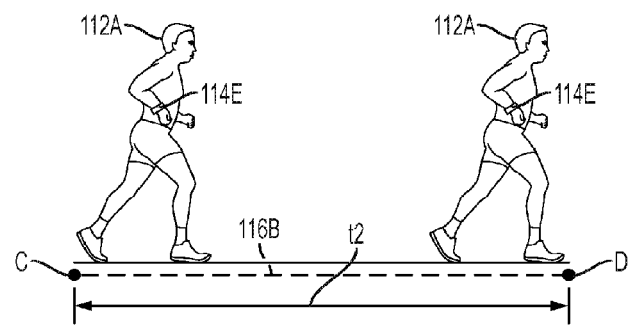
FIG. 1C is a diagram of a method for determining an amount of another type movement of a monitoring device over a period of time, in accordance with one embodiment described in the present disclosure.

FIG. 1C is a diagram of an embodiment of a method for determining an amount of movement 116B, e.g., an amount of distance traveled, a number of steps traveled, etc., of the monitoring device 114E over a period of time t2. For example, a position sensor determines that the user 112A wearing the monitoring device 114E on his hand has walked or ran a number of steps, e.g., four, fifty, hundred, etc., between positions C and D over the time period t2. The amount of movement 116B occurs when the user 112A is performing an activity of walking or running over the time period t2.

Figure 1D:
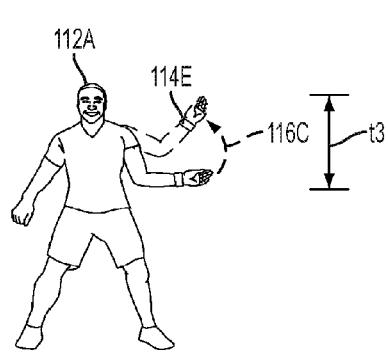
FIG. 1D is a diagram of a method for determining an amount of yet another type movement of a monitoring device over a period of time, in accordance with one embodiment described in the present disclosure.

FIG. 1D is a diagram of an embodiment of a method for determining an amount of movement 116C, e.g., an amount angular movement, etc., of the monitoring device 114E over a period of time t3. For example, a position sensor determines that a hand of the user 112A wearing the monitoring device 114E on his/her hand is displaced by an angle over the time period t3. The amount of movement 116C occurs when the user 112A is performing a sports activity, e.g., golfing, playing tennis, playing ping-pong, resistance training, etc., over the time period t3.

In some embodiments, a position sensor measures an angular displacement of a leg of the user 112A wearing the monitoring device 114G on his leg.

In various embodiments, a position sensor infers an activity performed by a user over a period of time based on one or more positions of a monitoring device that has the position sensor and that is worn by the user. For example, upon determining that a difference between a first y position and a second y position within a xyz co-ordinate system is greater than an amount and that x positions between the two y positions indicate a curved movement, a position sensor of a monitoring device determines that the user 112A is playing golf. As another example, upon determining that the user 112A covers less than a distance along an x-axis over a period of time, a position sensor of a monitoring device worn by the user 112A determines that the user 112A is walking and upon determining that the user 112A covers more than the distance along the x-axis over the period of time, the position sensor determines that the user 112A is running.

Figure 1E:
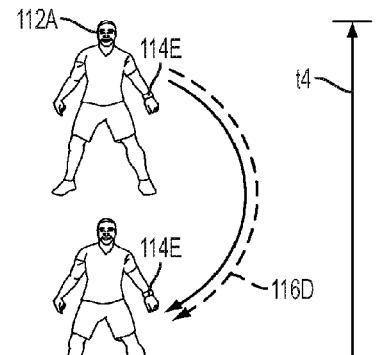
FIG. 1E is a diagram of a method for determining an amount of another type movement of a monitoring device over a period of time, in accordance with one embodiment described in the present disclosure.

FIG. 1E is a diagram of an embodiment of a method for determining an amount of movement 116D, e.g., an amount angular movement, etc., of the monitoring device 114E over a period of time t4. For example, a position sensor determines that the user 112A wearing the monitoring device 114E on his/her hand is displaced by an angle over the time period t4. The amount of movement 116D occurs when the user 112A is performing an activity, e.g., a sports activity, an exercise activity, etc., over the time period t4.

Examples of a period of time include a portion of a day, or a day, or a portion of a month, or a month, or a portion of a year, or a year, or a portion of a number of years, or a number of years.

Figure 2A:
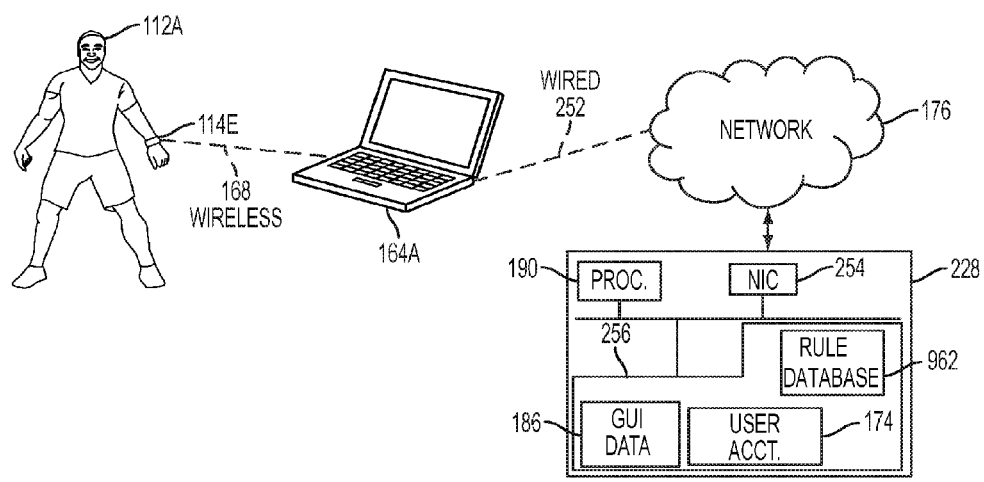
FIG. 2A is a diagram of a system for transferring data between a monitoring device and a server via a computing device and a network, in accordance with one embodiment described in the present disclosure.

FIG. 2A is a diagram of an embodiment of a system 250 for transferring data, e.g., activity data, geo-location data, etc., between the monitoring device 114E and a server 228 via a computing device 164A and the network 176. A wireless link 168 establishes a connection between the monitoring device 114E and the computing device 164A. For example, a Bluetooth device located within the monitoring device 114E establishes a Bluetooth connection with a Bluetooth dongle interfacing with the computing device 164A via a Universal Serial Bus (USB) interface. As another example, an ad hoc Wi-Fi transmission and reception is established between a Wi-Fi adapter of the monitoring device 114E and a Wi-Fi adapter of the computing device 164A. The wireless link 168 may be a Bluetooth or a Wi-Fi connection. A connection between the monitoring device 114E and the computing device 164A is used to transfer data between the monitoring device 114E and the computing device 164A.

In some embodiments, a geo-location and/or a position determined by the monitoring device 114E is sent from the monitoring device 114E via the computing device 164A to a server or a virtual machine for processing, e.g., analysis, determining event data, etc. The server or the virtual machine processes the geo-location and/or the position and sends processed data, e.g., event data, maps, routes, etc., to the computing device 164A for display on the computing device 164A.

In some embodiments, instead of the wireless link 168, a wired connection is used between the monitoring device 114E and the computing device 164A.

Moreover, a wired connection 252 is established between the computing device 164A and the server 228 via the network 176. A wired connection includes network components, e.g., one or more routers, one or more switches, one or more hubs, one or more repeaters, one or more servers, one or more cables, or a combination thereof, etc.

The server 228 includes a processor 190, a network interface controller (NIC) 254 and a memory device 256. The processor 190 is coupled with the memory device 256 and the NIC 254. An example of a NIC includes a network interface card. In some embodiments, a modem is used instead of a NIC.

The memory device 256 includes a user account 174 of the user 112A. The user 112A accesses the user account 174 when authentication information, e.g., username, password, fingerprints, footprints, thumbprints, or a combination thereof, etc., is authenticated by the processor 190 or another server of the network 176. The authentication information is provided by the user 112A via an input device, e.g., a mouse, a stylus, a keyboard, a keypad, a button, a touch screen, or a combination thereof, etc., of a monitoring device or of a computing device.

The user account 174 is accessed by the user 112A to review graphical user interface (GUI) data 186 on a display device of the computing device 164A or of the monitoring device 114E. The GUI data 186 includes geo-location data, a map, location in the form of location/activity identifiers, activity data in the form of activity levels, and/or physiological parameter of the user 112A. The activity data represents activities performed by the monitoring device 114E. The processor 190 associates, e.g., links, establishes a relationship between, etc., geo-location data, location, activity data, and/or physiological parameter of the user 112A with the user account 174 to allow access of the geo-location data, activity data, a map, location, and/or physiological parameter upon access of the user account 174. This relationship provides context to the activity, both in terms of what the activity was and where the activity occurred. This context can be used to define events that occur over a period of time, and the events can be presented on a GUI of a device, to provide useful information to a user regarding his or her activity over that period of time. Not only is the user provide with activity data, but the activity data is displayed in a graphical or data organized manner that identifies segmented activity data and associates it to the proper or inferred context.

In some embodiments, instead of using the monitoring device 114E to establish the wireless connection 168, any other monitoring device, e.g. the monitoring device 114A (FIG. 1A) or a monitoring scale is used.

It should be noted that in several embodiments, data is transferred from a monitoring device via a computing device and the network 176 to a virtual machine instead of the server 228.

In some embodiments, instead of the wired connection 252, a combination of a wireless connection and a wired connection is established.

In various embodiments, the user account 174 is stored in a memory device of a computing device or on a memory device of a monitoring device. In these embodiments, processing of a geo-location and/or position is not done on the server 228 or a virtual machine to generate processed data, e.g., event data, location identifier, activity identifier, etc. but is done by a processor of the computing device and/or by a processor of a monitoring device to generate the processed data.

Figure 2B:
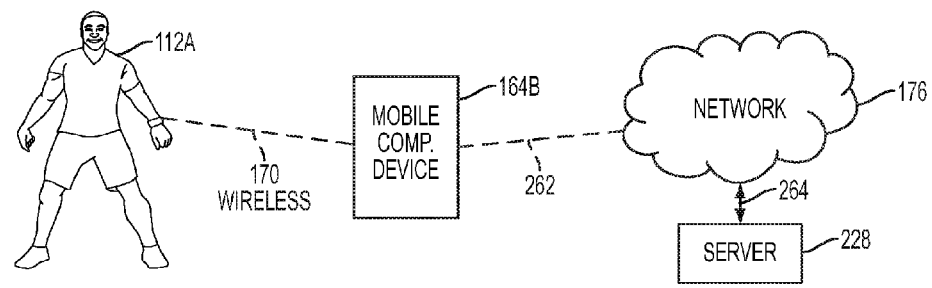
FIG. 2B is a diagram of an embodiment of a system for transferring data between a monitoring device and the server via a mobile computing device and the network, in accordance with one embodiment described in the present disclosure.

FIG. 2B is a diagram of an embodiment of a system 260 for transferring data, e.g., activity data, geo-location data, etc., between the monitoring device 114E and the server 228 via a mobile computing device 164B and the network 176. A wireless link 170 establishes a connection between the monitoring device 114E and the mobile computing device 164B. The wireless link 170 may be a Bluetooth connection, a Wi-Fi connection, a near field connection, a radio frequency connection, or an optical connection, etc. In some embodiments, instead of the wireless link 168, a wired connection is used between the monitoring device 114E and the mobile computing device 164B. A connection is used to transfer data between the monitoring device 114E and the mobile computing device 164B.

Moreover, the server 228 and the mobile computing device 164B are coupled with each other via a wireless connection 262, e.g., a Wi-Fi connection, etc., the network 176, and a connection 264. The connection 264 between the server 228 and the network 176 may be a wired or a wireless connection.

Figure 3A:
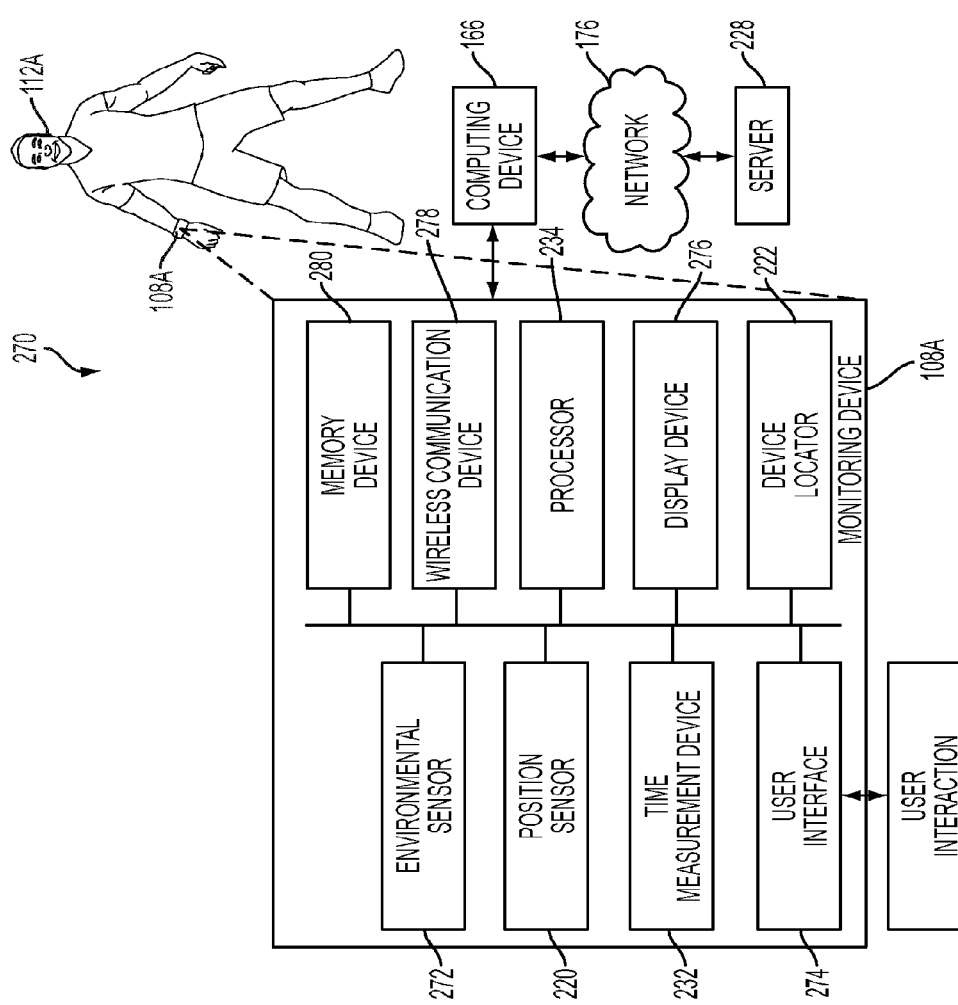
FIG. 3A is a diagram of a system to illustrate components of a monitoring device, in accordance with one embodiment described in the present disclosure.

FIG. 3A is a diagram of an embodiment of a system 270 to illustrate components of a monitoring device 108A. The system 270 includes the monitoring device 108A, a computing device 166, the network 176, and the server 228.

The monitoring device 108A is an example of any of the monitoring devices 114A, 114B, 114C, 114D, 114E, 114F, 114G, 114H, and 114I (FIG. 1A). The monitoring device 108A includes an environmental sensor 272, a position sensor 220, a time measurement device 232, a user interface 274, a device locator 222, a display device 276, a processor 234, a wireless communication device 278, and a memory device 280, all of which are coupled with each other.

Examples of the device locator 222 include a GPS transceiver, a mobile transceiver, etc. As used herein, a device locator may be referred to as a device or circuit or logic that can generate geo-location data. The geo-location data provides the appropriate coordinate location of the device or tracker, such as a location on a map or location in a room or building. In some embodiments, a GPS device provides the geo-location data. In other embodiments, the geo-location data can be obtained from various devices (e.g., cell towers, Wi-Fi device signals, other radio signals, etc., which can provide data points usable to locate or triangulate a location.

Examples of the environmental sensor 272 include a barometric pressure sensor, a weather condition sensor, a light exposure sensor, a noise exposure sensor, a radiation exposure sensor, and a magnetic field sensor. Examples of a weather condition include a temperature, humidity, a pollen count, air quality, rain conditions, snow conditions, wind speed, a combination thereof, etc. Examples of light exposure include ambient light exposure, ultraviolet (UV) light exposure, or a combination thereof, etc. Examples of air quality include particulate counts for varying sized particles, or level of carbon dioxide in air, or level of carbon monoxide in air, or level of methane in air, or level of other volatile organic compounds in air, or a combination thereof.

Examples of the position sensor 220 include an accelerometer, a gyroscope, a rotary encoder, a calorie measurement sensor, a heat measurement sensor, a moisture measurement sensor, a displacement sensor, an ultrasonic sensor, a pedometer, an altimeter, a linear position sensor, an angular position sensor, a multi-axis position sensor, or a combination thereof, etc. In some embodiments, the position sensor 220 measures a displacement, e.g., angular displacement, linear displacement, a combination thereof, etc., of the monitoring device 108A over a period of time with reference to an xyz co-ordinate system to determine an amount of activity performed by the user 112A during the period of time. In some embodiments, a position sensor includes a biological sensor, which is further described below. In various embodiments, a position sensor includes a motion sensor.

Examples of the time measurement device 232 include a watch, an oscillator, a clock, an atomic clock, etc. Examples of the user interface 274 include an input device for interacting with the user 112A. For example, the user interface 274 receives a selection of the GUI data 186 (FIG. 2A) from the user 112A. It should be noted that when the user interface 274 includes a touch screen, the touch screen 274 is integrated within the display device 276.

Examples of a display device includes a liquid crystal display (LCD) device, a light emitting diode (LED) display device, a plasma display device, etc. As an example, the display device 276 displays the GUI data 186. In some embodiments, all GUIs described herein are displayed by rendering the GUI data 186.

Examples of the memory device 280 are provided above. Examples of the wireless communication device 278 include a Wi-Fi adapter, a Bluetooth device, etc.

In some embodiments, the processor 234 receives one or more geo-locations measured by the device locator 222 over a period of time and determines a location of the monitoring device 108A based on the geo-locations and/or based on one or more selections made by the user 112A via the user interface 274 and/or based on information available within a geo-location-location database of the network 176. For example, the processor 234 determines that a location within the geo-location-location database corresponds to one or more geo-locations stored within the geo-location-location database. In this example, upon receiving the geo-locations from the device locator 222, the processor 234 determines the location based on the correspondence between the geo-locations and the location in the geo-location-location database. In some embodiments, the geo-location-location database includes a map of a geographical region, e.g., a city, a state, a county, a country, a continent, a geographical area, world, etc. The map is generated by the server 228 or another server based on one or more geo-locations.

The environmental sensor 272 senses and determines an environmental parameter, e.g., a barometric pressure, a weather condition, an amount of light exposure, an amount of noise, an amount of radiation, an amount of magnetic field, or a combination thereof, etc., of an environment in which the monitoring device 108A is placed. The device locator 222 determines a geo-location of the monitoring device 108A.

The time measurement device 232 determines an amount of time associated with one or more positions sensed by the position sensor 220, associated with one or more environmental parameters determined by the environmental sensor 272, associated with one or more geo-locations determined by the device locator 222, and/or associated with one or more locations determined by the processor 234. For example, the time measurement device 232 determines an amount of time for a number of positions that is reached by movement of the monitoring device 108A and that is determined by the position sensor 220. As another example, the time measurement device 232 determines an amount of time for a number of geo-locations reached by movement of the monitoring device 108A and that is determined by the device locator 222.

The wireless communication device 278 establishes a wireless link with the computing device 166 to send data, e.g., activity data, geo-location data, location data, a combination thereof, etc., to and/or receive the data and/or instructions from the computing device 166. Each computing device 164A and 164B (FIGS. 2A & 2B) is an example of the computing device 166. The instructions from the computing device 166 may be to send data, e.g., activity data, geo-location data, location data, a combination thereof, etc., to the computing device 166.

In some embodiments, the monitoring device 108A excludes the wireless communication device 278. In these embodiments, the monitoring device 108A communicates using a wired connection with the computing device 166.

In various embodiments, the time measurement device 232 is integrated as a part of the position sensor 220 and/or as a part of the environmental sensor 272 and/or as a part of the device locator 222.

In several embodiments, the monitoring device 108A excludes the environmental sensor 272.

In a number of embodiments, the monitoring device 108A includes a biological sensor coupled to the environmental sensor 272, the position sensor 220, the time measurement device 232, the user interface 274, the device locator 222, the display device 276, the processor 234, the wireless communication device 278, and the memory device 280. The biological sensor is further described below.

Figure 3B:
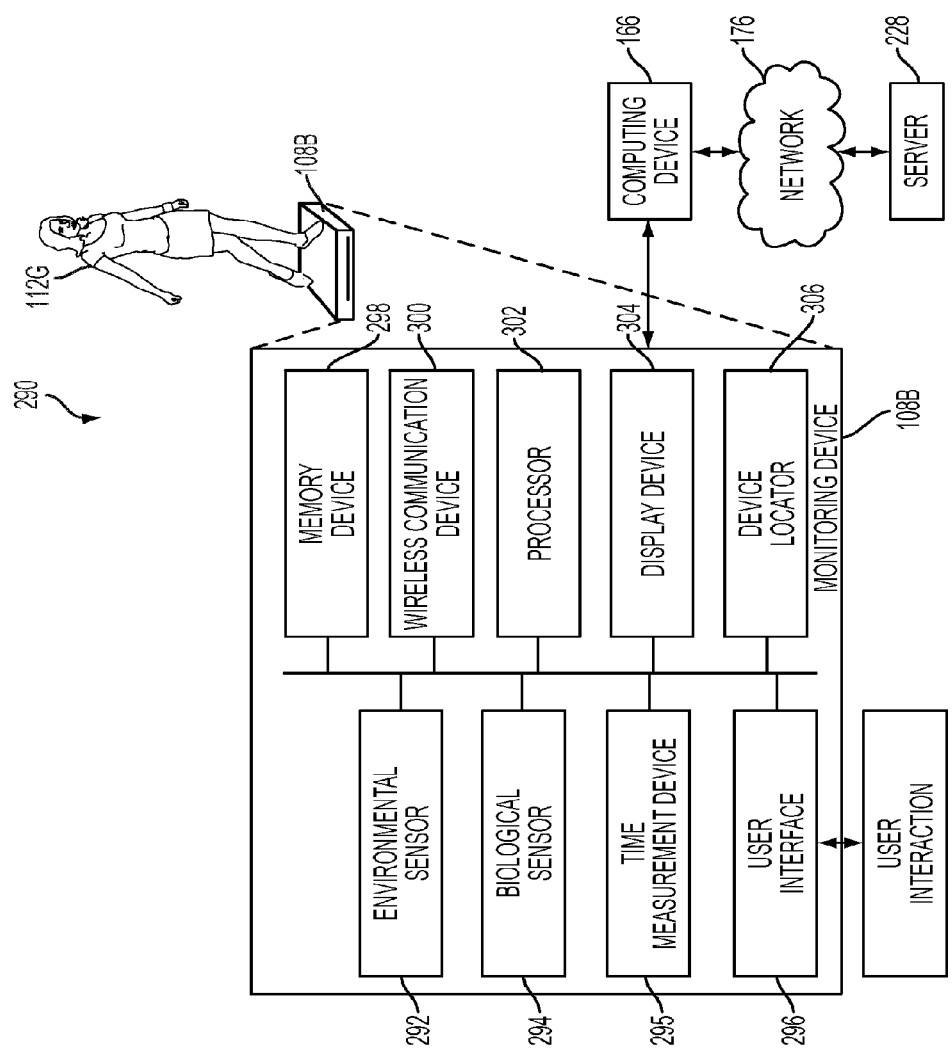
FIG. 3B is a diagram of a system to illustrate components of another monitoring device, in accordance with one embodiment described in the present disclosure.

FIG. 3B is a diagram of an embodiment of a system 290 to illustrate components of a monitoring device 108B. The system 290 includes the monitoring device 108B, the computing device 166, the network 176, and the server 228. An example of the monitoring device 108B includes a scale. The monitoring device 108B is placed on a floor and the user 112A stands on the monitoring device 108B. The monitoring device 108B includes an environmental sensor 292, a biological sensor 294, a time measurement device 295, a user interface 296, a device locator 306, a display device 304, a processor 302, a wireless communication device 300, and a memory device 298.

The environmental sensor 292 performs the same functions as that of the environmental sensor 272 (FIG. 3A) except that the environmental sensor 292 is of a different, e.g., larger, smaller, etc., size compared to a size of the environmental sensor 272. In some embodiments, the environmental sensor 272 is used in the monitoring device 108B instead of the environmental sensor 292.

The biological sensor 294 senses and determines a physiological parameter of the user 112A. For example, the biological sensor 294 determines a weight of the user 112A. As another example, the biological sensor 294 determines a body mass index of the user 112A. As yet another example, the biological sensor 294 determines a fingerprint or a footprint of the user 112A. As another example, the biological sensor 294 determines a heart rate, a hydration level, a body fat, a bone density, and/or a bioimpedance of the user 112A. Examples of the biological sensor 294 include a biometric sensor, a physiological parameter sensor, or a combination thereof.

The time measurement device 295 performs the same functions as that of the time measurement device 232 (FIG. 3A) except that the time measurement device 295 is different, e.g., larger, smaller, etc., in size compared to the time measurement device 232. As an example, the time measurement device 295 determines an amount of time for a number of physiological parameters measured by the biological sensor 294.

In some embodiments, the time measurement device 232 is used in the monitoring device 108B instead of the time measurement device 295.

Similarly, the user interface 296 performs the same functions as that of the user interface 274 (FIG. 3A) and is of a different size than that of the user interface 274. In various embodiments, the user interface 274 is used in the monitoring device 108B instead of the user interface 296.

Moreover, the memory device 298 performs the same functions as that of the memory device 280 (FIG. 3A) and is of a different size than that of the memory device 280. For example, the memory device 298 includes a different, e.g., larger, smaller, etc., number of memory cells compared to memory cells of the memory device 280. In various embodiments, the memory device 280 is used in the monitoring device 108B instead of the memory device 298.

Also, the wireless communication device 300 performs the same functions as that of the wireless communication device 278 (FIG. 3A) and is of a different size than that of the wireless communication device 278. For example, the wireless communication device 300 includes electrical components that allow a transfer data at a different, e.g., higher, lower, etc., rate with the computing device 166 compared to a rate of transfer of data between the wireless communication device 278 and the computing device 166. In various embodiments, the wireless communication device 278 is used in the monitoring device 108B instead of the wireless communication device 300.

Furthermore, the processor 302 performs the same functions as that of the processor 234 (FIG. 3A) and is of a different, e.g., larger, smaller, etc., size than that of the processor 234. For example, the processor 302 is of a size to achieve a different, e.g., higher, lower, etc., speed than that of the processor 234. In various embodiments, the processor 234 is used in the monitoring device 108B instead of the processor 302.

Moreover, the display device 304 performs the same functions as that of the display device 276 (FIG. 3A) and is of a different, e.g., larger, smaller, etc., size than that of the display device 276. In various embodiments, the display device 276 is used in the monitoring device 108B instead of the display device 304.

Also, the device locator 306 performs the same functions as that of the device locator 222 (FIG. 3A) and is of a different, e.g., larger, smaller, etc., size than that of the device locator 222. In various embodiments, the device locator 222 is used in the monitoring device 108B instead of the device locator 306.

In some embodiments, the monitoring device 108B includes a position sensor (not shown) that performs the same functions as that of the position sensor 220 (FIG. 3A). The position sensor of the monitoring device 108B is coupled to the environmental sensor 292, the biological sensor 294, the time measurement device 295, the user interface 296, the device locator 306, the display device 304, the processor 302, the wireless communication device 300, and the memory device 298. In various embodiments, the position sensor 220 is implemented within the monitoring device 108B.

Figure 4A:
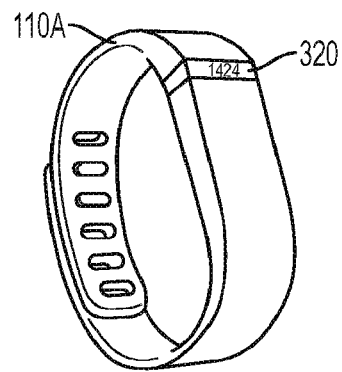
FIG. 4A is an isometric view of a monitoring device that is worn around a hand of a user or around a leg of the user, in accordance with one embodiment described in the present disclosure.

FIG. 4A is an isometric view of an embodiment of a monitoring device 110A that is worn around a hand of a user or around a leg of the user. For example, the monitoring device 110A has a band that is unclasped to allow the monitoring device 110A to extend around a wrist of a user or a leg of the user. After the monitoring device 110A extends around the wrist, the band is clasped to fit the monitoring device 110A to the wrist of the user or to the leg of the user. As another example, the monitoring device 110A has an elastic band that is stretched to allow a grip of the monitoring device 110A to expand. The monitoring device 110A is then slipped around a palm of a user to a wrist of the user or is slipped around a foot of the user to an ankle of the user. The elastic band is then released to fit the monitoring device 110A to the wrist of the user or the ankle of the user. In some embodiments, the monitoring device 110A is worn on a forearm or an upper arm of a user. In other embodiments, the monitoring device can be carried, held, stored in a bag, attached to a shoe, attached to a shirt or pants, etc. In other embodiments, a single person can hold or wear multiple devices. The multiple devices can track the same body part or object or can track/monitor multiple body parts, or objects. For instance, the user can wear one on his/her wrist, one in a shoe, one on his pants, a hat, a visor, or any other object that can track some movement and/or location of the user.

The monitoring device 110A includes a display screen 320 of a display device that displays activity data of one or more activities performed by a user over a period of time, chronological data, geo-location data, or a combination thereof. Examples of a display screen include an LCD screen, an LED screen, a plasma screen, etc. Examples of chronological data include a time of day, a day, a month, a year, etc. The monitoring device 110A is an example of any of the monitoring devices 114A, 114B, 114C, 114D, 114E, 114G, 114H, 114I (FIG. 1A), and 108A (FIG. 3A).

The monitoring device 110A includes one or more input devices that allows a user to switch between displaying different types of data, e.g., from activity data to chronological data, from chronological data to activity data, from one type of activity data to another type of activity data, from geo-location data to activity data, from activity data to geo-location data, etc., and to adjust or set chronological data. Types of activity data include calories burned by a user, weight gained by a user, weight lost by a user, stairs ascended by a user, stairs descended by a user, steps taken by a user during walking or running, floors descended by a user, floors climbed by a user, rotations of a bicycle pedal rotated by a user, distance covered by a vehicle operated by a user, golf swings taken by a user, forehands of a sport played by a user, backhands of a sport played by a user, or a combination thereof, etc.

Again, it should be noted that in some embodiments, the monitoring device 110A is implemented as a watch, a wristband, or a bracelet, that is worn/held by the user 112A.

Figure 4B:
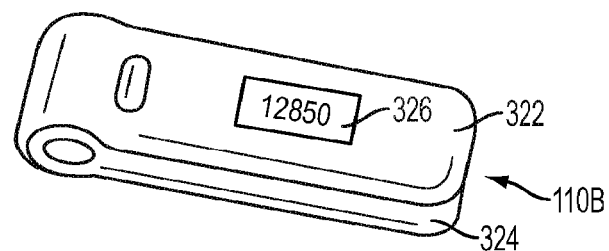
FIG. 4B is an isometric view of another monitoring device that fits to an article of clothing or a belt worn by a user, in accordance with one embodiment described in the present disclosure.

FIG. 4B is an isometric view of an embodiment of a monitoring device 110B that fits to an article of clothing or a belt worn by a user. For example, the monitoring device 110B has a pivoting clip that opens to allow the monitoring device 110B to extend with respect to a pocket of a shirt worn by a user. After the monitoring device 110B extends with respect to the pocket, the clip is retracted to fit the monitoring device 110B to the pocket. The clip may be located between an upper portion 322 and a lower portion 324 of the monitoring device 110B to allow the upper portion 322 to extend from and pivot with respect to the lower portion 324.

The monitoring device 110B includes a display screen 326 that displays activity data, chronological data, geo-location data, or a combination thereof. The monitoring device 110B is an example of the monitoring device 108A (FIG. 3A). The monitoring device 110B includes one or more input devices that allow a user to switch between displaying different types of data and to adjust or set chronological data.

Figure 4C:
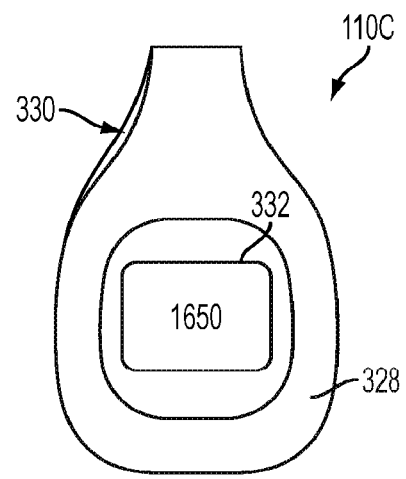
FIG. 4C is a view of yet another monitoring device that fits to an article of clothing or a belt worn by a user, in accordance with one embodiment described in the present disclosure.

FIG. 4C is a view of an embodiment of a monitoring device 110C that fits to an article of clothing or a belt worn by a user. For example, the monitoring device 110C has a flexible pivoting clip that opens to allow the monitoring device 110C to extend with respect to a pocket of a pant worn by a user. After the monitoring device 110C extends around the pocket, the clip is retracted to fit the monitoring device 110C to the pocket. The clip may be located between an upper portion 328 and a lower portion 330 of the monitoring device 110C to allow the upper portion 328 to extend from and pivot with respect to the lower portion 330.

The monitoring device 110C includes a display screen 332 that displays data, e.g., activity data, chronological data, geo-location data, or a combination thereof, etc. The monitoring device 110C is an example of the monitoring device 108A (FIG. 3A). The monitoring device 110C includes one or more input devices that allow a user to switch between displaying different types of data and to adjust or set chronological data.

Figure 4D:
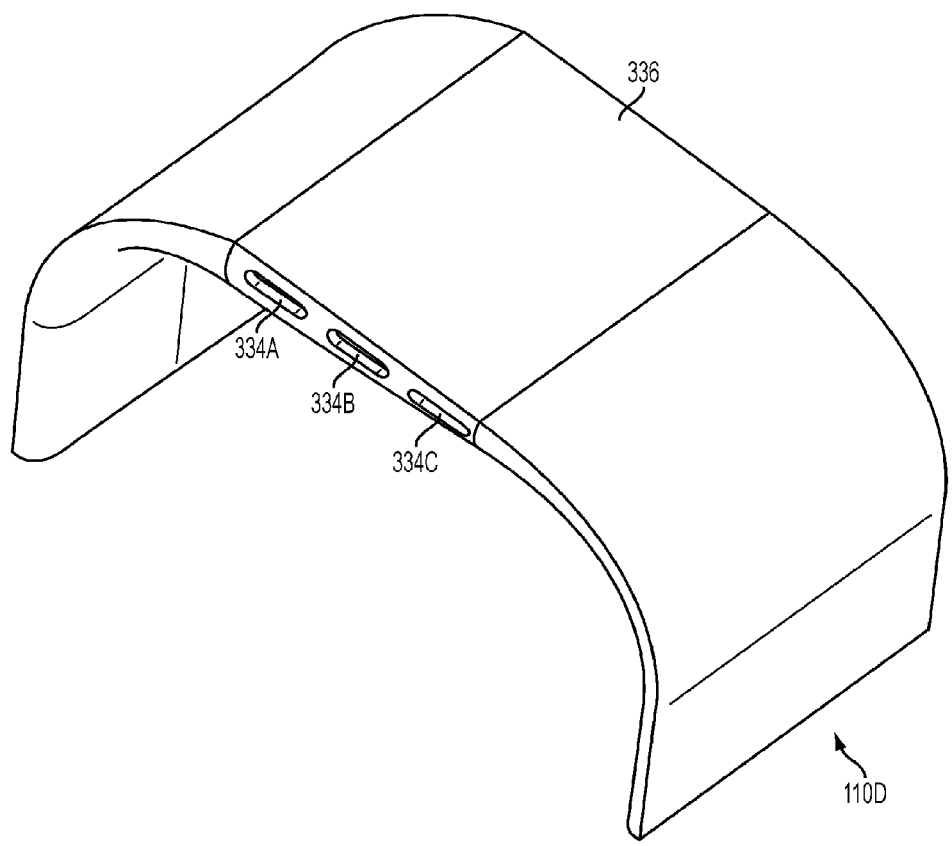
FIG. 4D is an isometric view of another monitoring device that fits to an arm of a user, in accordance with one embodiment described in the present disclosure.

FIG. 4D is an isometric view of an embodiment of a monitoring device 110D that fits with respect to an arm of a user. For example, the monitoring device 110D includes a hook and loop clasp that is extended to loop around a wrist of a user and is then retracted to hook to the wrist. In some embodiments, the monitoring device 110D is implemented within a wrist watch. The monitoring device 110D includes a number of buttons 334A, 334B, and 334C to allow the monitoring device 110D to switch between different types of data, e.g., geo-location data, location, chronological data, activity data, physiological parameter, etc., and to adjust or set chronological data.

The monitoring device 110D includes a display screen 336 that displays activity data, chronological data, geo-location data, physiological parameter, location data, the GUI data 186 (FIG. 2A), or a combination thereof. The monitoring device 110D is an example of any of the monitoring devices 114A, 114B, 114C, 114D, 114E, 114G, 114H, 114I (FIG. 1A), and 108A (FIG. 3A).

It should be noted that in some embodiments, instead of being implemented as a watch, the monitoring device 110D is implemented as a wristband or a bracelet that is worn by the user 112A.

Monitoring devices have shapes and sizes adapted for coupling to, e.g., secured to, worn, etc., the body or clothing of a user. The monitoring devices collect one or more types of physiological and/or environmental data from embedded sensors and/or external devices and communicate or relay the data to other devices, including devices capable of serving as an Internet-accessible data sources, thus permitting the collected data to be viewed, for example, using a web browser or network-based application. For example, while the user 112A is wearing or holding a monitoring device, the monitoring device may calculate and store the user's step count using one or more sensors. The monitoring device then transmits data representative of the user's step count to an account on a virtual machine, a computer, or a mobile phone, where the data may be stored, processed, and visualized by the user 112A.

Indeed, the monitoring device may measure or calculate a plurality of activity data and/or physiological parameters in addition to, or in place of, the user's step count. These activity data and/or physiological parameters include, but are not limited to, energy expenditure, e.g., calorie burn, etc., floors climbed, floors descended, heart rate, heart rate variability, heart rate recovery, geo-location, elevation, speed and/or distance traveled, swimming lap count, swimming stroke type and count detected, bicycle distance and/or speed, blood pressure, blood glucose, skin conduction, skin temperature, body temperature, electromyography, electroencephalography, weight, body fat, caloric intake, nutritional intake from food, medication intake, sleep periods, sleep phases, sleep quality, pH levels, hydration levels, respiration rate, or a combination thereof. The monitoring device may also measure or calculate parameters related to an environment around the user 112A, such as, e.g., barometric pressure, weather conditions (e.g., temperature, humidity, pollen count, air quality, rain/snow conditions, wind speed, etc.), light exposure (e.g., ambient light, UV light exposure, time and/or duration spent in darkness, etc.), noise exposure, radiation exposure, magnetic field, or a combination thereof.

In some embodiments, the monitoring device quantifies work productivity against noise levels and/or against air quality and/or against temperature and/or against pressure and/or against humidity and/or against pollen count and the quantification is identified as a level within event data. In several embodiments, the monitoring device quantifies stress levels against noise levels and/or against an amount of time spent by the user 112A at work and/or against an amount of time spent by the user 112A exercising outside a work location and/or against an amount of time spent by the user 112A in a gym and/or an amount of time spent by the user 112A at his parent's home, and the quantification is identified as a level within event data. In some embodiments, a stress level is quantified, e.g., measured, determined, etc., based on heart rate variability (HRV) and/or galvanic skin response (GSR). The HRV and/or the GSR are measured by a biological sensor.

Furthermore, a monitoring device or a computing device collating data streams may calculate parameters derived from the activity data and/or physiological parameters. For example, monitoring device or a computing device may calculate a user's stress and/or relaxation levels through a combination of heart rate variability, skin conduction, noise pollution, and sleep quality. In another example, a monitoring device or a computing device may determine an efficacy of a medical intervention (e.g., medication) through a combination of medication intake, sleep and/or activity data. In yet another example, the monitoring device or a computing device may determine an efficacy of an allergy medication through the combination of pollen data, medication intake, sleep and/or other activity data.

Figure 5:
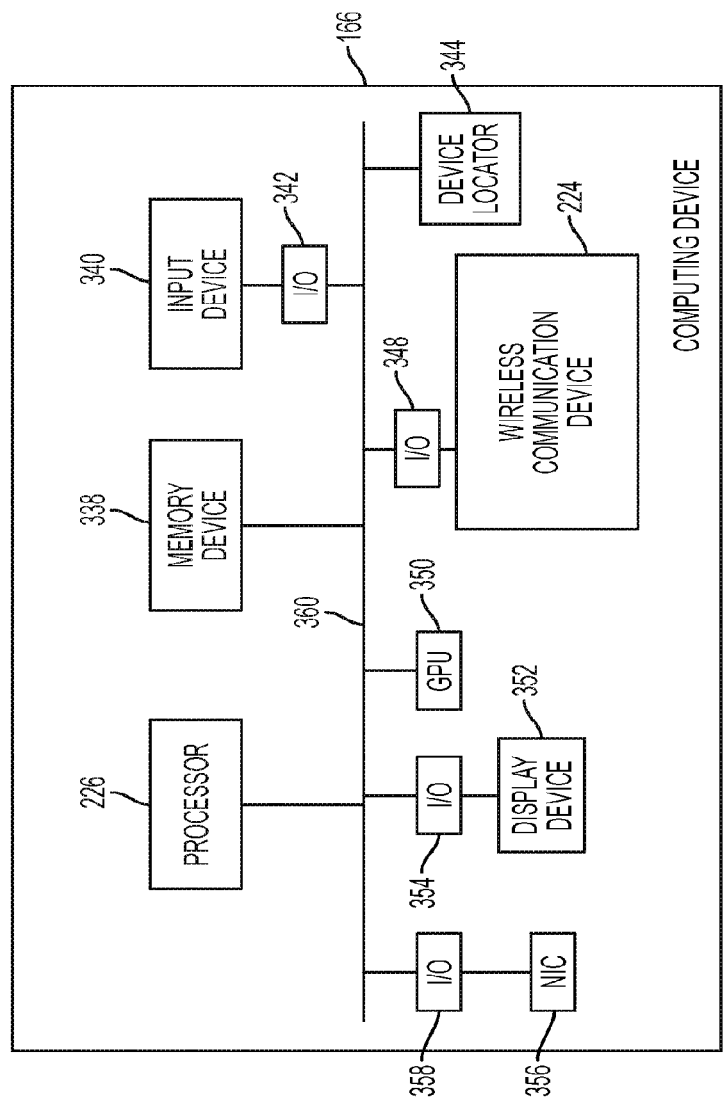
FIG. 5 is a block diagram of a computing device, in accordance with one embodiment described in the present disclosure.

FIG. 5 is a block diagram of an embodiment of the computing device 166. The computing device 166 includes a processor 226, a memory device 338, an input device 240, an input/output interface (I/O) 342, a device locator 344, a wireless communication device 346, an I/O 348, a graphical processing unit (GPU) 350, a display device 352, an I/O 354, a NIC 356, and an I/O 358, all of which are coupled to each other via a bus 360.

An I/O is a parallel interface, a serial interface, or a USB interface between two devices that are coupled to the I/O. For example, the I/O 358 is an interface between the NIC 356 and the bus 360.

Examples of the processor 226 and the memory device 338 are provided above. Moreover, examples of the input device 340 and the device locator 344 are provided above. Furthermore, examples of the wireless communication device 346, the display device 352, and the NIC 356 are provided above. The GPU 350 executes a rendering technique to display data, e.g., GUI, web page, etc., on the display device 352.

The wireless communication device 346 receives geo-location data and activity data from the wireless communication device 278 (FIG. 3A) of the monitoring device 108A and/or the wireless communication device 300 (FIG. 3B) of the monitoring device 108B. The processor 226 determines a group of activity data and a location/activity identifier based on the activity data and the geo-location data.

In some embodiments, the computing device 166 includes a wired communication device in addition to or instead of the wireless communication device 300. Examples of the wired communication device include a USB interface, a parallel interface, and a serial interface.

In several embodiments, the user 112A provides via the user interface 274 (FIG. 3A) of the monitoring device 108A to the processor 234 or via the input device 340 (FIG. 5) of the computing device 166 to the processor 226 one or more locations, e.g., a home of the user 112A, coffee shop, work, gym, a home of a friend of the user 112A, a home of a family member of the user 112A, a work place of the user 112A, a place, a street, a building, etc., that the user 112A visits over a period of time. In some embodiments, the user 112A provides via the user interface 274 (FIG. 3A) of the monitoring device 108A to the processor 234 or via the input device 340 (FIG. 5) of the computing device 166 to the processor 226 a size of a location and a type of a location, e.g., work place, sandwich place, pizza place, eatery, gym, golf course, park, running place, walking place, eating place, etc. Examples of a size of a location include a number of floors within the location, a square footage of a location, a number of offices in the location, a number of rooms in the location, a number of people that can fit in the location, a height of the location, a width of the location, a length of the location, a radius of a circle that identifies the location, a diameter of a circle that identifies the location, or a combination thereof.

The one or more locations, the type of location, and/or the size of the location received from the user 112A are sent by the monitoring device 108A or by the monitoring device 108B via the computing device 166 and the network 176 to the server 228 to be stored in the geo-location-location database. In some embodiments, the one or more locations, the type of location, and/or the size of the location received from the user 112A are sent by the monitoring device 108A or by the monitoring device 108B via the network 176 to the server 228 without using the computing device 166 to be stored in the geo-location-location database.

In some embodiments, upon accessing the geo-location-location database, the processor 226 or the processor 234 determines that the geo-location-location database does not include a location corresponding to one or more geo-locations visited by the user 112A over a period of time. The processor 226 determines whether the user 112A is within a radius that includes one or more geo-locations of the user 112A. Upon determining that the user 112A is within the radius for more than a number of instances of time, the processor 226 generates a prompt to provide to the user 112A via the display device 352 or the processor 234 generates the prompt to provide to the user 112A via the display device 276. The prompt requests the user 112A to provide the location corresponding to the one or more geo-locations that are within the radius and that are visited by the user 112A.

In a number of embodiments, the processor 234 determines that among multiple locations, a location within the geo-location-location database is closest to a geo-location of the user 112A wearing a monitoring device, and determines the location to correspond to the geo-location-location of the user 112A.

In some embodiments, the processor 234 receives a selection, e.g., an expansion of a bubble-shaped or another shaped graphical element or displayed on the display device 276, a contraction of a bubble-shaped or another shaped graphical element displayed on the display device 276, etc., from the user 112A and the selection indicates that a location corresponds to a different set of geo-locations than that indicated by the geo-location-location database. Upon receiving the selection, the processor 234 determines that the location corresponds to the different set of geo-locations than that indicated by the geo-location-location database.

It should be noted that a graphical element has one or more graphical properties, e.g., a shape, a color, a shade, a texture, or a combination thereof. For example, a graphical element includes a block, a line, a box, a dot, a pin, a circle, a bubble, or a combination thereof.

In various embodiments, the computing device 166 includes a position sensor that is coupled to the bus 360. The position sensor is similar to the position sensor 220 (FIG. 3A) except that the position sensor measures positions of the computing device 166.

Figure 6A:
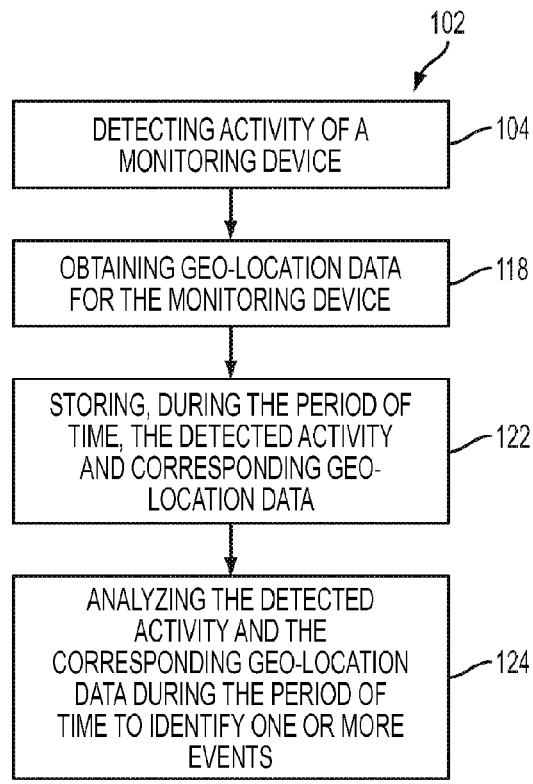
FIG. 6A is a flowchart of a method for segmenting a period of time into identification of locations of a user performing activities, in accordance with one embodiment described in the present disclosure.

FIG. 6A is a flowchart of an embodiment of a method 102 for segmenting a period of time into identification of locations of a user performing activities. The method 102 is executed by the monitoring device 108A (FIG. 3A).

The method 102 includes detecting, in an operation 104, an activity of the monitoring device 108A when the monitoring device 108A is worn by the user 112A (FIG. 1A). It should be noted that when the monitoring device 108A is worn by the user 112A, the activity of the monitoring device 108A is the same as that of the user 112A. The activity includes an amount of movement of the monitoring device 108A and is performed for a period of time. In some embodiments, the activity includes a number of calories burned by the user 112A. Examples of the activity of the user 112A detected by the monitoring device 108A include running, or walking, or jogging, or sleeping, or moving around, or a sports activity, or sleep, or a combination thereof.

The amount of movement of the user 112A includes an amount of movement of a body part of the user 112A. For example, the amount of movement of the user 112A includes an amount of stairs ascended by the user 112A, or an amount of stairs descended by the user 112A, a number of forehands of a sport played by the user 112A, or a number of backhands of the sport, or a number of serves of the sport made by the user 112A, or a number of times a golf swing is made by the user 112A, or a number of times a soccer ball is kicked by the user 112A, or a number of times a ball is thrown by the user 112A, a number of rotations of a bicycle made by the user 112A, or a number of times a paddle, e.g., a brake pedal, an accelerator pedal, etc., of a vehicle is pushed by the user 112A, or a number of times a hand movement is made by the user 112A, or a number of times a leg movement is made by the user 112A, or a number of times a steering wheel of a vehicle is rotated partially or fully by the user 112A, or an amount of calories burned by the user 112A, or an amount of distance traveled by the user 112A, an amount of steps walked or ran by the user 112A, or an amount of hours slept by the user 112A, or an amount of time for which the user 112A is active, or a combination thereof.

The detection of the activity is performed by the position sensor 220 (FIG. 3A) of the monitoring device 108A. For example, the position sensor 220 determines the amount of movement of the user 112A. The position sensor 220 determines the amount of movement at each amount of time, e.g., second, minute, hour, a fraction of a second, a fraction of a minute, a fraction of an hour, etc., that is measured by the time measurement device 232 (FIG. 3A) of the monitoring device 108A.

The method 102 further includes obtaining, in an operation 118, geo-location data for the monitoring device 108A. For example, the geo-location data includes a latitude, an altitude, and/or a longitude of the monitoring device 108A. The geo-location data is obtained by the device locator 222 (FIG. 3A) of the monitoring device 108A. For example, signals are sent between the device locator 222 and another device, e.g., a cell tower, a satellite, etc., to determine a geo-location of the device locator 222, and the geo-location of the device locator 222 is the same as a geo-location of the monitoring device 108A. The geo-location of the monitoring device 108A is the same as a geo-location of the user 112A when the user 112A is wearing the monitoring device 108A.

The method 102 also includes storing, in an operation 122, during the period of time of activity performed by the user 112A, the activity that is detected in the operation 104 and the corresponding geo-location data that is obtained in the operation 118. The geo-location data that is obtained in the operation 118 corresponds to the activity detected in the operation 104 when the geo-location is obtained and the activity is detected at the same time or during the same time period. For example, when the user 112A wearing the monitoring device 108A is performing an activity at a longitude 1 and a latitude 1, a geo-location that includes the longitude 1 and the latitude 1 corresponds to the activity. In this example, the position sensor 220 determines that the user 112A is performing the activity and the device locator 222 determines that the user 112 is at the longitude 1 and latitude 1 at the same time the user 112A is performing the activity. To further illustrate, the detected activity corresponds to the geo-location data when the activity is detected at a time the monitoring device 108A is located at the geo-location.

The operation 122 of storing is performed by the memory device 280 (FIG. 3A) of the monitoring device 108A or by a combination of the processor 234 of the monitoring device 108A and the memory device 280 of the monitoring device 108A. For example, the processor 234 writes, e.g., stores, etc., data to be stored in the memory device 280.

Figure 7A:
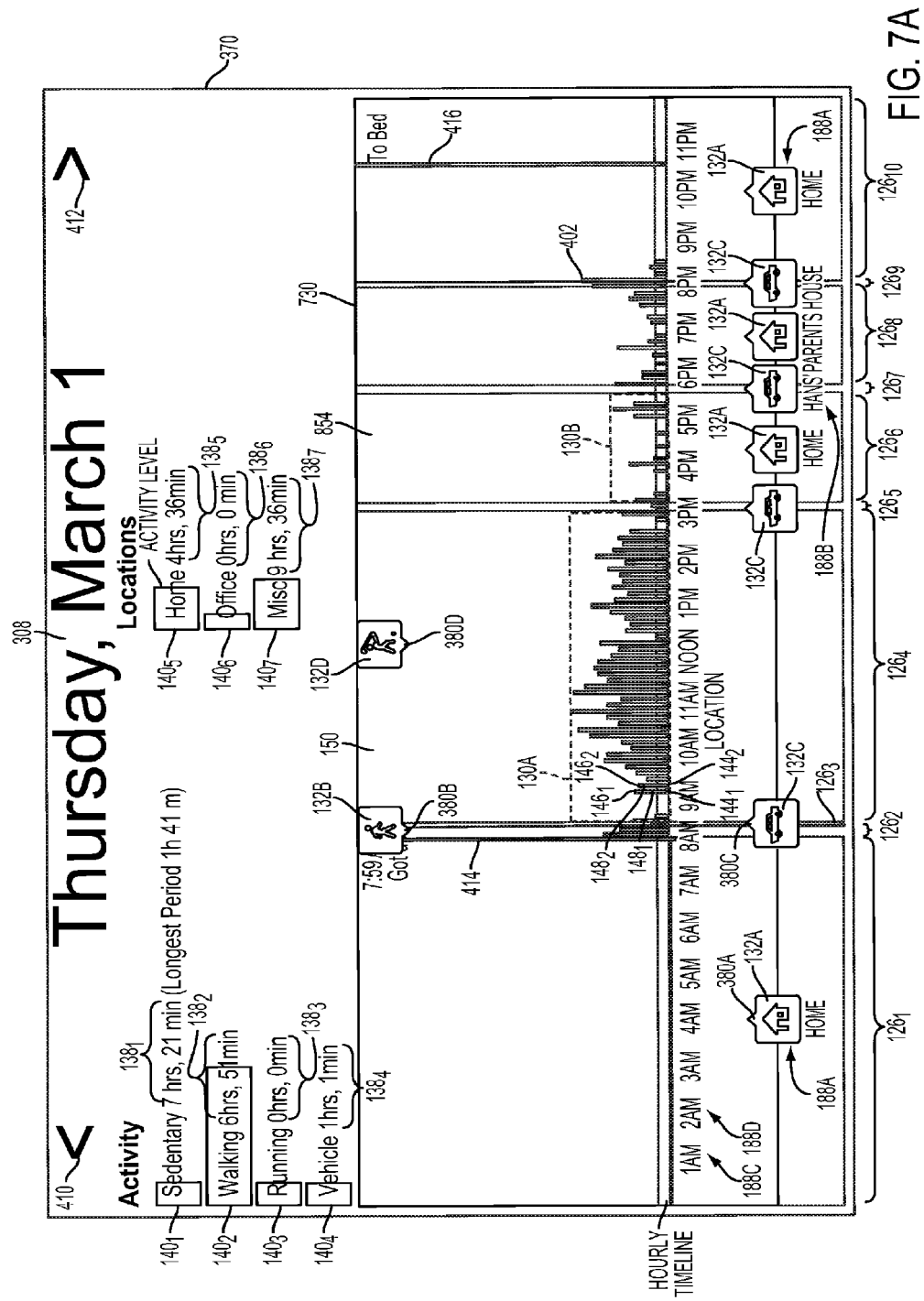
FIG. 7A is a graphical user interface (GUI) that displays one or more events and that is generated by executing the method of FIG. 6A, 6B, 6C, 6E, or 6F, in accordance with one embodiment described in the present disclosure.
Figure 7B:
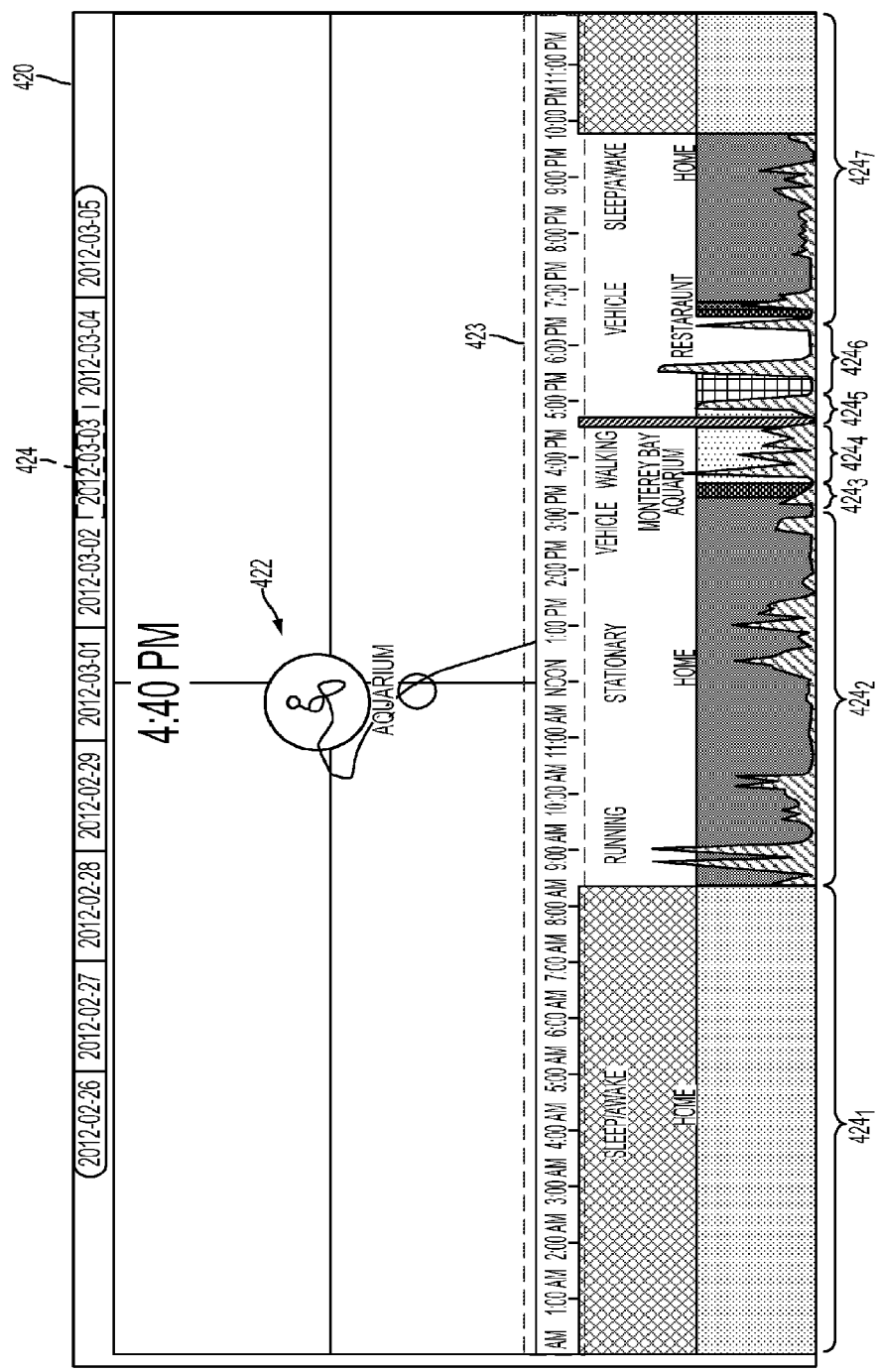
FIG. 7B is a diagram of another GUI that displays one or more events and that is generated by executing the method of FIG. 6A, 6B, 6C, 6E, or 6F in accordance with one embodiment described in the present disclosure.
Figure 7D:
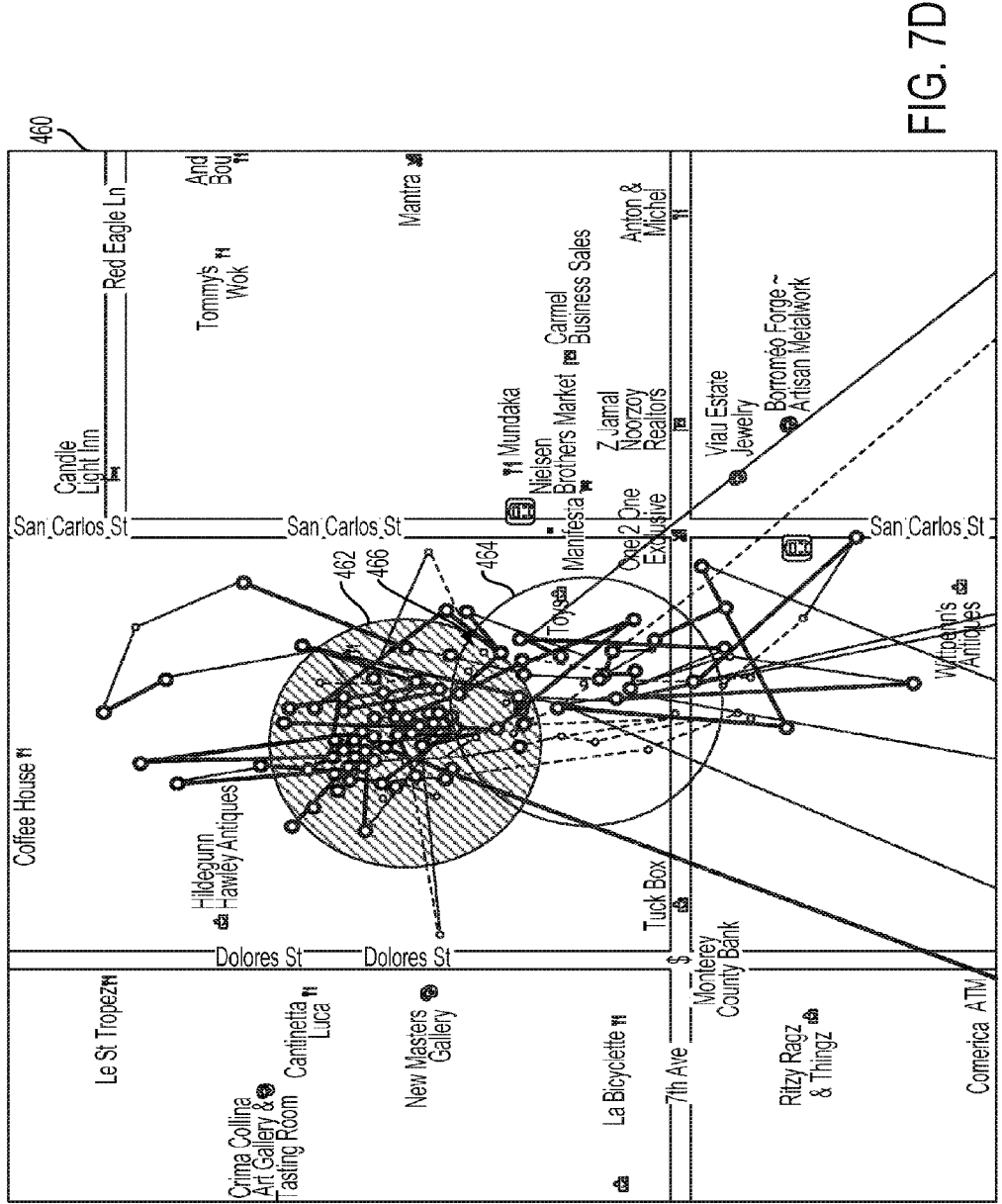
FIG. 7D is a diagram of a GUI to illustrate a method of allowing a user to choose a location in case of common geo-locations between multiple locations, in accordance with one embodiment described in the present disclosure.
Figure 7E:
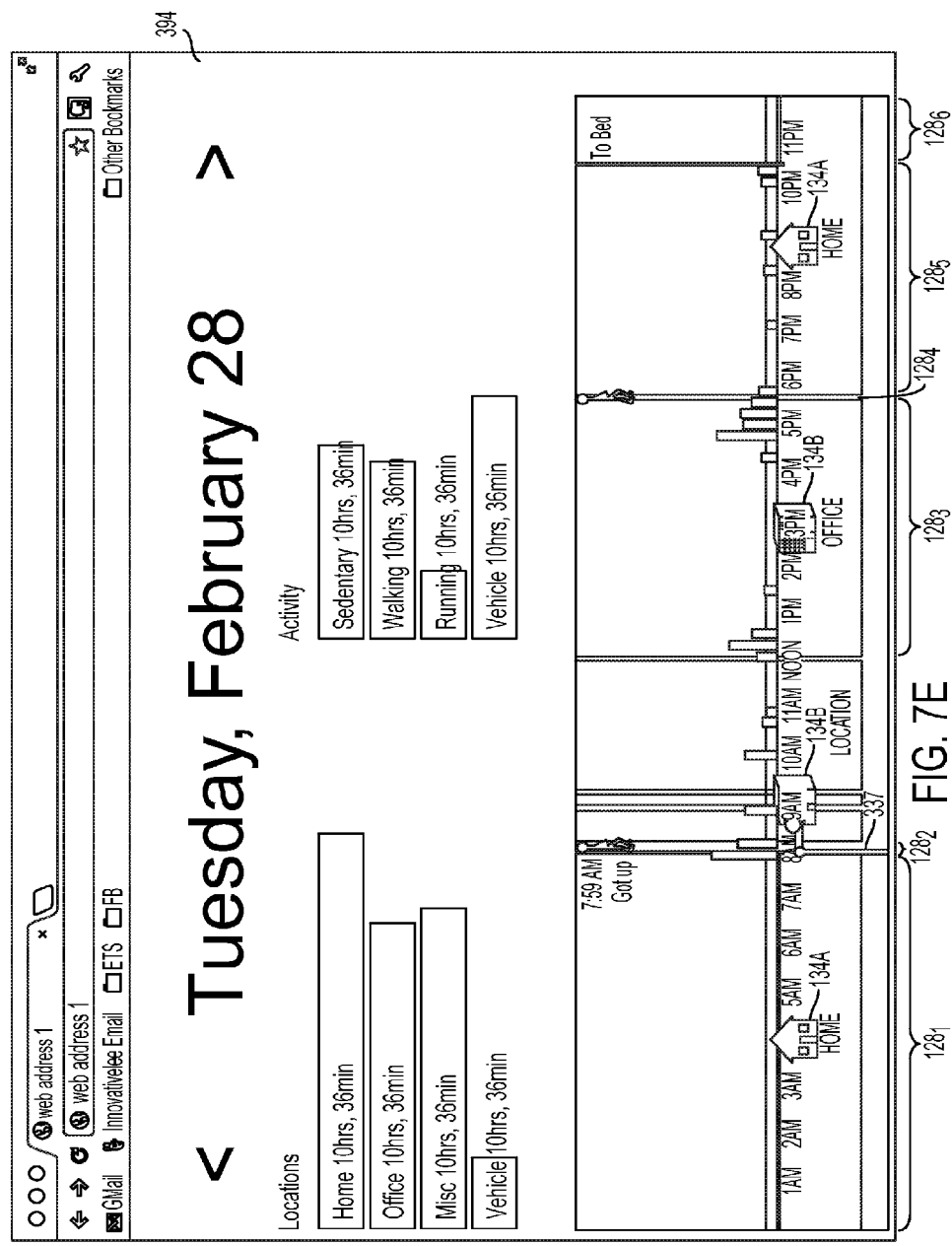
FIG. 7E is a diagram of a web page that includes a GUI that displays one or more events and that is generated by executing the method of FIG. 6A, 6B, 6C, 6E, or 6F, in accordance with one embodiment described in the present disclosure.

The method 102 further includes analyzing, in an operation 124, the activity detected in the operation 104 and the corresponding geo-location data obtained in the operation 118 to identify one or more events, e.g., an event $126_1$, an event $126_2$, an event $126_3$, an event $126_4$, an event $126_5$, an event $126_6$, an event $126_7$, an event $126_8$, an event $126_9$, an event $126_{10}$, an event $128_1$, an event $128_2$, an event $128_3$, an event $128_4$, an event $128_5$, an event $128_6$, etc., which are described with reference to FIGS. 7A and 7E. The events $126_1$, $126_2$, $126_3$, $126_4$ $126_5$, $126_6$, $126_7$, $126_8$, $126_9$, and $126_{10}$ are displayed within an event region 730 of FIG. 7A. The events $128_1$, $128_2$, $128_3$, $128_4$, $128_5$, and $128_6$ are displayed within a GUI 394 (FIG. 7E).

Each event occurs over a period of time. For example, the event $126_1$ occurs over a time period, e.g., from 12 AM to 8 AM, etc., and the event $126_4$ occurs over a time period, e.g., from a time between 8 AM and 9 AM to 3 PM, etc.

As further shown in FIG. 7A, each event $126_1$, $126_2$, $126_3$, $126_4$ $126_5$, $126_6$, $126_7$, $126_8$, $126_9$, and $126_{10}$ is a portion of a GUI 370, which is an example representation of the GUI data 186 (FIG. 2A). For example, each event $126_1$, $126_2$, $126_3$, $126_4$ $126_5$, $126_6$, $126_7$, $126_8$, $126_9$, and $126_{10}$ includes a textual and/or a graphical data portion of the GUI 370. To further illustrate, the event $126_4$ includes a graphical data portion that shows activity levels, e.g., amounts, etc., of an activity performed by the user 112A. Moreover, in this illustration, the event $126_4$ includes a time period during which the activity is performed and indicates the activity, e.g., golfing, etc. In this illustration, the activity indicates a location, e.g., a golf course. As another illustration, the event $126_6$ includes a graphical data portion that shows activity levels of an activity performed by the user 112A. Moreover, in this illustration, the event $126_6$ includes a time period during which the activity is performed and includes a location, e.g., a home of the user 112A, etc., at which the activity is performed.

Each event is associated, e.g., linked, corresponded, related, etc., with a group of activity data and each group of activity data is associated, e.g., linked, corresponded, etc., related, with a location/activity identifier. For example, referring to FIG. 7A, the event $126_4$ includes a group 130A of activity data and the event $126_6$ includes a group 130B of activity data. The group 130A includes activity levels of an activity performed by the user 112A during a period of time and the group 130A is associated with a location/activity identifier 132D. Similarly, the group 130B includes activity levels of an activity performed by the user 112A during a period of time, e.g., a time period between a time between 3 pm and 4 pm and a time between 5 pm and 6 pm, etc., and the group 130B is associated with a location/activity identifier 132A.

Moreover, similarly, a group of activity data of the event $126_1$ is associated with the location/activity identifier 132A, a group of activity data of the event $126_2$ is associated with a location/activity identifier 132B, a group of activity data of the event $126_3$ is associated with a location/activity identifier 132C, a group of activity data of the event $126_5$ is associated with the location/activity identifier 132C, a group of activity data of the event $126_7$ is associated with the location/activity identifier 132C, a group of activity data of the event $126_8$ is associated with the location/activity identifier 132A, a group of activity data of the event $126_9$ is associated with a location/activity identifier 132C, and a group of activity data of the event $126_{10}$ is associated with a location/activity identifier 132A. Furthermore, with reference to FIG. 7E, a group of activity data of the event $128_1$ is associated with a location/activity identifier 134A and a group of activity data of the event $128_3$ is associated with a location/activity identifier 134B. A group of activity data is associated with a location/activity identifier to provide a context as to which activity is performed and where. For example, an amount of calories burned by a user are displayed in a background in which an icon representing an activity of walking performed by the user is shown and/or an icon representing a public park is shown. The amount of calories is burned when the user is walking and/or in the public park and/or is walking in the public park.

Referring back to FIG. 6A, a location/activity identifier is generated by the processor 234 using the geo-location data, which is obtained in the operation 118, and/or activity data, which is obtained in the operation 104. For example, the processor 234 (FIG. 3A) of the monitoring device 108A determines that the geo-location-location database indicates a correspondence between a location of the user 112A and a set that includes one or more longitudes at which an activity is performed by the user 112A, one or more latitudes at which the activity is performed, and/or one or more altitudes at which the activity is performed, and assigns the location/activity identifier 132D to represent the location. As another example, the processor 234 determines that a distance traveled by the user 112A in a period of time is within an upper limit and a lower limit. The period of time is received from the time measurement device 232 of the monitoring device 108A. The distance traveled by the user 112A is received from the position sensor 220 and/or the device locator 222 of the monitoring device 108A. As another example, the processor 234 receives a selection from the user 112A via the user interface 274 (FIG. 3A) of the monitoring device 108A that one or more geo-locations at which the user 112A performs an activity correspond to a location of the user 112A, and assigns a location/activity identifier to represent the location.

The operation 124 is performed by the processor 234 (FIG. 3A) based on the activity detected in the operation 104 and/or the geo-location data obtained in the operation 118, and a time period during which the activity is performed. The processor 234 receives one or more amounts of time of performance of an activity during a time period from the time measurement device 232 (FIG. 3A), and/or receives one or more geo-locations at which the activity is performed during the time period from the device locator 222 (FIG. 3A), and receives one or more activity levels of the activity from the position sensor 220 (FIG. 3A) to perform the operation 124. For example, the processor 234 determines that the user 112A is in a vehicle upon determining that a speed of travel of the user 112A is greater than $s_1$ miles per hour. The speed $s_1$ is a running or walking speed of one or more users. The processor 234 determines a speed of travel of the user 112A based on geo-location data obtained in an hour of one or more geo-locations of the user 112. Geo-location data is received from the device locator 222 (FIG. 3A) of the monitoring device 108A and a measurement of the hour is received from the time measurement device 232 (FIG. 3A).

As another example, the processor 234 determines whether the user 112A is in a vehicle, or is riding a bicycle or a skateboard, or is undergoing ambulatory motion based on a speed of the user 112A and motion of a body portion of the user 112A. To illustrate, when the processor 234 determines that a speed of the user 112A is greater than a pre-determined number of miles per hour and motion of the body portion is less than a pre-determined amount of motion, the processor 234 determines that the user 112A is in a vehicle and is not walking or running. As another illustration, when the processor 234 determines that a speed of the user 112A is less than the pre-determined number of miles per hour and motion of the body portion is greater than the pre-determined amount of motion, the processor 234 determines that the user 112A is performing the ambulatory motion. Examples of ambulatory motion include walking, running, jogging, exercising, etc. An example of the body portion includes an arm of the user 112A. In various embodiments, a speed of the user 112A is determined by a device locator or a processor based on an amount of distance between two geo-locations and time of the user 112A at each of the geo-locations. In some embodiments, a speed of the user 112A is determined by a position sensor or a processor based an amount of distance between two positions and time of occurrence of each of the positions.

As yet another example, the processor 234 determines that the user 112A is running upon determining that a speed of travel of the user 112A is greater than $s_2$ miles per hour and a number of steps taken by the user 112A is greater than $ss_1$ per hour. The speed $s_2$ is a walking speed of one or more users. A number of steps are received by the processor 234 from the position sensor 220 (FIG. 3A) of the monitoring device 108A. As another example, the processor 234 determines that the user 112A is walking upon determining that a number of steps taken by the user 112A is less than $ss_1$ per hour and greater than $ss_2$ per hour. As yet another example, the processor 234 determines that the user 112A is in a vehicle upon determining that a speed of travel of the user 112A is greater than $s_3$ miles per hour and a number of steps taken by the user 112A is less than $ss_3$ per hour.

As another example, the processor 234 determines that the user 112A is moving around upon determining that a number of steps taken by the user 112A is less than $ss_4$ per hour. As yet another example, the processor 234 determines that the user 112A is sedentary upon determining that the user 112A is not walking, running, not moving around, and not in a vehicle. As another example, the processor 234 determines that the user 112A is sleeping upon determining that the user 112A is sedentary for greater than an amount of time.

In some embodiments, the processor 234 determines a speed of travel of the user 112A based on geo-location data obtained over a period of time of one or more geo-locations of the user 112 and the period of time.

The time period during which the activity is performed at a location is determined by the processor 234 based on a sum of amounts of time measured by the time measurement device 232 for performing the activity at one or more geo-locations corresponding to, e.g., included within, linked with, etc., the location.

The operation 124 of analyzing the detected activity and the corresponding geo-location data during the period of time includes determining a time element of segregation of the activity detected at the operation 104. For example, a period of time during which an activity is performed is segmented into one or more time elements. As another example, a period of time during which an activity is performed is segmented into one or more time elements, and each time element includes a graphical property and/or text to represent the time element. Examples of a time element include a fraction of a minute, or a minute, or a fraction of an hour, or an hour, etc. Further examples of a time element are shown as a time element $144_1$ and a time element $144_2$ in FIG. 7A. The time element $144_1$ is a time of day at which a golf activity having an activity level is performed by the user 112A. Moreover, the time element $144_2$ is another time of day at which a golf activity having an activity level is performed by the user 112A. The activity level at the time element $144_2$ is lower than the activity level at the time element $144_1$. In some embodiments, the activity level at the time element $144_2$ is higher than or the same as the activity level at the time element $144_1$. The time element $144_1$ includes text, e.g., 9 AM, etc.

The operation 124 of analyzing the detected activity and the corresponding geo-location data during the period of time further includes determining an activity level for each time element. For example, an activity level $146_1$ (FIG. 7A) is determined as being performed at the time element $144_1$ and an activity level $146_2$ (FIG. 7A) is determined as being performed at the time element $144_2$. As another example, the activity level $146_1$ (FIG. 7A) is determined as being performed at the time element $144_1$ and is determined to include text and/or a graphical property, e.g., a dark gray bar, etc., and the activity level $146_2$ (FIG. 7A) is determined as being performed at the time element $144_2$ and is determined to include text and/or a graphical property, a dark gray bar, etc.

The operation 124 of analyzing the detected activity and the corresponding geo-location data during the period of time also includes determining a location/activity identifier of a location and/or activity for each time element and for each activity level. For example, the processor 234 determines that an activity level that occurs at a time element is of an activity that occurs at one or more geo-locations that correspond to a location and/or that correspond to an activity, e.g., a home of the user 112, a building, a park, an office, golfing, walking, running, a commercial place, an eatery, a work place, a vehicle, a golf course, a sandwich shop, or any other location, etc., and determines a location/activity identifier that represents the location and/or activity.

As another example, the processor 234 determines that the activity level $146_1$ is of an activity that occurs at one or more geo-locations of a golf course and determines the location/activity identifier 132D that represents golfing. In this example, the processor 234 accesses correspondence between geo-location data and location data stored within the geo-location-location database to determine whether the one or more geo-locations correspond to the golf course and/or also accesses position data of the monitoring device 108A from the position sensor 220 to determine that the activity is golfing. As yet another example, the processor 234 determines that the activity level $146_2$ is of an activity that occurs at one or more geo-locations of a golf course and determines the location/activity identifier 132D. In this example, the processor 234 applies a selection received from the user 112A via the user interface 274 (FIG. 3A) to determine that one or more geo-locations at which the activity level $146_2$ occurs correspond to a golf course. In this example, the geo-locations at which the activity level $146_2$ occurs are the same or different from one or more geo-locations determined by the processor 234 from the geo-location-location database to correspond to a golf course.

Examples of a location/activity identifier include a graphical element, e.g. an icon, an icon having a pointer, a symbol, a symbol having a pointer, a trademark, a trademark having a pointer, a registered mark, a registered mark having a pointer, an animation icon, an animation icon having a pointer, an animation, an animation having a pointer, a video icon, a video icon having a pointer, a video, a video having a pointer, an audio icon, an audio icon having a pointer, an audio, an audio having a pointer, a multimedia icon, a multimedia icon having a pointer, a multimedia, a multimedia having a pointer, or a combination thereof, etc., that represents a location at which the activity is performed.

A location/activity identifier has a graphical element and/or text. For example, the location/activity identifier 380B includes an icon of a person walking. As another example, the location/activity identifier 380D includes an icon of a person golfing with a golf club.

The operation 124 of analyzing the detected activity and the corresponding geo-location data during the period of time further includes associating the activity level with the time element and the location/activity identifier. Upon determining the location/activity identifier for each time element and for each activity level, the processor 234 associates, e.g., establishes a link between, establishes a correspondence between, etc., the time element and the activity level with the location/activity identifier. For example, the processor 234 establishes a link between the time element $144_1$, the activity level $146_1$, and the location/activity identifier 132D. As another example, the processor 234 establishes a link between the time element $144_2$, the activity level $146_2$, and the location/activity identifier 132D.

The operation 124 of analyzing the detected activity and the corresponding geo-location data during the period of time also includes aggregating the associated activity levels and time elements over the period of time to indicate, using the associated location/activity identifier, a location of occurrence of the activity levels and of a group of activity data. The group of activity data includes the activity levels and the period of time. The processor 234 aggregates, e.g., combines, accumulates, etc., over a period of time the activity levels and time elements that are associated with a location/activity identifier of an activity. The period of time over which the processor 234 aggregates is continuous, e.g., from 1 pm to 2 pm on a day, from January to February of a year, from year 2000 to year 2004 of a decade, etc.

The aggregated activity levels, time elements, and the associated location/activity identifier are represented, by the processor 234, within one or more graphical elements and/or text of a background that represent an event to generate or identify the event. For example, the processor 234 assigns one or more graphical elements to an area, within the GUI 370 (FIG. 7A), to generate the event $126_4$ that includes the group 130A of activity data, the location/activity identifier 380D and a background 150, e.g., a gray-shaded area, a shaded area, an area having a graphical property, etc. The group 130A of activity data and the location/activity identifier 380D are overlaid on the background 150. The event $126_4$ includes the time element $144_1$ aligned, e.g., vertically, horizontally, oblique, etc., with the activity level $146_1$ and further includes the location/activity identifier 132D including or attached to a pointer 380D. The pointer 380D points to the event $126_4$ that includes the activity level $146_1$ and the time element $144_1$. Similarly, as shown in FIG. 7A, a pointer 380A that is included within or is attached to the location/activity identifier 132A points to the event $126_1$, a pointer 380B that is included within or is attached to the location/activity identifier 132B points to the event $126_2$, and a pointer 380C that is included within or is attached to the location/activity identifier 132C points to the event $126_3$.

It should be noted that in some embodiments, a location/activity identifier does not include and is not attached to a pointer. For example, the event $126_4$ includes the location/activity identifier 132D without the pointer 380D.

In various embodiments, a group of activity data includes a location/activity identifier in addition to one or more activity levels and one or more time elements. For example, the group 130A of activity data includes one or more activity levels, one or more time elements, and the location/activity identifier 380D.

In several embodiments, each activity level is assigned a graphical property by the processor 234. For example, as shown in FIG. 7A, the activity level $146_1$ is assigned a graphical property $148_1$ and the activity level $146_2$ is assigned a graphical property $148_2$. The graphical property $148_2$ may be the same or different from the graphical property $148_1$. For example, the graphical property $148_2$ has the same color as that of the graphical property $148_1$. As another example, the graphical property $148_2$ has the same texture and color as that of the graphical property $148_1$.

In some embodiments, the method 102 is performed by the monitoring device 108B (FIG. 3B) except instead of the operation 104, the biological sensor 294 performs an operation of detecting a physiological parameter of the user 112A who is located on the monitoring device 108B. Moreover, in these embodiments, the operation 118 of obtaining geo-location data for the monitoring device 108B is performed by the device locator 306 (FIG. 3B). Further, in these embodiments, the operation 122 of storing the detected physiological parameter and the corresponding geo-location data is performed by the processor 302 (FIG. 3B) or by a combination of the processor 302 and the memory device 298 (FIG. 3B). In these embodiments, the operation 124 of analyzing the detected physiological parameter and the corresponding geo-location data during the period of time to identify one or more events is performed by the processor 302 (FIG. 3B) of the monitoring device 108B.

Figure 6B:
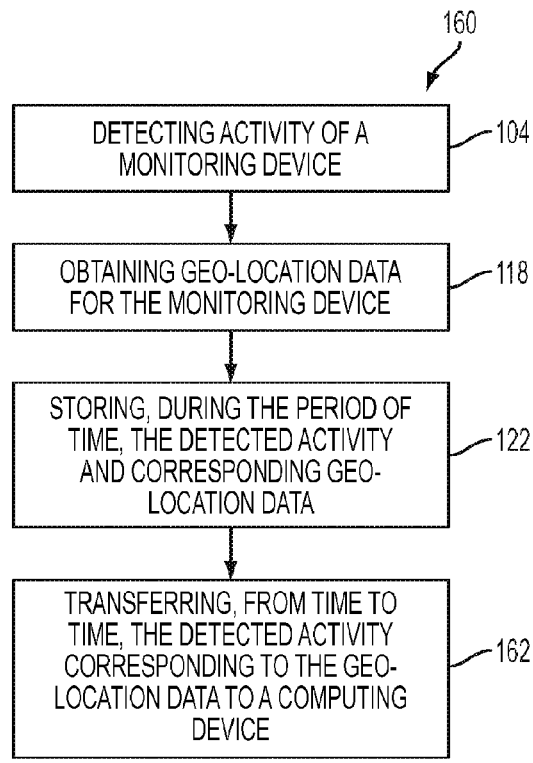
FIG. 6B is a flowchart of another method for segmenting a period of time into identification of locations of a user performing activities, in accordance with one embodiment described in the present disclosure.

FIG. 6B is a flowchart of an embodiment of a method 160 for segmenting a period of time into identification of locations of a user performing activities. The method 160 is executed by the monitoring device 108A (FIG. 3A). In the method 160, the operations 104, 118, and 122 are performed.

The method 160 includes transferring, e.g., sending, etc., in an operation 162, from time to time, to the computing device 166 (FIG. 5) the activity that is detected at the operation 104 and that corresponds to the geo-location data that is obtained at the operation 118. For example, activity data is transferred periodically, e.g., every fraction of a second, every second, every minute, every fraction of a minute, etc., or aperiodically, e.g., randomly, etc., to the computing device 166 upon reception of request from the computing device 166.

The operation 162 of transferring is performed by the wireless communication device 278 (FIG. 3A) via a wireless link, e.g., the wireless link 168 (FIG. 2A), the wireless link 170 (FIG. 2B), etc., between the monitoring device 108A (FIG. 3A) and the computing device 166. For example, the wireless communication device 278 executes a Bluetooth or a Wi-Fi protocol to transfer data to the computing device 166 via a wireless link. In some embodiments in which a wired link is used between the monitoring device 108A and the computing device 166, the operation 162 of transferring is performed by a wired communication device of the monitoring device 108A and the wired communication device is connected via a wired link to the wired communication device of the computing device 166. In various embodiments, the wireless communication device 278 transfers data via a wireless communication link and the network 176 (FIG. 3A) to the server 228 (FIG. 3A) without transferring data via the computing device 166. In several embodiments, a wired communication device of the monitoring device 108A transfers via a wired communication link and the network 176 to the server 228 without transferring data via the computing device 166. For example, the wired communication device of the monitoring device 108A executes a communication protocol, e.g., a Transmission Control Protocol over Internet Protocol (TCP/IP), a User Datagram Protocol over Internet Protocol (UDP/IP), etc., to communicate data with the server 228 via the network 176.

In some embodiments, the operations 104, 118, and 112 are performed by the monitoring device 108B (FIG. 3B) with the changes described above with respect to the method 102 (FIG. 6A). Moreover, in these embodiments, the operation 162 of transferring, from time to time, the detected activity corresponding to the geo-location data to the computing device 166 is performed by the wireless communication device 300 of the monitoring device 108B or by a wired communication device of the monitoring device 108B.

Figure 6C:
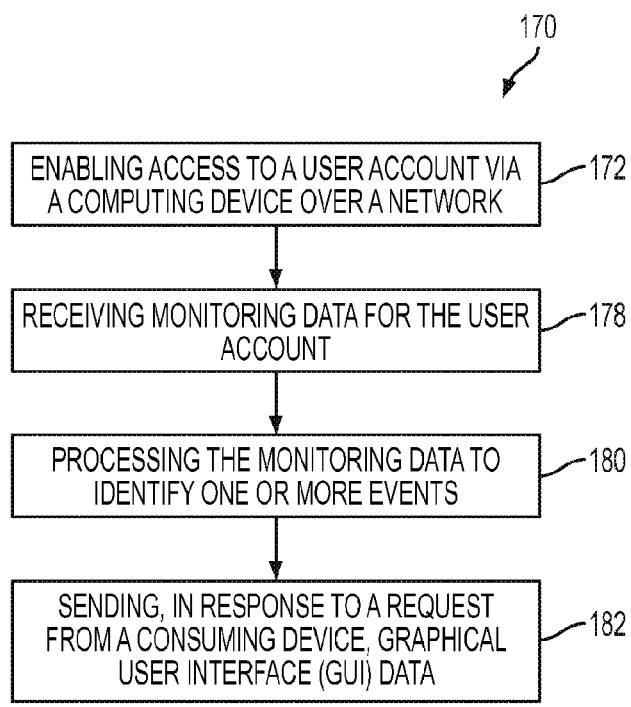
FIG. 6C is a flowchart of yet another method for segmenting a period of time into identification of locations of a user performing activities, in accordance with one embodiment described in the present disclosure.

FIG. 6C is a diagram of an embodiment of a method 170 for segmenting a period of time into identification of locations of a user performing activities. The method 170 is executed by the server 228 (FIGS. 2A & 2B). The method 170 includes an operation 172 of enabling access to the user account 174 (FIG. 2A) via the computing device 166 (FIG. 5) over the network 176 (FIG. 2A). The processor 190 (FIG.

2A) of the server 228 performs the operation 172 of enabling access to the user account 174.

The user 112A (FIG. 1A) uses the user interface 274 (FIG. 3A) of the monitoring device 108A or the input device 340 (FIG. 5) of the computing device 166 to provide the authentication information to access the user account 174. Upon receiving the authentication information via the network 176, the processor 190 (FIG. 2A) of the server 228 or another processor of another server determines whether the authentication information is authentic. Upon determining that the authentication information is authentic or upon receiving the determination from the other processor of the other server, the processor 190 enables access to the user account 174 to the user 112A. When access to the user account 174 is enabled, a representation of the user account 174 is rendered by the processor 234 on the display device 276 (FIG. 3A) of the monitoring device 108A or is rendered by the processor 226 of the computing device 166 on the display device 352 (FIG. 5) of the computing device 166.

The method 170 further includes receiving, in an operation 178, monitoring data for the user account 174. The monitoring data includes the activity detected at the operation 104 (FIGS. 6A & 6B) of the monitoring device 108A (FIG. 3A). The monitoring data includes geo-location data obtained at the operation 118 (FIG. 6A).

The operation of receiving 178 is performed by the NIC 254 (FIG. 2A) of the server 228. The monitoring data is received, via the network 176 (FIGS. 2A, 2B, & 3A), from the NIC 356 (FIG. 5) of the computing device 166 that has received the monitoring data from the wireless communication device 278 (FIG. 3A) of the monitoring device 108A or from a wired communication device of the monitoring device 108A. In some embodiments, the monitoring data is received from the wireless communication device 278 of the monitoring device 108A and the network 176 without use of the computing device 166.

In some embodiments, the NIC 254 applies a communication protocol to receive the monitoring data. For example, the NIC 254 depacketizes one or more packets to obtain the monitoring data.

The method 170 includes processing, in an operation 180, the monitoring data to identify one or more events. The operation 180 of processing is similar to the operation 124 (FIG. 6A) of analyzing the detected activity and the corresponding geo-location data during a period of time to identify one or more events. For example, the operation 180 is the same as the operation 124 except that the operation 180 is performed by the processor 190 (FIG. 2A) of the server 228. The operation 180 is performed to generate the GUI data 186 (FIG. 2A). The GUI data 186 includes event data of one or more events. For example, the GUI data 186 includes data that is rendered to display the GUI 370 (FIG. 7A). As another example, the GUI data 186 includes data that is rendered to display the GUI 394 (FIG. 7E).

The method 170 includes sending, in an operation 182, in response to a request from a consuming device the GUI data 186 (FIG. 2A). Examples of the consuming device include the computing device 166 (FIG. 5) or the monitoring device 108A (FIG. 3A). For example, when the user 112A is provided access to the user account 174 (FIG. 2A), a request is received from the NIC 356 (FIG. 5) to send the GUI data 186. Upon receiving the request, the NIC 254 (FIG. 2A) of the server 228 applies a communication protocol for sending the GUI data 186 via the network 176 to the NIC 356 of the computing device 166 for display on the display device 352 of the computing device 166. As another example, when the user 112A is provided access to the user account 174, a request is received from the wireless communication device 278 of the monitoring device 108A or a wired communication device of the monitoring device 108A via the network 176. Upon receiving the request, the NIC 254 (FIG. 2A) of the server 228 applies a communication protocol for sending the GUI data 186 via the network 176 to the wireless communication device 278 of the monitoring device 108A or to the wired communication device of the monitoring device 108A. The GUI data 186 is sent via the computing device 166 or without using the computing device 166.

The GUI data 186 includes graphics, e.g., graphical elements that represent the events 146₁ and 146₂ (FIG. 7A), that represent the background 150 (FIG. 7A), that represent the location/activity identifiers 132A, 132B, 132C, and 132D (FIG. 7A), etc. The GUI data 186 further includes text, e.g., text 188A ("e.g., HOME" in FIG. 7A) that describes, e.g., identifies, etc., a location that the user 112A has reached during a day, text 188B ("e.g., HANS' PARENTS HOUSE" in FIG. 7A) that describes another location that the user 112A has reached during the day another time of the day, text 188C (e.g., "1 AM" in FIG. 7A) that represents a time of the day, text 188D (e.g., "2 AM" in FIG. 7A) that represents yet another time of the day, etc.

The graphics and text segments a period of time over which one or more activities are performed into events that are graphically distinct from each other. For example, as shown in FIG. 7A, the event 126₂ that includes activity data of an activity of walking is graphically distinct, e.g., has a lighter shade, etc., than the event 126₄ that includes activity data of an activity of golfing. As another example, as shown in FIG. 7A, an event includes activity data representing an activity is represented by different graphical elements than an event that includes activity data representing the same or a different activity.

Figure 6D:
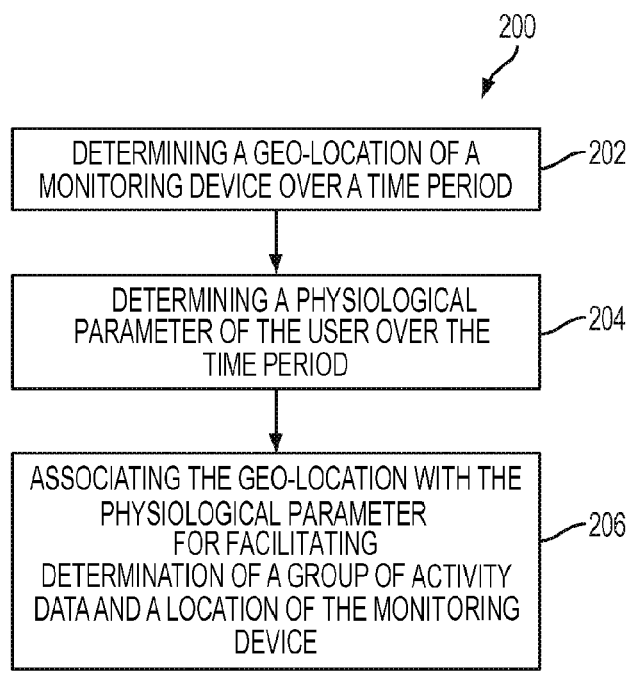
FIG. 6D is a flowchart of a method for segmenting a period of time into identification of locations of a user performing activities, in accordance with one embodiment described in the present disclosure.

FIG. 6D is a flowchart of an embodiment of a method 200 for segmenting a period of time into identification of locations of a user performing activities. The method 200 is executed by the monitoring device 108B (FIG. 3B).

The method 200 includes determining, in an operation 202, a geo-location of the monitoring device 108B over a time period. The geo-location of the monitoring device 108B is determined by the device locator 306 (FIG. 3B). The method 200 further includes determining, in an operation 204, a physiological parameter of the user 112A over a period of time. The operation 204 is performed by the biological sensor 294 (FIG. 3B) of the monitoring device 108B. For example, the biological sensor 294 measures a change in weight of the user 112A over a period of time for which the geo-location is determined in the operation 202. As another example, the biological sensor 294 measures a change in BMI of the user 112A over a period of time for which the geo-location is determined in the operation 202. A period of time is measured by the time measurement device 395 (FIG. 3B).

The method 200 also includes associating, in an operation 206, the geo-location determined in the operation 202 with the physiological parameter determined in the operation 204 to facilitate determination of a group of activity data and a location of the monitoring device 108B. The processor 302 (FIG. 3B) of the monitoring device 108B performs the operation 206. For example, the processor 302 establishes a link between the geo-location data and the physiological parameter. The processor 302 determines a location of the monitoring device 108B based on the geo-location data and the geo-location-location database. The processor 302 further determines a group of activity data that includes one or more amounts of a physiological parameter that provide a measure of an activity performed over a period of time. For example, when the user 112A exercises over a period of time, the user 112A may lose weight. As another example, when the user 112A is sedentary over a period of time, the user 112A may gain weight. The processor 302 then generates event data that includes a relation between the location and the group of activity data. For example, the processor 302 determines that one or more amounts of a physiological parameter occur at a location over a period of time and generates a relationship, e.g., correspondence, link, etc., between the amounts, the location, and the time period.

Figure 6E:
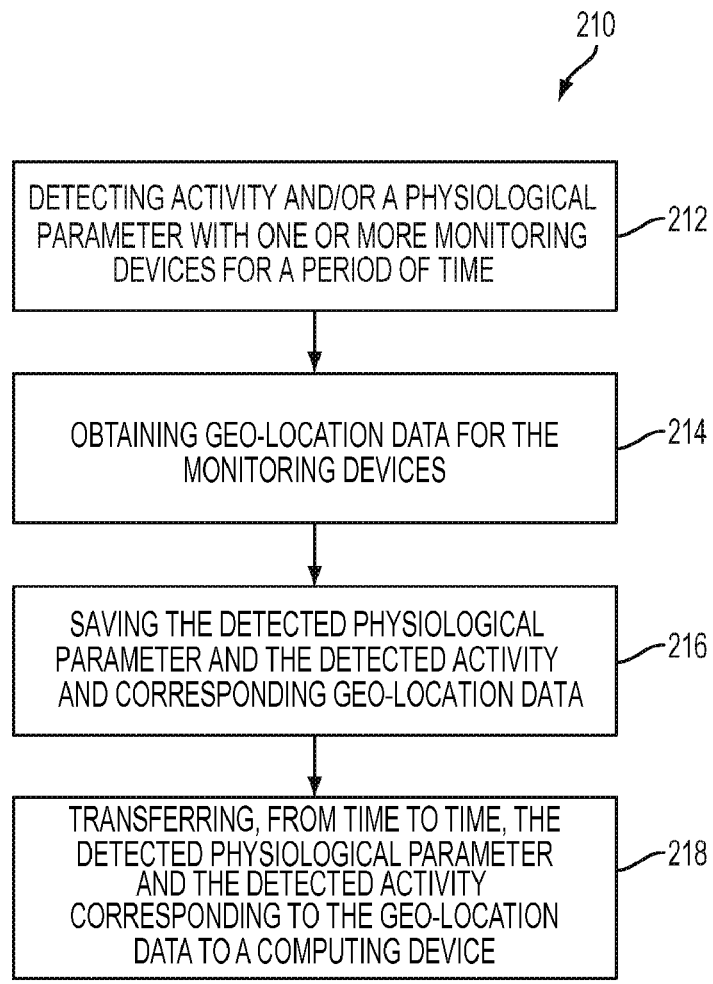
FIG. 6E is a flowchart of another method for segmenting a period of time into identification of locations of a user performing activities, in accordance with one embodiment described in the present disclosure.

FIG. 6E is a flowchart of an embodiment of a method 210 for segmenting a period of time into identification of locations of a user performing activities. The method 210 is performed by one or more monitoring devices, e.g., the monitoring device 108A, the monitoring device 108B, a combination thereof, etc.

The method 210 includes an operation 212 of detecting an activity and/or a physiological parameter of the user 112A with one or more monitoring devices for a period of time. For example, the position sensor 220 of the monitoring device 108A (FIG. 3A) detects an activity performed by the user 112A and the biological sensor 294 of the monitoring device 108B (FIG. 3B) detects a physiological parameter of the user 112A.

The method 210 further includes an operation 214 of obtaining geo-location data for the monitoring devices for the period of time for which the operation 212 is performed. For example, geo-location data of geo-location of the monitoring device 108A is measured by the device locator 222 of the monitoring device 108A (FIG. 3A) and geo-location data of geo-location of the monitoring device 108B is measured by the device locator 306 of the monitoring device 108B (FIG. 3B). A period of time is measured by the time measurement device 232 (FIG. 3A) of the monitoring device 108A and by the time measurement device 295 of the monitoring device 108B (FIG. 3B).

The method 210 includes an operation 216 of saving, in an operation 216, the detected physiological parameter and the detected activity in the operation 212. For example, the operation 216 of saving the detected activity is performed by the processor 234 of the monitoring device 108A and/or by the processor 234 and the memory device 280 of the monitoring device 108A. As another example, the operation 216 of saving the detected physiological parameter is performed by the processor 302 of the monitoring device 108B and/or by the memory device 298 (FIG. 3B) of the monitoring device 108B.

The method 210 includes an operation 218 of transferring, from time to time, the detected physiological parameter and the detected activity corresponding to the geo-location data to the computing device 166 (FIG. 5) and/or to the server 228. For example, the operation 218 of transferring is performed by the wireless communication device 278 (FIG. 3A) of the monitoring device 108A or by a wired communication device of the monitoring device 108A. As another example, the operation 218 of transferring is performed by the wireless communication device 300 of the monitoring device 108B or by a wired communication device of the monitoring device 108B. The detected activity and the detected physiological parameter are transferred wirelessly to the wireless communication device 224 (FIG. 5) of the computing device 166. In some embodiments, the detected activity and the detected physiological parameter are transferred via a wired link, e.g., a cable, a wire, etc., to the wired communication device (not shown) of the computing device 166. In several embodiments, the detected activity and the detected physiological parameter are transferred via a wired link or a combination of a wireless link and a wired link and the network 176 to the server 228 without use of the computing device 166.

Moreover, in some embodiments, the geo-location data is also transferred, from time to time, to the computing device 166 and/or to the server 228. For example, the wireless communication device 278 (FIG. 3A) of the monitoring device 108A transfers geo-location data to the wireless communication device 224 of the computing device 166 or a wired communication device of the monitoring device 108A transfers the geo-location data to the wired communication device of the computing device 166. As another example, the geo-location data is transferred wirelessly by the wireless communication device 300 of the monitoring device 108B or by a wired communication device of the monitoring device 108B to the computing device 166. In several embodiments, the geo-location data is transferred via a wired link or a combination of a wireless link and a wired link and the network 176 to the server 228 without use of the computing device 166.

Figure 6F:
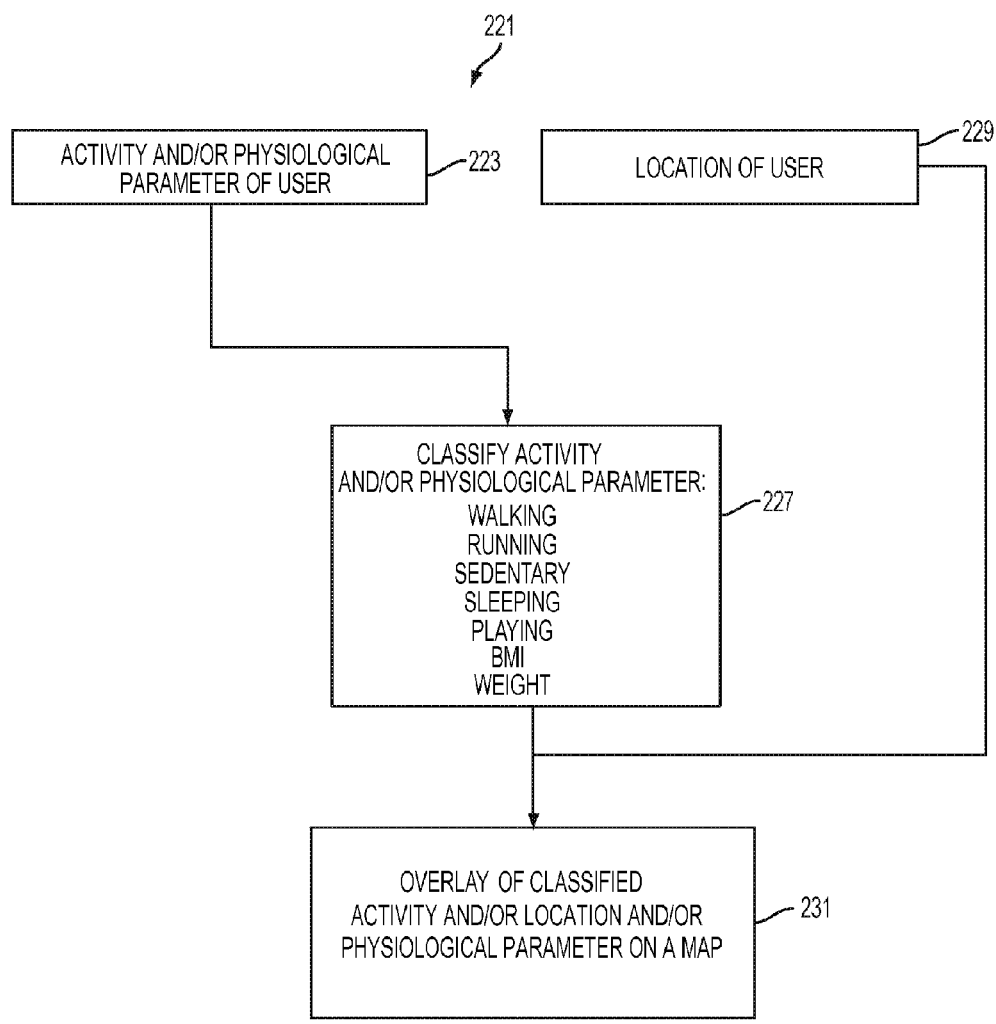
FIG. 6F is a flowchart of a method for combining a map with event data, in accordance with one embodiment described in the present disclosure.

FIG. 6F is a flowchart of an embodiment of a method 221 for segmenting a period of time into identification of locations of a user performing activities. The method 221 is performed by the monitoring device 108A, the monitoring device 108B, by the computing device 166, or a combination thereof.

The method 221 includes receiving, in an operation 223, detected activity and/or physiological parameter of the user 112A. For example, the processor 234 (FIG. 3A) of the monitoring device 108A receives detected activity from the position sensor 220 (FIG. 3A). As another example, the processor 302 of the monitoring device 108B receives detected physiological parameter from the biological sensor 294 (FIG. 3B) of the monitoring device 108B. As yet another example, the processor 226 of the computing device 166 (FIG. 5) receives the detected activity from the monitoring device 108A and/or receives the physiological parameter from the monitoring device 108B.

The method 221 includes an operation 227 of classifying detected activity and/or the physiological parameter. For example, the processor 234 (FIG. 3A) of the monitoring device 108A classifies the amount of movement into walking, running, sedentary, sleeping, moving around, or playing a sport. As another example, the processor 302 of the monitoring device 108B classifies the physiological parameter into a type of physiological parameter, e.g., BMI, heart rate, blood pressure, weight, etc. As another example, the processor 226 of the computing device 166 classifies the detected activity and/or the physiological parameter.

The method 221 further includes an operation 229 of determining a location of the user 112A. For example, the processor 234 of the monitoring device 108A determines a location of the user 112A based on geo-location data and/or based on detected activity and/or based on the geo-location-location database. The geo-location data is received by the processor 234 from the device locator 222 of the monitoring device 108A and the detected activity is received by the processor 234 from the position sensor 220 (FIG. 3A) of the monitoring device 108A. Moreover, a determination of a location based on the geo-location data is made by the processor 234 based on the geo-location data and/or the activity data and/or the geo-location-location database.

As another example, the processor 226 of the computing device 166 determines a location of the user 112A based on geo-location data and/or based on detected activity and/or based on a physiological parameter, and/or based on the geo-location-location database. The geo-location data is received by the processor 226 from the device locator 222 of the monitoring device 108A or from the device locator 306 of the monitoring device 108B and the detected activity is received by the processor 226 from the position sensor 220 (FIG. 3A) of the monitoring device 108A and/or a physiological parameter is received from the biological sensor 294 of the monitoring device 108B. Moreover, a determination of a location based on the geo-location data is made by the processor 234 based on the geo-location data and/or the activity data and/or the physiological parameter and/or the geo-location-location database. For example, upon determining that there is a lack of change beyond an amount in a physiological parameter over a period of time, the processor 234 determines that the user 112A has not left one or more geo-locations that corresponds to his/her home during the period of time.

In some embodiments, the processor 226 classifies an activity based on a physiological parameter of the user 112A, and/or a movement of the user 112A, and/or a location of the user 112A. For example, a heart rate of the user 112A is monitored, a movement of an arm of the user 112A is determined, and a location of the user 112A is determined to determine that the user 112A is training with weights in a gym and not swimming in the gym. As another example, an amount of calories burned by the user 112A is measured, a movement of an arm of the user 112A is determined, and a location of the user 112A is determined to indicate that the user 112A is swimming in a gym as opposed to running in the gym.

The method 221 further includes an operation 231 of overlaying of the classified activity performed by the user 112A and/or of the classified physiological parameter of the user 112A and/or of a location arrived at by the user 112A on a map. For example, the processor 234, the processor 302, or the processor 226 determines generates event data that includes the map, the classified activity, and/or the classified physiological parameter. In some embodiments, instead of the operation 231, an operation of overlaying the map is performed on the classified activity and/or the classified physiological parameter and/or the location arrived at by the user 112A.

In various embodiments, event data is generated based on positions that are obtained by a position sensor of a monitoring device and geo-locations obtained by a device locator of the computing device 166. The geo-locations are of the computing device 166 when carried by the user 112A. The computing device 166 transfers the geo-locations via a NIC and the network 176 to the server 228. Moreover, the monitoring device transfers the positions via a communication device and the network 176 to the server 228. The server 228 receives the geo-locations and the positions and generates the event data. In some embodiments, instead of the server 228, a virtual machine generates the event data.

In some embodiments, a monitoring device receives the geo-location data that is obtained by a device locator of the computing device 166 and generates event data based on positions and the geo-locations. The monitoring device includes a position sensor that determines the positions of the monitoring device. The monitoring device receives the geo-locations via a communication device of the monitoring device and a communication device of the computing device 166. The geo-locations are of the computing device 166 when carried by the user 112A.

In several embodiments, the computing device 166 receives positions that are obtained by a position sensor of a monitoring device and generates event data based on positions and the geo-locations. The geo-locations are of the computing device 166 when carried by the user 112A. The monitoring device includes a position sensor that determines the positions of the monitoring device.

In various embodiments, a portion of the event data is generated by a processor of a monitoring device and the remaining portion is generated by a processor of the computing device 166. In several embodiments, a portion of event data is generated by a processor of a monitoring device, another portion of the event data is generated by a processor of the computing device 166, and the remaining portion is generated by a processor of the server 228. In various embodiments, a portion of event data is generated by a processor of a monitoring device, another portion of the event data is generated by a processor of the computing device 166, and the remaining portion is generated by a virtual machine. In some embodiments, a portion of event data is generated by a processor of a monitoring device and the remaining portion is generated by a virtual machine or by the server 228. In various embodiments, a portion of event data is generated by a processor of the computing device 166 and the remaining portion is generated by a virtual machine or by the server 228.

FIG. 7A is an embodiment of the GUI 370 that displays the events $126_1$ thru $126_{10}$. In some embodiments, the processor 234 (FIG. 3A) highlights, e.g. bolds, colors, shades, etc., an activity level that is higher than or lower than the remaining activity levels by a threshold. The highlight distinguishes the activity level from one or more activity levels of one or more events that occur during a period of time. For example, the processor 234 provides a different color to an activity level 402 compared to remaining activity levels of the event $126_{10}$ when the processor 234 determines that the activity level 402 is greater than the remaining activity levels by a threshold.

The GUI 370 is rendered by the processor 234 of the monitoring device 108A to be displayed on the display device 276 (FIG. 3A) of the monitoring device 108A or by the processor 226 (FIG. 5) of the computing device 166 to be displayed on the display device 352 (FIG. 5) of the computing device 166.

The processor 234 or the processor 226 combines amounts of time of a common activity over one or more periods of time to indicate a combined amount of time, e.g., a combined amount of time $138_1$, a combined amount of time $138_2$, a combined amount of time $138_3$, a combined amount of time $138_4$, etc., of performance of the common activity and a level, e.g., a level $140_1$, a level $140_2$, a level $140_3$, a level $140_4$, etc., of the common activity performed. For example, as shown in FIG. 7A, the user 112A drove a vehicle for 1 hour and 1 minute on a date 308 of March 1, Thursday. As another example, the processor 234 or the processor 226 sums periods of time for which the user 112A performed the common activity on the date 308. To illustrate, a period of time of occurrence of the event $126_2$, a period of time of occurrence of the event $126_5$, a period of time of occurrence of the event $126_7$, and a period of time of occurrence of the event $126_9$ are summed to determine a total time period of occurrence of a common activity of driving a vehicle.

Examples of a common activity are the same as that of an activity except that the common activity is the same over multiple periods of time. For example, a common activity is walking, running, golfing, etc.

In various embodiments, the processor 234 or the processor 226 combines activity levels of performance of the common activity over the combined amount of time to generate a combined activity level for each common activity. For example, activity levels of the event $126_2$, activity levels of the event $126_5$, activity levels of the event $126_7$, and activity levels of the event $126_9$ are summed to generate a combined activity level of a common activity of driving over the total time period to generate a combined activity level $140_4$. Similarly, other combined activity levels $140_1$, $140_2$, and $140_3$ are generated.

Moreover, in some embodiments, the processor 234 or the processor 226 combines amounts of time of one or more activities performed at a common location over one or more periods of time to generate a combined amount of time, e.g., a combined amount of time $138_5$, a combined amount of time $138_6$, a combined amount of time $138_7$, etc., of performance of the one or more activities at the common location. For example, times of performance of all activities performed at a home of the user 112 on the date 308 are combined to generate the combined amount of time $138_5$. As another example, times of performance of all activities performed at an office of the user 112 on March 1 are combined to generate the combined amount of time $138_6$. A common location is a location at which one or more activities, e.g., a common activity, etc., are performed over one or more periods of time.

In several embodiments, the processor 234 or the processor 226 combines activity levels of performance of the one or more activities at the common location over a combined amount of time to generate a combined activity level, e.g., a combined activity level $140_5$, a combined activity level $140_6$, a combined activity level $140_7$, etc., of one or more activities performed at the common location. For example, activity levels of an activity of walking done by the user 112A at a home of the user 112A on the date 308 are combined to generate the combined activity level $140_5$. As another example, activity levels of one or more activities performed during the events $126_1$, $126_6$, and $126_{10}$ are combined to generate the combined activity level $140_5$.

The GUI 370 further includes a reverse button 410 and a forward button 412. The user 112A selects the reverse button 410 via the user interface 274 (FIG. 3A) or via the input device 340 (FIG. 5) to view a GUI that displays one or more events, one or more combined activity levels, and/or one or more combined amounts of time on a date prior to the date 308. Similarly, The user 112A selects the forward button 412 via the user interface 274 (FIG. 3A) or via the input device 340 (FIG. 5) to view a GUI that displays one or more events, one or more combined activity levels, and/or one or more combined amounts of time on a date after the date 308.

In various embodiments, the GUI 370 includes a time at which there is a change in an activity level beyond a limit in an amount of time. For example, the GUI 370 includes a wake-up time 414 and a bed time 416. The position sensor 220 (FIG. 3A) determines an amount of activity and based on the amount, the processor 234 or the processor 226 determines whether the amount of activity has crossed the limit in an amount of time. Upon determining that the amount of activity has crossed the limit in an amount of time, the processor 234 or the processor 226 indicates, e.g., highlights, etc., a time at which the level is crossed on the GUI 370. For example, the processor 234 highlights the wake-up time 414 and the bed time 316.

It should be noted that a GUI generated by the processor 234 is displayed on the display device 276 (FIG. 3A), a GUI generated by the processor 302 is displayed on the display device 304 (FIG. 3B), and a GUI generated by the processor 226 is displayed on the display device 352 (FIG. 5).

It should further be noted that in some embodiments, any GUI described herein as being generated by the processor 234 or by the processor 226 for display may instead be generated by the processor 302 of the monitoring device 108B for display on the display device 304.

In some embodiments, event data includes an environmental parameter that is received from the environmental sensor 272 of the monitoring device 108A by the processor 234 (FIG. 3A) or from the environmental sensor 292 of the monitoring device 108B by the processor 302 (FIG. 3B) or from the environmental sensor 272 via the wireless communication device 278 (FIG. 3A) of the monitoring device 108A by the NIC 356 (FIG. 5) of the computing device 166 or from the environmental sensor 292 via the wireless communication device 300 (FIG. 3A) of the monitoring device 108B by the NIC 356 (FIG. 5) of the computing device 166.

In several embodiments, the processor 226 or the processor 234 does not generate event data when an activity of the event data occurs for less than a period of time, e.g., two minutes, three minutes, etc.

In a number of embodiments, the processor 226 or the processor 234 replaces a current location identifier with a previous and a future location identifier when the user 112A is at the previous, current, and future locations within a time limit and when the previous location identifier and the future location identifier are the same. The previous location is a location at which the user 112A was before arriving at the current location. The current location is a location at which the user 112A is before the user 112A arrives at the future location. For example, the processor 234 determines based on the correspondence between one or more geo-locations, one or more positions of the user 112A, and the previous location and based on the correspondence between one or more geo-locations, one or more positions of the user 112A, and the future location that the previous location and the future location are the same.

In this example, the processor 234 further determines that the current location is different from the previous and future locations and the user 112A has arrived at the previous, current, and future locations within a time limit that is received from the time measurement device 232. In this example, the processor 234 determines that the current location is different from the previous locations based on the correspondence between one or more geo-locations, one or more positions of the user 112A, and the previous location and based on the correspondence between one or more geo-locations, one or more positions of the user 112A, and the future location and based on the correspondence between one or more geo-locations, one or more positions of the user 112A, and the current location. In this example, the processor 234 determines that the current location is the same as the previous and future locations upon determining that the previous and future locations are the same and that the user 112A arrives at the previous, current, and future locations within the time limit.

In several embodiments, the processor 226 or the processor 234 replaces a current activity identifier with a previous and a future activity identifier when the user 112A performs the previous, current, and future activities within a time limit and when the previous activity identifier and the future activity identifier are the same. The previous activity is an activity that the user 112A performs before performing the current activity and the current activity is an activity that the user 112A performs before performing the future activity. For example, the processor 234 determines based on positions of the user 112A and/or geo-location data of the user 112A that the previous activity and the future activity are the same and that the current activity is different from the previous and the future activities. In this example, the processor 234 further determines that the previous, current, and future activities are performed within a time limit that is received from the time measurement device 232. In this example, the processor 234 determines that the current activity is the same as the previous and future activities upon determining that the previous and future activities are the same and that the user 112A performs the previous, current, and future activities within the time limit.

In some embodiments, the processor 226 or the processor 234 applies a Markov model to determine whether to replace the current location identifier that is different from the previous and future location identifiers with the previous or future location identifier. In a number of embodiments, the processor 226 or the processor 234 applies a Markov model to determine whether to replace the current activity identifier that is different from the previous and future activity identifiers with the previous or future activity identifier.

In some embodiments, a user resizes and/or repositions an overlay, e.g., an activity identifier, a location identifier, etc., to improve the precision of an event. For example, an overlay indicates that the user 112A is performing an activity at a first activity level at a time. The user 112A changes a position and/or size of the overlay to indicate that the user 112A is performing the activity at a second activity level at the time. The first and second activity levels are displayed within the same GUI. The user 112A changes a position and/or size of an overlay via an input device of the computing device 166 or via a user interface of a monitoring device.

FIG. 7B is a diagram of a GUI 420 that is generated by executing the method 102 (FIG. 6A), 160 (FIG. 6B), 170 (FIG. 6C), 210 (FIG. 6E), or 221 (FIG. 6F). A map 422 includes a location, e.g., an aquarium, etc., visited by the user 112A and further includes a route to the location. The map 422 is displayed within the GUI 420. The map 422 is generated based on geo-location data. Moreover, the GUI 420 includes a timeline 423 of activities performed by the user 112A on a date 424 of Mar. 1, 2012. The date 424 is displayed within the GUI 420 on top of the map 422.

The user 112A selects the date 424 among multiple dates displayed on top of the map 422 via the user interface 274 (FIG. 3A) of the monitoring device 108A or via the input device 340 (FIG. 5) of the computing device 166. When the date 424 is selected, the processor 234 of the monitoring device 108A (FIG. 3A) generates the GUI 420 to display the GUI 420 on the display device 276 (FIG. 3A) or the processor 226 (FIG. 5) of the computing device 166 generates the GUI 420 to display the GUI 420 on the display device 352 (FIG. 5) of the computing device 166.

The GUI 420 includes events $424_1$, $424_2$, $424_3$, $424_4$, $424_4$, $424_5$, $424_6$, and $424_7$. The event $424_4$ includes activity levels of an activity performed at the aquarium by the user 112A.

FIG. 7C is a diagram illustrating a method for establishing boundaries between two locations over one or more periods of time. A boundary is a boundary of a location. A boundary also indicates a time at which the user 112A enters or exits a location having the boundary. For example, a boundary A includes outside walls of a home of the user 112A and a time at which the user 112A enters the home or exits the home. As another example, a boundary B includes outside walls of a building where the user 112A works and a time at which the user 112A enters the building or leaves the building. As yet another example, a boundary C includes outside walls of a sandwich shop and a time at which the user 112A enters the sandwich shop or leaves the sandwich shop. As another example, a boundary D includes a line that limits an area of a golf course and a time at which the user 112A enters the golf course or leaves the golf course. As an example, a boundary E includes a body of a vehicle and a time at which the user 112A enters the vehicle or leaves the vehicle.

The processor 234 of the monitoring device 108A (FIG. 3A) or the processor 226 (FIG. 5) of the computing device 166 determines boundaries where the user 112A arrives at, e.g., enters, etc., and departs from, e.g., exits, etc., a location. For example, the processor 234 receives from the device locator 222 (FIG. 3A) a geo-location 1 of the monitoring device 108A. Continuing with the example, the processor 234 determines that the geo-location 1 corresponds to a location 1, e.g., a street, a vehicle, etc., outside a location 2, e.g., a building, a street, etc. The location 2 corresponds to a geo-location 2. The processor 234 determines that the user 112A is at the location 1 at a time tx and at the location 2 at a time ty. In this example, the processor 226 receives the geo-location 1 from the device locator 222 and the geo-location 2 from the device locator 222 and the times tx and ty from the time measurement device 232 (FIG. 3A). In this example, there is a lack of geo-location data of the user 112A between the times tx and ty.

In the example, the processor 234 further determines a speed of an activity of the user 112A performed at the time tx or at the time ty. The processor 234 determines a speed of the user 112A between the times tx and ty. Further, in this example, the processor 234 calculates speed as a ratio of a distance between the geo-locations 2 and 1 and a difference between the times ty and tx. In this example, based on the speed, the processor 226 determines an amount of time taken by the user 112A to reach an entry of the location 2. A geo-location corresponding to the entry of the location 2 is obtained from the device locator 222 by the processor 234 and/or an amount of movement corresponding to the entry of the location 2 is obtained from the position sensor 220 of the monitoring device 108A, and the entry is determined from geo-location, the amount of movement, and/or the geo-location-location database by the processor 234. In this example, the processor 234 adds the amount of time taken to reach the entry from the time tx to determine a time of entry by the user 112A into the location 2 from the location 1.

In some embodiments, in the preceding example, based on the speed, the processor 226 determines an amount of time taken by the user 112A to reach an exit of the location 1. A geo-location corresponding to the exit of the location 1 is obtained from the device locator 222 by the processor 234 and/or an amount of movement corresponding to the exit of the location 1 is obtained from the position sensor 220 of the monitoring device 108A, and the exit is determined from geo-location, the amount of movement, and/or the geo-location-location database by the processor 234. In this example, without limitation to the methods, the processor 234 adds the amount of time taken to reach the exit from the time tx to determine a time of exit by the user 112A from the location 1.

It should be noted that the processor 234 of the monitoring device 108A or the processor 226 of the computing device 166 determines geo-location data as located along a straight line between two boundaries. For example, geo-location data is located on a straight line 440 between the boundary A and the boundary B, geo-location data is located on a straight line 442 between the boundary B and the boundary C, and geo-location data is located on a straight line 444 between a point 448 and the boundary D.

In some embodiments, geo-location data is determined for minute time intervals, e.g., times between the times tx and ty, every minute, every fraction of a minute, etc., is compared to the geo-location data on a straight line between two boundaries or between a boundary and a point. The processor 234 or the processor 226 performs the comparison. The geo-location data determined for the minute time intervals may be decimated by the processor 234 or the processor 226. The processor 234 or the processor 226 determines whether a divergence between the geo-location data obtained at the minute time intervals and geo-location data on a straight line between two boundaries exceeds a value. Upon determining that the divergence exceeds the value, the processor 234 or the processor 226 determines that there is a boundary at a point of the divergence.

For example, a divergence between geo-location data on the straight line 440 and geo-location data, obtained at minute time intervals, on a curve 446 exceeds a value. In this example, the boundary A exists at a point of the divergence. On the other hand, upon determining that the divergence does not exceed the value, the processor 234 or the processor 226 determines that there is no boundary at the point of lack of divergence. For example, a divergence between geo-location data on the straight line 444 and geo-location data, obtained at minute time intervals, on a straight line 446 does not exceed the value. In this example, there is no boundary formed at the point 448 at which the lines 444 and 446 start to intersect.

FIG. 7D is a diagram of a GUI 460 to illustrate a method of allowing a user to choose a location in case of common geo-locations between multiple locations. The GUI 460 is generated by executing the method 221 (FIG. 6F). As shown in the GUI 460, the processor 234 or the processor 226 determines that a location 462 and a location 464 has one or more common geo-locations 466. The locations 462 and 464 may be determined by the processor 226 or the processor 234 based on the geo-location-location database. The processor 234 generates a prompt and displays the prompt via the display device 276 (FIG. 3A) to the user 112A. Similarly, the processor 226 generates the prompt to display via the display device 352 (FIG. 5). The prompt indicates to the user 112A to select the location 462 or the location 464 as a location corresponding to the geo-locations 466. The user 112 selects via the user interface 274 (FIG. 3A) or via the input device 340 (FIG. 5) the location 462 or the location 464 as corresponding to the geo-locations 466. Upon receiving the selection of the location 462 or the location 464, the processor 226 or the processor 234 associates the selected location to correspond to the geo-locations 466.

In some embodiments, the user 112A expands a size of the location 462 via the user interface 274 (FIG. 3A) to indicate to include one or more geo-locations within the location 466 to indicate to the processor 226 that the one or more geo-locations within the location 466 are within the location 462. The processor 226 then associates the one or more geo-locations with the location 462 instead of with the location 466.

In various embodiments, one or more geo-locations are located outside the location 466. The user 112A expands a size of the location 462 via the user interface 274 (FIG. 3A) to indicate to include the one or more geo-locations to indicate to the processor 226 that the one or more geo-locations are within the location 462. The processor 226 then associates the one or more geo-locations with the location 462.

FIG. 7E is a diagram of an embodiment of a web page 470 that includes the GUI 394 that further includes the events $128_1$, $128_2$, $128_3$, $128_4$, $128_5$, and $128_6$. The GUI 394 is similar to the GUI 370 (FIG. 7A) except that the GUI 394 is displayed within the web page 470 and the GUI 394 includes a time 337 of exit by the user 112A of his/her home. In some embodiments, the GUI 394 includes a time of entry or exit by the user 112A of a location.

A web page is displayed when the wireless communication device 278 (FIG. 3A) or a wired communication device of the monitoring device 108A sends a request for the web page to the server 228 via the network 176 without using the computing device 166 (FIG. 3A). In some embodiments, the request for a web page is sent from the NIC 356 of the computing device 166 via the network 176 to the server 228.

Upon receiving the request for a web page, the server 228 sends the web page via the network 176 to the computing device 166. The NIC 356 of the computing device receives a web page and the web page is displayed on the display device 352 (FIG. 5) of the computing device 166.

Similarly, in some embodiments, upon receiving the request for a web page, the server 228 sends the web page via the network 176 to the monitoring device 108A. The wireless communication device 278 (FIG. 3A) or a wired communication device of the monitoring device 108A receives a web page and the web page is displayed on the display device 276 (FIG. 3A) of the monitoring device 108A.

Figures 1, 7F:
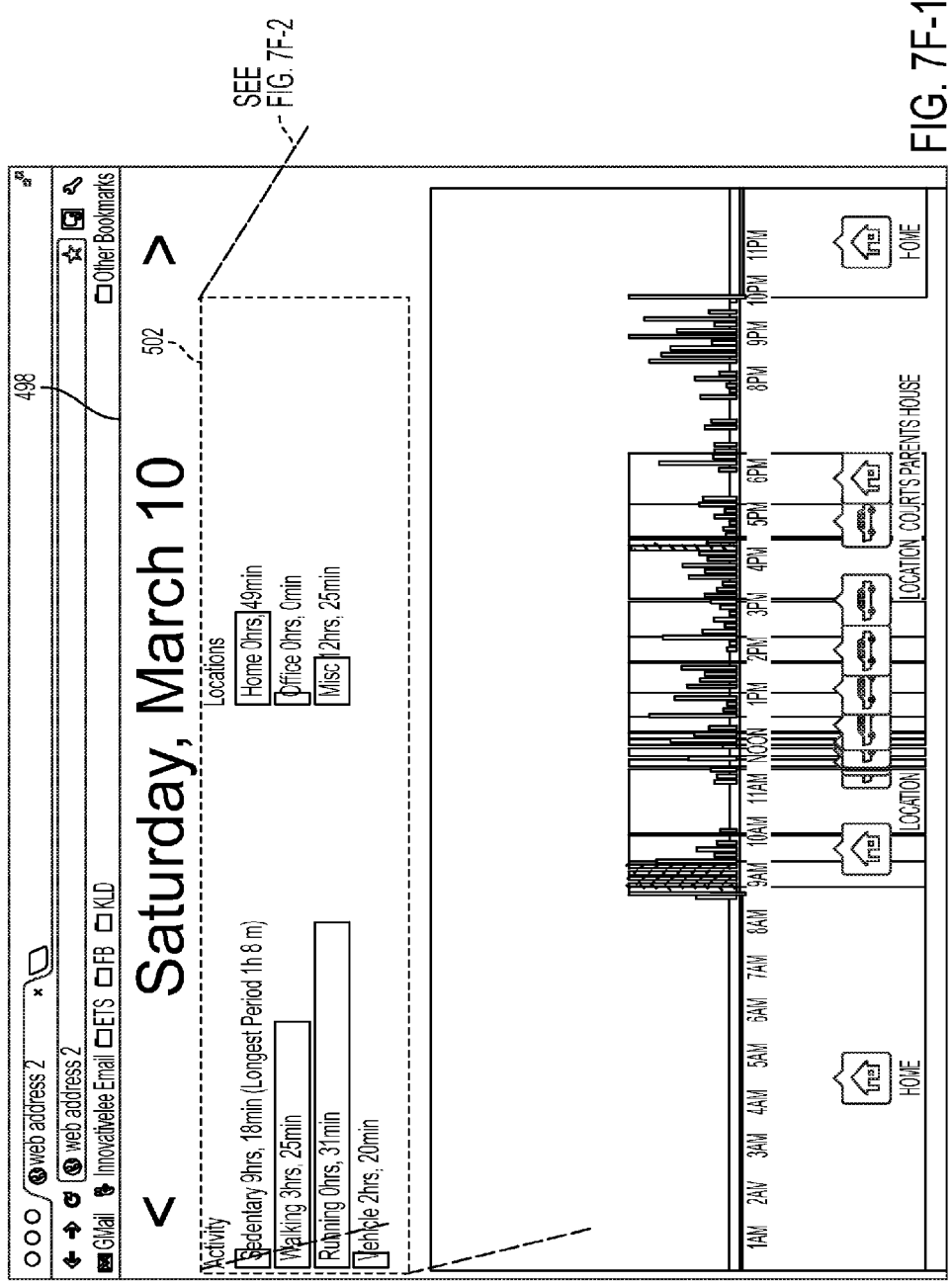
FIG. 7F-1 is a GUI to illustrate activity levels of one or activities performed by a user over a period of time and to illustrate activity levels associated with one or more locations at which the activities are performed, in accordance with one embodiment described in the present disclosure.
Figures 2, 7F:
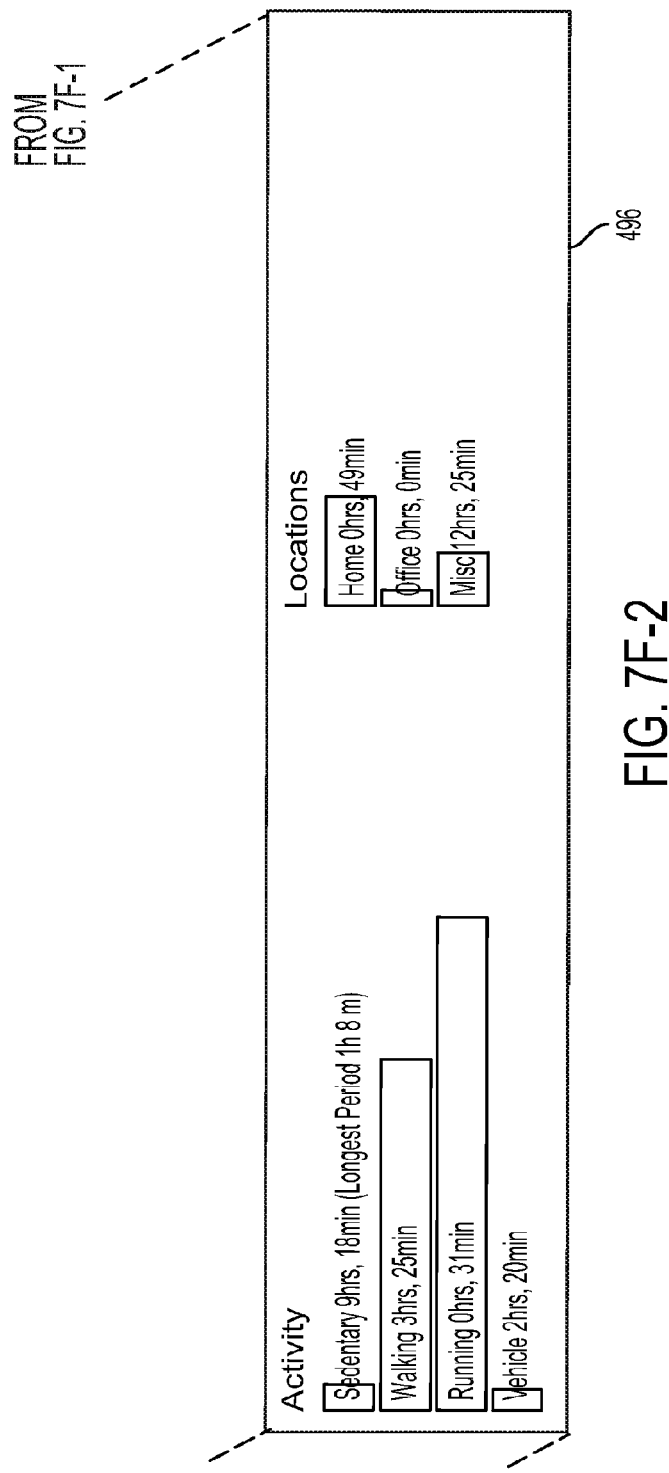
Figures 1, 7G:
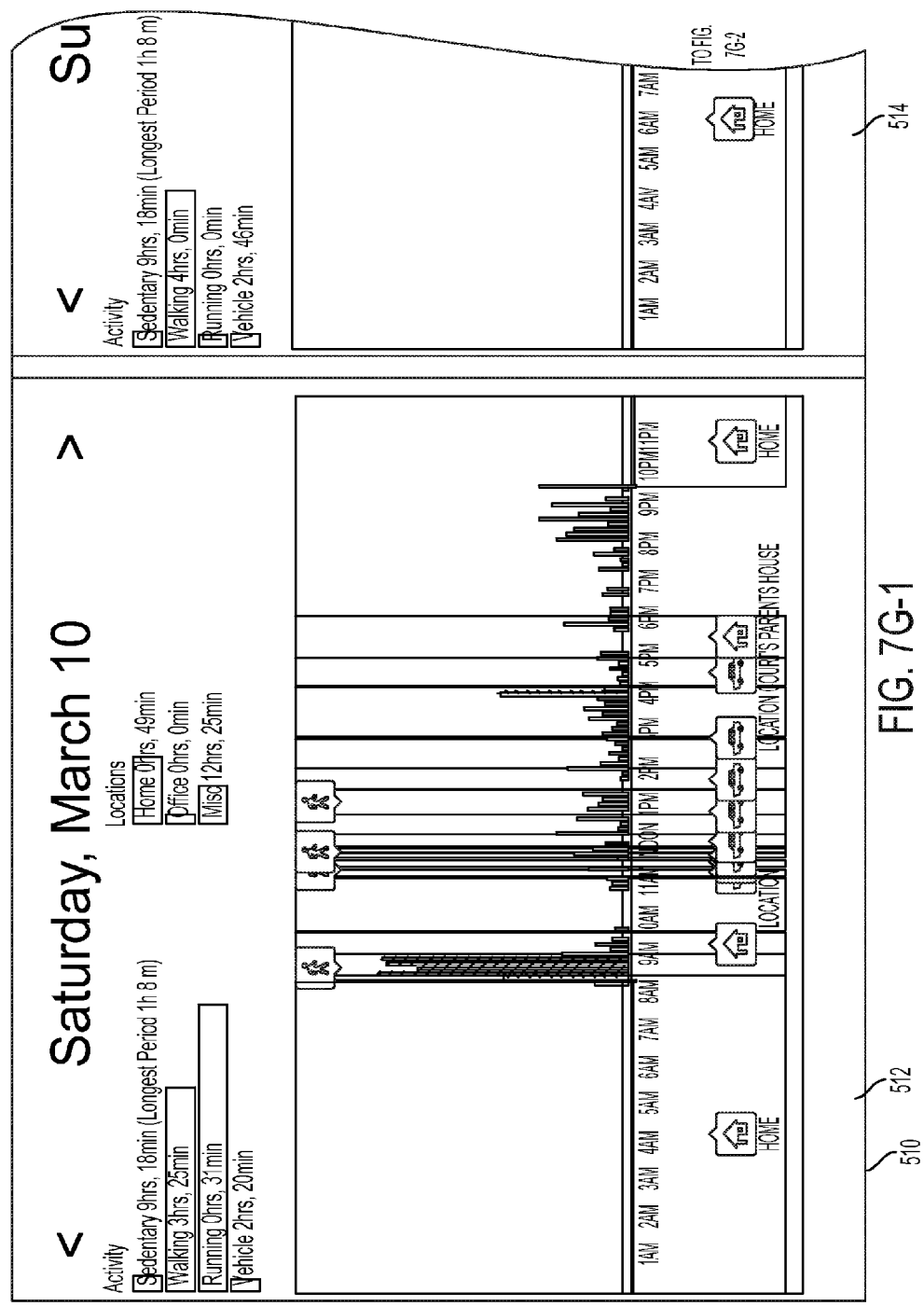
Figures 2, 7G:
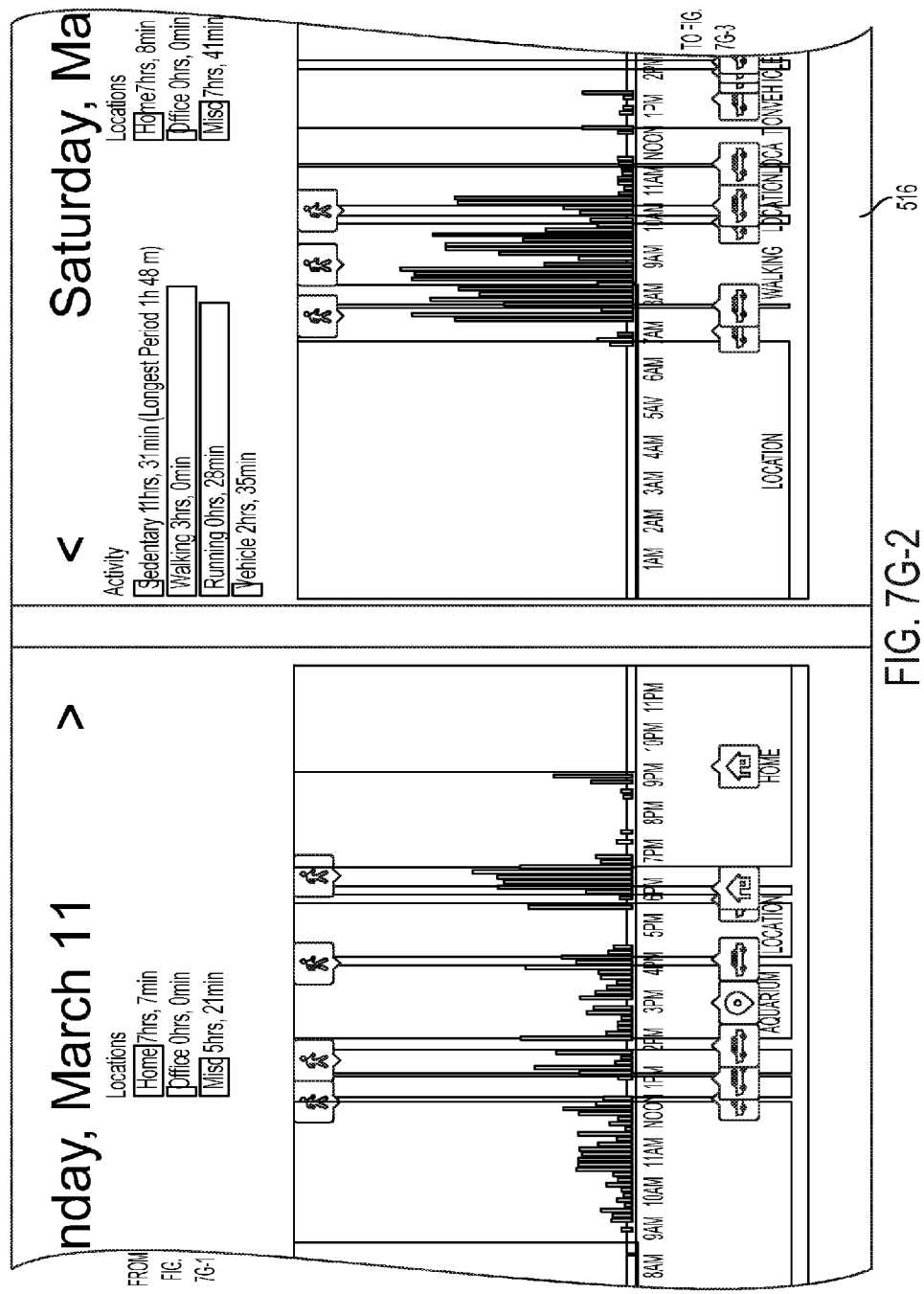
Figures 3, 7G:
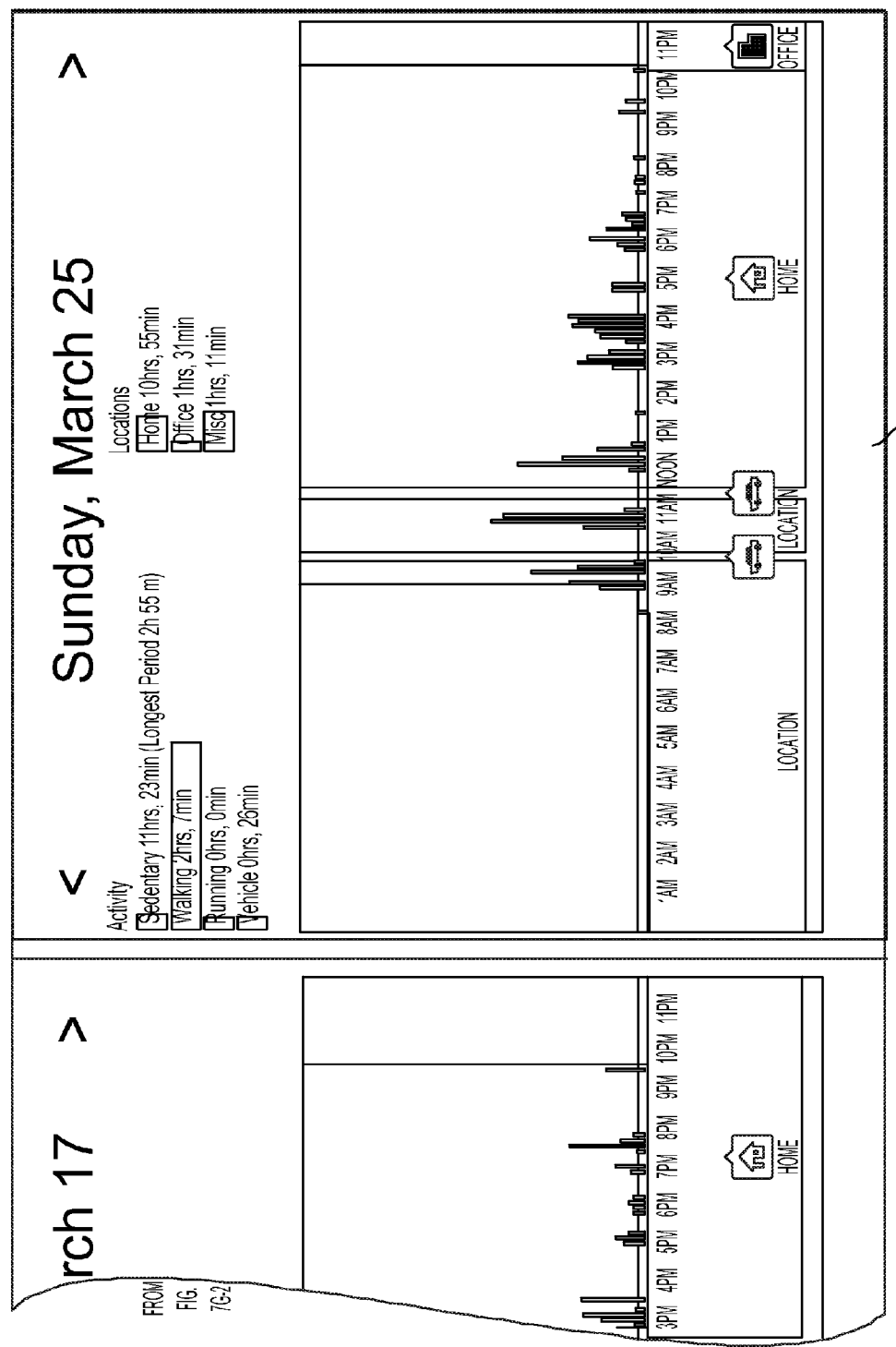

FIGS. 7F-1 and 7F-2 are diagrams used to illustrate an embodiment of a zoom-in 496 of a portion 502 of a GUI 498. The GUI 498 is generated by executing the method 102 (FIG. 6A), 160 (FIG. 6B), 170 (FIG. 6C), or 210 (FIG. 6E). In some embodiments, the zoom-in 496 is displayed on the display device 276 (FIG. 3A) of the monitoring device 108A or on the display device 352 (FIG. 5) of the computing device 166. The zoom-in 496 is displayed when the user 112A selects the portion 502 via the user interface 274 (FIG. 3A) or via the input device 340 (FIG. 5).

FIGS. 7G-1, 7G-2, and 7G-3 are diagrams used to illustrate an embodiment of a daily journal GUI 510. The daily journal GUI 510 is generated when the processor 234 or the processor 226 combines one or more GUIs 512, 514, 516, and 518. Each GUI 512, 514, 516, and 518 is generated by executing the method 102 (FIG. 6A), 160 (FIG. 6B), 170 (FIG. 6C), or 210 (FIG. 6E). The GUIs 512, 514, 516, and 518 have chronologically-ordered dates of one or more activities performed by the user 112A at one or more locations over one or more periods of time. In some embodiments, the GUIs 512, 514, 516, and 518 have consecutive dates, which are dates of activities performed by the user 112A. The daily journal GUI 510 is displayed by the processor 234 on the display device 276 (FIG. 3A) of the monitoring device 108A or is displayed by the processor 226 on the display device 352 (FIG. 5) of the computing device 166.

Each GUI 512, 514, 516, and 518 is displayed in a row. In some embodiments, each GUI 512, 514, 516, and 518 is displayed in a column or parallel to an oblique line.

Figure 7H:
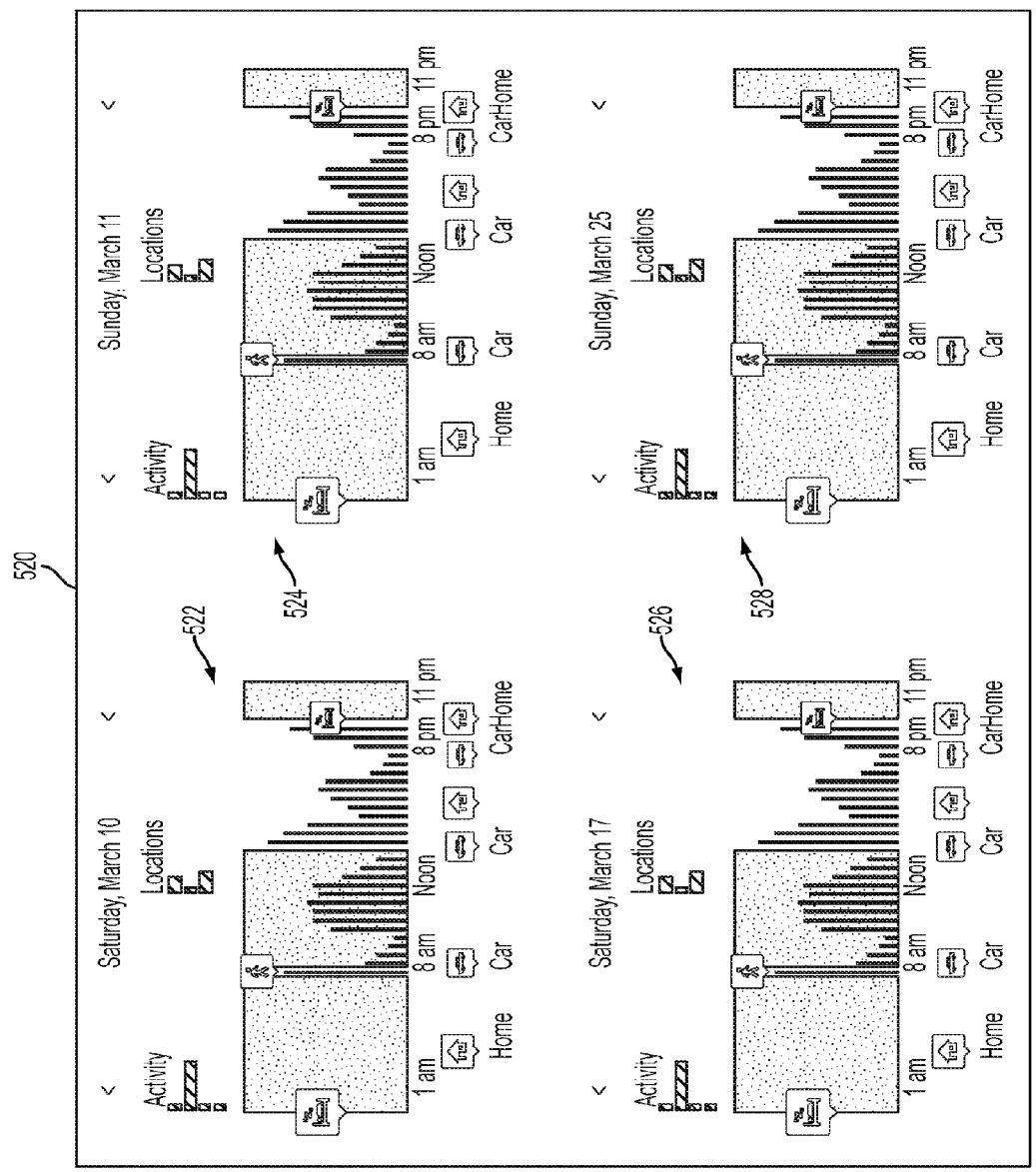
FIG. 7H is a diagram of another daily journal GUI that includes one or more GUIs that include event data for periods of time, in accordance with one embodiment described in the present disclosure.

FIG. 7H is a diagram of an embodiment of a daily journal GUI 520. The daily journal GUI 520 is generated when the processor 234 or the processor 226 combines one or more GUIs 522, 524, 526, and 528. Each GUI 522, 524, 526, and 528 is generated by executing the method 102 (FIG. 6A), 160 (FIG. 6B), 170 (FIG. 6C), or 210 (FIG. 6E). The GUIs 522, 524, 526, and 528 have chronologically-ordered dates of one or more activities performed by the user 112A at one or more locations over one or more periods of time. In some embodiments, the GUIs 522, 524, 526, and 528 have consecutive dates, which are dates of activities performed by the user 112A. The daily journal GUI 520 is displayed by the processor 234 on the display device 276 (FIG. 3A) of the monitoring device 108A or is displayed by the processor 226 on the display device 352 (FIG. 5) of the computing device 166.

Each GUI 522, 524, 526, and 528 is displayed in an orderly fashion.

Figure 7I:
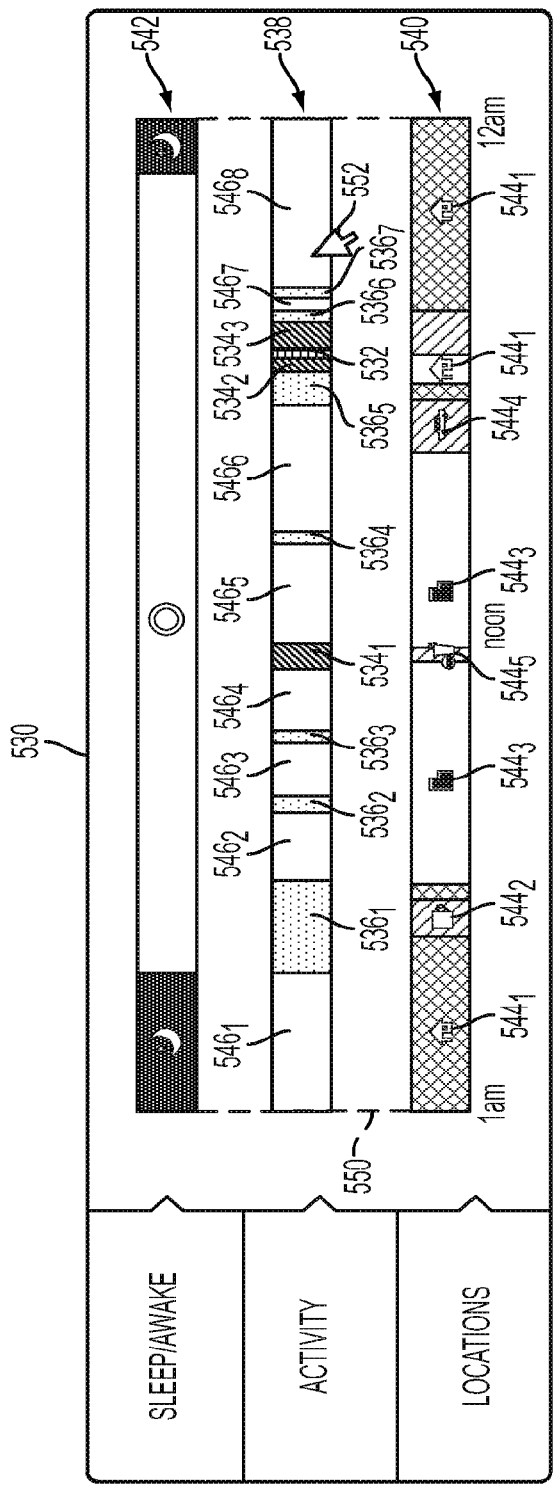
FIG. 7I is a GUI that provides an overview of one or more levels of one or more activities performed by a user at one or more locations over a period of time, in accordance with one embodiment described in the present disclosure.

FIG. 7I is a diagram of an embodiment of a GUI 530 that provides an overview of one or more activities 538 performed by the user 112A at one or more locations 540 over a period of time. The activities 538 are graphical elements. Similarly, the locations 540 are graphical elements. The GUI 530 is generated by executing the method 102 (FIG. 6A), 160 (FIG. 6B), 170 (FIG. 6C), or 210 (FIG. 6E). The GUI 530 also includes a time line 542 that shows a relationship of time periods, e.g., a night time period, a day time period, etc., with performance of the activities 538 and the locations 540. The activities 538, the locations 540, and the time line 542 are aligned with respect to each other along a column 550. The locations 540 include one or more location/activity identifiers $544_1$, $544_2$, $544_3$, and $544_4$.

The activities 538 include a sedentary activity $546_1$, a sedentary activity $546_2$, a sedentary activity $546_3$, a sedentary activity $546_4$, a sedentary activity $546_4$, a sedentary activity $546_5$, a sedentary activity $546_6$, a sedentary activity $546_7$, and a sedentary activity $546_8$. The activities 538 further include a lightly active activity $536_1$, a lightly active activity $536_2$, a lightly active activity $536_3$, a lightly active activity $536_4$, a lightly active activity $536_5$, a lightly active activity $536_6$, and a lightly active activity $536_7$. The activities 538 further includes a moderately active activity $534_1$, a moderately active activity $534_2$, a moderately active activity $534_3$, and a highly active activity 532.

It should be noted that an activity level of the sedentary active activity is lower than an activity level of the lightly active activity. An activity level of the lightly active activity is lower than an activity level of the moderately active activity and an activity level of the moderately active activity is lower than an activity level of the highly active activity. For example, a number of calories burned during the sedentary active activity is lower than a number of calories burned during the lightly active activity, a number of calories burned during the lightly active activity is lower than a number of calories burned during the moderately active activity, and a number of calories burned during the moderately active activity is lower than a number of calories burned during the highly active activity. As another example, an amount of activity performed at the sedentary active activity is lower than an amount of activity performed at the lightly active activity, an amount of activity performed at the lightly active activity is lower than an amount of activity performed at the moderately active activity, and an amount of activity performed at the moderately active activity is lower than an amount of activity performed at the highly active activity.

Each activity is vertically aligned with a location. For example, the sedentary activity $546_1$ is vertically aligned with the location $544_1$. As another example, the lightly active activity $536_1$ is vertically aligned with the locations $544_1$ and $544_2$.

In some embodiments, when an activity is aligned, e.g., vertically, horizontally, etc. with a location, the activity is performed at the location. For example, the monitoring device 108A worn by the user 112A captures positions used to determine an activity performed within a home of the user 112A.

Moreover, it should be noted that although four activities are shown in FIG. 7I, in some embodiments, any number of activities may be shown. Furthermore, in some embodiments, the activities 538, the locations 540, and the time line 542 are aligned with respect to each other along a row instead of the column 550. For example, each of the activities 538, the locations 540, and the time line 542 are made vertical instead of horizontal to be aligned with respect to each other along a row.

A cursor 552 is displayed on the GUI 530 by the processor 226 or by the processor 234. When the user 112A uses the user interface 274 (FIG. 3A) or the input device 340 (FIG. 5) to point the cursor 552 to a portion of the activities 538 and selects the portion, a progressively detailed GUI 560 is displayed. The GUI 560 is displayed in FIG. 7J.

Figure 7J:
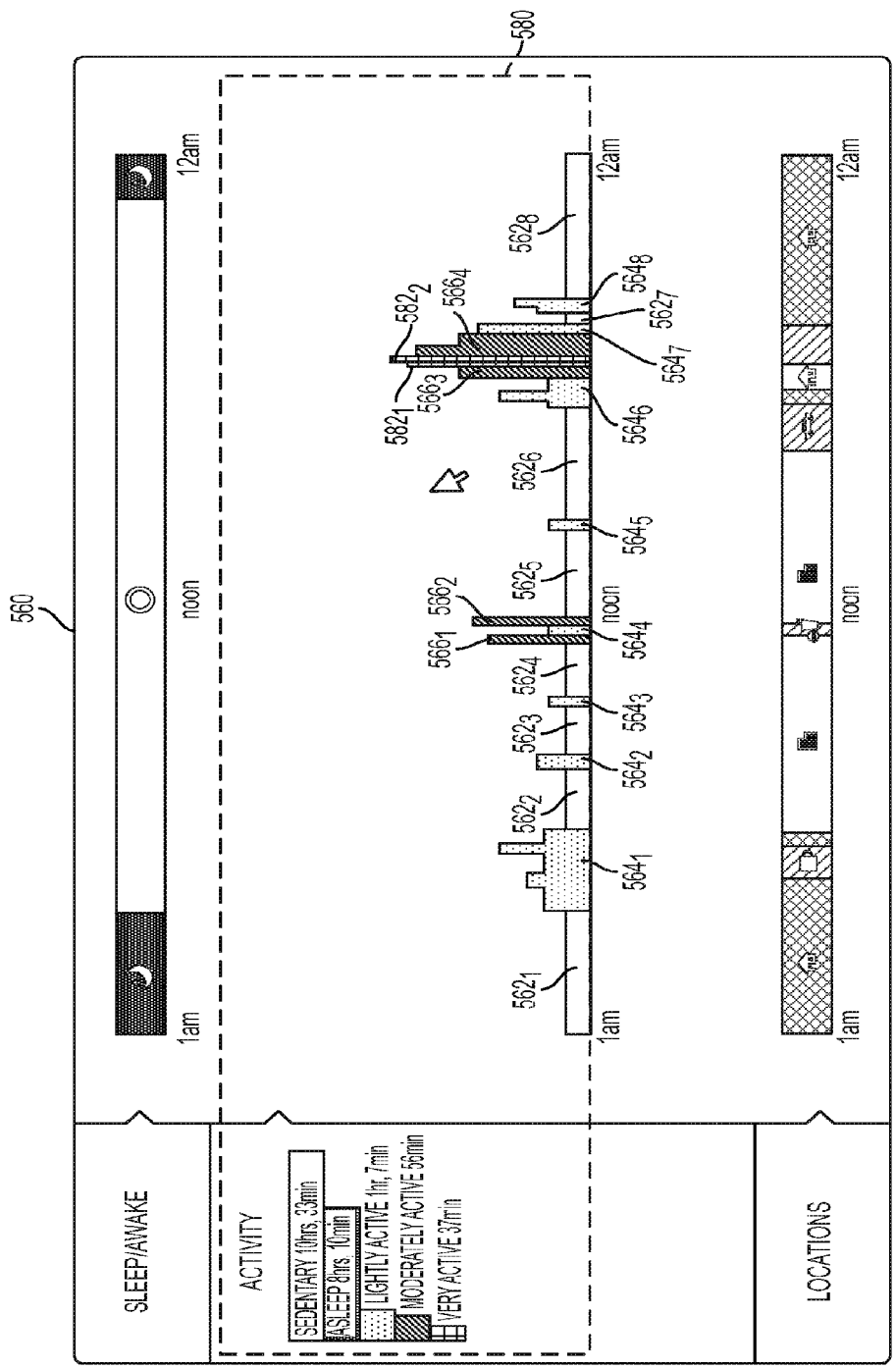
FIG. 7J is a diagram of a GUI that includes a detailed view of activities displayed in the GUI of FIG. 7I, in accordance with one embodiment described in the present disclosure.

FIG. 7J is a diagram of an embodiment of the GUI 560. The GUI 560 is generated by executing the method 102 (FIG. 6A), 160 (FIG. 6B), 170 (FIG. 6C), or 210 (FIG. 6E). The GUI 560 includes a detailed view of the activities 538 (FIG. 7I). The detailed view is shown as activities 580. For example, the GUI 560 includes a detailed view of each activity level of the GUI 530 (FIG. 7I). To illustrate, the highly active activity 532 (FIG. 7I) is detailed as one or more highly active activity levels $582_1$ and $582_2$ of the activity. As another illustration, the sedentary activities $546_1$ thru $546_8$ are detailed as one or more sedentary activity levels $562_1$, $562_2$, $562_3$, $562_4$, $562_5$, $562_6$, $562_7$, and $562_8$. As yet another illustration, the lightly active activities $536_1$ thru $536_7$ are detailed as one or more lightly active activity levels $564_1$, $564_2$, $564_3$, $564_4$, $564_5$, $564_6$, $564_7$, and $564_8$. As another illustration, the moderately active activities $534_1$ thru $534_3$ are detailed as one or more moderately active activity levels $566_1$, $566_2$, $566_3$, and $566_4$. In some embodiments the activities 580 are graphical elements.

In some embodiments, each location/activity identifier of the GUI 530 is detailed by the processor 226 or by the processor 234 into a detailed location/activity identifier within the GUI 560. For example, a building identifier within the GUI 530 is detailed, within the GUI 560 into one or more rooms of the building when the user 112A uses the user interface 274 (FIG. 3A) or the input device 340 (FIG. 5) to point the cursor 552 to a portion of the locations 540 (FIG. 7I) and to select the portion.

In various embodiments, the GUI 560 includes a detailed view, which includes one or more activity levels, of an activity of the GUI 530. The activity of the GUI 530 is one at which the user 112A points to and selects with the pointer 552. In some embodiments, the GUI 560 includes a detailed location/activity identifier of a location/activity identifier, on the GUI 530, at which the user 112A points to and selects with the pointer 552.

Figure 7K:
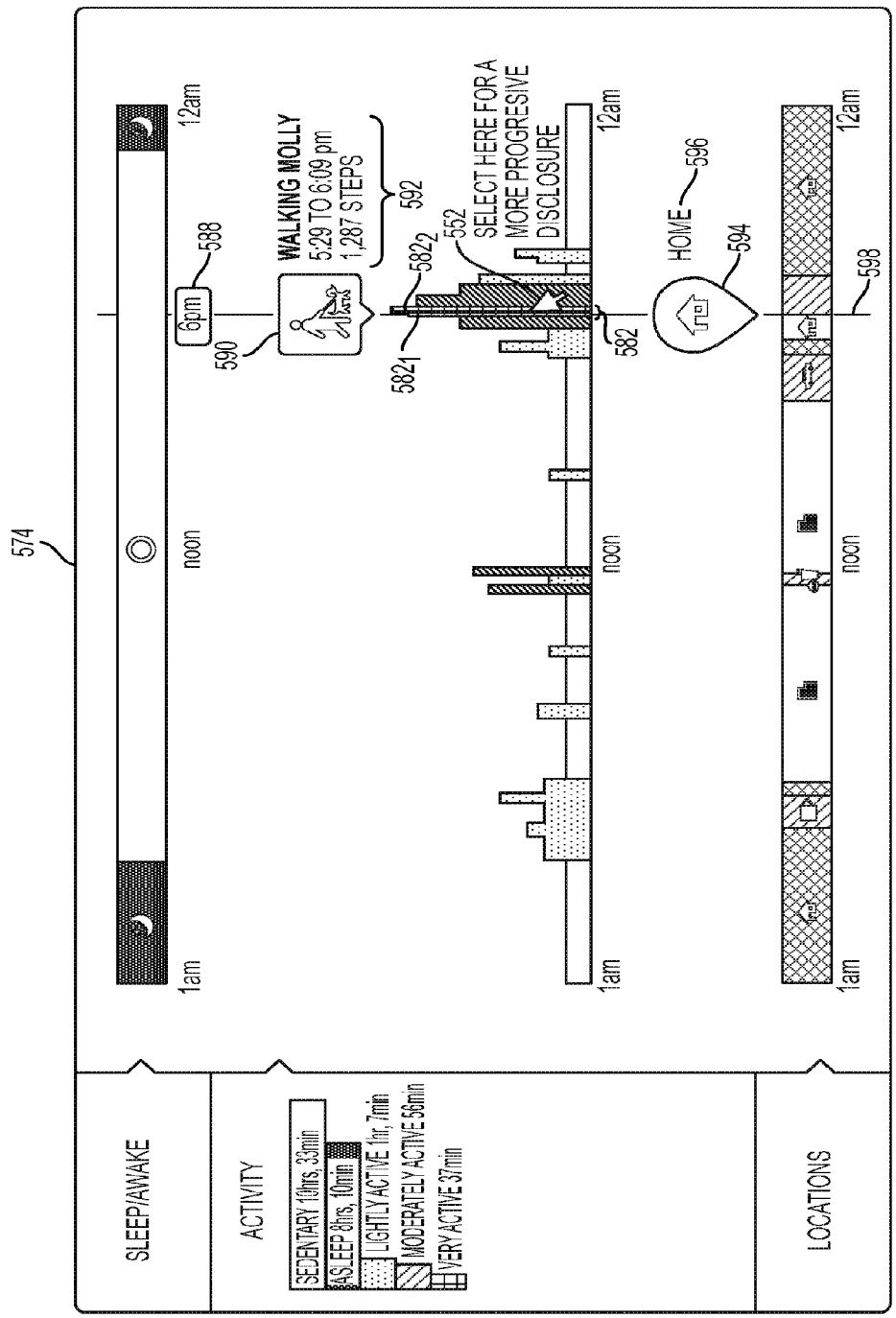
FIG. 7K is a diagram of a GUI that includes a more detailed view of activities displayed in the GUI of FIG. 7J, in accordance with one embodiment described in the present disclosure.

FIG. 7K is a diagram of an embodiment of the GUI 574. The GUI 574 is the same as the GUI 560 (FIG. 7J) except that the GUI 574 shows a more detailed view of one or more activities performed by the user 112A, of a time period during which the activities are performed, and/or of a location at which the activities are performed, compared to that shown in the GUI 560. For example, when the user 112A uses the user interface 274 (FIG. 3A) or the input device 340 (FIG. 5) to point the cursor 552 to a portion, e.g., an activity level $582_1$ (FIG. 7J), etc., of the activities 580 (FIG. 7J) and to select the portion, a detailed view of the portion is displayed within the GUI 574. To illustrate, the detailed view of the portion includes a graphical element 588 that displays a time at which the activity level $582_1$ occurs, a location/activity identifier 590 identifying an activity, e.g., walking, running, etc., performed at a location by the user 112A. The activity level $582_1$ and an activity level $582_2$ are portions of an activity level 582.

The detailed view further includes text 592 that describes the activity, having the activity level $582_1$, performed by the user 112A, time of occurrence of the activity, and activity data, e.g., number of steps, calories burned, etc., of the activity. The detailed view further includes a location/activity identifier 594 that represents a location closest to a location of performance of the activity identified by the location/activity identifier 590. For example, the location/activity identifier 594 is a home icon of a home of the user 112A and the home is at a location closest to a location where the user 112A walks a dog. The detailed view further includes text 596 describing a location identified by the location/activity identifier 594. The graphical element 588, the location/activity identifier 590, and the location/activity identifier 594 are aligned along a line 598. In some embodiments, the graphical element 588, the location/activity identifier 590, and the location/activity identifier 594 are not aligned with respect to each other. In various embodiments, the detailed view excludes the text 592 and/or excludes the text 596. In several embodiments, the detailed view excludes the location/activity identifier 590 and/or excludes the location/activity identifier 596. The GUI 574 is generated by executing the method 102 (FIG. 6A), 160 (FIG. 6B), 170 (FIG. 6C), or 210 (FIG. 6E).

Figure 7L:
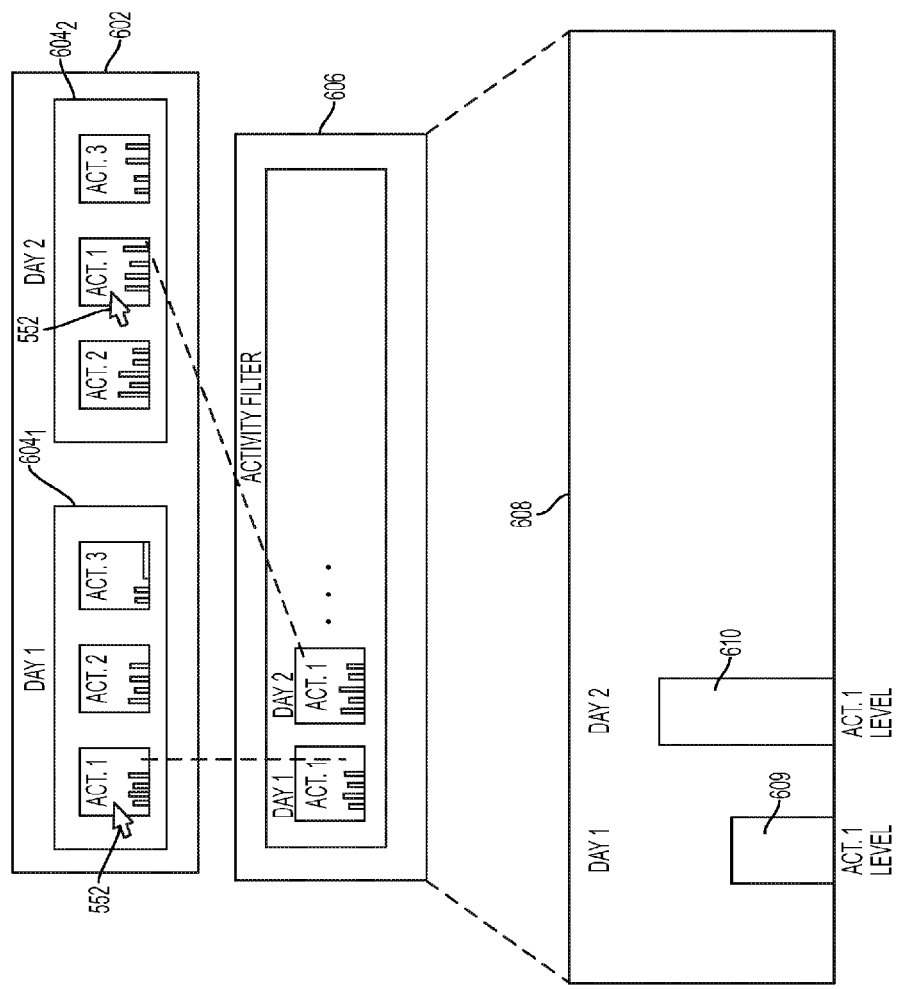
FIG. 7L is a diagram illustrating a method of combining activity levels over a period of time, in accordance with one embodiment described in the present disclosure.

FIG. 7L is a diagram illustrating an embodiment of a method of combining activity levels over a period of time. The method of combining activity levels over a period of time is performed by the processor 226 or by the processor 234. In the method of combining activity levels, a GUI 602 is displayed by the processor 226 or by the processor 234.

The GUI 602 includes a display $604_1$ of activity levels of a number of activities, e.g., an activity 1, an activity 2, and an activity 3, etc. performed by the user 112A during a day 1. The activities shown in the display $604_1$ are performed in the order shown. For example, the activity 1 is performed during the day 1 before the activity 2 is performed during the day 1 and the activity 2 is performed during the day 1 before the activity 3 is performed during the day 1.

Moreover, the GUI 602 includes a display $604_2$ of activity levels of a number of activities, e.g., an activity 2, an activity 1, and an activity 3, etc. performed by the user 112A during a day 2. The activities shown in the display $604_2$ are performed in the order shown. For example, the activity 2 is performed during the day 2 before the activity 1 is performed during the day 2 and the activity 1 is performed during the day 2 before the activity 3 is performed during the day 2.

The user 112A uses the user interface 274 (FIG. 3A) or the input device 340 (FIG. 5) to point the cursor 552 to the activity 1 performed during the day 1 to select the activity 1 performed during the day 1 and drag the activity 1 performed during the day 1 to a GUI 606, which is an activity filter. The user 112A then uses the user interface 274 (FIG. 3A) or the input device 340 (FIG. 5) to point the cursor 552 to the activity 1 performed during the day 2 to select the activity 1 performed during the day 2 and drag the activity 1 performed during the day 2 to the GUI 606. In some embodiments, the processor 226 or the processor 234 receives a selection from the user 112A via the user interface 274 (FIG. 3A) or the input device 340 (FIG. 5) of the activity 1, the activity 2, or the activity 3 over a period of time, e.g., day 1, day 2, etc., within the GUI 602 and the processor 234 drags the activities performed during the period of time to present in the GUI 606.

When the user 112A uses the user interface 274 (FIG. 3A) or the input device 340 (FIG. 5) to point the cursor 552 to the activity 1 performed during the day 1 within the GUI 606 and selects the activity 1 performed during the day 1 or to point the cursor 552 to the activity 1 performed during the day 2 and selects the activity 1 performed during the day 2 within the GUI 606, a GUI 608 is generated and displayed. The GUI 608 includes an aggregate, e.g., total, etc., activity level 609 of the activity 1 performed during the day 1 and includes an aggregate activity level 610 of the activity 1 performed during the day 2. Any aggregation of activity levels is performed by the processor 226 or by the processor 234.

In some embodiments, upon receiving the selection of the activity 1, the activity 2, or the activity 3 over a period of time, e.g., day 1, day 2, etc., within the GUI 602, the processor 226 or the processor 234 generates a GUI, e.g., the GUI 608, having aggregate activity levels of the activity over the period of time for which the activity is selected.

Figure 7M:
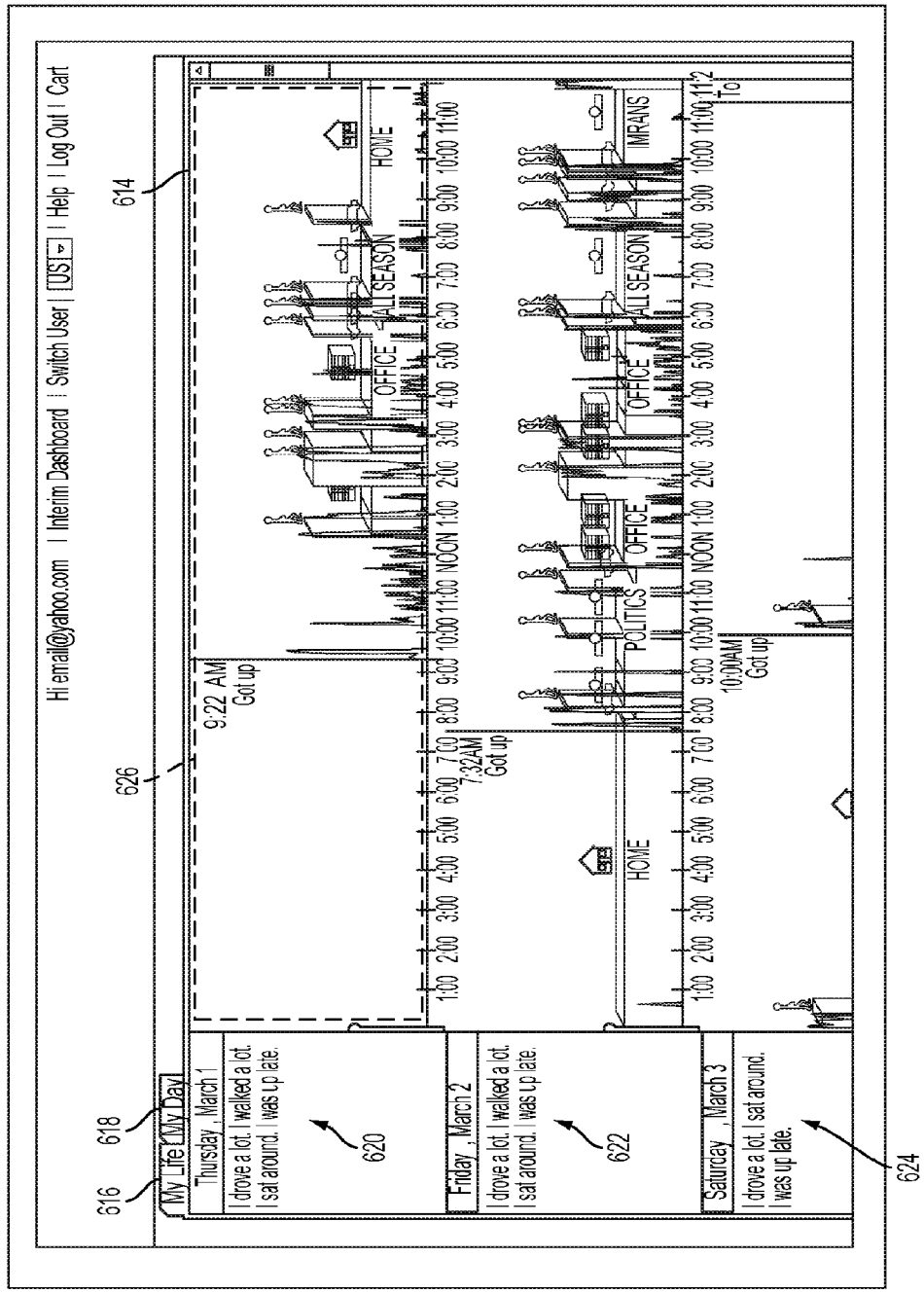
FIG. 7M is a diagram of a GUI that describes an aggregate level of one or more activities performed by a user over a period of time, in accordance with one embodiment described in the present disclosure.

FIG. 7M is a diagram of an embodiment of a GUI 614 that describes an aggregate level of one or more activities performed by the user 112A over a period of time. The processor 226 or the processor 234 determines an aggregate amount of an activity performed by the user 112A over a period of time. The processor 234 or the processor 234 generates a simplified description of the aggregate amount of the activity and displays the simplified description on a corresponding display device. For example, when the user 112A selects a tab 616 via the user interface 274 (FIG. 3A) or the input device 340 (FIG. 5), simplified descriptions 620, 622, and 624 are displayed within the GUI 614 for one or more periods of time. The simplified description 620 is of activities performed by the user 112A on Thursday, March 1, the simplified description 622 is of activities performed by the user 112A on Friday, March 2, and the simplified description 624 is of activities performed by the user 112A on Saturday, March 3.

Each simplified description of activities performed during a period of time is displayed besides a corresponding sequence of events occurring during the period of time. For example, the simplified description 620 of activities performed on Thursday, March 1 is displayed besides one or more events 626 occurring on Thursday, March 1.

Figure 7N:
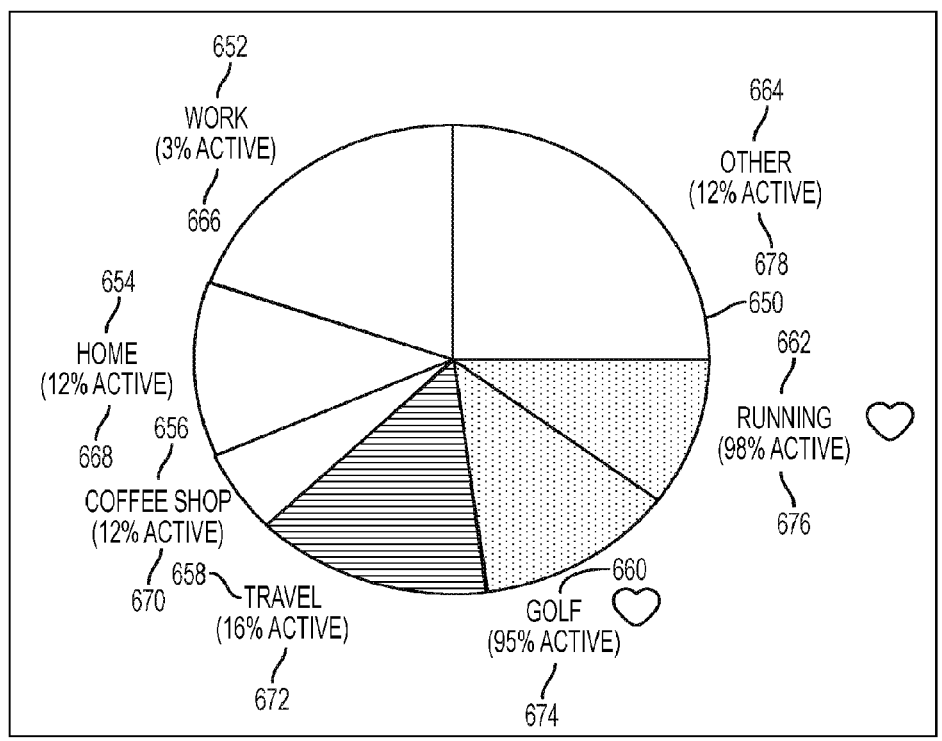
FIG. 7N is a diagram of a pie-chart of locations at which a user performs one or more activities and of percentages of activity levels at one or more locations over a period of time, in accordance with one embodiment described in the present disclosure.

FIG. 7N is a diagram of an embodiment of a pie-chart 650 of locations at which the user 112A performs one or more activities and of percentages of activity levels at the locations over a period of time. The period of time is represented by the pie-chart 650. The pie-chart 650 is generated by the processor 226 or the processor 234.

The pie-chart 650 is segmented into a location 652, a location 654, a location 656, an activity 658, an activity 660, an activity 662, and a location/activity 664. When the user 112A is at the location 652, the user 112A has an activity level of 666. Similarly, when the user 112A is at the location 654, the user 112A has an activity level of 668. When the user 112A is at the location 656, the user 112A has an activity level of 670. Moreover, when the user 112A is performing the activity 658, the user 112A has an activity level of 672. When the user 112A is performing the activity 660, the user 112A has an activity level of 674. Also, when the user 112A is performing the activity 662, the user 112A has an activity level of 676. When the user 112A is performing the activity 664 or is at the location 664, the user 112A has an activity level of 678.

In some embodiments, an activity level of an activity performed at a location by the user 112A is determined by the processor 226 or the processor 234 in terms of a percentage of an amount of activity that would have been performed at the location. For example, the processor 226 or 234 determines that a maximum amount of activity that can be performed by the user 112A or any other user at the location 652 is n. The processor 226 or 234 receives an amount of activity actually performed by the user 112A as m. The processor 226 or 234 determines a percentage (m/n)×100 as the activity level 666.

In various embodiments, any other type of graph, e.g., a bar graph, a line graph, etc., is generated by the processor 226 or the processor 234 instead of a pie chart.

Figure 7O:
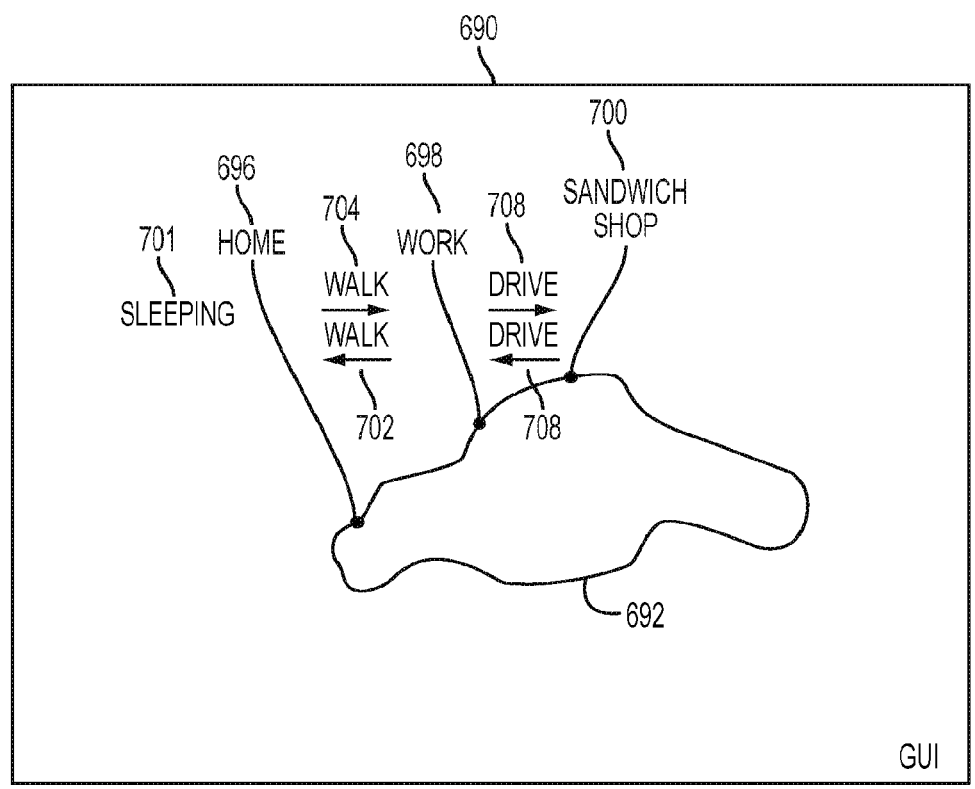
FIG. 7O is a diagram of a GUI that includes an overlay of a map on one or more locations that a user visits during a period of time to perform one or more activities performed by the user during a period of time, in accordance with one embodiment described in the present disclosure.

FIG. 7O is a diagram of an embodiment of a GUI 690 that includes an overlay of a map 692 on one or more locations 696, 698, and 700 that the user 112A visits during a period of time to perform one or more activities 701, 702, 704, and 708 performed by the user 112A during the period of time. The GUI 690 is generated by the processor 226 or by the processor 234. The GUI 690 is generated by executing the method 221 (FIG. 6F).

The GUI 690 includes a map 692 of a path traveled by the user 112A during a period of time, text describing the locations 696, 698, and 700 and text describing the activities 701, 702, 704, and 708.

In some embodiments, instead of text describing the locations 696, 698, and 700, one or more graphical elements or a combination of the graphical elements and text describing the locations are used within the GUI 690 to indicate the locations. In various embodiments, instead of text describing the activities 701, 702, 704, and 708, one or more graphical elements or a combination of the graphical elements and text describing the activities are used within the GUI 690 to indicate the activities.

In a number of embodiments, the one or more locations 696, 698, and 700 are overlaid on the map 692.

Figure 7P:
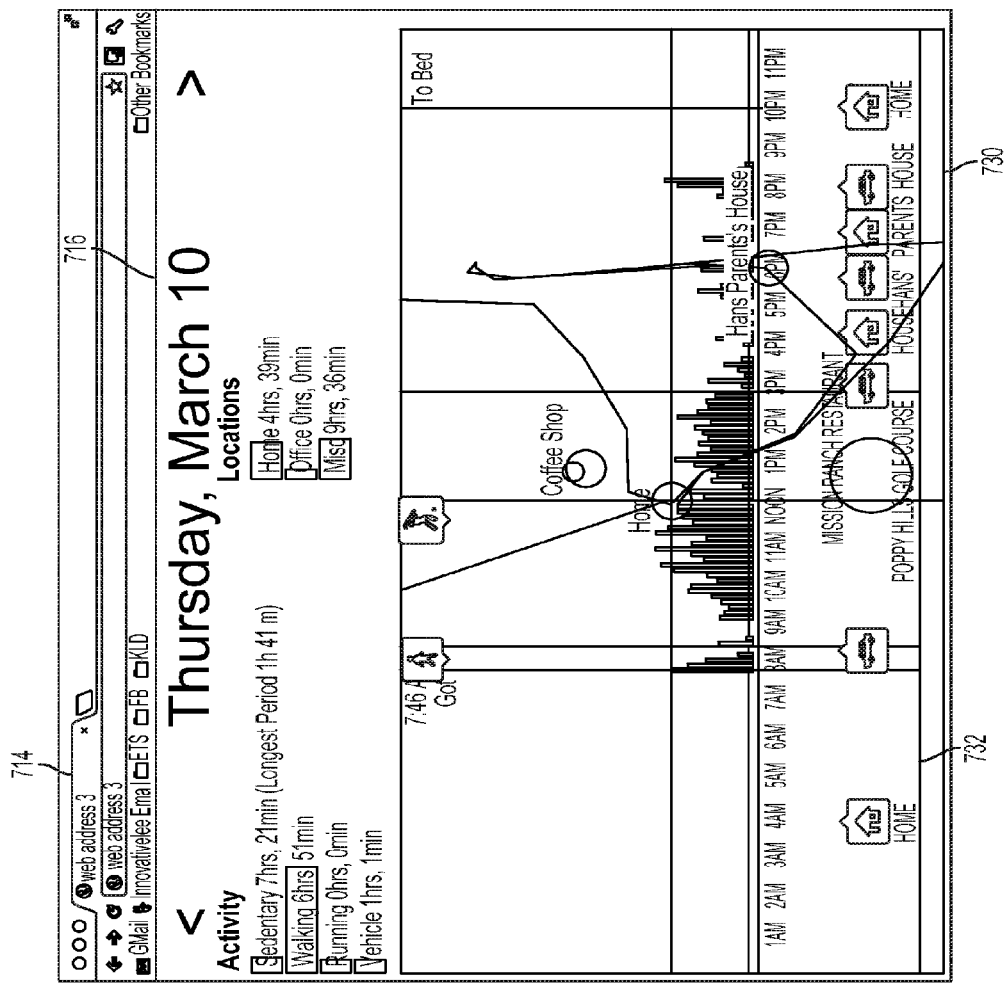
FIG. 7P is a diagram of a web page that illustrates that a map is overlaid on an event region to indicate a geo-location of a user at a time within a time period in which the user performs one or more activities, in accordance with one embodiment described in the present disclosure.

FIG. 7P is a diagram of an embodiment of a web page 714 that illustrates that a map 732 is overlaid on the event region 730 to indicate a geo-location of the user 112A at a time, e.g., an hour, a minute, etc., within a time period in which the user 112A performs one or more activities. The web page 714 includes a GUI 716 that further includes the map 732 and the event region 730. When the user 112A selects a time, e.g., 11 AM, NOON, 1 PM, etc., on the GUI 370 (FIG. 7A) via the user interface 274 (FIG. 3A) or the input device 340 (FIG. 5), a map, e.g., the map 732, etc., is overlaid by the processor 226 or the processor 234 on the GUI 370 to indicate a geo-location of the user 112A at the time. For example, the geo-location is indicated by centering the map at the geo-location of the user 112A at the time.

The GUI 716 is generated by executing the method 102 (FIG. 6A), 160 (FIG. 6B), 170 (FIG. 6C), or 210 (FIG. 6E) in combination with the method 221 (FIG. 6F).

In some embodiments, the event region 730 is overlaid on the map 732.

Figure 7Q:
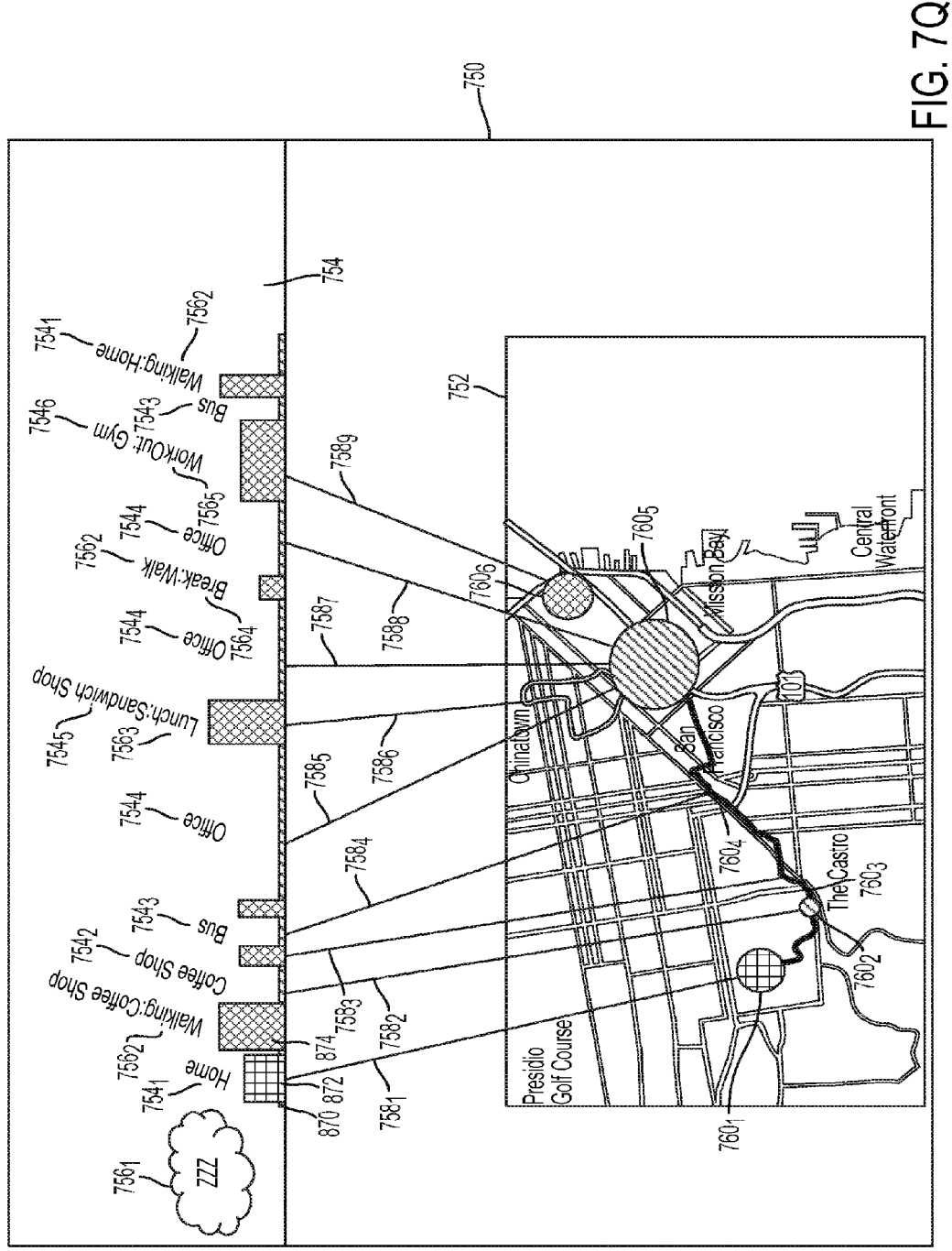
FIG. 7Q is a diagram of a GUI that includes a map below an event region, in accordance with one embodiment described in the present disclosure.

FIG. 7Q is a diagram of an embodiment of a GUI 750 that includes a map 752 below an event region 754. The GUI 750 is generated by the processor 226 or the processor 234. The event region 754 includes one or more location/activity identifiers $754_1$, $754_2$, $754_3$, $754_4$, $754_5$, and $754_6$ of locations visited by the user 112A during a period of time. Moreover, the event region 754 includes graphical elements and/or text that represent one or more activities $756_1$, $756_2$, $756_3$, $756_4$, and $756_5$ performed by the user 112A during the period of time.

The GUI 750 further includes links $758_1$, $758_2$, $758_3$, $758_4$, $758_5$, $758_6$, $758_7$, $758_8$, and $758_9$ between a set including one or more geo-locations $760_1$, one or more geo-locations $760_2$, one or more geo-locations $760_3$, one or more geo-locations $760_4$, one or more geo-locations $760_5$, and one or more geo-locations $760_6$ on the map 752 and a set including one or more of the location/activity identifiers $754_1$, $754_2$, $754_3$, $754_4$, $754_5$, and $754_6$ and/or one or more of the activities $756_1$, $756_2$, $756_3$, $756_4$, and $756_5$. For example, the link $758_1$ is established between the one or more geo-locations $760_1$ and the location $754_1$.

The GUI 750 is generated by executing the method 102 (FIG. 6A), 160 (FIG. 6B), 170 (FIG. 6C), or 210 (FIG. 6E) in combination with the method 221 (FIG. 6F).

In some embodiments, a geo-location is represented as a graphical element and/or as text by the processor 226 or by the processor 234.

In some embodiments, the map 752 is placed by the processor 236 or the processor 234 at any other place, e.g., above, to the left of, to the right of, etc., with respect to the event region 754.

Figure 7R:
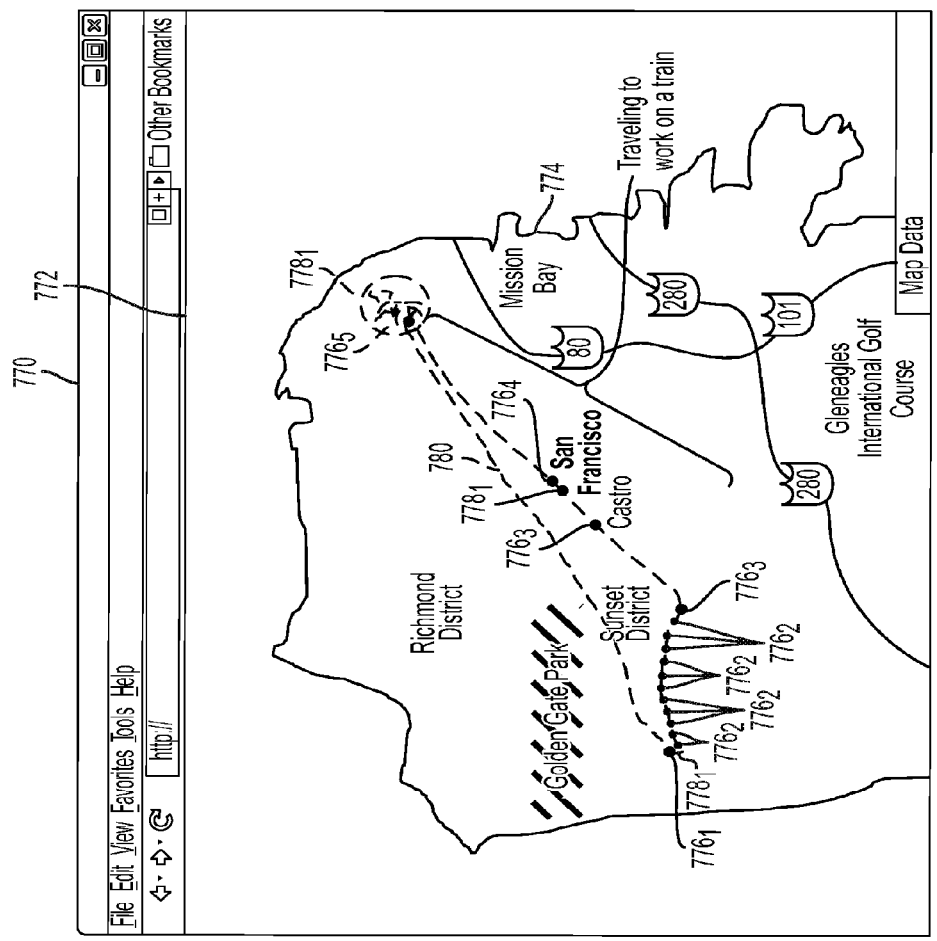
FIG. 7R is a diagram of a web page that is used to illustrate an overlay of event data on a map, in accordance with one embodiment described in the present disclosure.

FIG. 7R is a diagram of an embodiment of a web page 770 that is used to illustrate an overlay of event data on a map 774. A map is accessed by the processor 234 of the monitoring device 108A via the wireless communication device 278 (FIG. 3A) or a wired communication device of the monitoring device 108A and the network 176 (FIG. 3A) from the geo-location-location database of the server 228 (FIG. 3A) or another server without using the computing device 166 (FIG. 3A). In some embodiments, the map 774 is accessed by the processor 234 of the monitoring device 108A via the wireless communication device 278 (FIG. 3A) or a wired communication device of the monitoring device 108A, the computing device 166, and the network 176 (FIG. 3A) from the geo-location-location database of the server 228 (FIG. 3A) or another server. In a number of embodiments, the map 774 is accessed by the processor 226 of the computing device 166 via the NIC 356 (FIG. 5) of the computing device 166 and via the network 176 (FIG. 3A) from the geo-location-location database of the server 228 (FIG. 3A) or another server.

The web page 770 includes a GUI 772 that is displayed by the processor 226 or the processor 234. The GUI 772 is generated by the processor 226 or the processor 234. The GUI 772 is generated by executing the method 102 (FIG. 6A), 160 (FIG. 6B), 170 (FIG. 6C), or 210 (FIG. 6E) in combination with the method 221 (FIG. 6F).

The map 774 includes one or more geo-locations, names of landmarks accessed from the geo-location-location database, names of public places accessed from the geo-location-location database, names of streets accessed from the geo-location-location database, names of geo-locations accessed from the geo-location-location database, or a combination thereof, etc.

The event data is overlaid on the map 774 by the processor 226 or by the processor 234. The event data includes one or more of a location/activity identifier $776_1$, e.g., a home identifier, etc., a location/activity identifier $776_2$, e.g., an identifier of a bus, etc., a location/activity identifier $776_3$, e.g., an identifier of a railway station, etc., a location/activity identifier $776_4$, e.g., a vehicle identifier, etc., a location/activity identifier $776_5$, e.g., a work location/activity identifier, etc., of locations visited by the user 112A during a period of time and an activity identifier $778_1$ of an activity, e.g., walking, etc., performed by the user 112A during the period of time. The event data further includes a path 780 taken by the user 112A during the period of time in visiting the locations having the location/activity identifiers $776_1$, $776_2$, $776_3$, $776_4$, and $776_5$ and in performing an activity, e.g., walking, etc., represented by the activity identifier $778_1$.

In some embodiments, the event data includes activity data of any number of activities performed by the user 112A.

In several embodiments, the map 774 is overlaid on the event data.

Figure 7S:
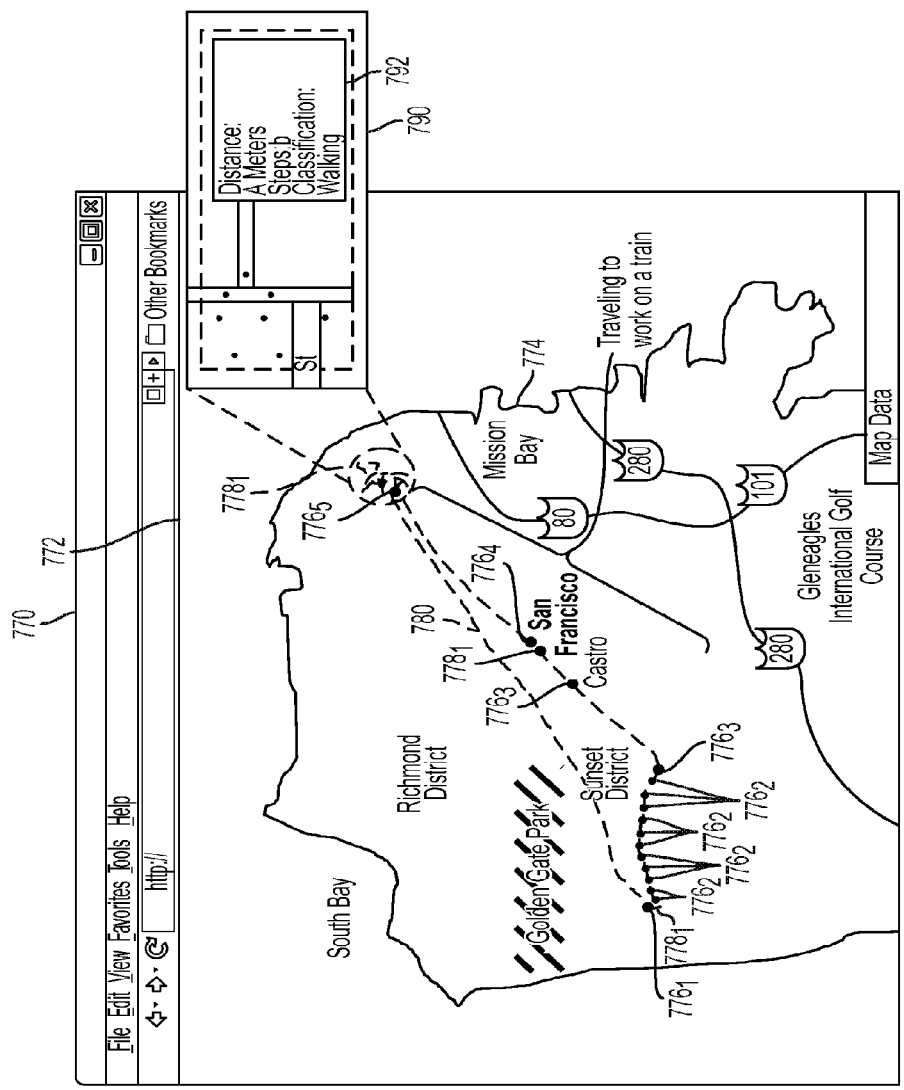
FIG. 7S is a diagram of a web page that is used to illustrate a zoom-in of a portion of the map of FIG. 7R and of activity data of an activity performed by a user while the user is at the portion, in accordance with one embodiment described in the present disclosure.

In various embodiments, the activity identifier $778_1$, the path 780, and/or the location/activity identifiers $776_1$, $776_2$, $776_3$, $776_4$, and $776_5$ are color-coded by the processor 226 or the processor 234. For example, the processor 226 or the processor 234 assigns a different color to the identifier $778_1$ than to one or more of the location/activity identifiers $776_1$, $776_2$, $776_3$, $776_4$, and $776_5$, and the path 780. As another example, the processor 226 or the processor 234 assigns a different color to the location/activity identifier $776_1$ than to one or more of the location/activity identifiers $776_2$, $776_3$, $776_4$, and $776_5$. As another example, the processor 226 or the processor 234 assigns a different color to the path 780 than to one or more of the location/activity identifiers $776_1$, $776_2$, $776_3$, $776_4$, and $776_5$ In some embodiments, the activity identifier $778_1$, the path 780, and/or the location/activity identifiers $776_1$, $776_2$, $776_3$, $776_4$, and $776_5$ are coded by the processor 226 or the processor 234 by using graphical properties. For example, the processor 226 or the processor 234 assigns a different graphical property to the activity identifier $778_1$ than to one or more of the location/activity identifiers $776_1$, $776_2$, $776_3$, $776_4$, and $776_5$, and the path 780. As another example, the processor 226 or the processor 234 assigns a different graphical property to the location/activity identifier $776_1$ than to one or more of the location/activity identifiers $776_2$, $776_3$, $776_4$, and $776_5$. As another example, the processor 226 or the processor 234 assigns a different graphical property to the path 780 than to one or more of the location/activity identifiers $776_1$, $776_2$, $776_3$, $776_4$, and $776_5$ FIG. 7S is a diagram of an embodiment of the web page 770 that is used to illustrate a zoom-in 790 of a portion of the map 774 and of event data of an event that occurs at the portion. When the user 112A uses the uses the user interface 274 (FIG. 3A) or the input device 340 (FIG. 5) to point the cursor 552 to the activity identifier $778_1$, the processor 226 or the processor 234 generates the zoom-in 790 to display the zoom-in 790. In some embodiments, a zoom-in is an example of a GUI.

The zoom-in 790 includes a detailed display 792 associated with the activity identifier $778_1$ of an activity performed by the user 112A at one or more geo-locations close to, e.g., within a vicinity of, within a radius of, etc., a location having the location/activity identifier $776_5$. The detailed display 792 includes a distance traveled by the user 112A close to a location having the location/activity identifier $776_5$, a number of steps taken by the user 112A close to the location, and a textual description of an activity that is identified by the activity identifier $778_1$ and that is close to, e.g., with a radius of, etc., the location.

In some embodiments, the zoom-in 790 includes any other activity data, e.g., a number of calories burned by the user 112A close to a location having the location/activity identifier $776_5$, an amount of golf swings taken by the user 112A close to the location, etc.

Figure 7U:
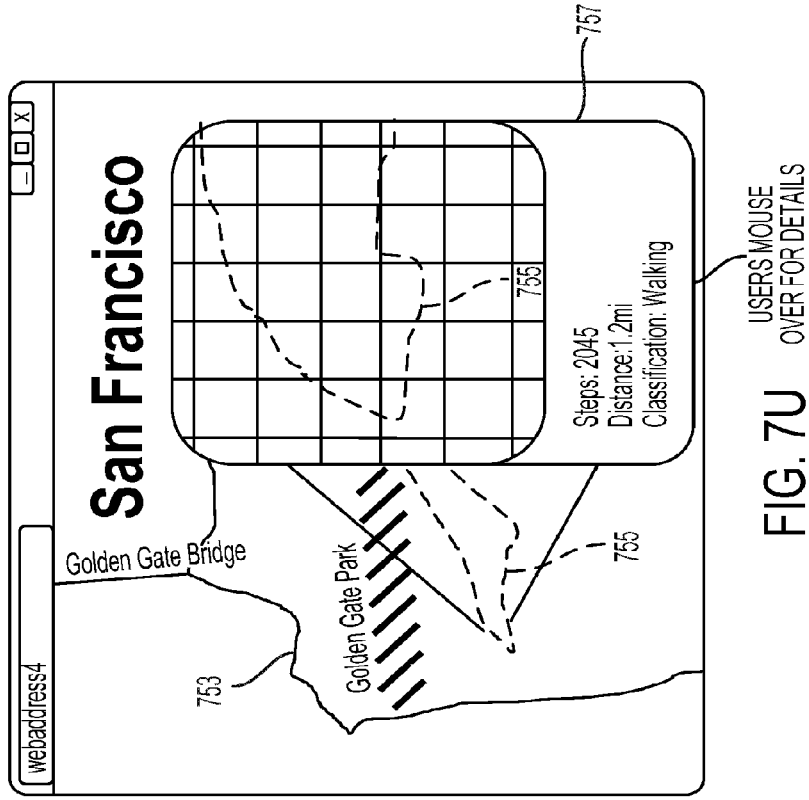
FIG. 7U is a diagram of an embodiment of the web page of FIG. 7T to illustrate a zoom-in of a portion of the map of FIG. 7T and to illustrate activity data associated with the zoom-in, in accordance with one embodiment described in the present disclosure.
Figure 7T:
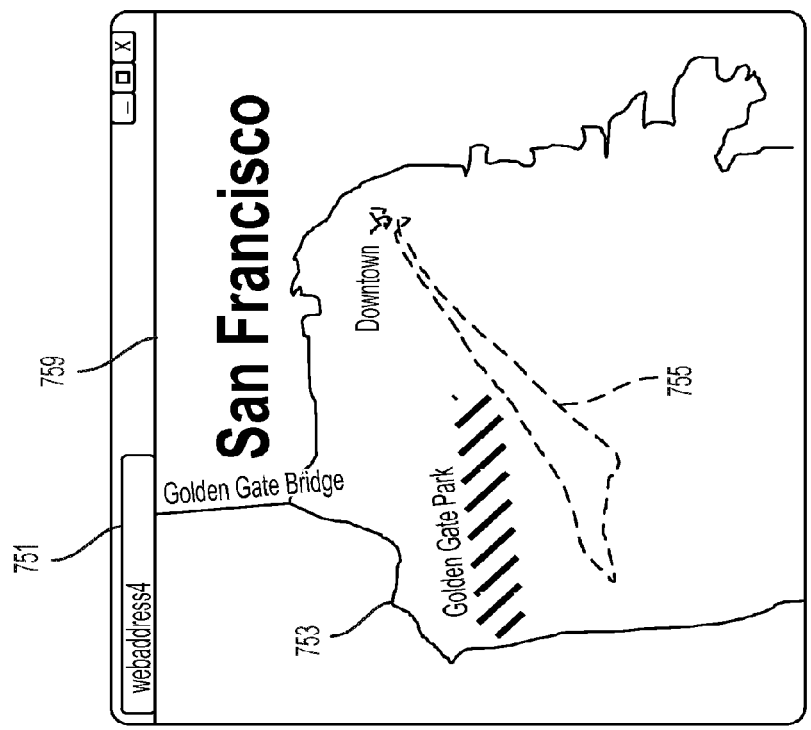
FIG. 7T is a diagram of an embodiment of a web page that includes a GUI that further includes an overlay of a map on a user's path, in accordance with one embodiment described in the present disclosure.

FIG. 7T is a diagram of an embodiment of a web page 751 that includes a GUI 759. The GUI 759 includes an overlay of a map 753 on a user's path 755. The user's path 755 is a path traveled by the user 112A during a period of time. The user's path 755 is coded to distinguish various locations and/or activities along the user's path 755. For example, a bus station is provided a different color by the processor 234 or by the processor 226 than that provided to a railway station. As another example, a walking activity of the user 112A along the user's path 755 is provided a different shade, text, and/or color by the processor 234 or by the processor 226 than that provided to a running activity of the user 112A along the user's path 755. The GUI 759 is generated by executing the method 102 (FIG. 6A), 160 (FIG. 6B), 170 (FIG. 6C), or 210 (FIG. 6E) in combination with the method 221 (FIG. 6F).

In some embodiments, the user's path 755 is overlaid on the map 753.

FIG. 7U is a diagram of an embodiment of a zoom-in 757 that includes a zoom-in of a portion of the user's path 755. The zoom-in 757 is generated when the user 112A points the cursor 552 (FIG. 7I) on a portion of the user's path 755 and selects the portion. The zoom-in 757 is of the portion of the user's path 755. The zoom-in 757 includes activity data, e.g., number of steps walked by the user 112A within the portion, a distance covered by the user 112A within the portion, and a type of activity, e.g., walking, running, etc., performed by the user 112A within the portion.

FIG. 7V is a diagram of an embodiment of the GUI 759 except that the GUI 759 indicates that a portion of the user's path 758 at which the user 112A takes bus to a train is coded differently than a portion of the user's path 758 at which the user 112A is traveling to work on a train and differently than a portion of the user's path 758 where the user 112A is walking around near his/her office.

Figure 8:
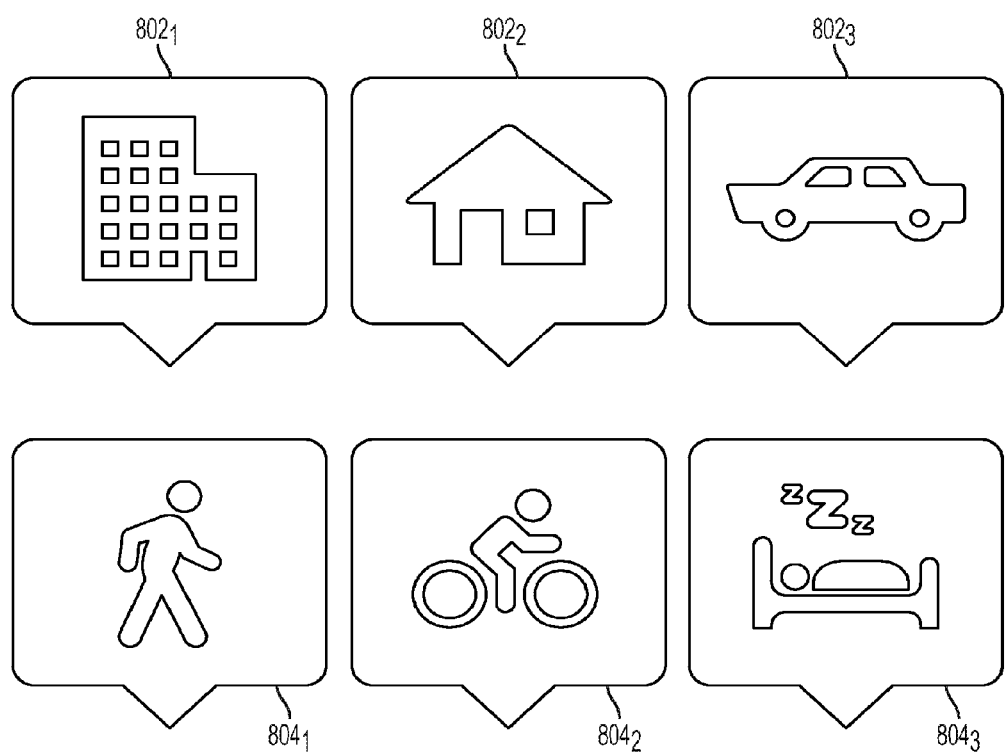
FIG. 8 is a diagram of one or more location identifiers and one or more activity identifiers, in accordance with one embodiment described in the present disclosure.

FIG. 8 is a diagram of an embodiment of one or more location/activity identifiers $802_1$, $802_2$, and $802_3$, and one or more activity identifiers $804_1$, $804_2$, and $804_3$. Each identifier $802_1$, $802_2$, $802_3$, $804_1$, $804_2$, and $804_3$ includes a pointer. For example, the identifier $802_1$ includes a pointer 806. In some embodiments, each identifier excludes a pointer.

Figure 9:
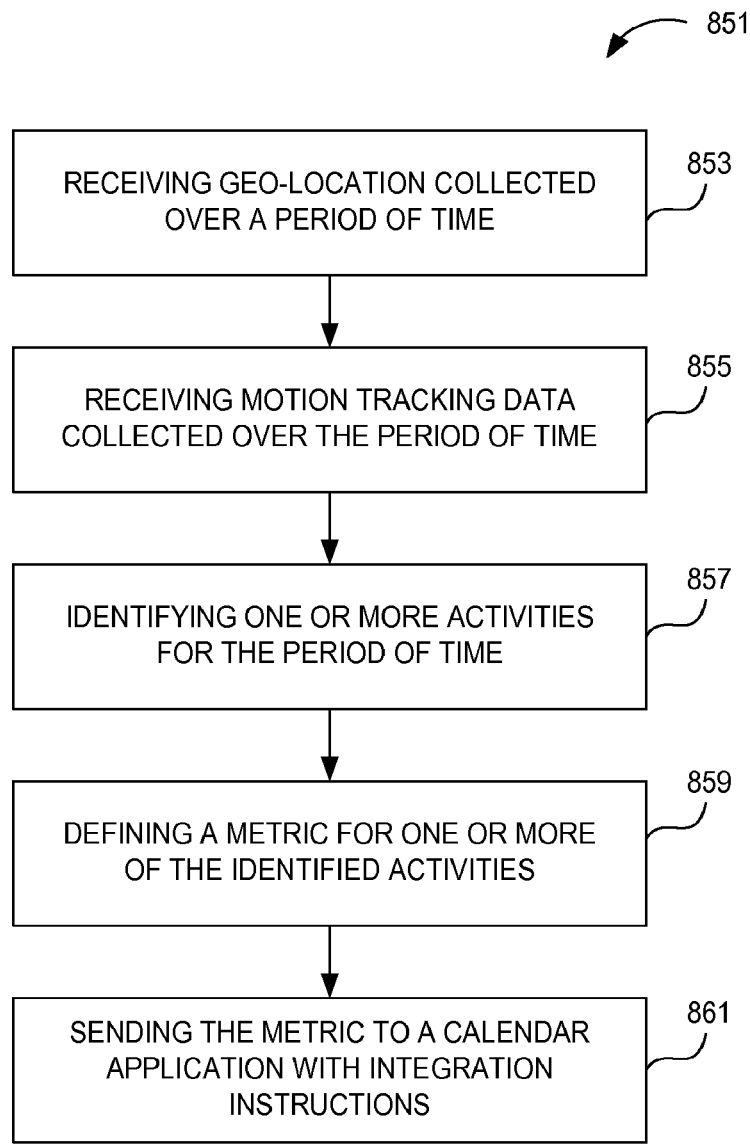
FIG. 9 is a flowchart of a method for facilitating generation of a calendar of activities performed by a user and of locations at which the activities are performed, in accordance with one embodiment described in the present disclosure.

FIG. 9 is a flowchart of an embodiment of a method 851 for facilitating generation of a calendar of activities performed by the user 112A and of locations at which the activities are performed. The method 851 is executed by the server 228 (FIG. 2B).

The method 851 includes receiving, in an operation 853, geo-location data that is collected over a period of time. For example, the geo-location data is received by the NIC of the server 228 via the network 176 from a communication device of a monitoring device. As yet another example, the geo-location data is received by the NIC of the server 228 (FIG. 2A) via the network 176 from the NIC of the computing device 166 (FIG. 5). In this example, the geo-location data is sent by the NIC of the computing device 166 to the server 228 after the wireless communication device of the computing device 166 receives the geo-location data from the wireless communication device of a monitoring device.

The operation 853 of receiving is performed by the NIC of the server 228.

The geo-location data is collected, e.g., obtained, etc., by the device locator of a monitoring device or of a computing device.

The geo-location data is associated with a monitoring device or with the computing device 166 from which the geo-location data is received. For example, the geo-location data is obtained by the device locator 222 of the monitoring device 108A to be sent to the server 228. As another example, the geo-location data is obtained by the device locator 306 of the monitoring device 108B to be sent to the server 228. As yet another example, the geo-location data is obtained by the device locator 344 of the computing device 166 (FIG. 5) to be sent to the server 228.

The method 851 includes receiving, in an operation 855, motion tracking data, e.g., the positions A, B, C, D, (FIGS. 1B, 1C), etc. of a monitoring device. For example, x, y, and z locations of the monitoring device 108A with reference to the xyz co-ordinate system are received. The operation 855 of receiving is performed by the NIC of the server 228.

The motion tracking data is collected over the period of time. For example, the motion tracking data is collected by the position sensor 220 of the monitoring device 108A (FIG. 3A) for 10 minutes, by a position sensor of the monitoring device 108B for 20 minutes, or by a position sensor of the computing device 166 (FIG. 5) for 2 hours.

The method 851 further includes identifying, e.g., characterizing, etc., in an operation 857, one or more activities for the period of time. The operation 857 is performed by the processor 190 of the server 228. The activities are identified based on inference rules that identify certain activities to have occurred when at least part of the motion tracking data is correlated to the received geo-location. For example, when the user 112A has a running speed of zero at a time the user 112A is moving his arm from an underarm position to an overarm position and is located at a golf course, the user 112A is playing golf.

The inference rules are used by the processor 190 to determine whether the received geo-location data identifies a location that is inconsistent with an activity identified using the received motion tracking data. For example, when the user 112A has a running speed of about zero at a time the user 112A is moving his arm from an underarm position to an overarm position and the user 112A is located at a baseball field, the user 112A is playing baseball and not golf. It is determined that the user 112A is playing golf based on the location of the user 112A. In this example, the movement from the underarm position to the overarm position is used to indicate that the user 112A is playing golf or baseball.

In one embodiment, the inference rules are stored in a rules database 962 (FIG. 2A) of the memory device 256 of the server 228 for access and execution by the processor of the server 228.

In some embodiments, the inference rules are executed by the processor 190 to compare stored motions, e.g., patterns of movement of a monitoring device, motions of the monitoring device, repeat motions of the monitoring device, motions of the monitoring device at some geo-locations, or a combination thereof, etc. The stored motions are compared with the motion tracking data and the geo-location data collected over the period of time. For example, when the geo-location data collected over the period of time indicates that the user 112A is traveling at a speed between 'a' miles per hour and 'b' miles per hour, it is determined by the processor 190 that the user 112A is walking. As another example, when the motion tracking data and the geo-location data collected over the period of time indicates that the user 112A is traveling at a speed of zero miles per hour and performing a motion between an underarm motion and an overarm motion, it is determined that the user 112A is playing golf or baseball. As another example, when the motion tracking data and the geo-location data collected over the period of time indicates that the user 112A is traveling at a speed of zero miles per hour and performing a motion between an underarm motion and an overarm motion and is located at a golf course, it is determined that the user 112A is playing golf.

It should be noted that in various embodiments, the geo-location data is used to determine a position of the user 112A.

In various embodiments, position and spatial position are used interchangeably herein. These positions or spatial positions can be one or more X, Y, Z coordinate points or a point, and a number of points over time can define some movement by the user wearing a tracking device.

In several embodiments, the stored motions are assigned tags by the processor 190 and the tags are used to identify and access the stored motions from the rules database 962.

In a number of embodiments, at least part of the motion tracking data is correlated to the received geo-location data when the geo-location data is collected at a time the user 112A is performing a motion. The motion of the user 112A is used to generate the motion tracking data. For example, when the user 112A performs a motion between the positions A and B (FIG. 1B), the position sensor of the monitoring device 108A generates the motion tracking data.

The method 851 includes performing an operation 859 of defining a metric for one or more of the identified activities. The operation 859 is performed by the processor of the server 228. The metric is associated with a calendar date. For example, as shown in FIG. 13, the sever processor determines that the user 112A has walked 52 steps per minute at a home of the user 112A on March, Saturday. As another example, the sever processor determines that the user 112A woke up at 10 AM on a calendar date of Saturday, March 3. As yet another example, the sever processor determines that the user 112A is walking in a park for 50 minutes. As another example, the processor 190 determines that the user 112A has swung for 20 times while golfing at a golf course.

Examples of metrics determined in the operation 859 include a metric 950, a metric 952, a metric 954, a metric 962, a metric 970, a metric 972, a metric 974, a metric 976, a metric 978, and a metric 966, a metric 956, a metric 958, a metric 960, a metric 964, a metric 980, a metric 982, a metric 984, a metric 986, a metric 988, and a metric 968, which are shown in FIG. 13. Examples of a calendar date include a calendar date 990 and a calendar date 992, which are shown in FIG. 13.

Other examples of a metric include a number of steps taken by the user 112A during the period of time, a number of stairs climbed by the user 112A during the period of time, a number of stairs descended by the user 112A during the time period, an amount of calories burned by the user 112A during the time period, or a wake-up time of the user, or a bed time of the user, or an amount of time of performing an activities, a location identifier, an activity identifier, or an amount of time of performing an activity at a location, or a combination thereof.

The server processor adds a metric determined for the user 112A over multiple periods of time to define a metric in the operation 859. For example, when the user 112A walks a first number of steps in a first period of time and a second number of steps in a second period of time, it is determined that the user 112A walks for a sum of the first and second numbers of steps over a sum of the first and second periods of time. The first and second periods of time occur on one calendar date. In this example, the number of steps are provided to the sever processor by a pedometer.

The method 851 includes an operation 861 of sending the metric to a calendar application with integration instructions. For example, the metric and the integration instructions are sent via the network 176 to the wireless communication device or a wired communication device of a monitoring device. As yet another example, the metric and the integration instructions are sent via the network 176 to the NIC of the computing device 166. In this example, a communication device, e.g., wired communication device, wireless communication device, etc., of the computing device 166 then sends the metric and the integration instructions to a corresponding communication device, e.g., wired communication device, wireless communication device, etc., of a monitoring device.

The calendar application includes an application executing on a virtual machine, or an application executing on the server 228, or an application executing on the computing device 166, or an application executing on a monitoring device. The calendar application is executed by a processor. For example, the calendar application is executed by the processor 234 (FIG. 3A), the processor 302 (FIG. 3B), the processor 226 (FIG. 5), or the processor 190 (FIG. 2A). The calendar application is executed by a processor to generate a calendar of dates, which may include a day of a week. Examples of a calendar include a calendar 1002 (FIGS. 14-1 and 14-2), a calendar 1004 (FIGS. 15-1 and 15-2), a calendar 1038 (FIGS. 17-1 and 17-2), and a calendar 1040 (FIGS. 18-1 and 18-2), each of which is a GUI. In a number of embodiments, the calendar application is executed by a processor to generate a calendar of weeks, months, years, etc.

The integration instructions define a calendar date to which the metric defined in the operation 859 is added. For example, the integration instructions provide that the 6000 steps be added to a calendar date of Saturday, March 3. As another example, the integration instructions provide that a bed time of 11:35 PM, which is a time at which the user 112A went to bed, be added to a calendar date of Saturday, March 4.

The integration instructions further include format data for presenting the metric on a calendar that is rendered by the calendar application. The format data includes a size of the metric, or a shape of the metric, or a color of the metric, or a shade of the metric, or a texture of the metric, or a graphical property of the metric, or a graphical element to represent the metric, or a combination thereof. In some embodiments, the integration instructions include a location of a metric on the calendar.

Figure 10:
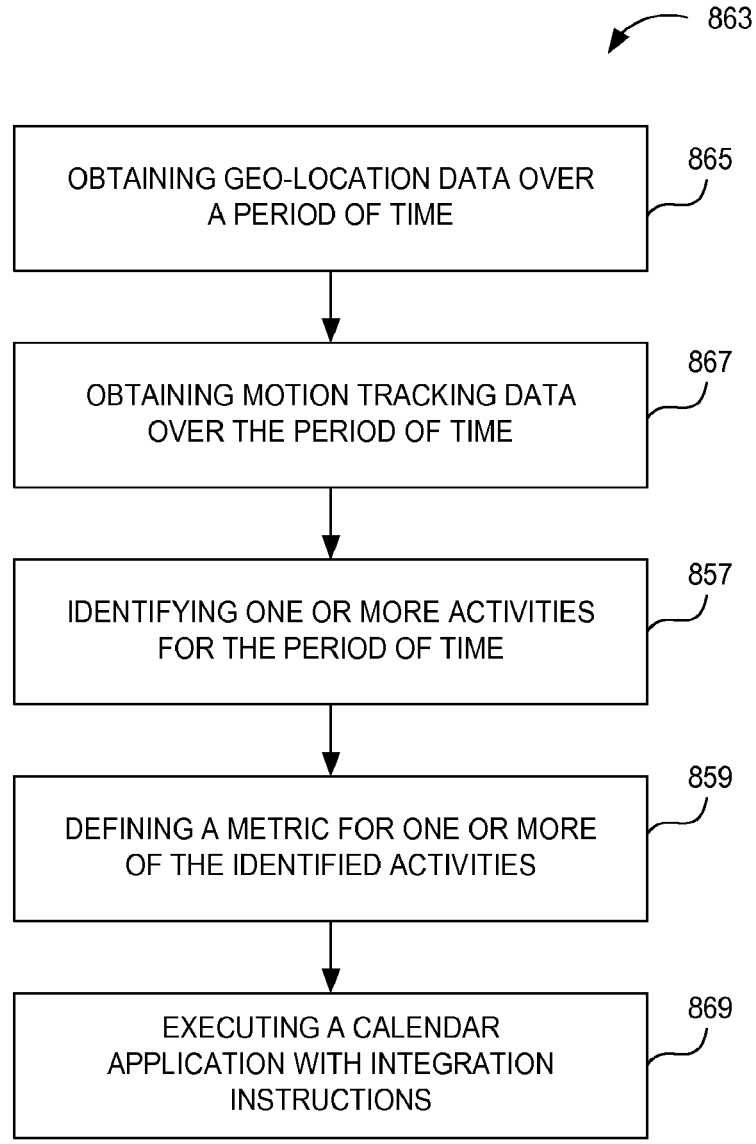
FIG. 10 is a flowchart of another method for generating a calendar of activities performed by a user and of locations at which the activities are performed, in accordance with one embodiment described in the present disclosure.

FIG. 10 is a flowchart of an embodiment of a method 863 for generating a calendar of activities performed by the user 112A and of locations at which the activities are performed. The method 863 is executed by a monitoring device or the computing device 166.

The method 863 includes an operation 865 of obtaining geo-location data over a period of time. The operation 865 is performed by the device locator of a monitoring device or by the device locator of the computing device 166 (FIG. 5). The operation 865 is the same as the operation 118 (FIG. 6A).

The method 863 includes obtaining, in an operation 867, motion tracking data over the period of time. The operation 867 is performed by the position sensor of a monitoring device or by a position sensor of the computing device 166. The operation 867 is the same as the operation 104 of FIG. 6A.

The method 863 includes the operations 857 and 859.

The method 863 includes an operation 869 of executing the calendar application and the integration instructions. The operation 869 is performed by the processor of the monitoring device or the processor of the computing device 166.

Figure 11A:
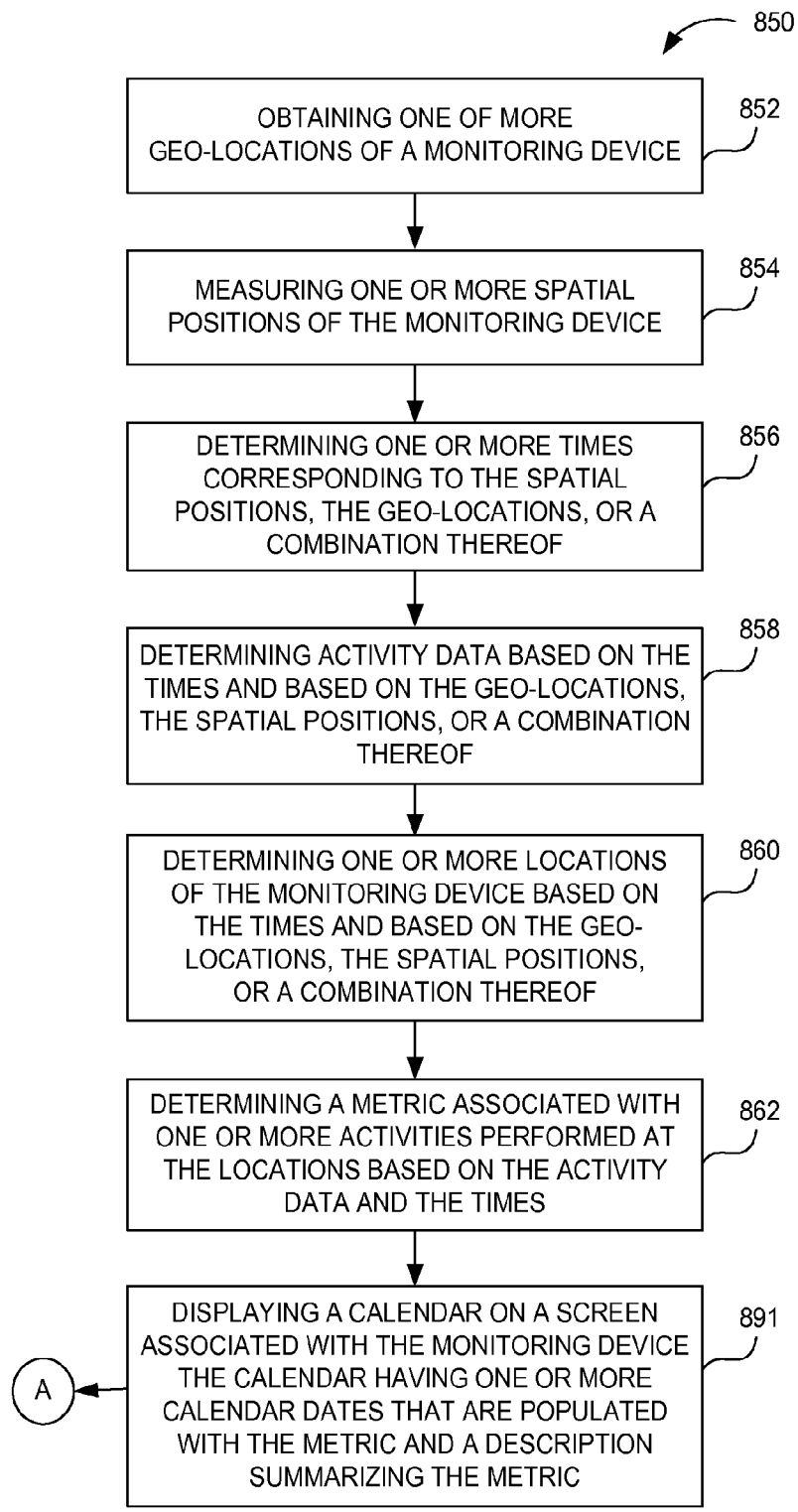
FIG. 11A is a flowchart of yet another method for generating a calendar of activities performed by a user and of locations visited by the user in performing the activities, in accordance with one embodiment described in the present disclosure.
Figure 11B:
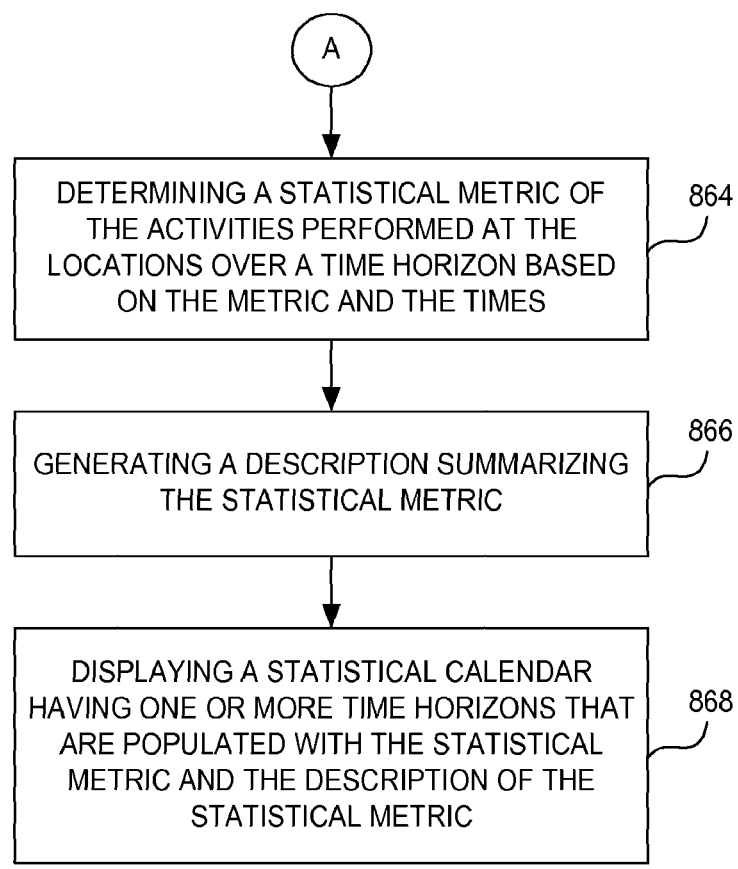
FIG. 11B is a continuation of the flowchart of FIG. 11A.

FIG. 11A is a flowchart of an embodiment of a method 850 for generating a calendar of activities performed by the user 112A and of locations visited by the user 112A in performing the activities. The method 850 is executed by a monitoring device or the computing device 166.

The method 850 includes an operation 852 of obtaining one or more geo-locations of a monitoring device. The operation 852 is performed by the device locator of a monitoring device or by the device locator of the computing device 166 (FIG. 5). In the operation 852, a longitude and a latitude of a monitoring device is measured. In some embodiments, in the operation 852, an altitude of a monitoring device is measured. In various embodiments, a longitude, a latitude, and an altitude of a monitoring device are measured.

The method 850 further includes an operation 854 of obtaining, e.g., measuring, etc., one or more spatial positions of a monitoring device. In several embodiments, the spatial positions of the computing device 166 are measured. The operation 854 is performed by the position sensor of a monitoring device, or by a position sensor of the computing device 166. In the operation 867, spatial positions of a monitoring device with reference to the xyz co-ordinate system are measured.

The method 850 includes an operation 856 of determining one or more times, e.g., the times $t_A$, $t_B$, $t_C$, $t_D$, (FIGS. 1B, 1C, 1D, 1E), etc., corresponding to the spatial positions, the geo-locations, or a combination thereof. The operation 856 is performed by the time measurement device of a monitoring device, or a time measurement device (not shown) of the computing device 166 (FIG. 5). The time measurement device of the computing device 166 is coupled to the bus 360 (FIG. 5).

In the operation 856, a time at which a monitoring device is at a position is measured. Moreover, in some embodiments, in the operation 856, a time at which a monitoring device is at a geo-location is measured. In various embodiments, in the operation 856, a time at which a monitoring device is at a position and is at a geo-location is measured.

The method 850 further includes determining, in an operation 858, activity data based on the times and the geo-locations, or the spatial positions, or a combination of the geo-locations and the spatial positions. For example, in the operation 858, an activity performed by the user 112A is determined based on the times and the geo-locations. To illustrate, when the user 112A travels from a first geo-location to a second geo-location in an amount of time ranging between t1 and t2, the user 112A is walking. As another example, when the user 112A travels from the first geo-location to the second geo-location in an amount of time between t3 and t4, the user 112A is running. As yet another example, when the user 112A travels from the first geo-location to the second geo-location in an amount of time between t5 and t6, the user 112A is in a vehicle.

As another example, in the operation 858, an activity performed by the user 112A is determined based on the times and the spatial positions. For example, when all positions of a hand motion performed by the user 112A in a period of time lie within a standard deviation of a plane parallel to the x-axis and is within a range of positions along a z-axis of the xyz co-ordinate system, and the positions are repeated periodically, the user 112A is playing a sport. As another example, when all positions of a hand motion over a time period performed by the user 112A are between an underarm and an overarm, the user 112A is playing softball or baseball or golf. As another example, when all positions of a hand of the user 112A are at the same xyz co-ordinate over a period of time, the user 112A is sleeping or resting.

As yet another example, in the operation 858, an activity performed by the user 112A is determined based on the times, the spatial positions, and the geo-locations. For example, when all positions of a hand motion performed by the user 112A are between an underarm and an overarm and all geo-locations at which the positions occur indicate a softball field, the user 112A is playing softball. As another example, when all positions of a hand motion performed by the user 112A are between an underarm and an overarm and all geo-locations at which the positions occur indicate a golf course, the user 112A is playing golf.

The operation 858 is performed by the processor of a monitoring device or by the processor of the computing device 166.

The activity data determined in the operation 858 includes one or more activity levels, e.g., the activity levels $146_1$ and $146_2$ (FIG. 7A), etc., and one or more classes of activities, e.g., walking, running, sports, sleeping, sedentary, active, passive, jogging, strolling, standing, sitting, etc., detected by a monitoring device. For example, the position sensor of a monitoring device measures an amount of calories burned by the user 112A, or a number of steps walked or ran by the user 112A, or a number of stairs climbed by the user 112A, or a number of stairs descended by the user 112A, or a combination thereof, etc.

The method 850 includes an operation 860 of determining one or more locations of the monitoring device 108A based on the times and based on the geo-locations, the spatial positions, or a combination of the spatial positions and the geo-locations. For example, when all positions of a hand motion performed by the user 112A between times t1 and t2 are between an underarm and an overarm and all geo-locations at which the positions indicate that the user 112A is standing and at a golf course while performing the hand motion, the user 112A is at the golf course between the times t1 and t2. As another example, when all geo-locations of the user 112A between times t1 and t2 correspond to a golf course as determined from the geo-location-location database, the user 112A is at the golf course between times t1 and t2.

In some embodiments, the one or more locations determined in the operation 860 are of the monitoring device 108B. In various embodiments, the one or more locations determined in the operation 860 are of the computing device 166.

The operation 860 is performed by the processor of a monitoring device or by the processor of the computing device 166.

The method 850 includes an operation 862 of determining the metric and a description summarizing the metric. The metric is associated with the activities performed at the locations based on the activity data and the times that are determined in the operation 856. For example, it is determined that the user 112A has taken 52 steps per minute while at home on March 3, Saturday. As another example, it is determined that the user 112A is at his home for 0.11 hours on March 3, Saturday. As yet another example, it is determined that the user 112A went to bed at 11:26 PM on March 3, Saturday. As yet another example, it is determined that the user was sedentary for 1:05 hours on March 3, Saturday and based on this determination, it is further determined that the user 112A sat around on March 3, Saturday. As another example, it is determined that the user 112A was in a vehicle for 201 minutes on March 3, Saturday and based on this determination, it is also determined that the user 112A drove a lot on March 3, Saturday. As yet another example, it is determined that the user 112A woke up at 10:00 AM on March 3, Saturday and this determination is compared with a threshold time, e.g., 7 AM, 8 AM, etc., to determine that the user 112A woke up late.

Examples of a description summarizing a metric include a description $994_1$, a description $994_2$, a description $994_3$, a description $996_1$, a description $996_2$, a description $996_3$, a description 1004, a description 1006, a description 1008, a description $1010_1$, and a description $1010_2$. The descriptions $994_1$, $994_2$, $994_3$, $996_1$, $996_2$, and $996_3$ are shown below in FIG. 13. The descriptions 1004, 1006, 1008, $1010_1$, and $1010_2$ are shown below in FIG. 14.

A summary of a metric is generated based on activity levels of one or more activities performed for one or more time periods. For example, it is determined that the metric determined in the operation 862 is less than a boundary, is equal to the boundary, or is greater than the boundary. In this example, when the metric is less than the boundary, a description, e.g. "I did not drive a lot", "I woke up late", "I went to bed late", "I sat around", etc., is generated based on an activity performed by the user 112A. To illustrate, when the user 112A has walked 10,000 steps in a day, a description, "I did not walk a lot" is generated for the day. As another illustration, when the user 112A is driving less than 10 miles in a day, a description, "I did not drive a lot" is generated for the day.

Moreover, in this example, when the metric is equal to the boundary, a description, e.g. "I drove", "I woke up", "I went to bed", "I went to bed on time", etc., is generated based on an activity performed by the user 112A. To illustrate, when the user 112A has walked 12,000 steps in a day, a description, "I walked" is generated for the day. As another illustration, when the user 112A is has driven 20 miles in a day, a description, "I drove" is generated for the day.

In some embodiments, the boundary is a range between two numbers. For example, instead of a boundary of 12,000 steps a day, the boundary is between 11,000 and 13,000 steps a day. As another example, instead of a boundary of 15 miles a day, the boundary is between 11 and 19 miles a day.

Furthermore, in this example, when the metric is greater than the boundary, a description, e.g. "I drove a lot", "I woke up early", "I went to bed early", etc., is generated based on an activity performed by the user 112A. To illustrate, when the user 112A has walked 25,000 steps a day, a description, "I walked a lot" is generated for the day. As another illustration, when the user 112A has driven 40 miles in a day, a description, "I drove a lot" is generated for the day.

The operation 862 is performed by the processor of a monitoring device or by the processor of the computing device 166.

The method 850 includes an operation 891 of displaying a calendar on a display screen associated with a monitoring device or with the computing device 166. For example, the calendar 1004 (FIGS. 15-1 and 15-2) is displayed on a display screen of the display device of the monitoring device 108A (FIG. 3A). As another example, the calendar 1002 is displayed on a display screen of the display device of the monitoring device 108B (FIG. 3B). As another example, the calendar 1002 is displayed on a display screen of the display device of the computing device 166. The operation 891 is performed by the display device 276, the display device 304, or by the display device 352 of the computing device 166. In some embodiments, the operation 863 is performed by the processor of a monitoring device 108B or by the processor of the computing device 166.

The calendar has one or more calendar dates, e.g., the calendar date 990 (FIG. 13), the calendar date 992 (FIG. 13), etc., that are populated with the metric and the description summarizing the metric. The operation of populating a calendar is performed by the processor of a monitoring device or by the processor of the computing device 166. In some embodiments, a calendar has one or more calendar dates that are populated with the metric or a description summarizing the metric.

The method 850 further includes an operation 864 of determining a statistical metric of the activities performed at the locations over a time horizon. For example, an average number of steps taken by the user 112A at a home of the user over a course of a week is calculated. As another example, an average wake-up time over a course of a month is calculated. As another example, an average bed time and an average wake-up time during a week are calculated. As another example, an average amount of time spent in a vehicle during a month is calculated. As an example, an average amount of time spent at a location each day during a course of a week or a month is calculated. As an example, an average amount of time spent performing an activity each day during a course of a week or a month is calculated. As yet another example, an average amount of time spent by the user 112A in a vehicle over a course of a year is calculated. Other examples of a statistical metric include a median of metrics of multiple activities performed at a location over the time horizon, a standard deviation of metrics of multiple activities performed at a location over the time horizon, a moving average of metrics of multiple activities performed at a location over the time horizon, or a combination thereof, etc. Yet other examples of a statistical metric include a median of metrics of an activity determined at multiple locations over the time horizon, a standard deviation of metrics of an activity determined at multiple locations over the time horizon, a moving average of metrics of an activity determined at multiple locations over the time horizon, or a combination thereof, etc.

The operation 864 is performed by the processor of a monitoring device or by the processor of the computing device 166.

Examples of a time horizon include a number of days of a week, a number of weeks, a number of months in a year, a number of years, etc.

The method 850 includes an operation 866 of generating a description summarizing the statistical metric over the time horizon. For example, it is determined that the statistical metric determined in the operation 864 is less than a limit, is equal to the limit, or is greater than the limit. In this example, when the statistical metric is less than the limit, a description, e.g. "I did not drive a lot", "I woke up late", "I went to bed late", "I sat around", etc., is generated based on an activity performed by the user 112A. To illustrate, when the user 112A is walking for an average of 10,000 steps a day in a week, a description, "I did not walk a lot" is generated for the week. As another illustration, when the user 112A is driving less than an average of 10 miles a day for a month, a description, "I did not drive a lot" is generated for the month.

Moreover, in this example, when the statistical metric is equal to the limit, a description, e.g. "I drove", "I woke up", "I went to bed", "I went to bed on time", etc., is generated based on an activity performed by the user 112A. To illustrate, when the user 112A is walking for an average of 12,000 steps a day in a week, a description, "I walked" is generated for the week. As another illustration, when the user 112A is driving an average of 20 miles a day for a month, a description, "I drove" is generated for the month.

In some embodiments, the limit is a range between two numbers. For example, instead of a limit of 12,000 steps a day, the limit is between 11,000 and 13,000 steps a day. As another example, instead of a limit of 15 miles a day, the limit is between 11 and 19 miles a day.

Furthermore, in this example, when the statistical metric is greater than the limit, a description, e.g. "I drove a lot", "I woke up early", "I went to bed early", etc., is generated based on an activity performed by the user 112A. To illustrate, when the user 112A is walking for an average of 25,000 steps a day in a week, a description, "I walked a lot" is generated for the week. As another illustration, when the user 112A is driving an average of 40 miles a day for a month, a description, "I drove a lot" is generated for the month.

Figure 16:
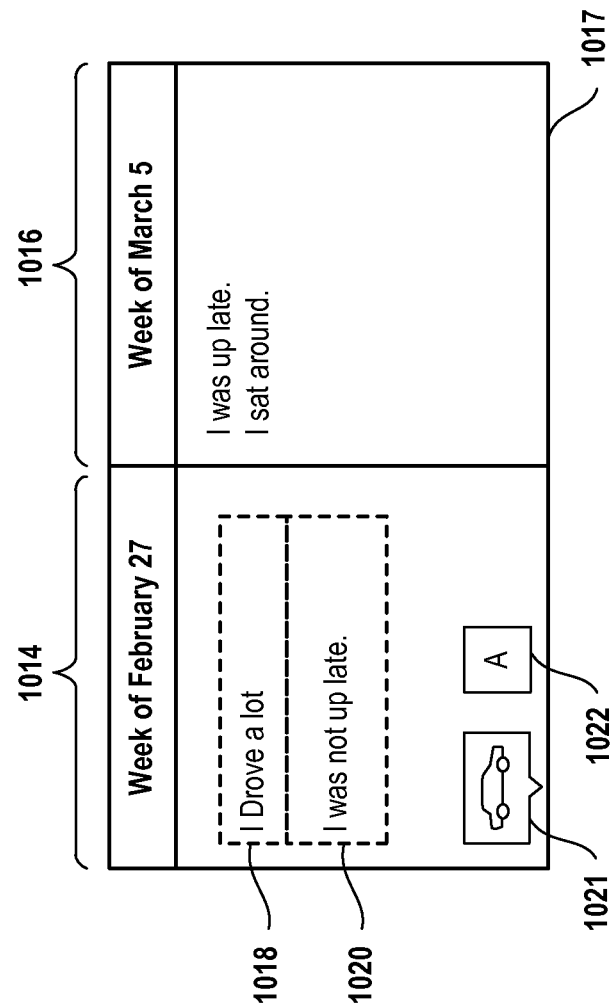
FIG. 16 is a diagram of a calendar representing weeks of activities performed by a user, in accordance with one embodiment described in the present disclosure.

Examples of a description summarizing the statistical metric are provided as a description 1018 (FIG. 16) and a description 1020 (FIG. 16).

The operation 866 is performed by the processor of a monitoring device or by the processor of the computing device 166.

The method 850 includes an operation 868 of displaying a statistical calendar on the screen associated with a monitoring device or with the computing device 166. For example, a statistical calendar 1017 (FIG. 16) is displayed on a display screen of the display device of the monitoring device 108A (FIG. 3A). The statistical calendar includes one or more time horizons that are populated with the statistical metric determined in the operation 864 and with the description generated in the operation 866.

The operation 868 is performed by the display device of a monitoring device or by the display device 352 of the computing device 166. In some embodiments, the operation 868 is performed by the processor of a monitoring device 108B or by the processor of the computing device 166.

The statistical calendar has one or more time horizons, e.g., a calendar week 1014 (FIG. 16), a calendar week 1016 (FIG. 16), etc., that are populated with the statistical metric and the description summarizing the statistical metric. Each calendar week 1014 and 1016 is a GUI. The operation of populating a statistical calendar is performed by the processor of a monitoring device or by the processor of the computing device 166. In some embodiments, a statistical calendar has one or more time horizons that are populated with the statistical metric or a description summarizing the statistical metric.

Figure 12A:
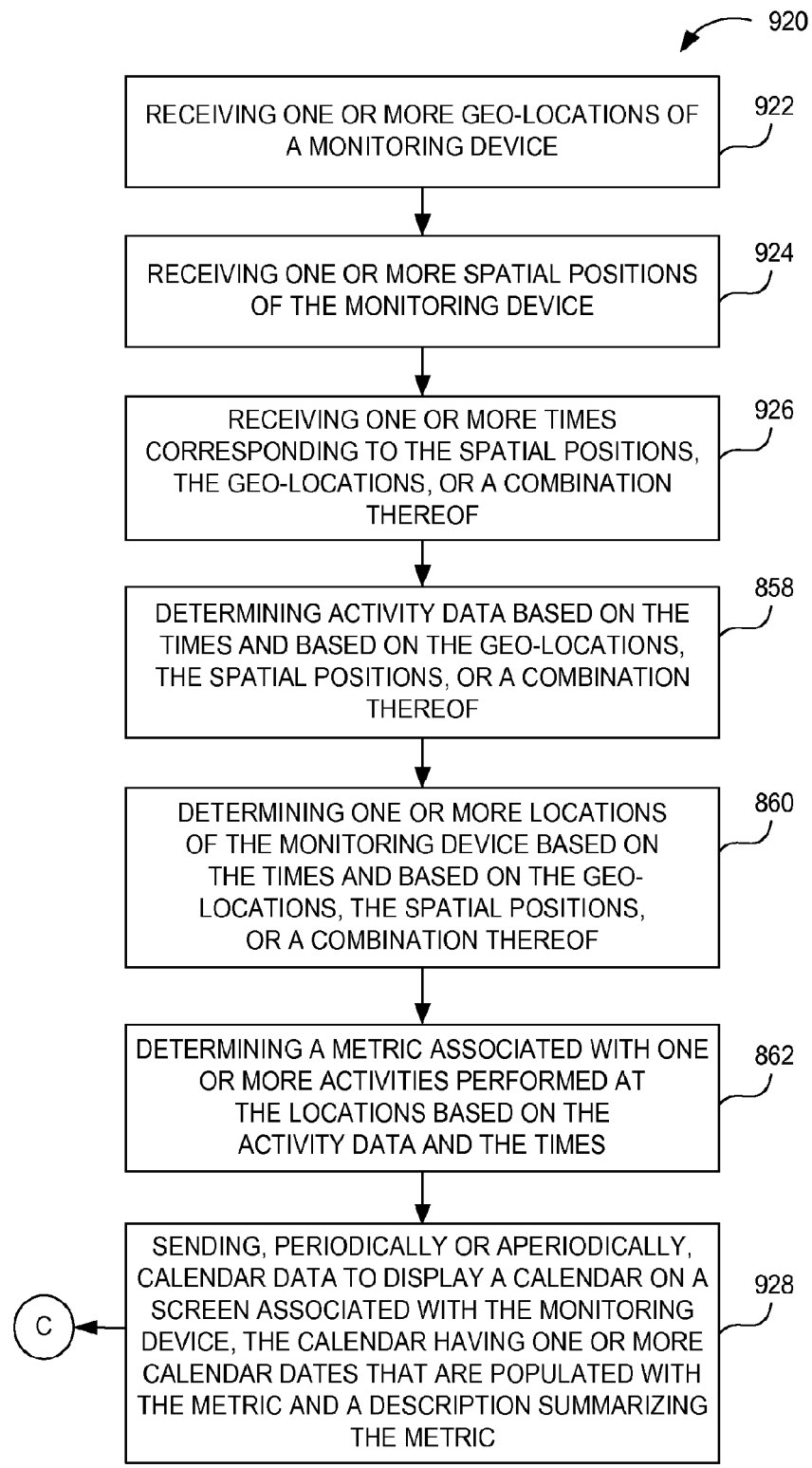
FIG. 12A is a flowchart of another method for generating a calendar of activities performed by a user and of locations visited by the user in performing the activities, in accordance with one embodiment described in the present disclosure.

FIG. 12A is a flowchart of an embodiment of a method 920 facilitating display of a calendar of activities performed by the user 112A and of locations visited by the user 112A in performing the activities. The method 920 is executed by the server 228.

The method 920 includes an operation of receiving 922 one or more geo-locations of a monitoring device. The operation 922 is the same as the operation 853 (FIG. 9) except that times at which the geo-location data is collected is received in an operation 926.

The method 920 further includes an operation 924 of receiving one or more spatial positions of a monitoring device. The operation 924 is the same as the operation 855 except that times at which motion tracking data is collected is received in the operation 926.

The method 920 includes an operation 926 of receiving one or more times corresponding to the spatial positions, the geo-locations, or a combination thereof. For example, times at which geo-locations are measured are received by the NIC of the server 228 via the network 176 from a communication device of a monitoring device. As yet another example, times at which spatial positions are measured are received by the NIC of the server 228 (FIG. 2A) via the network 176 from the NIC of the computing device 166 (FIG. 5). In this example, the geo-location data and the spatial positions are sent by the NIC of the computing device 166 to the server 228 after a communication device of the computing device 166 receives the geo-location data and the spatial positions from a communication device of a monitoring device.

The operation 926 of receiving is performed by the NIC of the server 228.

The method 920 includes performing the operations 860 and 862.

The method 920 includes performing an operation 928 of sending, periodically or aperiodically, calendar data to display a calendar. For example, the calendar data is sent via the network 176 to the wireless communication device or a wired communication device of a monitoring device. As yet another example, the calendar data is sent via the network 176 to the NIC of the computing device 166. In this example, a communication device of the computing device 166 then sends the calendar data to a communication device of a monitoring device.

Figure 12B:
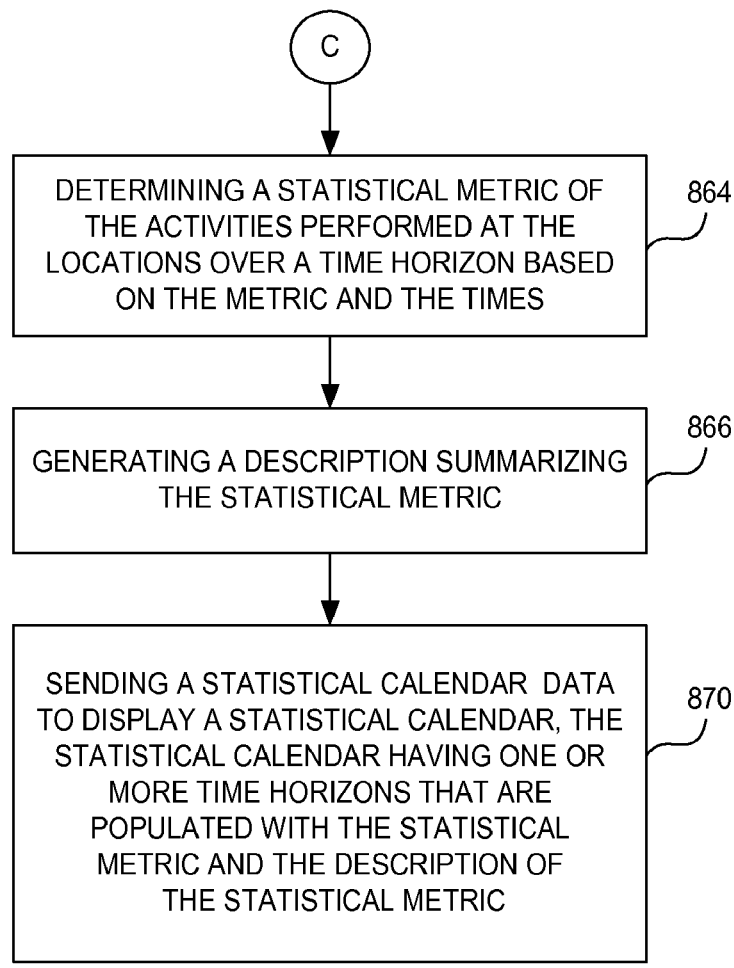
FIG. 12B is a continuation of the flowchart of FIG. 12A.

FIG. 12B is a continuation of the flowchart of FIG. 12A. The method 920 includes performing the operations 864 and 866.

The method 920 includes performing an operation 870 of sending the statistical calendar data. For example, the statistical calendar data is sent via the network 176 to the wireless communication device or a wired communication device of a monitoring device. As yet another example, the statistical calendar data is sent via the network 176 to the NIC of the computing device 166. In this example, a communication device of the computing device 166 then sends the statistical calendar data to a communication device of a monitoring device.

In some embodiments, calendar data is sent for display when a selection is received from the user 112A indicating that the calendar having the calendar data is to be displayed on the display device of a monitoring device or on the display device of the computing device 166. The user 112A selects the calendar for display by selecting the user interface of a monitoring device or by selecting the input device of the computing device 166. The selection indicating that the calendar is to be displayed is received from the wireless communication device or a wired communication device of a monitoring device, or from the NIC of the computing device 166. The selection is received by the NIC of the server 228.

Similarly, in various embodiments, statistical calendar data is sent for display when a selection is received from the user 112A indicating that the statistical calendar having the statistical calendar data is to be displayed on the display device of a monitoring device or on the display device of the computing device 166.

FIG. 13 is a diagram of an embodiment of a calendar GUI 1070 and another calendar GUI 1072. The calendar GUI 1070 includes the calendar date 990, the descriptions 994$_1$, 994$_2$, and 994$_3$, and the metrics 950, 952, 954, 962, 970, 972, 974, 976, 978, and 966.

Each metric of the calendar GUI 1070 is an amount of activity, e.g., an activity level, etc., performed by the user 112A on March 3, Saturday. For example, the metric 950 is a number of steps taken by the user 112A on March 3, Saturday. As another example, the metric 52 steps per minute is an amount of steps per minute taken by the user 112A at a home of the user 112A on March 3.

Similarly, each metric of the calendar GUI 1072 is an amount of activity performed by the user 112A on March 4. The calendar GUI 1072 includes the calendar date 992, the descriptions 996$_1$, 996$_2$, and 996$_3$, and the metrics 956, 958, 960, 964, 980, 982, 984, 986, 988, and 968.

In some embodiments, each of calendar GUI 1070 and GUI 1072 is coded, e.g., color-coded, shade-coded, texture-coded, shape-coded, etc., to distinguish an activity level or a metric represented with the GUI 1070 from an activity level or metric represented with the GUI 1072. For example, the GUI 1072 is coded as green and the GUI 1070 is coded as yellow to indicate the user 112A walked more steps on the calendar date 992 than that walked on the calendar date 990. As another example, the GUI 1072 is color-coded differently than the GUI 1070 when a weighted combination, e.g., a weighted sum, etc., of the metrics represented within the GUI 1070 is greater than a weighted combination of the metrics represented within the GUI 1072.

Any coding of a calendar GUI is performed by the processor of a monitoring device, the processor of the computing device 166, or the processor of the server 228. Moreover, a weighted combination of metrics of statistical metrics is calculated by the processor of a monitoring device, the processor of the computing device 166, or the processor of the server 228.

In several embodiments, a calendar GUI does not display metrics until an action to display the metrics is received from the user 112A. For example, when the user 112A uses the user interface of a monitoring device or the input device of the computing device 166 to hover over or select a description summarizing metrics, the metrics are displayed within the calendar GUI. An indication of hovering or the selection is received by the processor of a monitoring device or the processor of the computing device 166. Also, the displaying is performed by the processor of a monitoring device or the processor of the computing device 166.

In some embodiments, a calendar GUI does not display statistical metrics until an action to display the statistical metrics is received from the user 112A. For example, when the user 112A uses the user interface of a monitoring device or the input device of the computing device 166 to hover over or select a description summarizing statistical metrics, the statistical metrics are displayed within the calendar GUI. An indication of hovering or the selection is received by the processor of a monitoring device or the processor of the computing device 166. Also, the displaying is performed by the processor of a monitoring device or the processor of the computing device 166.

FIGS. 14-1 and 14-2 are diagrams of an embodiment of the calendar 1002. The calendar 1002 includes descriptions of metrics of activities performed by the user 112A for a week ranging from Sunday, February 26 thru Saturday, March 3. For example, the calendar 1002 includes the descriptions 1004, 1006, 1008, 1010$_1$, and 1010$_2$. In addition the calendar 1002 includes descriptions "I drove a lot", "I walked a lot", and "I sat around" of metrics of activities performed by the user 112A on Thursday, March 1. Moreover, the calendar 1002 includes descriptions "I did not walk a lot", "I worked late", and "I was up late" of metrics of activities performed by the user 112A on Friday, March 2. The calendar 1002 includes descriptions "I went for a run!", "I drove a lot", "I walked a lot", and "I sat around" of metrics of activities performed by the user 112A on Saturday, March 3.

FIGS. 15-1 and 15-2 are diagrams of an embodiment of the calendar 1004. The calendar 1004 includes descriptions of summaries of metrics of activities performed by the user 112A. Moreover, the calendar 1004 includes activity identifiers 132B and 132D.

Each activity identifier of the calendar 1004 identifies a summary of the metrics for a calendar date. For example, the activity identifier 132D indicates that the user 112A walked a lot on Sunday, February 28. As another example, the activity identifier 132B indicates that the user 112A walked a lot on Saturday, March 3 and the activity identifier 132D indicates that the user 112A played golf on Saturday, March 3. As another example, an activity identifier 1005 indicates that the user 112A did not walk a lot on Monday, February 27.

Moreover, each location identifier identifies a summary of one or more locations visited by the user 112A for a calendar date. For example, the location identifier $802_1$ indicates that the user 112A spend most of Monday, February 27 in his office.

In some embodiments, a summary of a location of a user on a calendar date is determined in a manner similar to determining a summary of an activity performed by the user on the calendar date. For example, upon determining that a majority of hours of a day are spent at home, a summary is generated indicating that the user spent most of his time on the day at his home. The majority of hours and the location are determined based on geo-location data, the geo-location-location database, and times, which are measured by a time measurement device. In some embodiments, the location is inferred from activity data. The summary of the location is determined by the processor of a monitoring device, the processor of the computing device 166, or the processor of the server 228. Examples of a summary of a location include "I was at work most of my day", "I was mainly at home today", etc.

Upon determining a summary of a location of the user 112A on a calendar date, the calendar 1004 is populated with a location identifier identifying the summary. The population of a calendar with the summary of the location and with the location identifier is performed by the processor of a monitoring device, the processor of the computing device 166, or the processor of the server 228.

Each activity identifier and each location identifier of the calendar 1004 is generated by the processor of a monitoring device, the processor of the computing device 166, or the processor of the server 228.

The calendar 1004 includes an award identifier 1012 that identifies a reward provided to the user 112 for achieving a milestone or a goal. One or more milestones are achieved to achieve a goal. In some embodiments, a milestone is a goal.

A goal is related to an activity, a location, or a time period, or a combination thereof. For example, a goal is to walk 20,000 steps at home. Another goal is to walk 20,000 steps today. Yet another goal is to burn an amount of calories by a date.

Similarly, a milestone is related to an activity, a location, or a time period. For example, a milestone is to walk 100 steps in 15 minutes. Another milestone is to run 3 miles each day at a park.

An award identifier, e.g., a badge, etc., is generated by the processor of a monitoring device, the processor of the computing device 166, or the processor of the server 228, when the processor determines that a goal or a milestone is achieved by the user 112A. The award identifier 1012 is generated when the user 112A walked a lot on Sunday, February 26.

FIG. 16 is a diagram of an embodiment of the calendar week 1014 and the calendar week 1016. The calendar weeks 1014 and 1016 are parts of the statistical calendar 1017, which is also a GUI. The calendar week 1014 includes the description 1018 and the description 1020. Similarly, the calendar week 1016 includes a description "I was up late" of a statistical metric, e.g., waking up after a time, etc., of an activity, e.g., waking up, etc., The calendar week 1016 also includes a description "I sat around" of a statistical metric, e.g., calories burned, steps walked, etc., of an activity, e.g. walking, etc.

In various embodiments, a description of an activity performed by the user 112A during the time horizon is identified using an activity identifier. For example, an activity identifier 1021 is generated to indicate that the user 112A drove a lot during the week of February 27. An activity identifier identifying one or more activities performed by the user 112A during the time horizon is generated by the processor of a monitoring device, the processor of the computing device 166, or the processor of the server 228.

In some embodiments, a summary of a location of a user during the time horizon is determined in a manner similar to determining a summary of a location of the user on a calendar date. For example, upon determining that a majority of hours of a week are spent at home, a summary is generated indicating that the user spent most of his time during the week at his home. The majority of hours and the location during the time horizon are determined based on geo-location data, the geo-location-location database, and times, which are measured by a time measurement device. In some embodiments, the location is inferred from activity data. The summary of the location during the time horizon is determined by the processor of a monitoring device, the processor of the computing device 166, or the processor of the server 228. Examples of a summary of a location visited by the user 112A during the time horizon include "I was at work most of my week", "I was mainly at home during this month", etc.

Upon determining a summary of a location of the user 112A during the time horizon, a calendar, the calendar 1014, the calendar 1016, etc., is populated with a location identifier identifying the summary. The population of a calendar with the summary of the location and with the location identifier associated with the time horizon is performed by the processor of a monitoring device, the processor of the computing device 166, or the processor of the server 228.

Each activity identifier and each location identifier of the calendars 1014 and 1016 is generated by the processor of a monitoring device, the processor of the computing device 166, or the processor of the server 228.

The calendar 1014 includes an award identifier, e.g., an award identifier 1022 etc., that identifies a reward provided to the user 112 for achieving a milestone or a goal during the time horizon. For example, the award identifier 1022 is generated when the user 112A drove a lot during the week of February 27. The award identifier is generated based on the statistical metric. For example, upon determining that the user 112A achieved a milestone or a goal during the time horizon, an award identified with an award identifier is generated and provided to the user account 174 (FIG. 2A).

An award identifier associated with the time horizon is generated based on the statistical metric by the processor of a monitoring device, the processor of the computing device 166, or the processor of the server 228. For example, upon determining that the user 112A walked an average of 10,000 steps a day for a week, an award identifier associated with the week is generated. As another example, upon determining that the user 112A ran 5 miles a day on average for two months, an award is provided to the user 112A by generation of an award identifier.

In some embodiments, each of calendar GUI 1014 and GUI 1016 is coded, e.g., color-coded, shade-coded, texture-coded, shape-coded, etc., to distinguish an activity level or a metric represented with the GUI 1016 from a statistical activity level or a statistical metric represented with the GUI 1072. For example, the GUI 1014 is coded as yellow and the GUI 1016 is coded as red to indicate the user 112A was more active during the week of February 27 than that during the week of March 5. As another example, a first calendar GUI is color-coded differently than a second calendar GUI when a weighted combination of statistical metrics represented within the first calendar GUI is greater than a weighted combination of statistical metrics represented within the second calendar GUI.

In some embodiments, the user 112A is more active for a period of time compared to another period of time when an activity level of the user 112A for the period of time is greater than an activity level of the user 112A for the other period of time. Similarly, in various embodiments, the user 112A is more active for a time horizon compared to another time horizon when an activity level of the user 112A for the time horizon is greater than an activity level of the user 112A for the other time horizon.

Figures 1, 17:
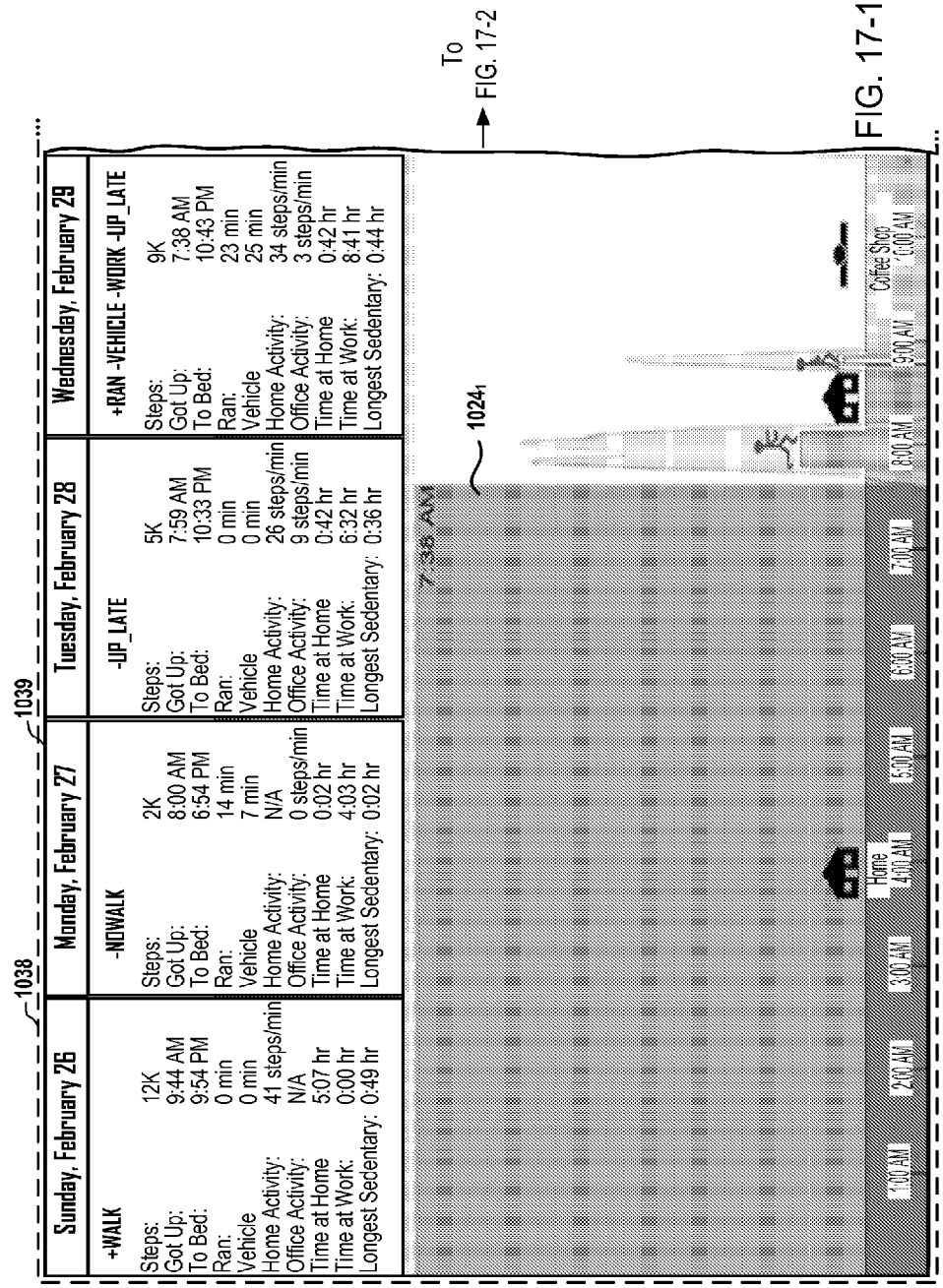
Figures 2, 17:
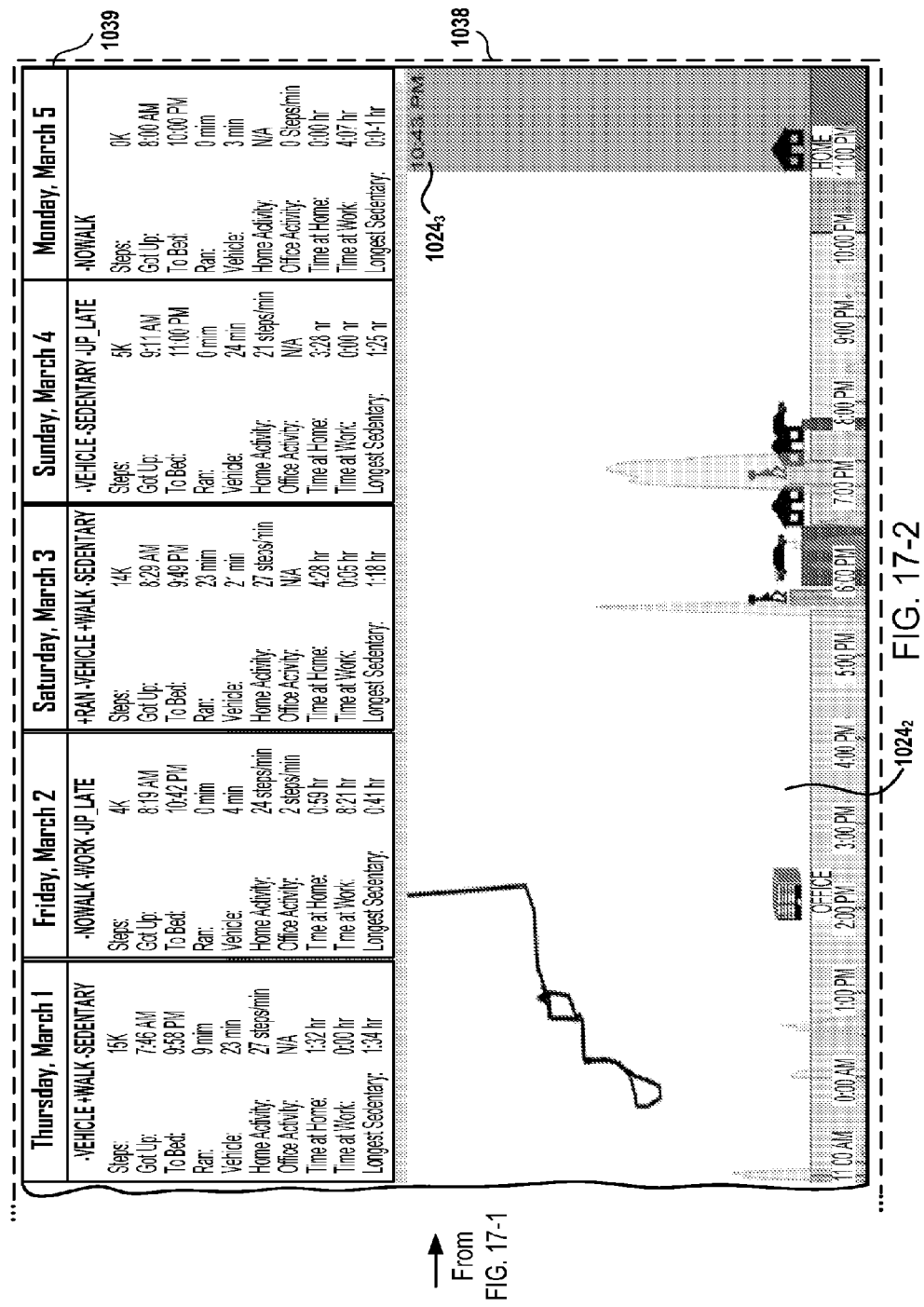

FIGS. 17-1 and 17-2 are diagrams of an embodiment of a GUI 1038. The GUI 1038 includes a calendar GUI 1039 and a group of event data $1024_1$, $1024_2$, and $1024_3$ in relation to the calendar GUI 1039. For example, the event data $1024_1$, $1024_2$, and $1024_3$ is below the calendar GUI 1039. In some embodiments, the event data $1024_1$, $1024_2$, and $1024_3$ is to the right of the calendar GUI 1039, or to the left of the calendar GUI 1039, or at any other position with respect to the calendar GUI 1039.

Figures 1, 18:
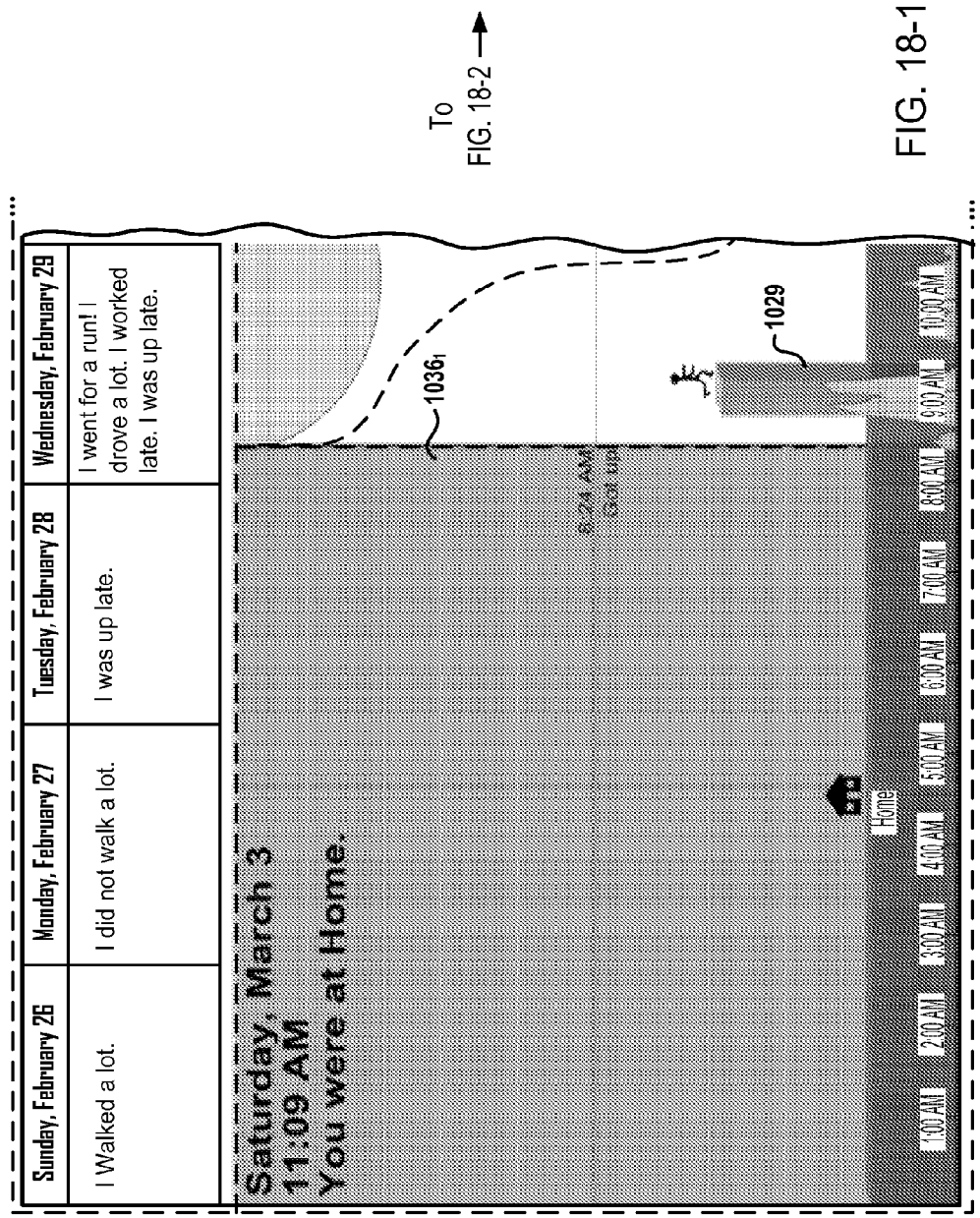
Figures 2, 18:
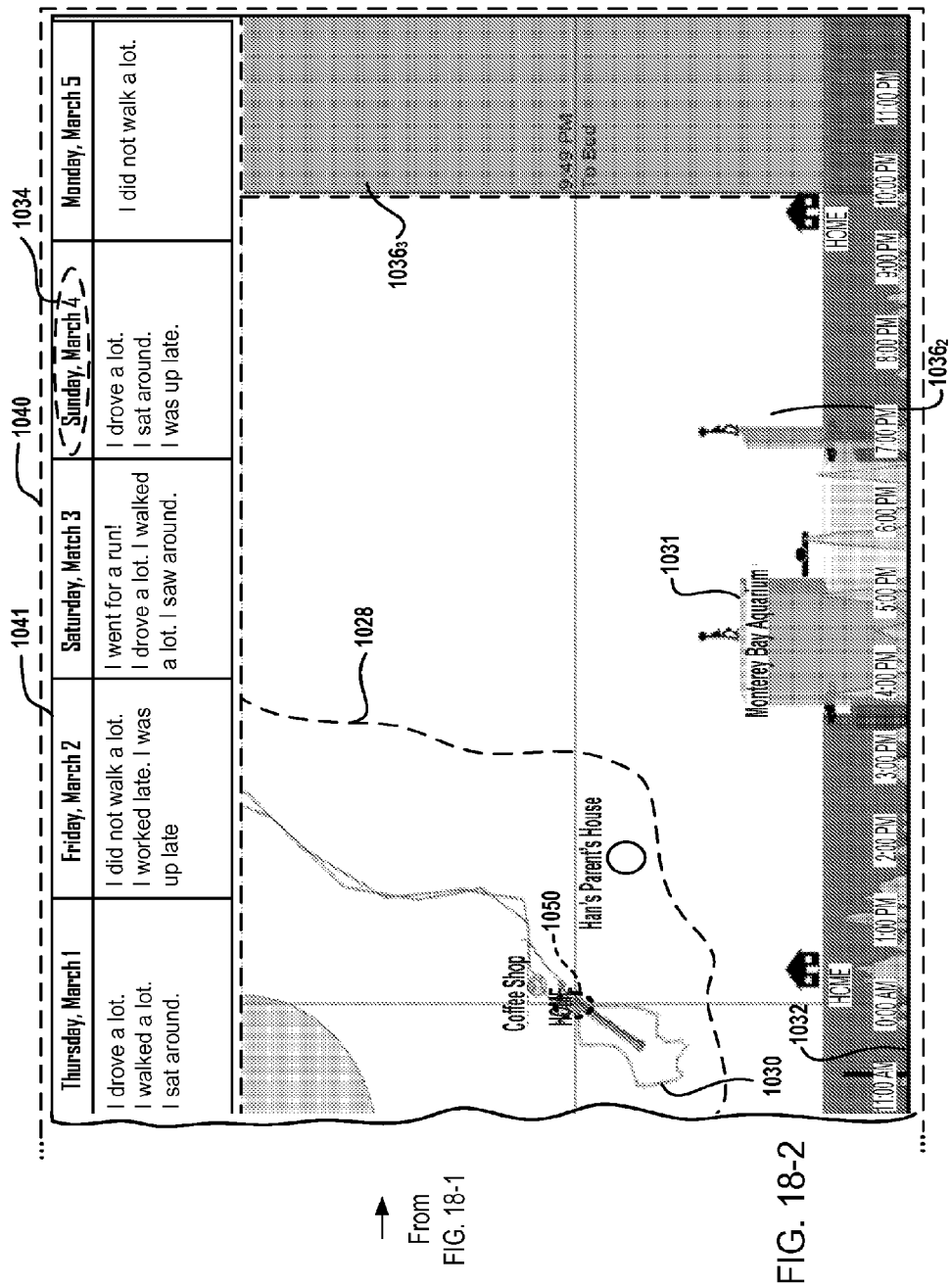

FIGS. 18-1 and 18-2 are diagrams of an embodiment of a GUI 1040. In the GUI 1040, a group of event data $1036_1$, $1036_2$, and $1036_3$ is generated in relation to, e.g., above, below, to the right of, to the left of, in any other relation, etc., a calendar GUI 1041.

In the GUI 1040, a map 1028 is overlaid on the event data $1036_2$. In some embodiments, the event data $1036_2$ is overlaid on the map 1028.

The map includes a route 1030 recorded using a monitoring device during performance of activities by the user 112A. The route 1030 is one followed by the user 112A on a calendar date of Saturday, March 3.

In some embodiments, the route 1030 shows activities performed by the user 112A on the route 1030 and locations visited by the user 112A on the route 1030. For example, an activity shown on the route 1030 is coded differently than another activity performed on the route 1030. As another example, a location on the route 1030 is coded differently than another location on the route 1030.

When a selection of an activity level 1032 is received from the user 112A via the user interface of a monitoring device or via the input device of the computing device 166, the map 1028 is centered on a location, e.g., a house, etc., at which an activity having the activity level is performed. The centering is performed by the processor of a monitoring device, the processor of the server 228, or by the processor of the computing device 166.

As shown in FIGS. 18-1 and 18-2, the map 1028 is of a different dimension than the activity data within event data. For example, activity levels 1029 and 1031 within the event data $1036_2$ are three-dimensional and the map 1028 is two-dimensional. In some embodiments, the map 1028 is three-dimensional and activity levels of event data are two-dimensional. In various embodiments, both the map 1028 and activity levels of event data are of the same dimension.

In some embodiments, the event data $1036_1$, $1036_2$, and $1036_3$ are generated when a selection of a calendar date 1034 is received from the user 112A via the user interface of a monitoring device or via the input device of the computing device 166.

The event data of FIGS. 18-1 and 18-2 is associated with the calendar date of Saturday, March 3. For example, the event data of FIGS. 18-1 and 18-2 shows activity levels of the user 112A on March 3, location identifiers identifying locations visited by the user 112A on March 3, and activity identifiers identifying activities performed by the user 112A on March 3.

Moreover, in some embodiments, upon receiving the selection of the calendar date 1034, the map 1028 is displayed with respect to, e.g., is overlaid on, is overlaid with, etc., the event data shown in FIGS. 18-1 and 18-2.

Figure 19:
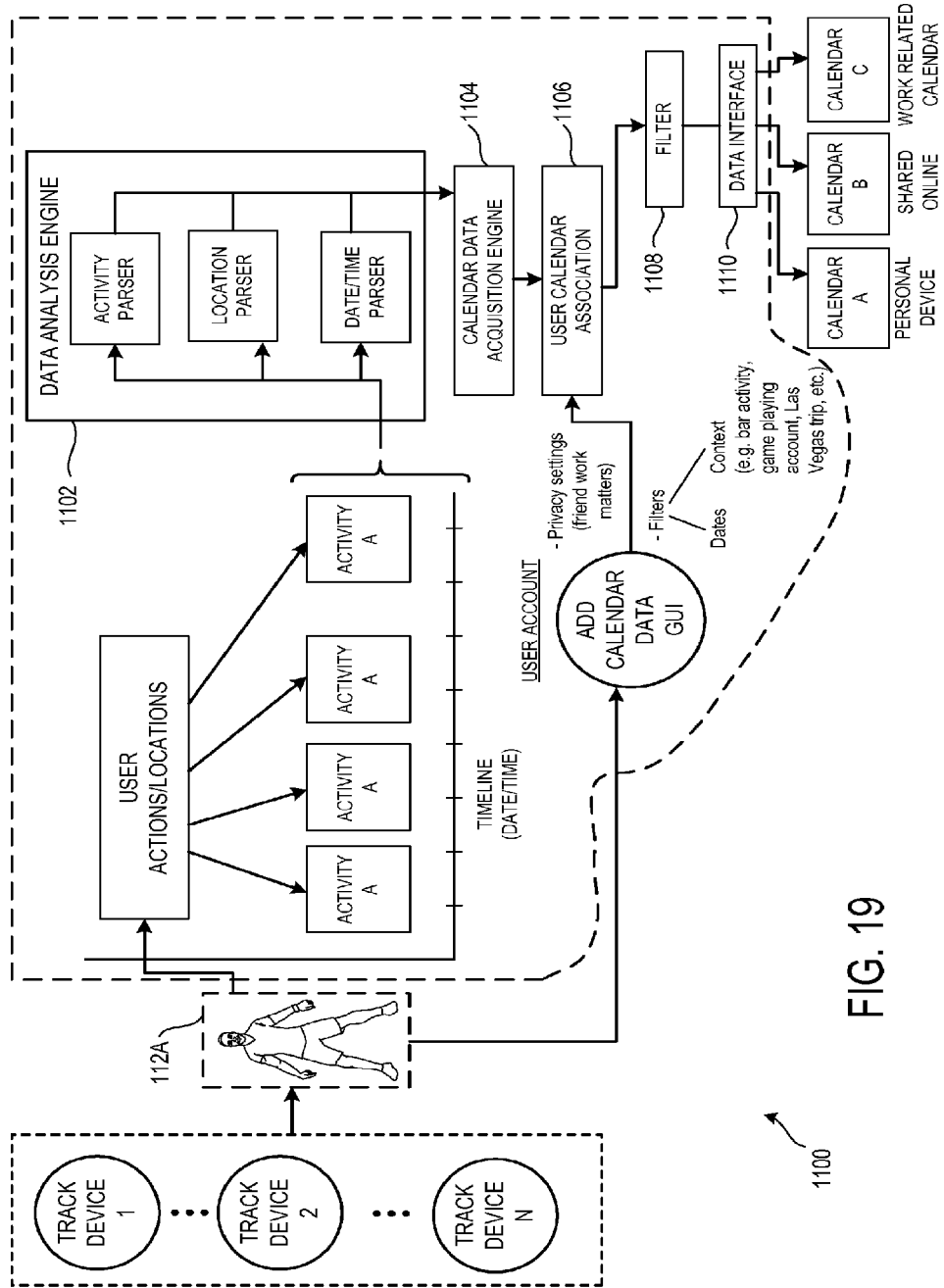
FIG. 19 is a diagram of an embodiment of a system for filtering calendar data based on filters provided by a user, in accordance with one embodiment described in the present disclosure.

FIG. 19 is a diagram of an embodiment of a system 1100 for filtering calendar data based on filters provided by the user 112A.

The user 112A is wearing one or more track devices, e.g., a track device 1, a track device 2, a track device n, where n is an integer greater than zero. The user 112A performs actions at one or more locations. Based on the actions and locations, activities A thru N are generated. Each activity A thru N includes one or more activity levels, e.g., number of calories burned, number of steps taken, number of stairs climbed, etc. The activities A thru N are plotted along a timeline that includes dates and/or times of day.

A data analysis engine 1102 parses the activities A thru N, the locations at which the activities are performed, and dates/times at which the activities are performed at the locations. For example, the data analysis engine 1102 determines that an activity is performed at a location at a time on a calendar date.

A calendar data acquisition engine 1104 acquires, e.g., receives, reads, etc., the parsed activities, the parsed locations, and the parsed dates/times from the data analysis engine 1102.

Within the user account 174 (FIG. 2A), the user 112A uses the user interface of a monitoring device or the input device of the computing device 166 to provide filters and privacy settings to the user account 174. Examples of the filters include dates of a calendar and a context of activities performed by the user 112A. For example, the user 112A provides dates between U and V to filter a GUI to remove from a calendar GUI all activities performed by the user 112A and/or all locations visited by the user 112A between the dates U and V. As another example, the user 112A provides locations to remove all activities performed at the locations by the user 112A from a calendar GUI. Examples of locations to be removed include Las Vegas, Reno, sin city, etc. As yet another example, the user 112A provides activities to be removed from a calendar GUI. Examples of activities to be removed include sleeping at work, sedentary activity at work, etc.

As another example, the user 112A provides the privacy settings that determine which group of people can view activities performed by the user 112A and/or, locations visited by the user 112A. For example, the user 112A designates that social network friends of the user 112A may view activities performed by the user 112A in Las Vegas. As another example, the user 112A designates that the user's work mates may view active activities performed by the user 112A at work. As yet another example, the user 112A designates that the user 112A may view, by accessing the user account 174, all activities performed by the user 112A at all locations.

A user calendar associator 1106 associates a calendar GUI with the filters and the privacy settings provided by the user 112A. For example, it is determined whether dates provided by the user 112A for filtering out are dates of a timeline of event data. As another example, it is determined whether activities provided by the user 112A to be filtered out are the same as those having metrics represented within a calendar. As yet another example, it is determined whether locations provided by the user 112A to be filtered out are the same as locations identified by location identifiers within a calendar. As another example, it is determined whether activities provided by the user 112A to be filtered out are the same as activities identified by activity identifiers within a calendar.

A filter 1108 is applied to a calendar GUI to filter out activities and/or locations identified by the user 112A from a calendar GUI based on the privacy settings. For example, upon determining that a calendar is to be shared online with work mates, activities related to being sedentary at work, sleeping at work, etc., are filtered out from the calendar. As another example, upon determining that a calendar is to be shared online with a social network family or social network friends, activities performed at some locations, e.g., Las Vegas, Reno, Atlantic city, etc., are filtered out. As yet another example, upon determining that a calendar is to be accessed by the user 112A via the user account 174, none of the activities and locations are filtered. In this example, no filtering of an activity and/or a location within a calendar GUI is performed by the filter 1108.

A data interface 1110 receives the filtered activities and locations from the filter 1108, and sends some of the filtered activities and locations for populating a calendar B and some of the filtered activities and locations for populating a calendar C. The data interface 1110 sends all activities and locations received without any filtering for populating a calendar A. The calendar A is a personal calendar of the user 112A and the calendar A is accessible to the user 112A via the user account 174. The calendar B is another calendar of the user 112A and the calendar is accessible by social network friends and/or social network family of the user 112A. The calendar C is yet another calendar of the user 112A and the calendar C is accessible by work mates or work social network friends of the user 112A.

It should be noted that in some embodiments, the data analysis engine 1102, the calendar data acquisition engine 1104, the user calendar associator 1106, and the filter 1106 are implemented within the processor of the server 228 and the data interface 1108 is implemented within the NIC of the server 228. For example, the data interface 1110 sends filtered activities and locations to the wireless communication device of a monitoring device or to a wired communication device of the monitoring device for populating a calendar displayed on a monitoring device. As another example, the data interface 1110 sends filtered activities and locations to the NIC of the computing device 166 and the wireless communication device or a wired communication device of the computing device 166 sends the filtered activities and locations for populating a calendar displayed on a monitoring device.

In various embodiments, the data analysis engine 1102, the calendar data acquisition engine 1104, the user calendar associator 1106, and the filter 1106 are implemented within the processor of the computing device 166 and the data interface 1108 is implemented within the wireless communication device or a wired communication device of the computing device 166. For example, the data interface 1110 sends filtered activities and locations to the wireless communication device of a monitoring device or to a wired communication device of the monitoring device.

In several embodiments, the data analysis engine 1102, the calendar data acquisition engine 1104, the user calendar associator 1106, the filter 1106, and the data interface 1110 are implemented within the processor of a monitoring device. In these embodiments, the data interface 1110 sends the filtered activities and/or the filtered locations to a display device of the monitoring device for populating a calendar with the filtered locations and/or filtered activities.

In a number of embodiments, the user 112A accesses the user account 174 to update a metric or a statistical metric that is represented in a calendar. For example, the user 112A selects an edit button besides a metric on a calendar GUI to change the metric. The selection is made by the user 112A via the user interface of a monitoring device or via the input device of the computing device 166. The updated metric or updated statistical metric is sent via the network 176 to the server 228. The processor of the server 228 updates within the user account 174 the metric or the statistical metric based on the update received. The server 228 then sends the updated metric or the updated statistical metric via the network 176 to the computing device 166 or to a monitoring device to populate a calendar, e.g., calendar A, B, C, etc., with the updated metric or the updated statistical metric.

Figure 20:
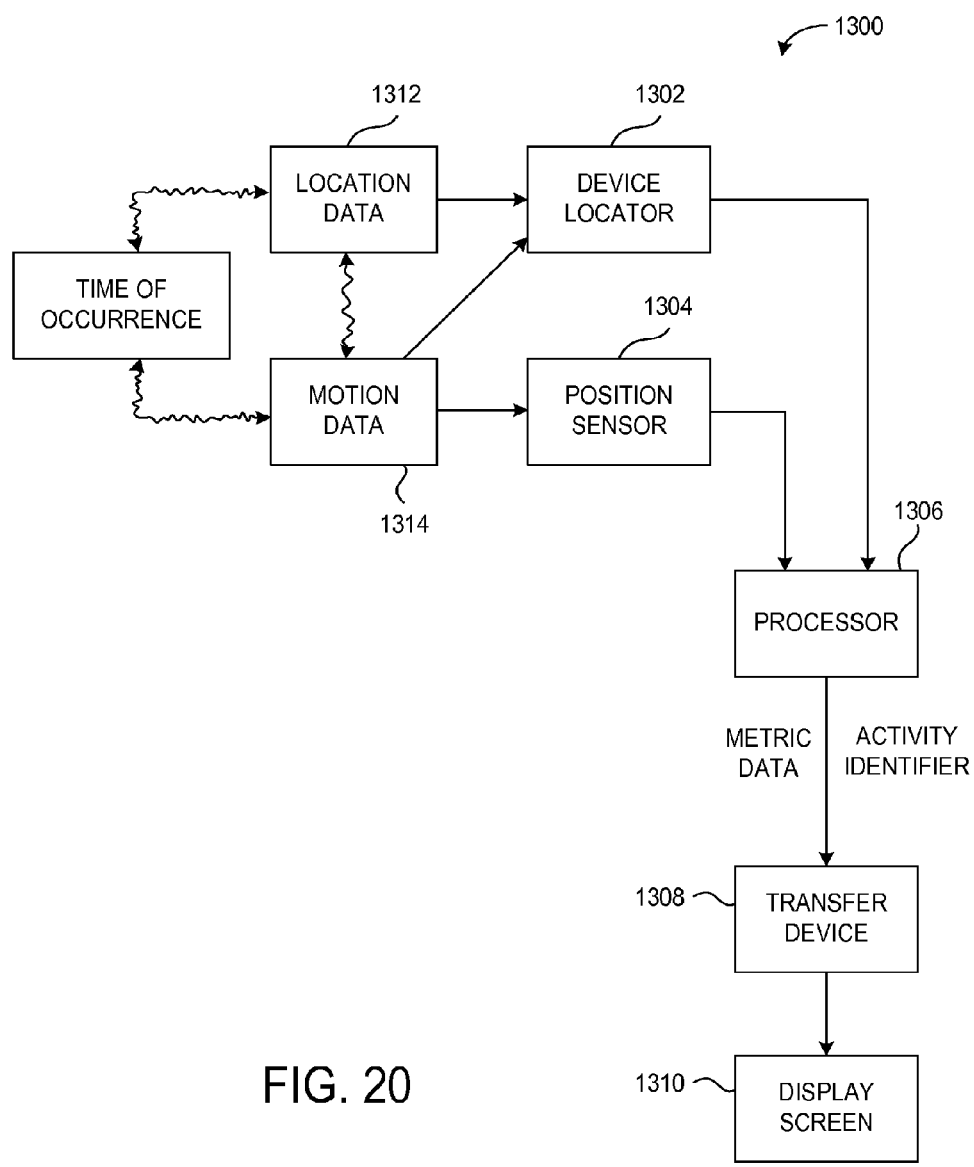
FIG. 20 is a diagram of a system for generating a metric, in accordance with one embodiment described in the present disclosure.

FIG. 20 is a diagram of an embodiment of a system 1300 for generating a metric. The system 1300 includes a device locator 1302, a position sensor 1304, a processor 1306, a transfer device 1308, and a display screen 1310.

Examples of the device locator 1302 include a device locator of a monitoring device or a device locator of the computing device 166. Examples of the processor 1306 include a processor of a monitoring device, a processor of the computing device 166, or a processor of the server 228. Examples of the transfer device 1308 include a communication device of a monitoring device, or a NIC of the computing device 166, or a communication device of the computing device 166, or a NIC of the server 228. Examples of the display screen 1310 include a display screen of a display device of a monitoring device or a display screen of a display device of the computing device 166.

The device locator 1302 obtains location data 1312, e.g., geo-locations, etc., of a monitoring device or of the computing device 166.

In one embodiment, the position sensor 1304 determines one or more positions of movement of a monitoring device or of the computing device 166. The one or more positions are indicated as motion data 1314. It should be noted that a time at which the motion data 1314, e.g., a position, another position, etc., is determined is a time of occurrence of the motion data 1314. Moreover, in some embodiments, a time at which the location data 1312, e.g., a geo-location, another geo-location, etc., is determined is a time of occurrence of the location data 1312.

The motion data 1314 is associated with a time of occurrence and the location data 1312 of a monitoring device. For example, the location data 1312 includes one or more geo-locations at which one or more positions of the motion data 1314 occur.

In some embodiments, the motion data 1314 is determined by the device locator 1302. For example, the device locator 1302 determines one or more geo-locations of a monitoring device when carried, e.g., worn, held, wrapped around an arm, etc., by the user 112A. In this example, the motion data 1314 includes the geo-location data. The geo-locations determined by the device locator 1302 provide positions of the user 112A at various times.

In various embodiments, the motion data 1314 includes geo-locations and positions of a monitoring device.

The processor 1302 receives the location data 1312 from the device locator 1302. Moreover, the processor 1302 receives the motion data 1314 from the position sensor 1304 and/or the device locator 1302. For example, a processor of the server 228 receives data, e.g., the location data 1312, the motion data 1314, etc., from a communication device of a monitoring device via the network 176 and a NIC of the server 228. As another example, a processor of the computing device 166 receives data, e.g., the location data 1312, the motion data 1314, etc., from a communication device of a monitoring device via the network 176 and a communication device of the computing device 166.

The processor 1306 processes the received motion data 1314 to identify a group of the motion data 1314 having a substantially common characteristic. For example, the processor 1306 determines whether the received motion data 1314 includes common positions of a monitoring device over a period of time or a common amount of change in positions of the monitoring device over a period of time. To illustrate the common positions, the processor 1306 determines whether the motion data 1314 repeats one or more of the substantial same co-ordinates over a period of time or repeats a pattern of co-ordinates over a period of time. To further illustrate the repetition of one or more of the substantially same co-ordinates, when the user 112A is playing golf, the user 112A repeats one or more of the same co-ordinates of a swing between an underhand position and an overhand position over a period of time. As another illustration of the repetition of one or more of the substantial same co-ordinates, when the user 112A is pitching while playing baseball, the user 112A repeats one or more of the substantial same co-ordinates between an overhand position and an underhand position over a period of time. As an illustration of the repetition of the pattern, when the user 112A is walking, a pattern of positions of the user 112A is repeated at each step taken by the user 112A.

As an illustration of the common amount of change in positions of the monitoring device over a period of time, the processor 1306 determines whether the motion data 1314 repeats substantially the same co-ordinates within a pre-determined standard deviation over a period of time or repeats a pattern of co-ordinates within a pre-determined standard deviation over a period of time. To further illustrate the repetition of the co-ordinates within a pre-determined standard deviation, when the user 112A is playing golf, the user 112A repeats co-ordinates that lie within a standard deviation that is pre-determined based on previous swings of the user 112A or of other users. As another illustration of the repetition of the co-ordinates within a pre-determined standard deviation, when the user 112A is pitching while playing baseball, the user 112A repeats co-ordinates that lie within a standard deviation that is pre-determined based on previous pitches of the user 112A or of other users. As an illustration of the repetition of the pattern within a pre-determined standard deviation, when the user 112A is walking, at each step taken by the user 112A, a pattern of positions of the user 112A is within a standard deviation of a pre-determined pattern of walking. The pre-determined pattern of walking is of the user 112A or of other users.

The processor 1306 processes the location data 1312 for the group of the motion data. The group of motion data 1314 by way of processing the location data 1312 provides an activity identifier. For example, the processor 1306 determines one or more geo-locations of the user 112A at which the user 112A is performing an activity identified by the group of motion data 1312. To illustrate, the processor 1306 determines whether the user 112A has traveled a distance greater than a pre-determined distance between two geo-locations in a period of time. In this illustration, it is identified by the position sensor 1304 that the user 112A is engaging in a repeatable pattern. In this illustration, it is determined that the user 112A is running. The processor 1306 generates an activity identifier that identifies an activity of running being performed by the user 112A. As another illustration, the processor 1306 determines based on the geo-location-location database that the user 112A is at a golf course. In this illustration, it is identified by the position sensor 1304 that a motion of the user 112A repeats co-ordinates between an underhand position and an overhand position within a pre-determined standard deviation over a period of time. In this illustration, it is determined that the user 112A is playing golf. The processor 1306 generates an activity identifier that identifies an activity of baseball being performed by the user 112A. As yet another illustration, the processor 1306 determines based on the geo-location-location database that the user 112A is at a baseball field. In this illustration, it is identified by the position sensor 1304 that a motion of the user 112A repeats co-ordinates between an overhand position and an underhand position within a pre-determined standard deviation over a period of time. In this illustration, it is determined that the user 112A is playing baseball. The processor 1306 generates an activity identifier that identifies an activity of baseball being performed by the user 112A.

The motion data 1314 includes metric data that identifies detailed characteristics of the motion data 1314 for the activity identifier. For example, the motion data may include number of swings taken while playing golf, a number of steps taken by the user 112A while walking, or a number of steps taken by the user 112A while running, or a number of stairs climbed by the user 112A while walking, or a number of stairs descended by the user 112A while walking, or a number of stairs climbed by the user 112A while running, or a number of stairs descended by the user 112A while running, or an amount of calories burned by the user 112A while walking, or an amount of calories burned by the user 112A while running, an amount of calories burned by the user 112A while performing an activity, or an amount of distance traveled by the user 112A while walking, or an amount of distance traveled by the user 112A while performing an activity, or an amount of hours slept by the user 112A, or an amount of time for which the user 112A is active, or an amount of time for which the user 112A is passive, or an amount of time for which the user 112A is sedentary, or an amount of time for which the user 112A is at a location, or a time at which the user 112A wakes up, or a time at which the user 112A goes to bed, or an amount of time the user 112A is performing an activity, or a combination thereof.

In some embodiments, to determine a number of stairs climbed by the user 112A, a processor determines whether a change in an x position of an arm of the user 112A occurs simultaneous with a change in a y position of the arm. Upon determining that the change in the x position occurs simultaneous with the change in the y position, the processor determines a number of times the change in the y position has occurred. The number of time is equal to a number of stairs ascended or descended by the user 112A. The changes in the x and y positions are received by the processor from a position sensor.

In several embodiments, to determine whether the user 112A is ascending or descending stairs, a processor determines whether a y2 position of an arm of the user 112A that occurs after an occurrence of a y1 position is higher than the y1 position. Upon determining that the y2 position is higher than the y1 position, the processor determines that the user 112A is climbing stairs. On the other hand, upon determining that the y 2 position is lower than the y1 position, the processor determines that the user 112A is descending stairs. In another embodiment, an altimeter of the monitoring device or other portable device held, carried or worn by the user can detect altitude, which can be used to strengthen the determination of a metric.

The transfer device 1308 receives the activity identifier and the metric data from the processor 1306 and sends the activity identifier and the metric data to a screen of a device for display. For example, the transfer device 1308 sends the activity identifier and the metric data via the network 176 to the NIC of the computing device 166 and the processor of the computing device 166 applies a rendering program to display the activity identifier and the metric data on the display device of the computing device 166. As another example, the transfer device 1308 sends the activity identifier and the metric data via the network 176 to a communication device of a monitoring device and a processor of the computing device 166 applies a rendering program to display the activity identifier and the metric data on a display device of the monitoring device.

In some embodiments, the activity identifier is a GUI that receives an input for rendering more or less of the detailed characteristics of the motion data. For example, when the activity identifier displayed on a screen is selected by the user 112A via a user interface of a monitoring device or via an input device of the computing device 166, a number of the detailed characteristics displayed on the screen are reduced. For example, instead of an amount of time for which the user 112A walked on Monday, May 1 and an amount of calories burned by the user 112A by the walking, the amount of time or the amount of calories are displayed on a screen. As another example, instead of an amount of time for which the user 112A walked on Monday, May 1 and an amount of calories burned by the user 112A by the walking, a summary of the metric data is displayed on a screen. In this example, it may be summarized that the user 112A walked a lot on Monday, May 1. As yet another example, in addition to an amount of time for which the user 112A walked on Monday, May 1 and an amount of calories burned by the user 112A by the walking, upon receiving an input of an activity identifier, a summary of the metric data for Monday, May 1 is displayed. In this example, it may be displayed that the user 112A walked a lot on Monday, May 1 and/or that the user 112A walked at a park and/or a time at which the user 112A started to walk and/or an amount of time the user 112A finished walking.

In some embodiments in which the processor 1306 and the display screen 1310 are parts of the same device, e.g., a monitoring device, the computing device 166, etc., the transfer device 1308 does not couple the processor 1306 with the display screen 1310. In these embodiments, the processor 1306 is coupled to the display screen 1310.

In some embodiments, a method, system or combinations of methods and system are provided to gather and process metric data related to user activity. The metric data can include captured or tracked motions, movements, travel or combinations thereof. The metric data that is captured can, from time to time, be transferred to one or more computing devices. The computing devices can include those that are connected to the Internet, where cloud processing can be performed in accordance with defined logic and algorithms. The tracked data can take on many forms, such as tracked motions, tracked patterns of motions, tracked locations associated with the motions, and/or associated geo-location data associated with the tracked motions or activities.

Broadly speaking, the monitoring device, when worn by a user or held/carried by a user will track activity data, which defines metric data. The metric data may be associated to particular times of day and then rendered on a graphical user interface. In one embodiment, the metric data is also correlated to location information. Each metric data or groups of metric data can be graphically displayed in a way that conveys location for the metric data. For example, the location information can identify a place where certain tracked activity occurred.

In one embodiment, the system will automatically group certain metric data to particular events. An event, in one embodiment, defines a type of activity and location for that activity. The event can be, for instance, jogging in Central Park in New York City. In some embodiments, the metric data, which is automatically associated or related to an event can provide information that is not accurate, information that might need fine tuning or information that the user does not want to share or store with the tracked metric data.

In one example, if a user is tracked at a playground jogging, and the user was supposed to be at a company meeting, the user may wish to edit the event or modify the metric for privacy concerns. Thus, the systems and methods provide ways for editing, modifying, correcting, adjusting, or removing events tagged or identified for certain metric data collected with the monitoring device. In one embodiment, some of these functions can be performed using user interfaces provided with graphical user interfaces (GUI) and controls. The GUIs and controls can be on any device connected to the Internet or a network, or a device that can communicate with another device that has or can later obtain Internet or network access.

Figure 21:
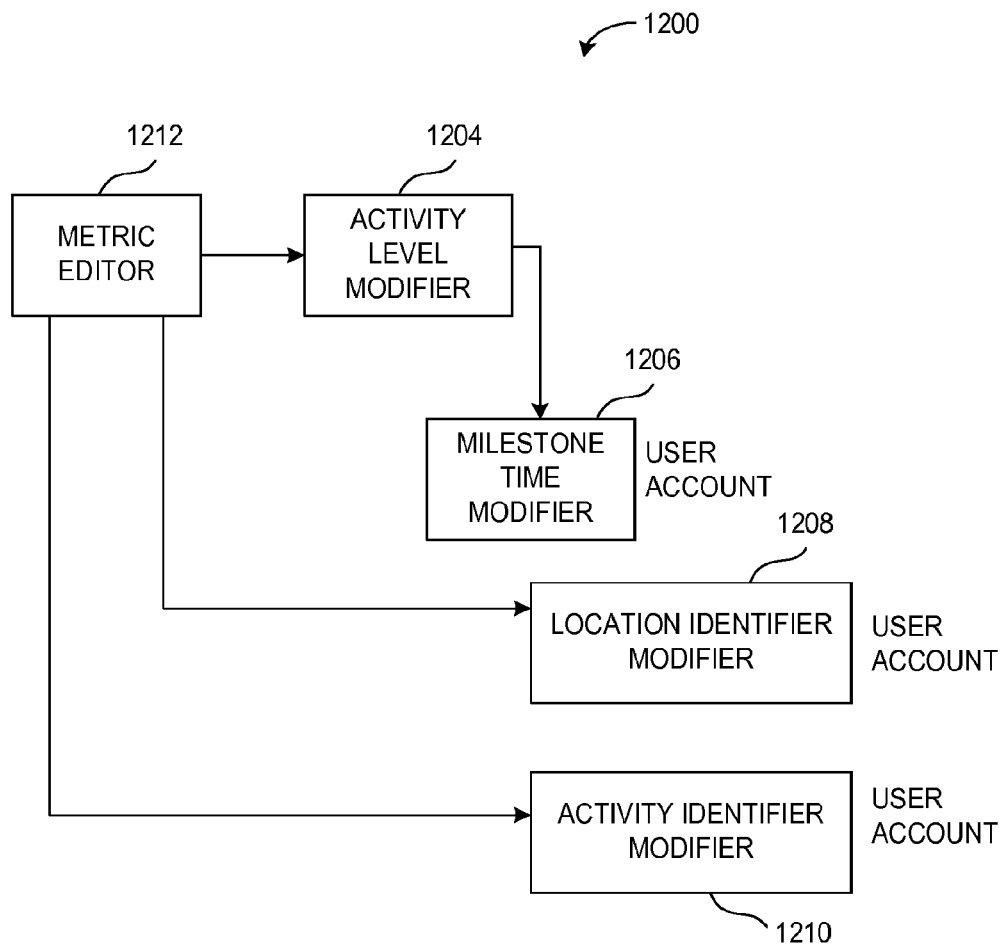
FIG. 21 is a diagram of a system for editing a metric and changing a time associated with achieving a milestone, changing a location identifier, and changing an activity identifier based on the edited metric, in accordance with one embodiment described in the present disclosure.

FIG. 21 is a diagram of an embodiment of a system 1200 for editing a metric and changing a milestone based on the edited metric. The system 1200 includes a metric editor 1202, an activity level modifier 1204, a milestone time modifier 1206, a location identifier modifier 1208, and an activity level modifier 1210. In some embodiments, each or selected ones of the metric editor 1202, the activity level modifier 1204, the milestone time modifier 1206, the location identifier modifier 1208, and the activity level modifier 1210 may be implemented within a processor of a monitoring device, the processor of the computing device 166, or the processor of the server 228. In some embodiments, the editor and modifiers can be implemented as code, software or hardware and software. In some embodiments, the code or software can be implemented in firmware of a device, where special digital signal processors (DSPs) are used, field programmable gate arrays (FPGAs), programmable logic devices (PLDs), or specialized circuits, logic, gates, transistors, chips, chip sets, batteries, clocks, etc.

The metric editor 1202 receives a change to a metric from the user 112A. For example, the user 112A accesses the user account 174 and edits a metric, e.g., an activity level, a time for which an activity is performed, a time at which an activity is started by the user 112A, a time at which an activity is finished by the user 112A, a location at which an activity is performed, a type of activity, etc. The user 112A may select an edit button displayed besides a metric on a GUI of a monitoring device or of the computing device 166 to edit the metric. In some embodiments, the user 112A selects a metric that is displayed on a GUI to edit the metric. In various embodiments, a type of activity includes a class of the activity.

The user 112A provides a change to a metric via the user interface of a monitoring device or via the input device of the computing device 166. The metric editor 1202 executes a change to a metric upon receiving the change from the user 112A.

Any edits to a metric are communicated from the metric editor 1202 to the activity level modifier 1204, the milestone time modifier 1206, the location identifier modifier 1208, and/or to the activity identifier modifier 1210.

The activity level modifier 1204 changes an activity level that is displayed on a display device to represent the edited metric. For example, the activity level modifier 1204 increases or decreases an amplitude of the activity level $146_1$ (FIG. 7A) to represent the edited metric.

Moreover, the milestone time modifier 1206 modifies a remaining time period of achievement of a milestone by the user 112A based on the change in the activity level. In one embodiment, the entire time period is allocated for achievement of the milestone by a processor. For example, the milestone modifier 1206 calculates a sum of activity levels to be achieved during a remainder of a period of time. The sum is calculated after one or more activity levels are changed by the activity level modifier 1204. The change in the sum after the change in the activity levels changes the remainder time period of achieving the milestone.

In some embodiments, a milestone is a goal.

In various embodiments, a milestone is a sub-goal for achieving a goal. For example, a milestone to achieve a goal of walking 360,000 steps a month is to walk 12,000 steps a day. As another example, a milestone to achieve a goal of losing 5 pounds in a month is to run for 20 minutes a day.

In some embodiments, a milestone is a number of times an activity is performed in a time period or a sum of one or more activity levels of one or more activities performed by the user 112A in a time period. For example, a milestone includes a number of walks per time period, or a number of runs per time period, or a number of times the user 112A bicycled per time period, or a number of times the user 112A went to a gym per time period, or a length of time that the user 112A is at work per time period, or a length of time for which the user 112A slept during a time period, or a change in weight of the user 112A per time period, a weight to be achieved at an end of a time period, a number of calories to be burned at an end of a time period, or a change in calories of the user 112A per time period, or a combination thereof.

In various embodiments, a milestone is associated with a subset of an amount of time in which a goal is to be achieved. For example, when a goal is to be achieved in a month, each milestone is to be achieved in a day or a week. As another example, when a goal is to be achieved in a year, a milestone is to be achieved in a week, or a month, or six months, or ten months, etc.

In some embodiments, a milestone is provided to the user account 174 to be achieved each day, or each week, or each month, or each year to help the user 112A identify good and bad habits and to help achieve a lifestyle change in the life of the user 112A.

Examples of a goal include achieving an activity level of one or more activities within an amount of time. To illustrate, a goal may be to achieve a number of calories burned within a week. To further illustrate, a goal may be to achieve an amount of weight loss within a month. As another illustration, a goal may be to run or walk a number of steps every day. As another example, a goal includes achieving an activity level of one or more activities at one or more locations within an amount of time. As yet another example, a goal includes achieving an activity level of one or more activities at one or more locations.

Other examples of a goal include achieving an activity level at a location within an amount of time. To illustrate, a goal may be to walk a number of steps at work each day. As another illustration, a goal may be to go to bed at 9 PM at home each night.

In some embodiments, a goal is associated with an activity that is trackable via a monitoring device. For example, a goal is to walk a number of steps, which is trackable by the position sensor or the device locator of a monitoring device. As another example, a goal is to walk at a geo-location for an amount of time and the goal is trackable by the device locator and the time measurement device of a monitoring device.

A goal is provided by the user 112A via the user interface of a monitoring device or via the input device of the computing device 166. For example, the user 112A logs into a representation of the user account 174 to provide the goal.

A goal is received from the NIC of the computing device 166 and the network 176 by the NIC of the server 228. In some embodiments, a goal is received from a communication device, e.g., wireless communication device, wired communication device, etc., of a monitoring device via the network 176 by the NIC of the server 228. In various embodiments, a goal is received by the processor of the computing device 166 from the input device of the computing device 166.

In some embodiments, a goal is received by a communication device of the computing device 166 from a communication device of a monitoring device.

Continuing further with FIG. 21, upon receiving an edit to a metric from the metric editor 202, the location identifier modifier 1208 modifies a location identifier that is associated with the metric that is edited. For example, when the metric editor 1202 indicates that an amount of time spent by the user 112A at home of the user 112A is 0 minutes instead of 10 minutes, the location identifier modifier 1208 removes a location identifier that identifies a home of the user 112A for the 10 minutes from a GUI. As another example, when the metric editor 1202 indicates that the user 112A is at a home of the user 112A at a time instead of at a golf course, the location identifier modifier 1208 changes a location identifier that indicates that the user 112A is at home to indicate that the user 112A is at the golf course at that time. As yet another example, when the metric editor 1202 indicates that the user 112A is at a home of the user 112A between 9 AM and 10 AM instead of between 12 PM and 1 PM, the location identifier modifier 1208 moves a location identifier identifying that the user 112A is at his home from pointing between 12 PM and 1 PM to pointing between 9 AM and 10 AM.

Upon receiving an edit to a metric from the metric editor 1202, the activity identifier modifier 1210 modifies an activity identifier that is associated with the metric that is edited. As an example, when the metric editor 1202 indicates that an amount of time spent by the user 112A playing a sport between 11 AM and 12 PM is 0 minutes instead of 20 minutes, the activity identifier modifier 1210 removes from a GUI an activity identifier that identifies the activity of sport being performed for the 20 minutes by the user 112A. As another example, when the metric editor 1202 indicates that the user 112A is walking instead of being sedentary at a time, the activity identifier modifier 1210 changes an activity identifier that indicates that the user 112A is being sedentary to indicate that the user 112A is walking at that time. As yet another example, when the metric editor 1202 indicates that the user 112A is playing golf between 2 PM and 3 PM instead of between 12 PM and 1 PM, the activity identifier modifier 1210 moves an activity identifier identifying that the user 112A is playing golf from pointing between 12 PM and 1 PM to pointing between 2 PM and 3 PM.

In some embodiments, a processor applies adaptive learning of locations. For example, a processor determines that a user is at a location and/or achieves an activity level of an activity at the location for a number of times greater than a pre-determined number. The processor further determines a range of times at which the user is at the location for the number of times and/or achieves the activity level at the location. When the user visits the location on a day after the processor determines the range of times, the processor determines whether a time at which the user visits the location falls within the range of times. Upon determining that the time at which the user visits the location at a time that falls within the range of times, the processor determines that the user is at the location and/or will achieve the activity level at the location.

In several embodiments, a processor applies refined learning of location and size. For example, a processor determines that the user 112A visits an inside the user's home and determines that one or more geo-locations within the inside of the home corresponds to the home. In this example, the processor determines that the one or more geo-locations within the inside of the home corresponds to the home based on the geo-location-location database or based on a selection received from the user indicating that the geo-locations correspond to the home. In this example, a processor determines that the user 112A visits a backyard of the user's home and determines that one or more geo-locations of the backyard of the home correspond to the home. In this example, the processor determines that one or more geo-locations of the backyard corresponds to the home based on the geo-location-location database or based on a selection received from the user indicating that the geo-locations correspond to the home. When the user visits a geo-location within the backyard or the inside of the home for a next time, the processor determines that the user is at his/her home. It should be noted that although home is used as an example, in some embodiments, other locations, e.g., a gym, a work place, a golf course, a race track, etc., may be used.

In several embodiments, a processor determines a favorite route of a user based on a number of times the user follows the route. For example, a processor determines that a user follows a route for greater than a pre-determined number of times. In this example, the processor determines that the route is a favorite route of the user. In this example, the processor determines data associate with the route, e.g., a statistical amount of time taken to complete the route, or a location close to the route, or a destination of the route, or a combination thereof, etc. In some embodiments, the processor determines the destination of the route from a maps service or from the geo-location-location database. Examples of the statistical amount of time taken to complete the route include an average amount of time to complete the route, a maximum amount of time to complete the route, a minimum amount of time taken to complete the route, etc. In this example, the processor labels, within a GUI, the route with the data associated with the route. To illustrate, the processor labels a route as "walk to a train" instead of "walk". As another illustration, the processor labels a route as "morning walk to work" instead of "walk". As another illustration, the processor labels a route as "3 mile run down Cedar street" instead of "run". As another illustration, the processor labels a route as "6 mile beach run" instead of "run". Examples of the route include a dog walking route, a commute to work route, a running route, a route to a bus station, a route to a train station, a route to work, a route to home, a route to a friend's home, etc.

In some embodiments, a processor quantifies an emotional response when a user is responsive to a piece of entertainment. The emotional response includes a combination of the HRV and/or the GSR. Based on the emotional response, the processor assigns a rating to the piece of entertainment. For example, when the HRV and/or the GSR indicate to the processor that the user is sleeping during a movie, the processor assigns a low rating to the movie. On the other hand, when the HRV and/or the GSR indicate to the processor that the user is excited during the movie, the processor assigns a high rating to the movie. Based on the HRV and/or the GSR, the processor determines a type of the piece of entertainment that the user likes. In some embodiments, the processor prompts a user to provide the rating. The piece of entertainment may be a movie, an opera, a ballet, a concert, a song, a multimedia presentation, a television show, news, etc. Examples of a type of the piece of entertainment include a horror piece, an action piece, a drama piece, a sad piece, a comedy piece, etc.

In various embodiments, a processor determines that a user is at a location at which the piece of entertainment is presented, e.g., publicly displayed, shown, etc., and displays within a GUI that includes event data information regarding the location. For example, a processor determines that a user is at a movie theater and populates a GUI with show times of movies at the theater. The show times of the movies are obtained from a website or a database that is used to present the show times. Other examples of information regarding the location include video games available at a theater, types of food available at a concert, etc.

In various embodiments, a processor determines motion and location features from users to build a network database. For example, the processor determines that a user performs an activity at a location for a number of times and performs a motion signature that identifies the activity for the number of times. The motion signature is a motion of a user that is substantially repeated over a time period. For example, a first swimming motion when the user is at a swimming pool in a gym is performed on day 1 and a second swimming motion when the user is at the swimming pool at the gym is performed on day 2. The first and second motions are within a standard deviation. When the user visits, e.g., enters, etc., the location at another time, e.g., day 3, etc., the processor determines that the user is going to perform the same activity that the user has performed for the number of times. For example, the processor determines based on the motion signature and the location visited for the number of times as soon as the user enters a gym that the user will swim at the gym. As another example, the processor determines that the user will do yoga at a yoga place based on the motion signature and the location visited for the number of times.

It should be noted that in some embodiments, any method or function or operation that is described herein as being performed by the processor 226 of the monitoring device 108A (FIG. 3A) or by the processor 234 of the computing device 166 (FIG. 5) may be performed by the processor 302 (FIG. 3B) of the monitoring device 108B or by the processor 190 (FIG. 2A) of the server 228.

In various embodiments, functions or methods or operations described herein as being performed by a processor of a device are performed by one or more processors of the device. For example, a function of displaying a GUI is performed by a GPU (not shown) of the monitoring device 108A instead of by the processor 234 (FIG. 3A).

In a number of embodiments, any GUI, described herein, is generated by a virtual machine, the processor of the server 228, the processor of a monitoring device, the processor of the computing device 166, a processor of a server of the network 176, a GPU of the computing device 166, a GPU of a monitoring device, or a combination thereof.

In a number of embodiments, all GUIs, described herein, are accessed by the user 112A when the user 112A accesses the user account 174 (FIG. 2A).

In various embodiments, a web page is a GUI.

It should be noted that although a limited number of identifiers are shown in Figures described herein, in some embodiments, any number of identifiers are used.

Embodiments described in the present disclosure may be practiced with various computer system configurations including hand-held devices, microprocessor systems, microprocessor-based or programmable consumer electronics, minicomputers, mainframe computers and the like. Several embodiments described in the present disclosure can also be practiced in distributed computing environments where tasks are performed by remote processing devices that are linked through a wire-based or wireless network.

With the above embodiments in mind, it should be understood that a number of embodiments described in the present disclosure can employ various computer-implemented operations involving data stored in computer systems. These operations are those requiring physical manipulation of physical quantities. Any of the operations described herein that form part of various embodiments described in the present disclosure are useful machine operations. Several embodiments described in the present disclosure also relates to a device or an apparatus for performing these operations. The apparatus can be specially constructed for a purpose, or the apparatus can be a computer selectively activated or configured by a computer program stored in the computer. In particular, various machines can be used with computer programs written in accordance with the teachings herein, or it may be more convenient to construct a more specialized apparatus to perform the required operations.

Various embodiments described in the present disclosure can also be embodied as computer-readable code on a non-transitory computer-readable medium. The computer-readable medium is any data storage device that can store data, which can be thereafter be read by a computer system. Examples of the computer-readable medium include hard drives, network attached storage (NAS), ROM, RAM, compact disc-ROMs (CD-ROMs), CD-recordable (CD-Rs), CD-rewritable's (RWs), magnetic tapes and other optical and non-optical data storage devices. The computer-readable medium can include computer-readable tangible medium distributed over a network-coupled computer system so that the computer-readable code is stored and executed in a distributed fashion.

Although the method operations were described in a specific order, it should be understood that other housekeeping operations may be performed in between operations, or operations may be performed in an order other than that shown, or operations may be adjusted so that they occur at slightly different times, or may be distributed in a system which allows the occurrence of the processing operations at various intervals associated with the processing, as long as the processing of the overlay operations are performed in the desired way. For example, the operations 104 and 118 in FIG. 6A are performed simultaneously or the operation 118 is performed before the operation 104. As another example, the operations 202 and 204 of FIG. 6D are performed simultaneously or the operation 204 is performed before performing the operation 202. As yet another example, the operation 223 of FIG. 6F may be performed before, or after, or simultaneous with the performance of the operation 229.

Although the foregoing embodiments have been described in some detail for purposes of clarity of understanding, it will be apparent that certain changes and modifications can be practiced within the scope of the appended claims. Accordingly, the present embodiments are to be considered as illustrative and not restrictive, and the various embodiments described in the present disclosure is not to be limited to the details given herein, but may be modified within the scope and equivalents of the appended claims.

What is claimed is:

1. A method operable by a server, the server comprising a network interface configured to communicate with a monitoring device via a computer network, a memory device configured to store a rules database including inference rules of the monitoring device, and a processor, the method comprising:
receiving, via the network interface, one or more geo-locations associated with the monitoring device of a user;
receiving, from the monitoring device via the network interface, data regarding a movement of a body part of the user, the movement occurring within a time period, the monitoring device configured to attach to the user and including one or more sensors configured to collect the data regarding the movement of the body part;
identifying, by the processor, a first type of activity and a second type of activity based on a comparison of the data regarding the movement to patterns of movement corresponding to a plurality of predefined activity types, the second type of activity being different than the first type of activity;
determining, by the processor based on the inference rules, that the identified first and second types of activities are consistent with the one or more geo-locations, the inference rules correlating the data regarding the movement of the body part and the geo-location information of the monitoring device to the types of activities;
determining, by the processor, an amount of each of the first and second types of activities;
determining, by the processor, that the amount of the first type of activity is above a first threshold level;
determining, by the processor, that the amount of the second type of activity is above a second threshold level;
generating, by the processor, first and second textual descriptions indicative of the amounts of the first and second types of activities being above the first and second threshold levels, respectively, without including the amounts of the first and second types of activities;
associating, by the processor, the first and second textual descriptions with a calendar of an account of the user; and
providing, via the computer network and the network interface, access to the account to allow viewing of the first and second textual descriptions on a graphical user interface of a device associated with the account.

2. The method of claim 1, wherein the calendar of the user is identified by the account.

3. The method of claim 1, further comprising:
including at least one additional an activity identifier for a calendar date of the calendar of the user, the calendar being identified by the account.

4. The method of claim 1, further comprising:
including at least one additional activity identifier associated with one of the first and second textual descriptions for a calendar date of the calendar of the user, the calendar being identified by the account.

5. The method of claim 1, further comprising:
generating a location identifier that corresponds to the one or more geo-locations; and
associating the location identifier with the amount of the first type of activity.

6. The method of claim 1, wherein the amount of the activity of the first type is to be represented as a level of the activity of the first type during the time period.

7. The method of claim 1, further comprising:
identifying an activity identifier, and for the activity identifier generating a level of the activity of the second type,
wherein access to the account of the user enables viewing of the activity identifier and level of the activity of the second type.

8. The method of claim 1, further comprising identifying a graphical icon representing the first type of activity.

9. The method of claim 1, further comprising:
analyzing the one or more geo-locations of where the movement of the body part occurred, the analyzing of the one or more geo-locations used to select a location identifier for the one or more geo-locations;
associating the location identifier with a calendar date of the calendar, wherein providing access to the account of the user is performed to allow viewing of the location identifier as being associated with the calendar date.

10. The method of claim 1, further comprising:
associating the first type of activity identified by an activity identifier with a calendar date of the calendar and a calendar time of the calendar,
wherein providing access to the account is performed to allow viewing of the activity identifier as being associated with the calendar date and the calendar time.

11. A system comprising:
a network interface configured to communicate with a monitoring device via a computer network;
a memory device configured to store a rules database including inference rules of the monitoring device; and
a processor coupled to the memory device, the processor configured to:
  receive, via the network interface, one or more geo-locations associated with the monitoring device of a user;
  receive, from the monitoring device via the network interface, data regarding a movement of a body part of the user, the movement occurring within a time period, the monitoring device configured to attach to the user and including one or more sensors configured to collect the data regarding the movement of the body part;
  identify a first type of activity and a second type of activity based on a comparison of the data regarding the movement to patterns of movement corresponding to a plurality of predefined activity types, the second type of activity being different than the first type of activity;
  determine, based on the inference rules, that the identified first and second types of activities are consistent with the one or more geo-locations, the inference rules correlating the data regarding the movement of the body part and the geo-location information of the monitoring device to the types of activities;
  determine an amount of each of the first and second types of activities;
  determine that the amount of the first type of activity is above a first threshold level;
  determine that the amount of the second type of activity is above a second threshold level;
  generate first and second textual descriptions indicative of the amounts of the first and second types of activities being above the first and second threshold levels, respectively, without including the amounts of the first and second types of activities;
  associate the first and second textual descriptions with a calendar of an account of the user; and
  provide, via the computer network and the network interface, access to the account to allow viewing of the first and second textual descriptions on a graphical user interface of a device associated with the account.

12. The system of claim 11, wherein the calendar of the user is identified by the account.

13. The system of claim 11, wherein the processor is configured to include an activity identifier for a calendar date of the calendar of the user, the calendar being identified by the account.

14. The system of claim 11, wherein the processor is configured to include an activity identifier associated with one of the first and second textual descriptions for a calendar date of the calendar of the user, the calendar being identified by the account.

15. The system of claim 11, wherein the processor is configured to:
generate a location identifier that corresponds to the one or more geo-locations; and
associate the location identifier with the amount of the first type of activity.

16. The system of claim 11, wherein the amount of the activity of the first type is to be represented as a level of the activity of the first type during the time period.

17. The system of claim 11, wherein the processor is configured to:
identify an activity identifier, and for the activity identifier generate a level of the activity of the second type,
wherein access to the account of the user enables viewing of the activity identifier and level of the activity of the second type.

18. The system of claim 11, wherein the processor is configured to identify a graphical icon representing of the first type of activity.

19. The system of claim 11, wherein the processor is configured to:
analyze the one or more geo-locations of where the movement of the body part occurred, the analyzing of the one or more geo-locations used to select a location identifier for the one or more geo-locations;
associate the location identifier with a calendar date of the calendar,
wherein providing access to the account of the user is performed to allow viewing of the location identifier as being associated with the calendar date.

20. The system of claim 11, wherein the processor is configured to:
- associate the first type of activity identified by an activity identifier with a calendar date of the calendar and a calendar time of the calendar,
- wherein the access to the account is performed to allow viewing of the activity identifier as being associated with the calendar date and the calendar time.

21. A non-transitory computer readable medium containing program instructions, wherein execution of the program instructions by one or more processors of a computer system causes the one or more processors to carry out a plurality of operations of:
- receiving, via a network interface of the computer system, one or more geo-locations associated with a monitoring device of a user;
- receiving, from the monitoring device via the network interface, data regarding a movement of a body part of the user, the movement occurring within a time period, the monitoring device configured to attach to the user and including one or more sensors configured to collect the data regarding the movement of the body part;
- identifying a first type of activity and a second type of activity the user based on a comparison of the data regarding the movement to patterns of movement corresponding to a plurality of predefined activity types, the second type of activity being different than the first type of activity;
- determining, based on inference rules of the monitoring device stored in a rules database on the non-transitory computer readable medium, that the identified first and second types of activities are consistent with the one or more geo-locations, the inference rules correlating the data regarding the movement of the body part and the geo-location information of the monitoring device to the types of activities;
- determining an amount of each of the first and second types of activities;
- determining that the amount of the first type of activity is above a first threshold level;
- determining that the amount of the second type of activity is above a second threshold level;
- generating first and second textual descriptions indicative of the amounts of the first and second types of activities being above the first and second threshold levels without including the amounts of the first and second types of activities;
- associating the first and second textual descriptions with a calendar of an account of the user; and
- providing, via a computer network and the network interface, access to the account to allow viewing of the first and second textual descriptions on a graphical user interface of a device associated with the account.

22. The non-transitory computer readable medium of claim 21, wherein the calendar of the user is identified by the account.

23. The non-transitory computer readable medium of claim 21, wherein the operations further comprise:
- including an activity identifier for a calendar date of the calendar of the user, the calendar being identified by the account.

24. The non-transitory computer readable medium of claim 21, wherein the operations further comprise:
- including an activity identifier associated with one of the first and second textual descriptions for a calendar date of the calendar of the user, the calendar being identified by the account.

25. The non-transitory computer readable medium of claim 21, wherein the operations further comprise:
- generating a location identifier that corresponds to the one or more geo-locations; and
- associating the location identifier with the amount of the first type of activity.

26. The non-transitory computer readable medium of claim 21, wherein the amount of the activity of the first type is to be represented as a level of the activity of the first type during the time period.

27. The non-transitory computer readable medium of claim 21, wherein the operations further comprise:
- identifying an activity identifier, and for the activity identifier generating a level of the activity of the second type,
- wherein access to the account of the user enables viewing of the activity identifier and level of the activity of the second type.

28. The non-transitory computer readable medium of claim 21, further comprising identifying a graphical icon representing the first type of activity.

29. The non-transitory computer readable medium of claim 21, wherein the operations further comprise:
- analyzing the one or more geo-locations of where the movement of the body part occurred, the analyzing of the one or more geo-locations used to select a location identifier for the one or more geo-locations;
- associating the location identifier with a calendar date of the calendar,
- wherein providing access to the account of the is performed to allow viewing of the location identifier as being associated with the calendar date.

30. The non-transitory computer readable medium of claim 21, wherein the operations further comprise:
- associating the first type of activity identified by the activity identifier with a calendar date of the calendar and a calendar time of the calendar,
- wherein providing access to the account is performed to allow viewing of the activity identifier as being associated with the calendar date and the calendar time.

* * * * *